(12) United States Patent
Nagaswamy et al.

(10) Patent No.: US 10,336,723 B2
(45) Date of Patent: Jul. 2, 2019

(54) INHIBITORS OF TRKA KINASE

(71) Applicant: GVK BIOSCIENCES PRIVATE LIMITED, Hyderabad (IN)

(72) Inventors: Kumaragurubaran Nagaswamy, Hyderabad (IN); Vijaya G. Tirunagaru, Hyderabad (IN)

(73) Assignee: GVK BIOSCIENCES PRIVATE LIMITED, Hyderabad (IN)

( * ) Notice: Subject to any disclaimer, the term of this patent is extended or adjusted under 35 U.S.C. 154(b) by 0 days.

(21) Appl. No.: 15/545,061

(22) PCT Filed: Jan. 22, 2016

(86) PCT No.: PCT/IB2016/050328
§ 371 (c)(1),
(2) Date: Jul. 20, 2017

(87) PCT Pub. No.: WO2016/116900
PCT Pub. Date: Jul. 28, 2016

(65) Prior Publication Data
US 2018/0009781 A1 Jan. 11, 2018

(30) Foreign Application Priority Data
Jan. 23, 2015 (IN) .............................. 362/CHE/2015

(51) Int. Cl.
| | | |
|---|---|---|
| *C07D 401/12* | (2006.01) | |
| *C07D 403/12* | (2006.01) | |
| *C07D 401/14* | (2006.01) | |
| *C07D 405/14* | (2006.01) | |
| *C07D 405/12* | (2006.01) | |
| *C07D 409/12* | (2006.01) | |
| *C07D 417/14* | (2006.01) | |
| *C07D 471/04* | (2006.01) | |
| *C07D 491/056* | (2006.01) | |
| *C07D 207/14* | (2006.01) | |
| *A61K 31/4375* | (2006.01) | |
| *A61K 31/4709* | (2006.01) | |

(52) U.S. Cl.
CPC ......... *C07D 401/12* (2013.01); *C07D 207/14* (2013.01); *C07D 401/14* (2013.01); *C07D 403/12* (2013.01); *C07D 405/12* (2013.01); *C07D 405/14* (2013.01); *C07D 409/12* (2013.01); *C07D 417/14* (2013.01); *C07D 471/04* (2013.01); *C07D 491/056* (2013.01)

(58) Field of Classification Search
CPC ................ C07D 401/12; C07D 207/14; C07D 491/056; C07D 471/04; C07D 417/14; C07D 403/12; C07D 405/12; C07D 405/14; C07D 401/14; C07D 409/12
See application file for complete search history.

(56) References Cited

FOREIGN PATENT DOCUMENTS

| | | | |
|---|---|---|---|
| EP | 1499607 B1 | 12/2005 | |
| EP | 1364212 B1 | 2/2011 | |
| WO | 2004026836 A2 | 4/2004 | |
| WO | WO-2006070284 A1 * | 7/2006 | ........... C07D 401/12 |
| WO | 2008021924 A1 | 2/2008 | |
| WO | 2014078372 A1 | 5/2014 | |

OTHER PUBLICATIONS

Wiesner, T et al., Kinase fusions are frequent in Spitz tumors and spitzoid melanomas. Nature Communications. vol. 5, 2014, 3116; abstract; p. 3, paragraph 3; p. 4, paragraph 4.
Mardy, S. et al., Congenital Insensitivity to Pain with Anhldrosis: Novel Mutations in the TRKA (NTRK1) Gene Encoding a High-Affinity Receptor for Nerve Grown Factor. American Journal of Human Genetics, vol. 64, 1999,. pp. 1570-1579; p. 1570, col. 2, paragraph 2.
Eiro, N. et al, Inflammation and cancer. World Journal of Gastrointestinal Surgery, vol. 4, No. 3, Mar. 27, 2012, pp. 62-72; abstract.
Jimenez-Andrade, JM et al, Pathological Sprouting of Adult Nociceptors in Chronic Prostate Cancer-Induced Bone Pain. The Journal of Neuroscience, vol. 30, No. 44, Nov. 3, 2010, pp. 14649-14656; abstract.

(Continued)

*Primary Examiner* — John M Mauro
(74) *Attorney, Agent, or Firm* — Barnes & Thornburg LLP; Jeffrey R. Stone

(57) ABSTRACT

The present invention is directed to the compounds of Formula I which are inhibitors of tropomyosin-related kinase A (TrkA): Formula (I) or stereoisomers, tautomers or a pharmaceutically acceptable salts, metabolites, isotopes, solvates or prodrugs thereof, wherein, Ra, Rb, Rc, Rd, R1, R2, L and Het-Ar are as defined herein. These compounds can be used for the preventive and/or therapeutic treatment of diseases or disorders associated with abnormal activities of nerve growth factor (NGF) receptor TrkA such as Pain, inflammation or an inflammatory diseases, Cancer, atherosclerosis, restenosis, thrombosis, Neurodegenerative diseases, Erectile Dysfunction (ED), Skin disorders, Autoimmune disease like Multiple sclerosis, Sjögren's syndrome, endometriosis, diabetic peripheral neuropathy, prostatitis, Infectious diseases, diseases related to an imbalance of the regulation of bone remodeling, endometriosis, pelvic pain syndrome and diseases resulting from abnormal tissue remodelling and fibrotic disorders; or a disease, disorder, injury, or malfunction relating to dysmyelination or demyelination.

9 Claims, No Drawings

(56) References Cited

OTHER PUBLICATIONS

Talamas, FX et al, Discovery of N-[4-[6[tert-Butyl-5-methoxy-8-(6-methoxy-2-oxo-1H-pyridin-3-yl)-3-quinoly-phenyl-methanesulfonamide (RG7109), a Potent Inhibitor of the Hepatitis C Virus NS5B Polymerase. Journal of Medical Chemistry, vol. 57, No. 5, Mar. 13, 2014, pp. 1914-1931; p. 1, paragraph 1; p. 2, paragraph 5.

Castello, G. et al, HCV-related hepatocellular carcinoma; From chronic inflammation to cancer. Clinical Immunology, vol. 134, 2010, pp. 237-250; abstract.

International Search Report, dated May 4, 2016, for PCT Application No. PCT/IB2016/050328, filed Jan. 22, 2016.

\* cited by examiner

INHIBITORS OF TRKA KINASE

CROSS-REFERENCE TO RELATED APPLICATIONS

This application is a Section 371 national stage application of International application number PCT/IB2016/050328, filed Jan. 22, 2016, and published as WO2016/116900 on Jul. 28, 2016, which claims priority from Indian application number 362/CHE/2015 filed Jan. 23, 2015, the contents of which are incorporated herein in their entirety for all purposes.

FIELD OF THE INVENTION

The present invention relates to novel compounds that act as inhibitors of the members of Trk family protein kinases. Particularly, the invention discloses compounds possessing inhibitory activity against TrkA.

BACKGROUND OF THE INVENTION

The current available therapies for the treatment of pain utilize several classes of compounds like Non-steroidal anti-inflammatory drugs (NSAID's) and opioids. Most NSAIDs have one or more side effects such as irritation of the gastrointestinal (GI) tract leading to Nausea/Vomiting, Gastric ulceration/bleeding, Dyspepsia, inflammatory bowel disease, altered renal function, deleterious effects on the cardiovascular system and many more. Opioids result in emetic, constipatory and negative respiratory effects, as well as the potential for addiction. Hence, there is a great unmet need for drugs that alleviate pain without the adverse effects caused by the current pain therapies.

Trks and neurotrophins are well known for their effects on neuronal growth and survival through their regulation of cell proliferation, differentiation, apoptosis, and survival of neurons in both the central and peripheral nervous systems. Trk kinases, with three highly homologous isoforms, TrkA, TrkB, and TrkC are activated by high affinity growth factors named neurotrophins with Nerve growth factor (NGF), which activates TrkA; brain-derived neurotrophic factor (BDNF) and NT-4/5, which activate TrkB; and NT-3, which activates TrkC. The binding of neurotrophins to the extracellular domain of Trks causes the Trk kinase to autophosphorylate at several intracellular tyrosine sites and triggers downstream signal transduction pathways such as PI3K, Ras and PLC-γ pathways (Molecules 2015, 20(6), 10657-10688).

NGF signaling via TrkA is recognized to play an important role in pain sensation. Genetic studies in humans with TrkA loss of function mutations have provided evidence of the significant role of NGF signaling in pain sensation (ClinAuton Res 2002; 12 Suppl 1: 120-32). Currently, novel pain treatments are highly desired due to low efficacy and/or undesirable gastrointestinal, renal and psychotropic side effects of NSAIDS and opiates. NGF expression is increased in various pain conditions and administration of NGF increases pain sensitivity. Inhibition of NGF signaling via TrkA using a variety of antibody and small molecule based approaches have been shown to be effective in preclinical animal models for pain (Anesthesiology. 2011 July; 115(1): 189-204). Selective TrkA inhibition demonstrated equivalent efficacy to nonselective Trk inhibitors. Intermittent TrkA inhibition using a small molecule results in comparable efficacy to NGF antibodies in pain models (Andrews IASP, 2012). NGF mab, Tanezumab demonstrated excellent clinical efficacy in Osteoarthritis, chronic low back pain and diabetic peripheral neuropathy. TrkA selective small molecule inhibitors have therapeutic utility for various pain conditions. Efficacy of Anti-TrkA antibodies and anti-NGF antibodies for treatment of inflammatory and neuropathic pain have been demonstrated in vivo models in WO2006/131952 and WO2005/061540.

Trks play key role in malignant transformation, chemotaxis, metastasis, and survival signaling in human tumors (Cancer Lett 2001; 169:107-14). Oncogenic activation of TRKA occurs through genomic rearrangement and the creation of a gene fusion where extracellular domain of TrkA is replaced by fusion with another gene with the kinase domain intact results in constitutive activation of TrkA pathway. A number of NTRK1 gene fusions have been reported in a variety of cancers such as NSCLC, spitz melanoma, colorectal cancer, cholangiocarcinoma, soft tissue sarcoma, glioblastoma and papillary thyroid carcinoma (Cancer Discovery Jan. 1, 2015 5; 25) with more new fusions being reported based on the NGS sequencing of patient DNA. Trk inhibitors such as Entrectinib and LOXO-101 have demonstrated significant tumor regression in patients with Trk fusions (Cancer Discov. 2015 October; 5(10):1049-57, J Natl Cancer Inst. 2015 Nov. 12; 108(1)).

In addition to gene fusions, molecular alterations such as an in-frame deletion of NTRK1 (ΔTRKA) in acute myeloid leukemia (AML) and a splice variant of NTRK1 (TRKAIII) in neuroblastoma have been functionally characterized as oncogenic. Autocrine and paracrine signalling by Trk receptors have been implicated as protumorigenic in several different tumor types. An autocrine loop involving TrkA and NGF is associated with protumorigenic activity in both breast and prostate carcinomas (Mol Cell Biol. 2000 December; 20(23):8655-66, Clin Cancer Res 2001; 7:2237-45). Expression of TrkA and TrkC wild-type receptors is associated with a positive prognosis in patients with neuroblastoma (excluding expression of the splice variant TRKAIII) (N Engl J Med. 1993 Mar. 25; 328(12):847-54). Hence, TrkA inhibitors have potential for cancers driven by activated TrkA signaling due to molecular alterations or autocrine/paracrine signalling due to increased expression of TrkA and/or NGF.

TrkA is expressed in the bone forming area in mouse models of bone fracture (Bone. 2000 June; 26(6):625-33) and Trk inhibitors induce apoptosis of proliferating osteoblasts (Cancer Res. 2002 Feb. 15; 62(4):986-9) suggesting use of Trk inhibitors for bone remodelling diseases such as bone metastases in cancer patients.

NGF and TrkA are expressed in immune cells and a localized increase in NGF at the sites of inflammation is observed during the inflammatory process. Inflammatory cytokines such as IL-1beta, TNF-alpha and IL-6 are able to modify the basal production of NGF in the organism and induce the synthesis of NGF in a variety of cell types and tissues. TrkA-NGF pathway is also involved in a number of disorders such as Osteoarthritis, Multiple Sclerosis (J Clin Immunol. December 2011; 31(6): 1010-1020) and in inflammatory diseases including Asthma (Pharmacology & Therapeutics 2008, 117(1), 52-76), Interstitial Cystitis (The Journal of Urology 2005, 173(3), 1016-21), inflammatory bowel diseases including Ulcerative Colitis and Crohn's disease (Gut 2000, 46(5), 670-678), neurodegenerative diseases like Alzheimer's disease, Huntington's disease, Progressive Supranuclear Palsy (J Alzheimers Dis. 2014; 40(3): 605-617, ActaNeuropathol. 1998 November; 96(5):495-501) and Neurogenic Erectile Dysfunction (European Urology, November 2014). Inhibition of Trk pathway has been shown to be effective in preclinical models of inflammatory diseases. Therefore, TrkA kinase inhibition can be used as a new methodology for the treatment of these diseases.

Trk kinases are also involved in skin diseases like atopic dermatitis (Archives of Dermatological Research 2006, 298 (1), 31-37), Eczema, Psoriasis (J. Investigative Dermatology 2004, 122(3), 812-819), Pruritis (Acta Derm Venereol 2015; 95: 542-548), restenosis and Atherosclerosis. TrkA inhibition is also implicated for the treatment of fibrotic disorders based on the ability of Connective Tissue Growth Factor (CTGF) to activate TrkA signaling (Fibrogenesis Tissue Repair. 2012 Jun. 6; 5(Suppl 1):S24). TrkA inhibitors may also be useful in treatment of endometriosis (Reprod Sci. 2011 December; 18(12):1202-10, Hum Reprod. 2009 April; 24(4):827-34), diabetic peripheral neuropathy (Brain Res. 2000 Jun. 9; 867(1-2):149-56, Diabet Med. 2009 December; 26(12):1228-34), chronic prostatitis/chronic pelvic pain syndrome (Urology. 2002 April; 59(4):603-8, BJU Int. 2011 July; 108(2):248-51) and Chagas' disease (Cell Host Microbe. 2007 Jun. 14; 1(4):251-61).

Several classes of small molecule inhibitors of Trk kinases are known to be useful for treating pain or cancer. International Publication No. WO2014/078378, WO2012/125668, Patent publication numbers US20150336970, AU2015200511 and Expert Opinion on Therapeutic Patents (2009) 19, 305-19 and Expert Opinion on Therapeutic Patents (2014), 24(7):731-744 discloses the classes of compounds that are said to be inhibitors of Trk kinases which could be useful for treating diseases such as pain, cancer, restenosis, Psoriasis, thrombosis, atherosclerosis, Inflammatory diseases, neurodegenerative diseases or the like.

Hence, pharmacological inhibition of TrkA pathway offers promising approaches for the treatment of a variety of diseases dependent on hyperactivation of TrkA pathway.

SUMMARY OF THE INVENTION

The invention provides to the compounds of Formula I which are inhibitors of tropomyosin-related kinase A (TrkA):

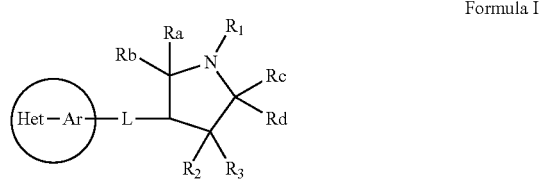

Formula I

Where, Ra, Rb, Rc, Rd, R1, R2, L and Het-Ar are as defined herein.

The invention further provides for the pharmaceutical compositions which include an effective amount of a compound of formula I, or stereoisomers, tautomers or pharmaceutically acceptable salts, solvates, metabolites, isotopes or prodrugs thereof, and a pharmaceutically acceptable carrier.

The invention further provides to the use of pharmaceutical compositions for the treatment and/or prevention of diseases associated with abnormal or deregulated TrkA kinase activity in a patient in need thereof, like Pain, Inflammation or inflammatory diseases, Cancer, Atherosclerosis, Restenosis, Thrombosis, Neurodegenerative diseases like Alzheimer's Disease, Huntington's disease or Progressive supranuclear palsy, Erectile Dysfunction (ED), Skin disorders like Atopic Dermatitis, Eczema, Pruritis or Psoriasis, Autoimmune diseases like Multiple sclerosis, Sjögren's syndrome, endometriosis, diabetic peripheral neuropathy, prostatitis, Infectious diseases, diseases related to an imbalance of the regulation of bone remodeling, endometriosis, pelvic pain syndrome and diseases resulting from abnormal tissue remodelling and fibrotic disorders; or a disease, disorder, injury or malfunction relating to dysmyelination or demyelination or a disease or disorder associated with abnormal activities of nerve growth factor (NGF) receptor TrkA.

The invention further provides for a method for treating a disease or disorder mediated by the Trk receptors or associated with abnormal or deregulated TrkA kinase activity wherein said disease or disorder is selected from the group consisting of Pain, inflammation or inflammatory diseases, Cancer, atherosclerosis, restenosis, thrombosis, Neurodegenerative diseases, Erectile Dysfunction (ED), Skin disorders, Autoimmune disease, Sjögren's syndrome, endometriosis, diabetic peripheral neuropathy, prostatitis, Infectious diseases, diseases related to an imbalance of the regulation of bone remodeling, endometriosis, pelvic pain syndrome and diseases resulting from abnormal tissue remodelling and fibrotic disorders; or a disease, disorder, injury, or malfunction relating to dysmyelination or demyelination or a disease or disorder associated with abnormal activities of nerve growth factor (NGF) receptor Trk A in a patient in need thereof, comprising administering to the patient a therapeutically effective amount of a compound of Formula I or a pharmaceutically acceptable salt thereof, and a pharmaceutically acceptable carrier.

The invention further provides a method for treating a disease or a disorder modulated by TrkA or in which the NGF receptor TrkA kinases are involved. The method further comprises administering to a patient, in need thereof, a therapeutically effective amount of a compound of this invention or their stereoisomers, tautomers, or pharmaceutically acceptable salts, isotopes, metabolites, solvates or prodrugs.

The invention further provides intermediates required for synthesis of the compounds of Formula I.

The invention further provides for a method of synthesis, separation, and purification of the compounds of the invention.

The invention further provides the use of novel compounds of Formula I which act as TrkA inhibitor and/or antagonist for the preparation of a medicament useful in the treatment of disorders like Pain, Inflammation or inflammatory diseases, Cancer, Atherosclerosis, Restenosis, Thrombosis, Neurodegenerative diseases like Alzheimer's Disease, Parkinson's disease, Huntington's disease or Progressive supranuclear palsy, Erectile Dysfunction (ED), Skin disorders like Atopic Dermatitis, Eczema, Pruritis or Psoriasis, Autoimmune diseases like Multiple sclerosis, Sjogren's syndrome, endometriosis, diabetic peripheral neuropathy, prostatitis, Infectious diseases, diseases related to an imbalance of the regulation of bone remodeling, endometriosis, pelvic pain syndrome and diseases resulting from abnormal tissue remodelling and fibrotic disorders; or a disease, disorder, injury, or malfunction relating to dysmyelination or demyelination or a disease or disorder associated with abnormal activities of nerve growth factor (NGF) receptor Trk-A.

Additional features and advantages of the invention will be apparent from the detailed description which follows, taken in conjunction by way of examples, features of the invention.

DETAILED DESCRIPTION OF THE INVENTION

From the foregoing detailed description of certain embodiments, reference will now be made to the exemplary embodiments and examples, it will be apparent that various modifications, additions and other alternative embodiments, examples are possible without departing from the true scope and spirit of the invention. The embodiments and examples discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention.

DEFINITIONS

As used herein, the term "alkyl," by itself or as part of another substituent, refers to linear or branched alkyl group with 1 to 10 carbon atoms.

As used herein, the term "alkenyl," by itself or as part of another substituent, means a straight or branched chain hydrocarbon radical having a single carbon-carbon double bond As used herein, the term "Alkoxy" group refers to an —O(alkyl) group, wherein alkyl group is as defined above.

As used herein, the term "Alkynyl" refers to hydrocarbon chain which is straight or branched and contains at least one degree of unsaturation, i.e., at least one carbon-carbon triple bond.

As used herein, the term "Halogen or Halo" represents fluorine, chlorine, bromine, or iodine.

As used herein, the term "Haloalkyl" means at least one halogen atom is substituted on an alkyl group. Both halogen and alkyl have the meaning as defined above.

As used herein, the term "Hydroxy' or 'Hydroxyl" represents —OH.

As used herein, the term "Hydroxyalkyl" means at least one hydrogen atom of an alkyl group is replaced by a hydroxyl group. Alkyl group is as defined above.

As used herein, the term "Haloalkoxy" means at least one halogen atom is substituted on an alkoxy group, wherein alkoxy and halogen groups are as defined above.

As used herein, the term "alkoxycarbonyl" and as used herein denotes a group of formula —C(=O)OR wherein R is alkyl; alkyl as defined herein.

As used herein, the term "3-10 membered heterocyclic ring" refers to a monocyclic or polycyclic ring system, saturated or unsaturated or aromatic; containing one nitrogen atom and optionally 1-3 additional heteroatoms or heterogroups independently selected from O, S, N, CO, SO, or $SO_2$.

As used herein, the term "hetero-aromatic ring" or "Het-Ar ring" is understood to encompass any heterocyclic aromatic ring having 5 or 6 atoms, containing one or more independent hetero-atoms selected from nitrogen, oxygen and sulfur. It should be noted that a hetero-atom may be positioned on any position on the fused 5 to 6 membered hetero-aromatic ring formed.

As used herein, the term "cycloalkyl" denotes a saturated carbocyclic ring containing 3 to 6 carbon atoms.

As used herein, the term "heteroatom" refers to a sulfur, nitrogen, or oxygen atom.

As used herein, the term "aminocarbonyl" refers to a monovalent group of formula —(CO)N(R2)2 where each R2 is independently hydrogen or alkyl.

As used herein, the term "Aryl" refers to monocyclic or polycyclic aromatic ring system. Exemplary aryl groups include, but are not limited to, phenyl, naphthyl, and the like.

As used herein, the terms "heterocyclyl", "heterocycle" or "heterocyclic", represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, or S, and including any bicyclic group in which any of the above-defined heterocyclic rings is fused to a benzene ring As used herein, the term "carbocyclic ring" refers to a saturated or non-aromatic unsaturated ring. The term "3-6-membered carbocyclic ring" refers to a carbocyclic ring wherein the number of ring carbon atoms is from 3 to 6.

As used herein, the term "cyano" refers to a substituent having a carbon atom joined to a nitrogen atom by a triple bond.

As used herein, the term "nitro" refers to the group —$NO_2$.

As used herein, the term "amino" refers to the group —$NH_2$

As used herein, the term "Carbonyl" refers to the divalent group —C(O)—.

As used herein, the term "cyano (1-3Calkyl)" denotes an alkyl group as defined above wherein a hydrogen atom of the alkyl group is replaced by a cyano (—CN) group.

As used herein, the term "Ligand" or "L" denotes a linker molecule or ligand molecule. Exemplary Ligand or linker molecules include, but not limited to —O—, —NH—, —$SO_2$N(R')—, —C(O)N(R')—; —N(R')C(O)—, —C(O)N(R')C(O)—, —N(R')$SO_2$—, —N(R')$SO_2$N(R')—, —NR'C(O)N(R')—, —NR'C(S)N(R')—, or —N(R')C(O)O—.

As used herein, the term "heteroaryl", as used herein except where noted, represents a stable 5- to 7-membered monocyclic- or stable 9- to 10-membered fused bicyclic heterocyclic ring system which contains an aromatic ring, any ring of which may be saturated, partially saturated, or unsaturated and which consists of carbon atoms and from one to four heteroatoms selected from the group consisting of N, O and S.

As used herein, unless otherwise specifically defined, substituted alkyl, substituted aryl, substituted heteroaryl, and substituted heterocycle include moieties containing from 1 to 3 substituents in addition to the point of attachment to the rest of the compound.

As used herein, the term "Optionally substituted" means that the substitution is optional and therefore it is possible for the designated atom or group to be unsubstituted. When more than one substituent is present on an atom or group, the chosen substituents are independent of each other (i.e. same or different).

As used herein, the term "stereoisomers" is a general term used for all isomers of an individual molecule that differ only in the orientation of their atoms in space. It is to be understood that all stereoisomeric forms of the compounds of the invention, including but not limited to, diastereomers, enantiomers and atropsiomers, as well as mixtures thereof such as forms, are included in the scope of the present application.

As used herein, the term "tautomer" refers to the coexistence of two (or more) compounds that differ from each other only in the position of one (or more) mobile atoms and in electron distribution, for example, keto-enol tautomers.

As used herein, the term "pharmaceutically acceptable" refers to the carrier, diluent, salts, solvates or excipient must be compatible with the other ingredients of the formulation and not deleterious to the recipient thereof.

As used herein, the term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives.

As used herein, the term "prodrug" refers to compounds that are rapidly transformed in vivo to yield the parent compound of the above formula, for example by hydrolysis in blood as well as the zwitterionic forms of the compounds of the invention As used herein, the term 'a therapeutically effective amount' refers to the amount of the compound of the present invention that, when administered to a subject, is effective in (i) at least partially alleviating, inhibiting, preventing and/or ameliorating a condition, or a disorder or a disease mediated by TrkA, TrkB and/or TrkC, associated with TrkA, TrkB and/or TrkC activity or characterized by activity (normal or abnormal) of TrkA, TrkB and/or TrkC; (ii) reducing or inhibiting the activity of TrkA, TrkB and/or TrkC; or (iii) reducing or inhibiting the expression of TrkA, TrkB and/or TrkC.

As used herein, the term "fusion" or "fusion protein" refers to a co-linear, covalent linkage of two or more proteins or fragments thereof via their individual peptide backbones, most preferably through genetic expression of a polynucleotide molecule encoding those proteins.

As used herein, the term "TrkA" refers to one of Trk's high affinity binding protein kinase receptors that are activated by Neurotrophins (NT), a group of soluble growth factors Nerve Growth Factor (NGF), Brain-Derived Neurotrophic Factor (BDNF) and Neurotrophin 3-5 (NT 3-5). The Trk's are made up of three family members TrkA, TrkB and TrkC that bind to and mediate the signal transduction derived from the Neurotrophins. Inhibitors of the Trk/neurotrophin pathway have been demonstrated to be highly effective in numerous pre-clinical animal models of pain. The compounds of the invention are modulators of the Trk receptors, particularly TrkA.

The present invention relates to novel compounds that act as inhibitors of the members of Trk family protein kinases. Particularly, the present invention discloses compounds possessing inhibitory activity against TrkA. The compounds of the present invention are useful as an active ingredient of a medicament for preventive and/or therapeutic treatment of the aforementioned diseases.

According to an embodiment of the present invention, the compounds are represented by general formula I:

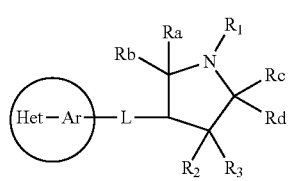

Formula I or stereoisomers, tautomers, or pharmaceutically acceptable salts, solvates, metabolites, isotopes, or prodrugs thereof, wherein:

Ra and Rb are each independently selected from H, alkyl, alkenyl, alkynyl, haloalkyl, halogen, hydroxy, hydroxyalkyl, alkoxy, haloalkoxy, optionally substituted phenyl, optionally substituted 5-6 membered aromatic ring having 1-3 heteroatoms selected from O, N, and S or Ra and Rb together forms carbonyl group, optionally substituted phenyl which is further optionally substituted with a halogen;

Rc and Rd is H, alkyl, alkenyl, alkynyl, haloalkyl, hydroxy, alkoxy, haloalkoxy, optionally substituted phenyl, optionally substituted 5-6 membered aromatic ring having 1-3 heteroatoms selected from O, N, and S or Rc and Rd together to form a ring (4-6 membered) with or without a hetero atom;

R1 is H, alkyl, alkenyl, alkynyl, haloalkyl, hydroxy, alkoxy, haloalkoxy, (1-3C alkoxy)(1-3C)alkyl, (1-4C alkoxycarbonyl) (1-6Calkyl), mono, di, tri halo(1-4C alkyl), (1-3C alkyl)aminocarbonyl, Cyano(1-3C alkyl), (1-3C haloalkoxy)(1-3C)alkyl, optionally substituted phenyl, 3-6 membered carbocyclic or heterocyclic ring with one or more heteroatom selected from O, N or S and optionally substituted with one or more substituents independently selected from H, alkyl, alkenyl, alkynyl, haloalkyl, halogen, hydroxy, alkoxy, haloalkoxy, nitro or amino, a 9-10 membered bicyclic heteroaryl having 1-3 ring nitrogen atoms;

R2 and R3 are independently selected from H, alkyl, alkenyl, alkynyl, isopropyl, tert butyl, haloalkyl, halogen, hydroxy, alkoxy, haloalkoxy, optionally substituted phenyl, or optionally substituted 5-6 membered aromatic ring having 1-3 heteroatoms selected from O, N or S or R2 and R3 can be combined to form a ring (5/6-membered) with 1-2 hetero atoms.

L is a ligand selected from —O—, —NH—, —SO$_2$N(R')—, —C(O)N(R')—; —N(R')C(O)—, —C(O)N(R')C(O)—, —N(R')SO$_2$—, —N(R')SO$_2$N(R')—, —NR'C(O)N(R')—, —NR'C(S)N(R')—, or —N(R')C(O)O—;

each R' is independently selected from H or alkyl;

Het-Ar ring is selected from H1 or H2;

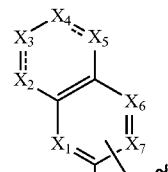

H1

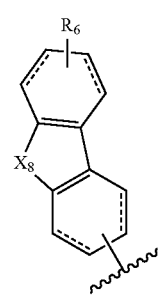

H2

X1-X7 at each occurrence is a bond, —CR5-, —CH2- or an heteroatom selected from N, O or S;

X8 is selected from O, S, NH, N-alkyl, SO, SO$_2$ or C=O

R4, R5 and R6 are each independently selected from the group consisting of H, alkyl, alkenyl, alkynyl, isopropyl, tert. Butyl, haloalkyl, halogen, mono, di, tri halo(1-4C alkyl) hydroxy, alkoxy, haloalkoxy, cyano, cycloalkyl(3-7 carbon), optionally substituted phenyl, optionally substituted 5-6 membered heterocyclic ring having 1-3 heteroatoms selected from O, N, or S or 3-6 membered carbocyclic ring having one or more heteroatom selected from O, N or S, —NH$_2$, —N(H)(alkyl), —N(alkyl)$_2$, —N(H)C(O)alkyl, —N(alkyl)C(O)alkyl, —N(H)C(O)O alkyl, —N(alkyl)C(O)Oalkyl, —N(H)SO$_2$(alkyl), —N(alkyl)SO$_2$(alkyl), —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$.

In another exemplary embodiment, wherein L is urea or optionally substituted urea.

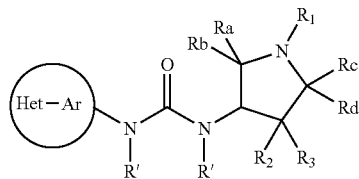

In another exemplary embodiment, wherein L is substituted urea and each R' can be joined together to form 5-6 membered ring structure.

According to an exemplary embodiment, wherein the H1 is selected from the group consisting of but not limited to:

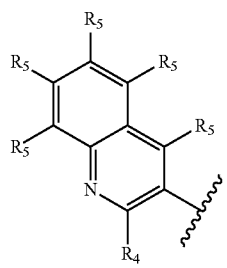
H1A

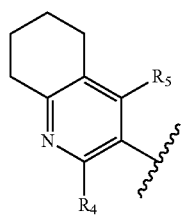
H1B

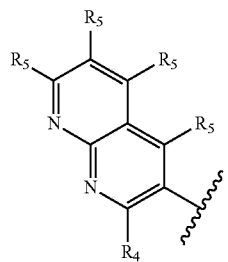
H1C

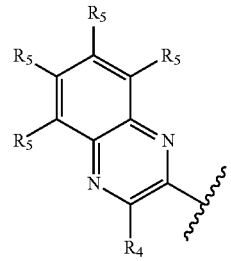
H1D

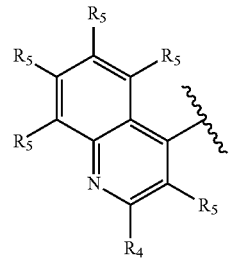
H1E

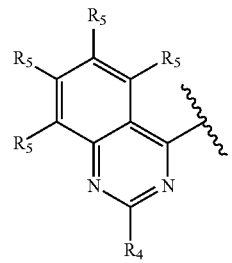
H1F

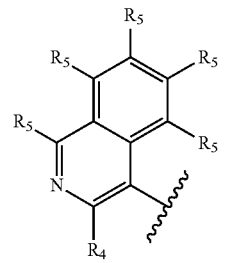
H1G and R4, R5 are each independently selected from the group consisting of H, alkyl, alkenyl, alkynyl, isopropyl, tert. Butyl, haloalkyl, halogen, mono, di, tri halo(1-4C alkyl) hydroxy, alkoxy, haloalkoxy, cyano, cycloalkyl(3-7 carbon), optionally substituted phenyl, optionally substituted 5-6 membered heterocyclic ring having 1-3 heteroatoms selected from O, N, or S or 3-6 membered carbocyclic ring having one or more heteroatom selected from O, N or S, —NH$_2$, —N(H)(alkyl), —N(alkyl)$_2$, —N(H)C(O)alkyl, —N(alkyl)C(O)alkyl, —N(H)C(O)O alkyl, —N(alkyl)C(O)Oalkyl, —N(H)SO$_2$(alkyl), —N(alkyl)SO$_2$(alkyl), —C(O)alkyl, —C(O)OH, —C(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$.

According to another exemplary embodiment, wherein the H2 is selected from the group consisting of but not limited to:

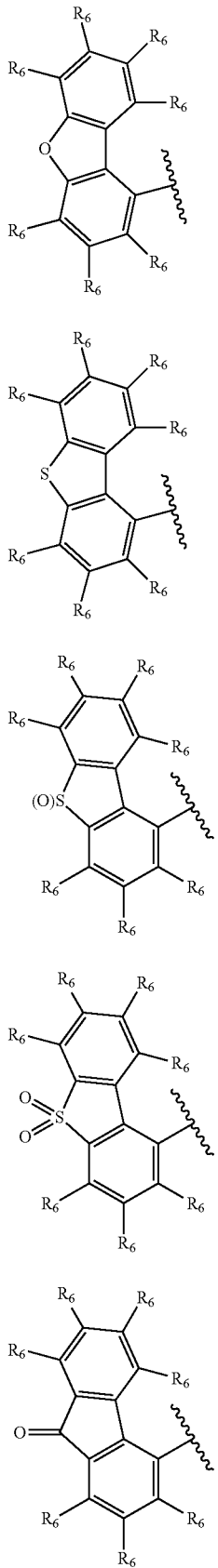

H2A

H2B

H2C

H2D

H2E

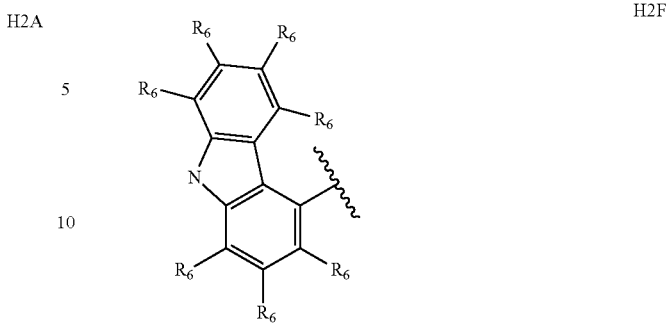

H2F and each R6 is independently selected from the group consisting of H, alkyl, alkenyl, alkynyl, isopropyl, tert. Butyl, haloalkyl, halogen, mono, di, tri halo(1-4C alkyl) hydroxy, alkoxy, haloalkoxy, cyano, cycloalkyl(3-7 carbon), optionally substituted phenyl, optionally substituted 5-6 membered heterocyclic ring having 1-3 heteroatoms selected from O, N, or S or 3-6 membered carbocyclic ring having one or more heteroatom selected from O, N or S, —NH$_2$, —N(H)(alkyl), —N(alkyl)$_2$, —N(H)C(O)alkyl, —N(alkyl)C(O)alkyl, —N(H)C(O)O alkyl, —N(alkyl)C(O) Oalkyl, —N(H)SO$_2$(alkyl), —N(alkyl)SO$_2$(alkyl), —C(O) alkyl, —C(O)OH, —C(O)Oalkyl, —C(O)NH$_2$, —C(O)N (H)(alkyl), —C(O)N(alkyl)$_2$, —S(alkyl), —S(O)alkyl, —S(O)$_2$alkyl, —S(O)$_2$N(H)$_2$, —S(O)$_2$N(H)(alkyl) and —S(O)$_2$N(alkyl)$_2$.

According to an embodiment, the invention provides a pharmaceutical composition comprising a therapeutically effective amount of a compound selected of the Formula I or physiologically acceptable salts thereof, stereoisomers thereof, solvates thereof or the hydrates thereof, or metabolites thereof or isotopes as an active ingredient. The aforementioned pharmaceutical composition is used for preventive and/or therapeutic treatment of diseases caused by abnormal or deregulated TrkA activity. Diseases involving abnormal TrkA activity can be one or more of the following but not limited to Pain, inflammation or inflammatory diseases, Cancer, atherosclerosis, restenosis, thrombosis, Neurodegenerative diseases, Erectile Dysfunction (ED), Skin disorders, Autoimmune disease like Multiple sclerosis, Sjögren's syndrome, endometriosis, diabetic peripheral neuropathy, prostatitis, Infectious diseases, diseases related to an imbalance of the regulation of bone remodeling, endometriosis, pelvic pain syndrome and diseases resulting from abnormal tissue remodelling and fibrotic disorders; or a disease, disorder, injury, or malfunction relating to dysmyelination or demyelination or a disease or disorder associated with abnormal activities of nerve growth factor (NGF) receptor TrkA.

According to another embodiment of the invention, a method is provided for the prevention and/or therapeutic treatment of a disease or a disorder selected from the group comprising of Pain, inflammation or inflammatory diseases, Cancer, atherosclerosis, restenosis, thrombosis, Neurodegenerative diseases, Erectile Dysfunction (ED), Skin disorders, Autoimmune disease like Multiple sclerosis, Sjögren's syndrome, endometriosis, diabetic peripheral neuropathy, prostatitis, Infectious diseases, diseases related to an imbalance of the regulation of bone remodeling, endometriosis, pelvic pain syndrome and diseases resulting from abnormal tissue remodelling and fibrotic disorders; or a disease, disorder, injury, or malfunction relating to dysmyelination or demyelination or a disease or disorder associated with abnormal activities of nerve growth factor (NGF) receptor Trk A.

According to another embodiment of the present invention, a method is provided for inhibiting tropomyosin receptor kinase A (TrkA) in a patient, by administering a therapeutically effective amount of a compound of the Formula I to the patient.

According to yet another embodiment of the present invention, a method is provided for the prevention and/or therapeutic treatment of diseases or disorders mentioned above by administering to a patient a therapeutically effective amount of a compound of the Formula I or a pharmaceutically acceptable salt and a pharmaceutically acceptable carrier.

According to yet another embodiment of the present invention, a medicament is provided which can be used for preventive and/or therapeutic treatment of inflammatory diseases. Specifically, compounds of the present invention are used for preventive and/or therapeutic treatment of inflammatory diseases selected from the lung diseases, bowel diseases, interstitial cystitis, and painful bladder syndrome The Inflammatory lung disease is Asthma or Interstitial Cystitis and Inflammatory bowel disease is Ulcerative Colitis, Crohn's disease or urinary incontinence.

According to yet another embodiment of the present invention, a method is provided for preventive and/or therapeutic treatment of acute or chronic pain. Specifically, compounds of the present invention are used for preventive and/or therapeutic treatment of acute pain and chronic pain selected from cancer induced pain, bone fracture pain, inflammatory pain, neuropathic pain, surgery, bone fracture, skeletal pain caused by tumor metastasis, osteoarthritis, psoriatic arthritis, rheumatoid arthritis, interstitial cystitis, chronic pancreatitis, visceral pain, inflammatory pain, migraine, chronic lower back pain, bladder pain syndrome, femur fracture pain, hyperalgesia, repetitive motion pain, dental pain, myofascial pain, dysraennorhea, as well as pain associated with angina.

According to yet another embodiment of the present invention, a method is provided for preventive and/or therapeutic treatment of an imbalance of the regulation of bone remodelling. Specifically, compounds of the present invention are used for preventive and/or therapeutic treatment of osteoporosis, rheumatoid arthritis, and bone metastases, Osteolytic metastases, life-threatening hypercalcemia, spinal cord compression, ankylosing spondylitis, tumor-induced osteolysis, periodontal disease.

According to yet another embodiment of the present invention, compounds of the invention may be used to decrease tolerance and/or dependence to opioid treatment of pain, and for treatment of withdrawal syndrome of e.g., alcohol, opioids, and cocaine.

According to yet another embodiment of the present invention, a method is provided for preventive and/or therapeutic treatment of abnormal tissue remodelling and fibrotic disorders. Specifically, compounds of the present invention are used for preventive and/or therapeutic treatment of abnormal tissue remodelling and fibrotic disorders selected from Idiopathic pulmonary fibrosis, Raynaud's syndrome, endometrial fibrosis, atrial fibrosis, myelofibrosis, progressive massive fibrosis, nephrogenic systemic fibrosis, scleroderma, systemic sclerosis, atherofibrosis, ocular fibrosis, scarring and cirrhosis.

According to yet another embodiment of the present invention, a medicament is provided which can be used for preventive and/or therapeutic treatment of cancer related to dysregulation of TrkA. The dysregulation of TrkA is due to chromosomal rearrangements like one or more chromosome translocations, over-expression, inversions, insertions, deletions or mutations in the TrkA protein. These rearrangements have been shown to be oncogenic driver in a number of cancers like Non Small cell Lung Cancer, colorectal carcinoma, papillary thyroid carcinoma, Glioblastoma, Melanoma, Acute Myeloid Leukemia, Large Cell Neuroendocrine Carcinoma, Gastric Carcinoma, Pancreatic Carcinoma, Prostrate Carcinoma, Head and Neck squamous cell carcinoma.

The dysregulation of TrkA as a result of one or more chromosome translocations or inversions leads to formation of TrkA gene fusions. The TrkA gene fusion can be LMNA-TrkA, TFG-TrkA, TPM3-TrkA, CD74-TrkA, NFASC-TrkA, MPRIP-TrkA, BCAN-TrkA, TP53-TrkA, RNF213-TrkA, RABGAP1L-TrkA, IRF2BP2-TrkA, SQSTMI-TrkA, SSBP2-TrkA, or TPR-TrkA.

According to yet another embodiment of the present invention, a medicament is provided which can be used for preventive and/or therapeutic treatment of cancer. Specifically, compounds of the present invention are used for preventive and/or therapeutic treatment of cancer selected from lung adenocarcinomas, breast cancer, thyroid carcinoma, pancreatic cancer, ovarian carcinoma, gastric carcinoma, malignant mesothelioma, prostate carcinoma, neuroblastic tumors, colorectal carcinoma, spitzoid melanoma, salivary adenoid cystic carcinoma, stomach cancer, kidney cancer, urethral cancer, glioblastoma multiforme, oral squamous cell carcinoma, Acute Myeloid Leukemia, cholangiocarcinoma, mastocytosis or extramammary Paget's disease.

According to yet another embodiment of the present invention, depending upon the particular conditions to be treated or prevented, additional therapeutic agents may be administered together with the compounds of this invention. In some cases, these additional therapeutic agents are normally administered to treat or prevent the same condition. For example, methotrexate may be combined with the compounds of this invention to treat leukemia.

According to one embodiment, additional therapeutic agent is selected from anti-TNF drugs, or with a circulating receptor fusion protein such as etanercept (Enbrel), targeted kinase inhibitors, these additional therapeutic agents may be administered with Compound of the Formula I or a pharmaceutically acceptable salt thereof as part of the same or separate dosage forms, via the same or different routes of administration, and on the same or different administration schedules according to standard pharmaceutical practice known to one skilled in the art.

According to another embodiment, additional therapeutic agent is selected from anti-inflammatory compounds, steroids, analgesics, opioids, calcitonin gene-related peptide receptor antagonists, subtype-selective ion channel modulators, anticonvulsants, dual serotonin-norepinephrine reuptake inhibitors, KSP (kinesin spindle protein) inhibitors, JAK family kinase inhibitors, and tricyclic antidepressants, cabozantinib, crizotinib, erlotinib, gefitinib, imatinib, lapatinib, nilotinib, pazopanib, pertuzumab, regorafenib, sunitinib, and trastuzumab. sorafenib, trametinib, vemurafenib arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine, Aflibercept, bevacizumab, aldesleukin, ipilimumab, lambrolizumab, nivolumab and sipuleucel-T.

One or more compounds of Formula I can be supplied in the form of a therapeutic composition that is within the scope of the present application.

Unless defined otherwise, all technical and scientific terms used herein have the same meaning as commonly understood to one of ordinary skill in the art.

EXAMPLES

Examples of the compounds of the present invention are shown in Table 1.

TABLE 1

Exemplary compounds from Formula I (Examples 1-202)

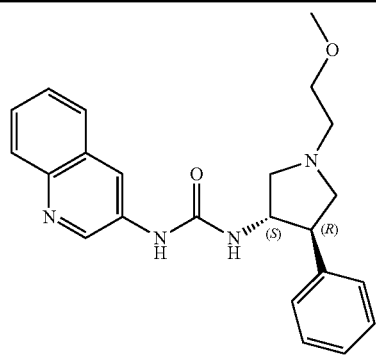

Example 1

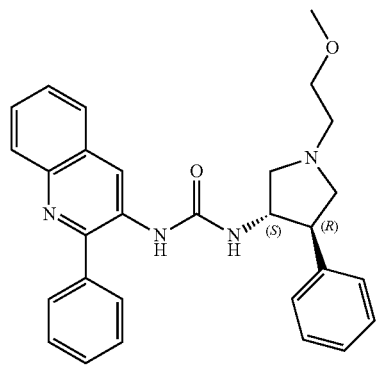

Example 2

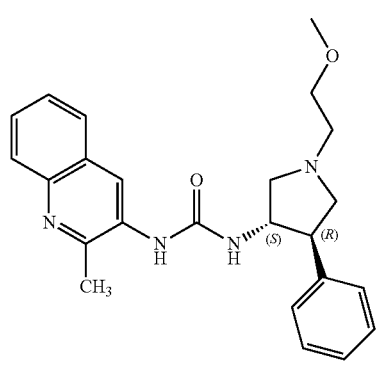

Example 3

TABLE 1-continued

Exemplary compounds from Formula I (Examples 1-202)

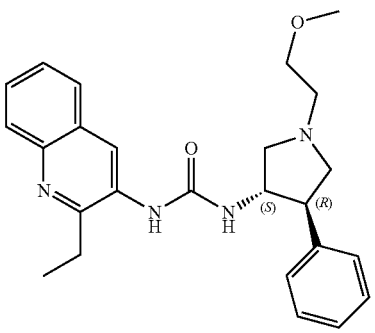

Example 4

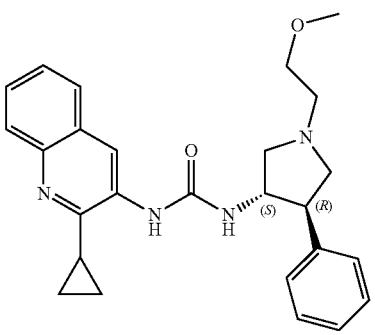

Example 5

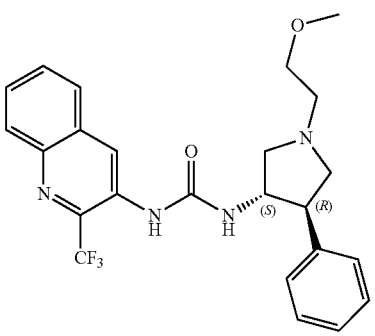

Example 6

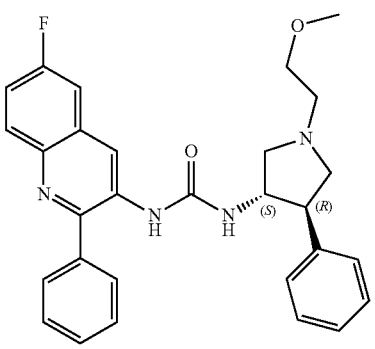

Example 7

TABLE 1-continued
Exemplary compounds from Formula I (Examples 1-202)
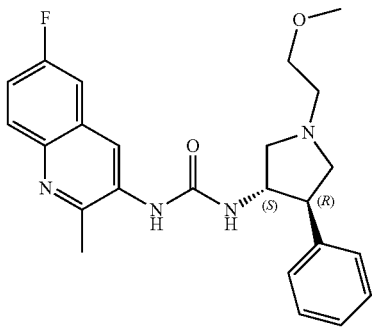
Example 8
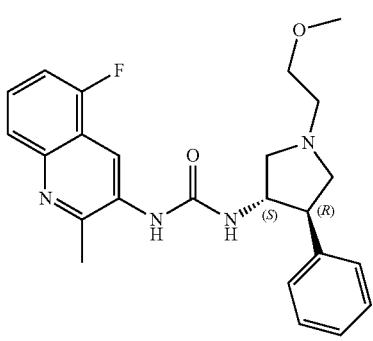
Example 9
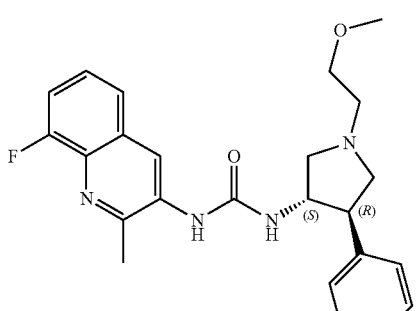
Example 10
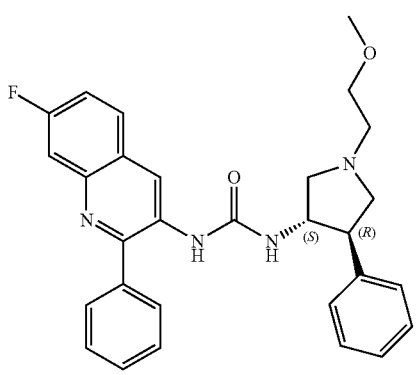
Example 11
TABLE 1-continued
Exemplary compounds from Formula I (Examples 1-202)
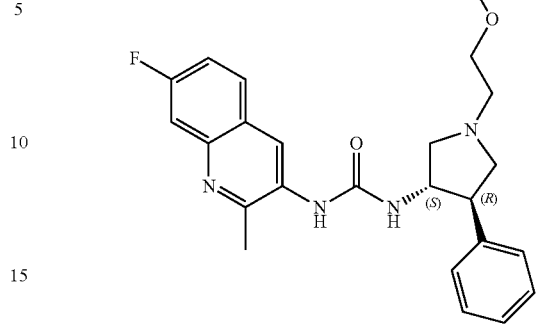
Example 12
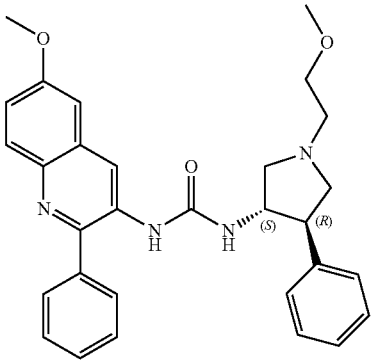
Example 13
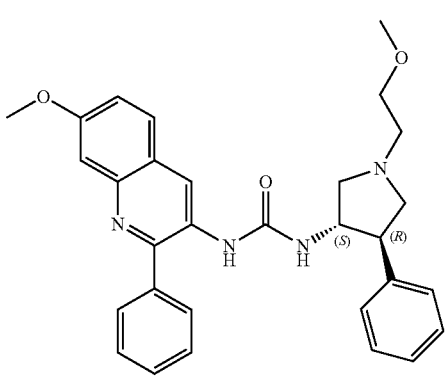
Example 14
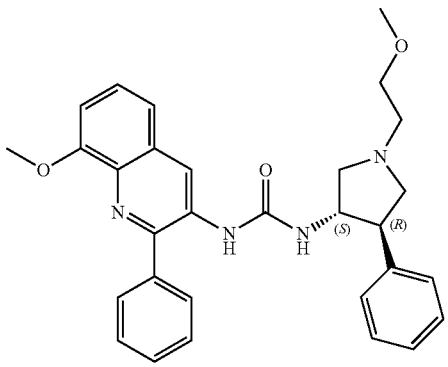
Example 15

TABLE 1-continued
Exemplary compounds from Formula I (Examples 1-202)
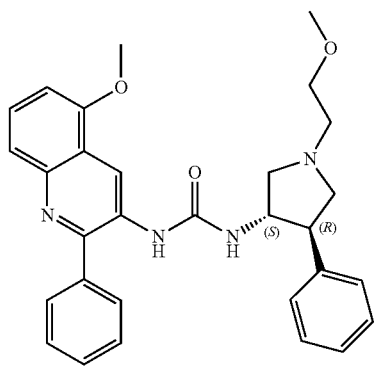
Example 16
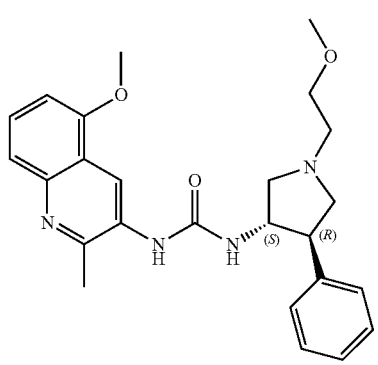
Example 17
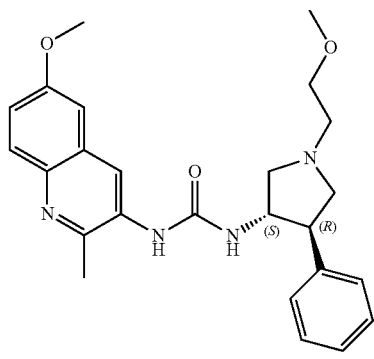
Example 18
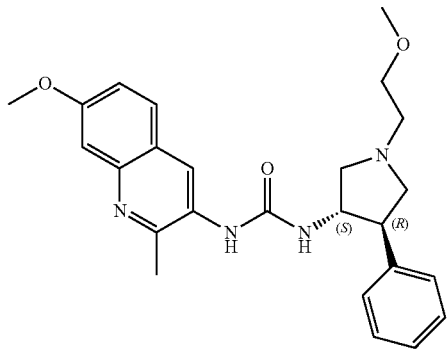
Example 19
TABLE 1-continued
Exemplary compounds from Formula I (Examples 1-202)
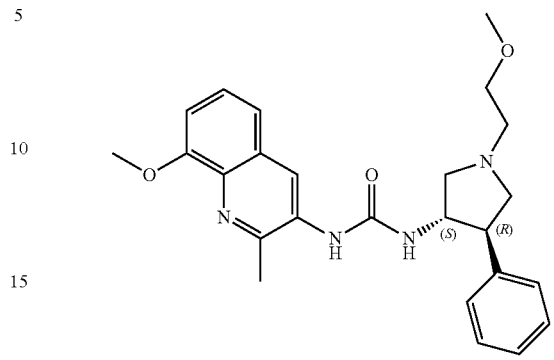
Example 20
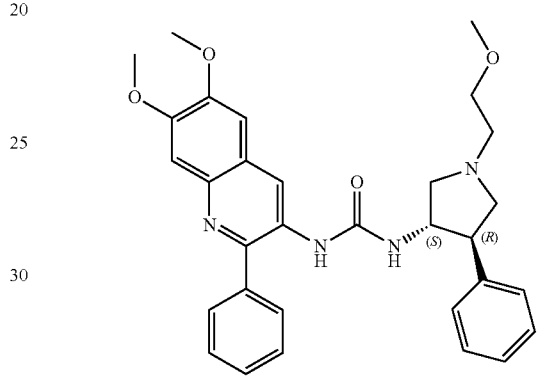
Example 21
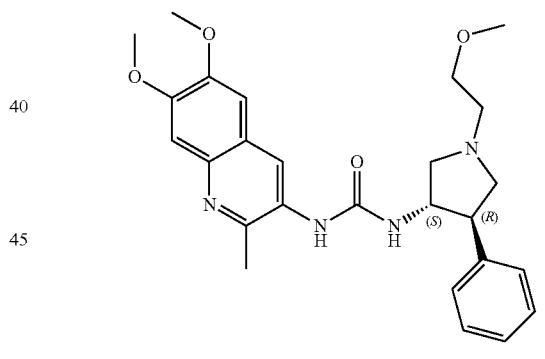
Example 22
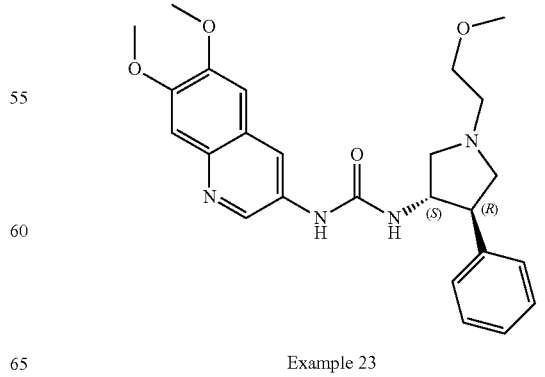
Example 23

TABLE 1-continued
Exemplary compounds from Formula I (Examples 1-202)
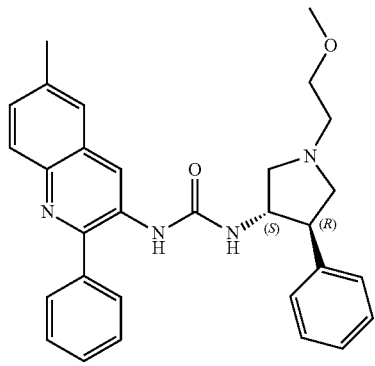
Example 24
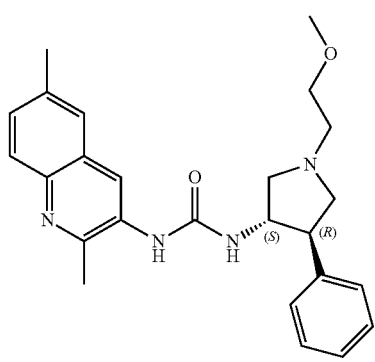
Example 25
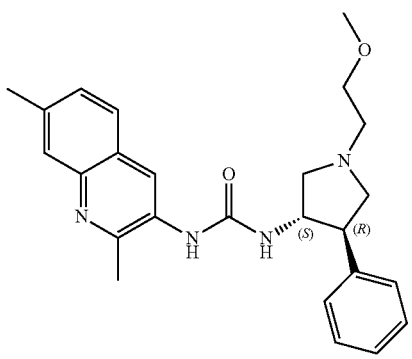
Example 26
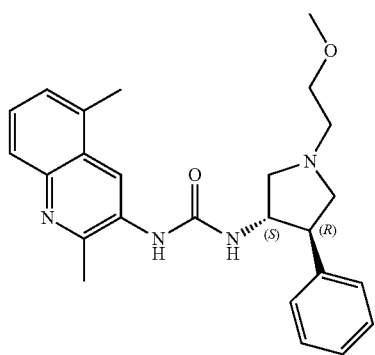
Example 27
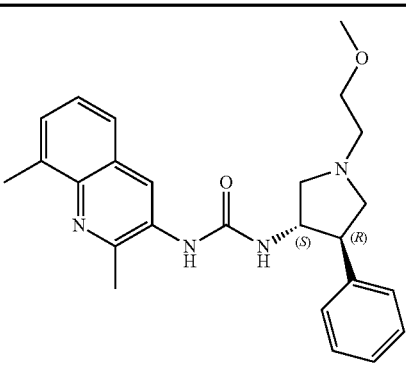
Example 28
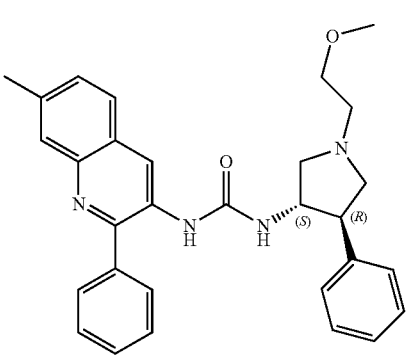
Example 29
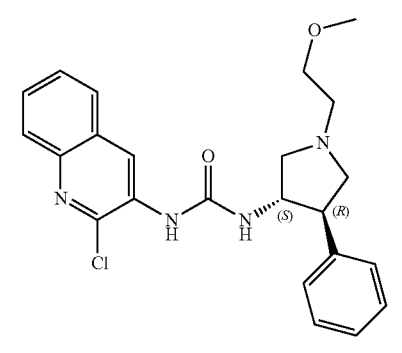
Example 30
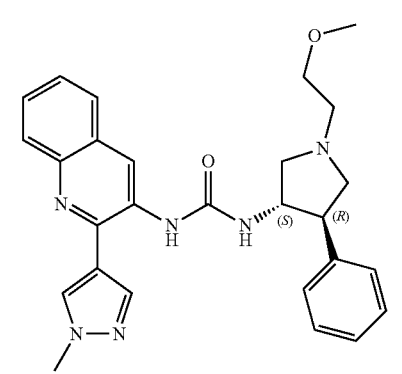
Example 31

TABLE 1-continued
Exemplary compounds from Formula I (Examples 1-202)
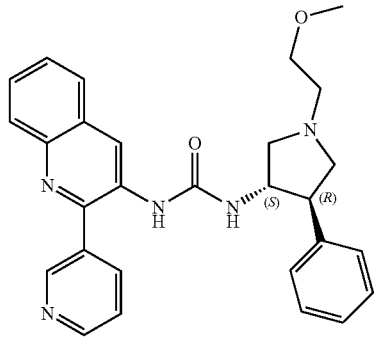
Example 32
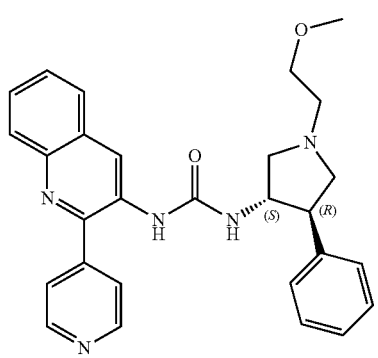
Example 33
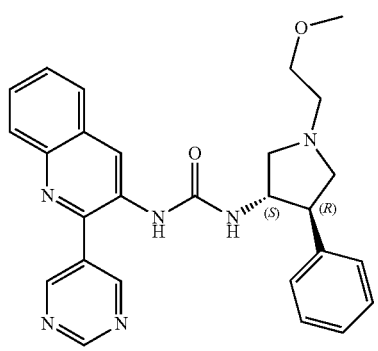
Example 34
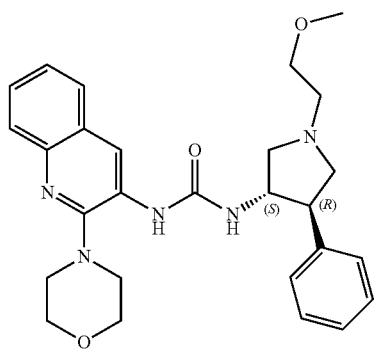
Example 35
TABLE 1-continued
Exemplary compounds from Formula I (Examples 1-202)
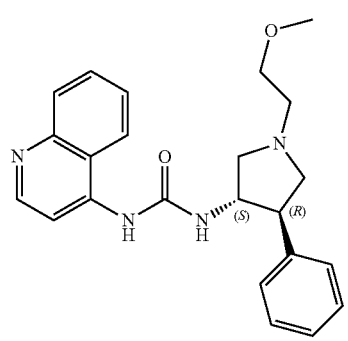
Example 36
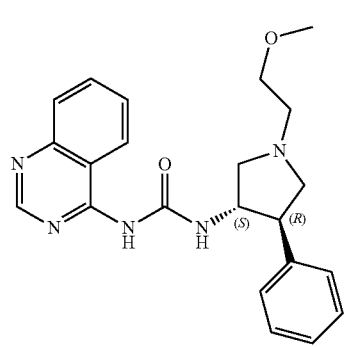
Example 37
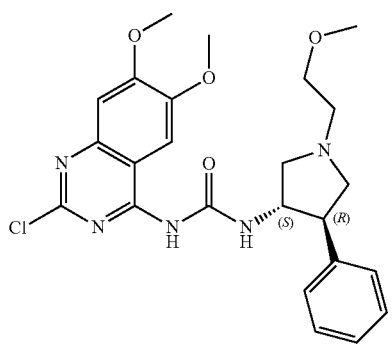
Example 38
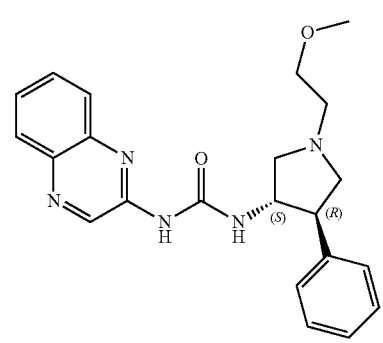
Example 39

TABLE 1-continued
Exemplary compounds from Formula I (Examples 1-202)
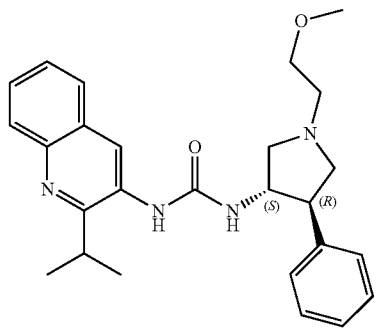
Example 40
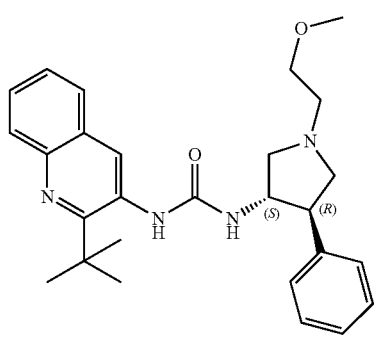
Example 41
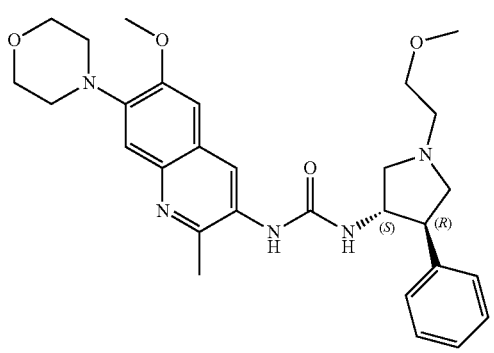
Example 42
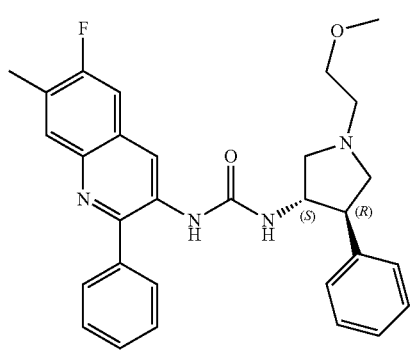
Example 43
TABLE 1-continued
Exemplary compounds from Formula I (Examples 1-202)
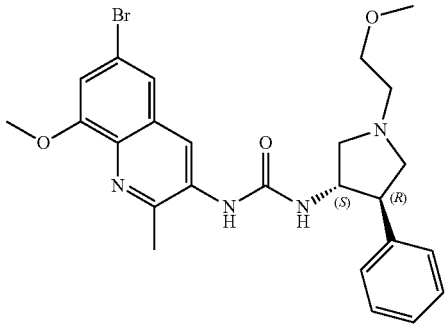
Example 44
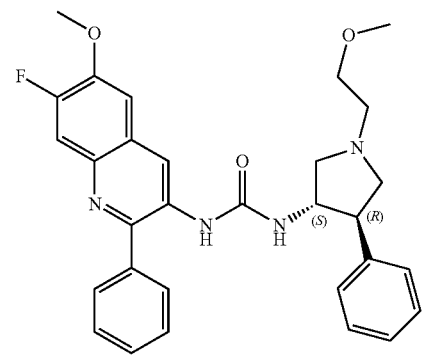
Example 45
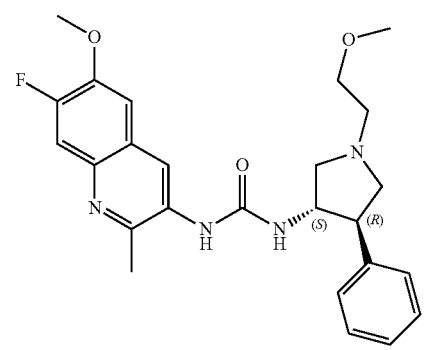
Example 46
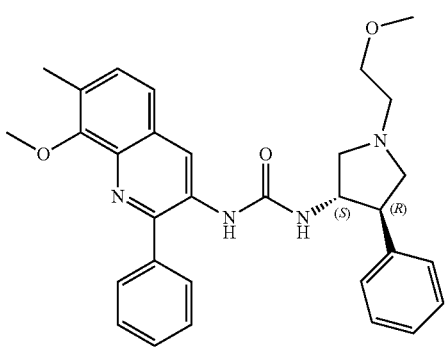
Example 47

TABLE 1-continued
Exemplary compounds from Formula I (Examples 1-202)
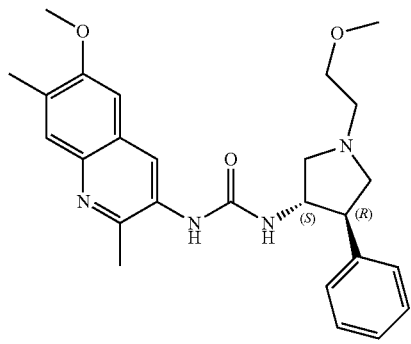
Example 48
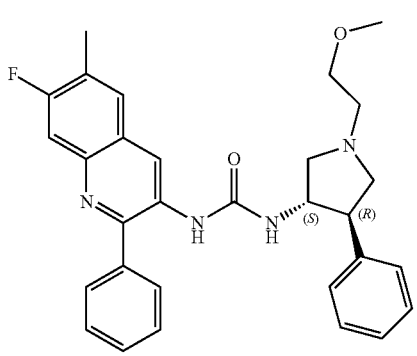
Example 49
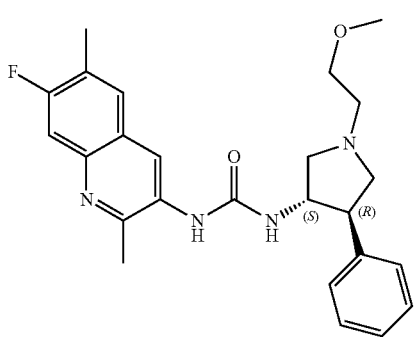
Example 50
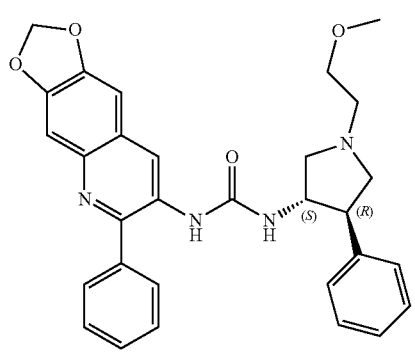
Example 51
TABLE 1-continued
Exemplary compounds from Formula I (Examples 1-202)
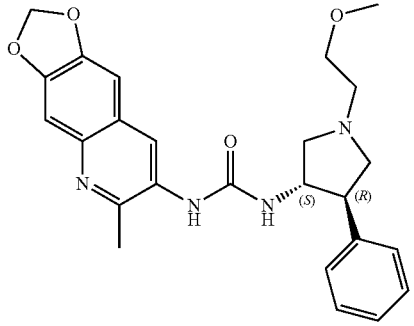
Example 52
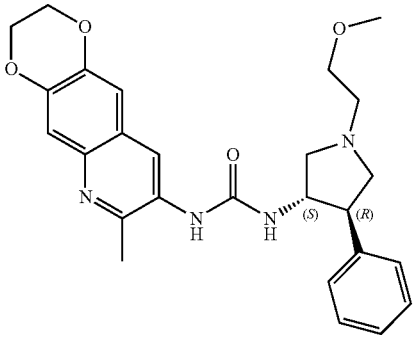
Example 53
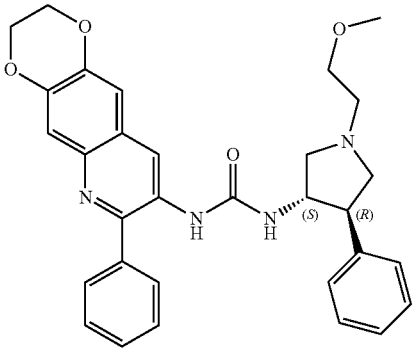
Example 54
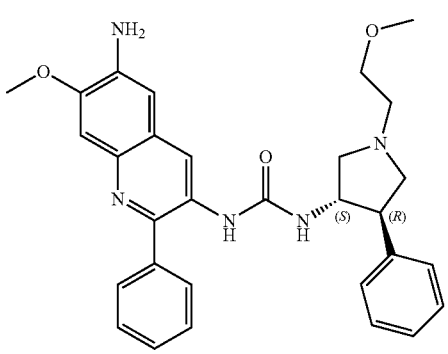
Example 55

TABLE 1-continued
Exemplary compounds from Formula I (Examples 1-202)
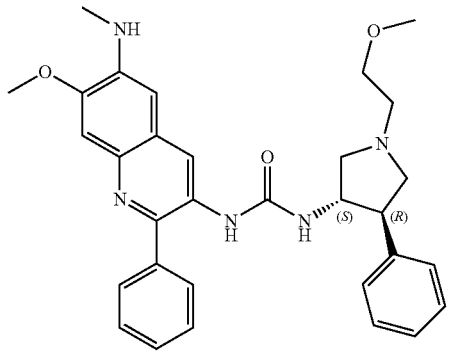
Example 56
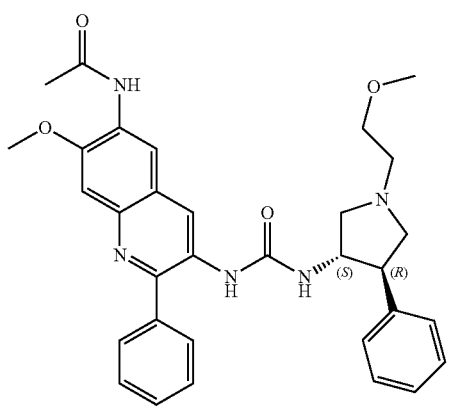
Example 57
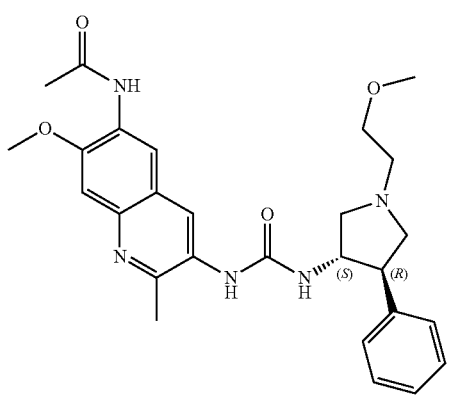
Example 58
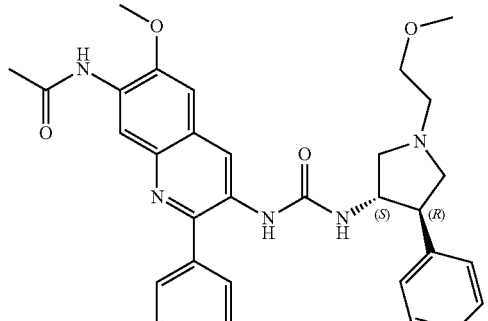
Example 59
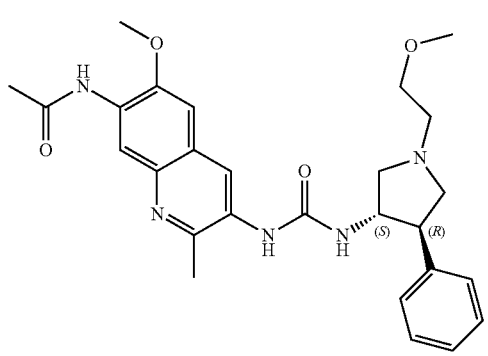
Example 60
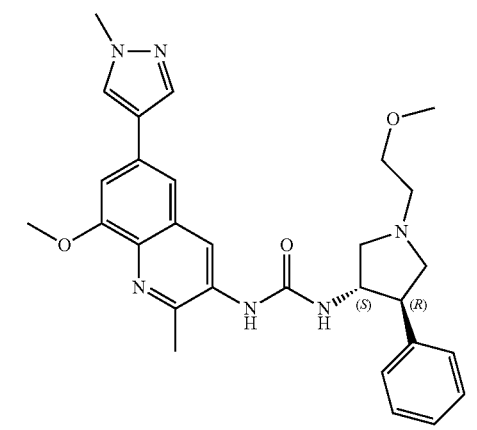
Example 61
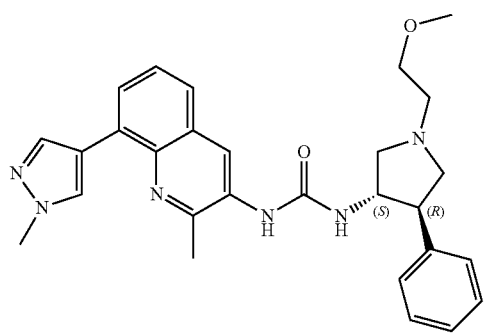
Example 62

TABLE 1-continued
Exemplary compounds from Formula I (Examples 1-202)
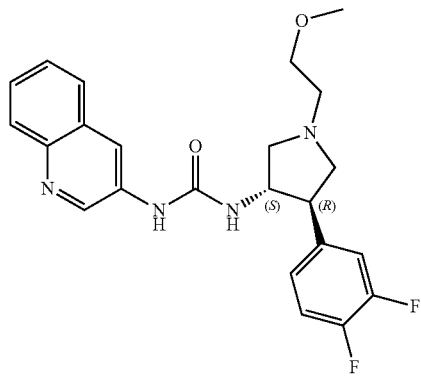
Example 63
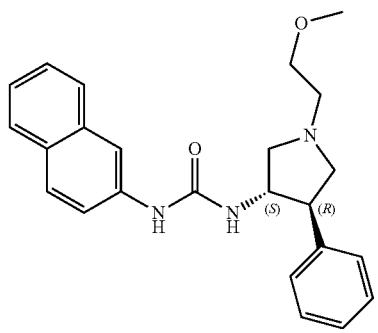
Example 64
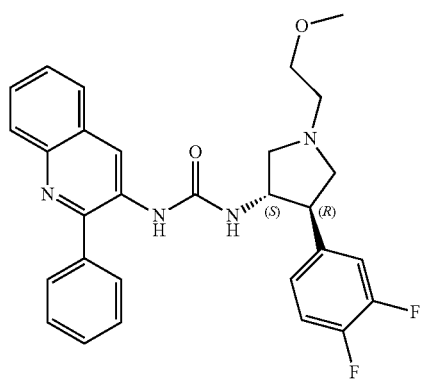
Example 65
TABLE 1-continued
Exemplary compounds from Formula I (Examples 1-202)
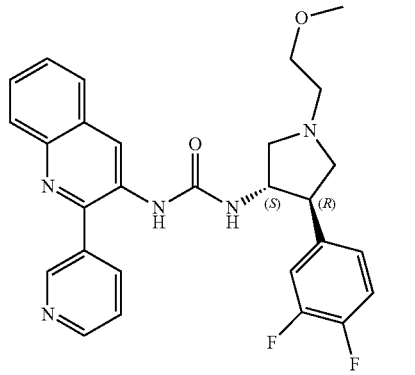
Example 66
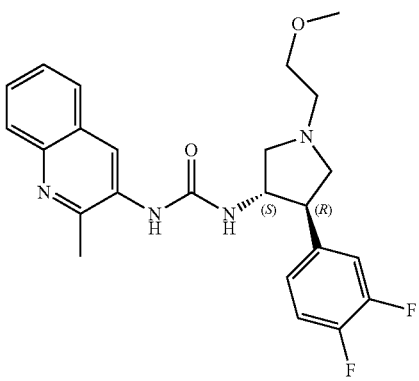
Example 67
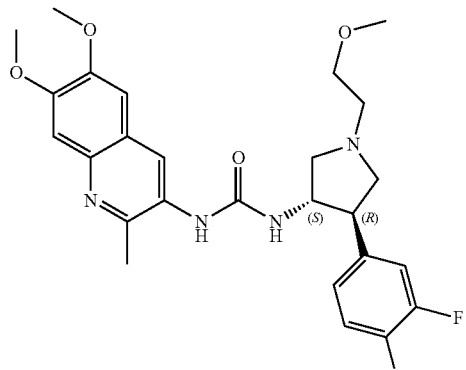
Example 68

TABLE 1-continued
Exemplary compounds from Formula I (Examples 1-202)
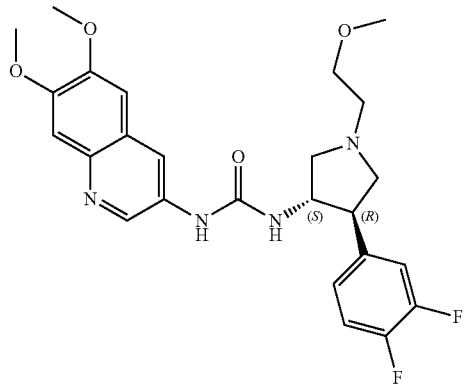
Example 69
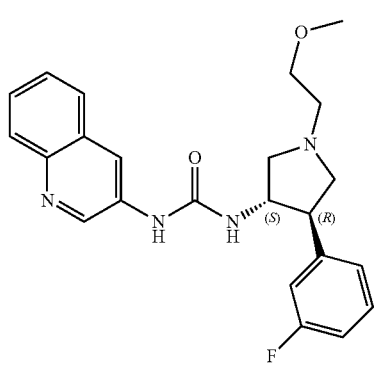
Example 70
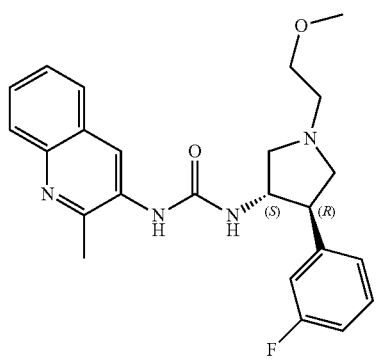
Example 71
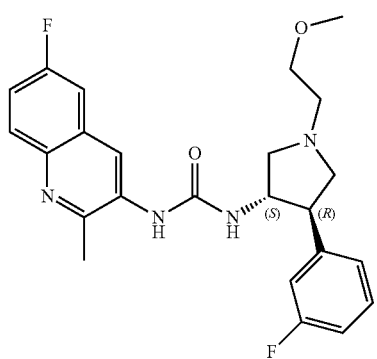
Example 72
TABLE 1-continued
Exemplary compounds from Formula I (Examples 1-202)
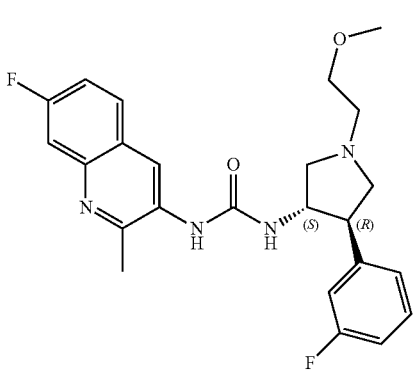
Example 73
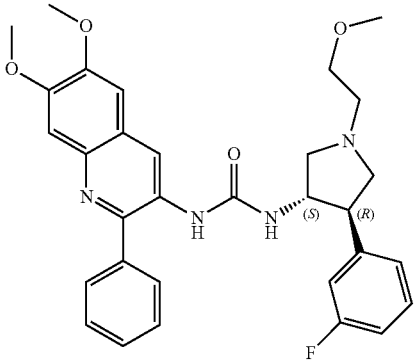
Example 74
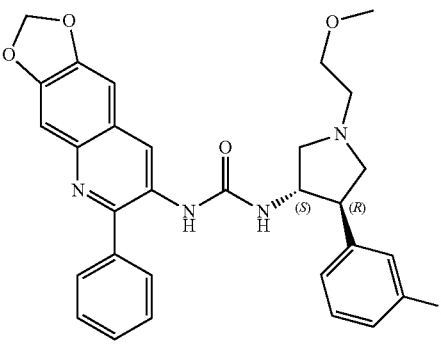
Example 75
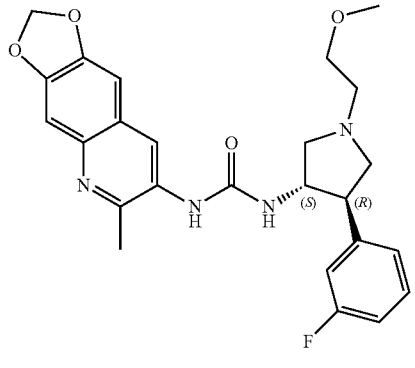
Example 76

TABLE 1-continued
Exemplary compounds from Formula I (Examples 1-202)
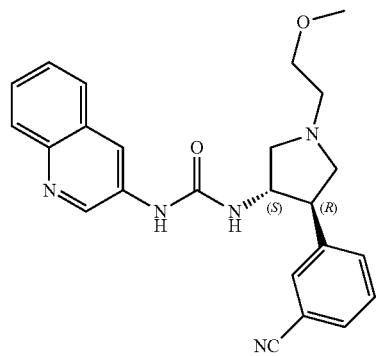
Example 77
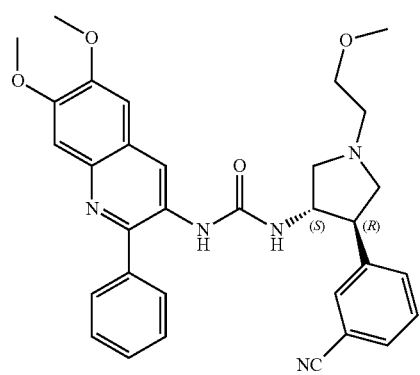
Example 78
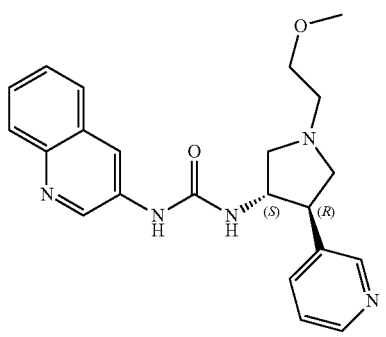
Example 79
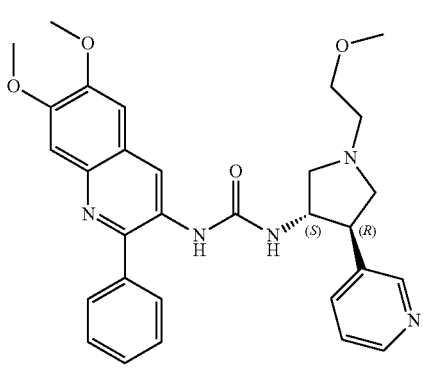
Example 80
TABLE 1-continued
Exemplary compounds from Formula I (Examples 1-202)
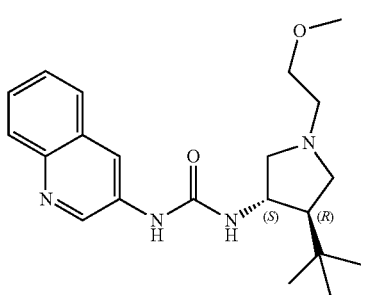
Example 81
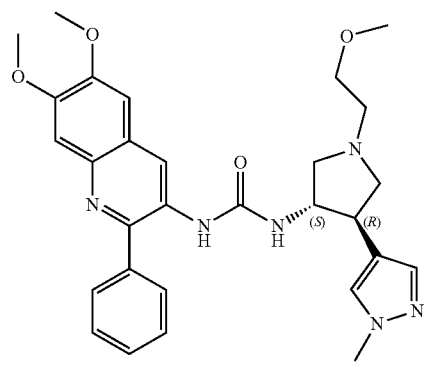
Example 82
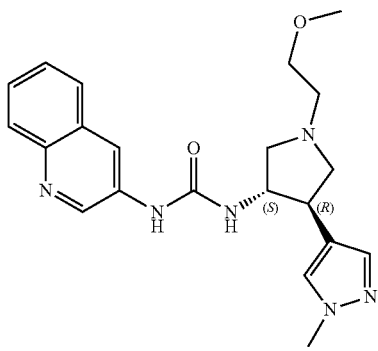
Example 83
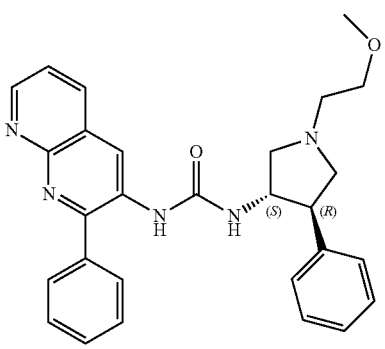
Example 84

TABLE 1-continued
Exemplary compounds from Formula I (Examples 1-202)
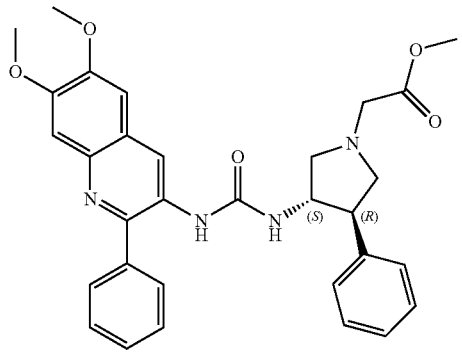
Example 85
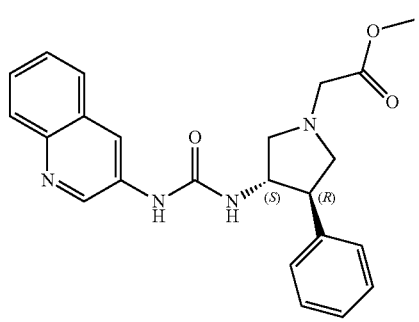
Example 86
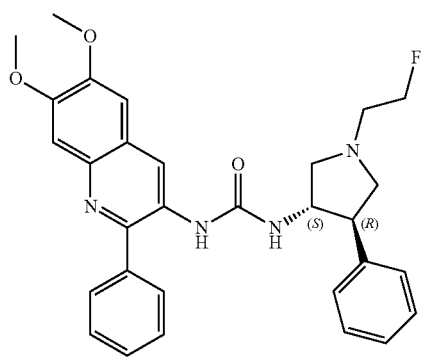
Example 87
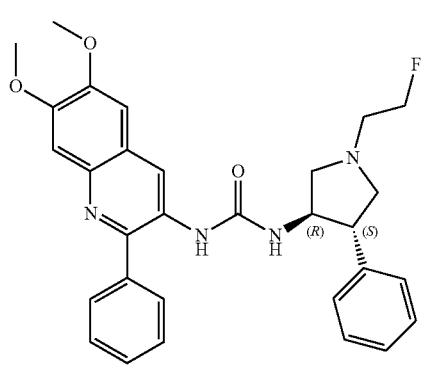
Example 88
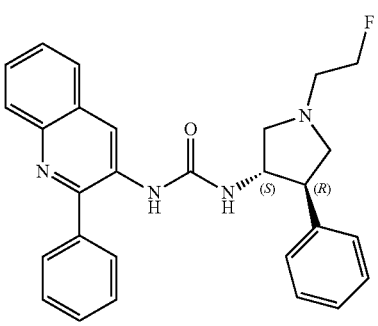
Example 89
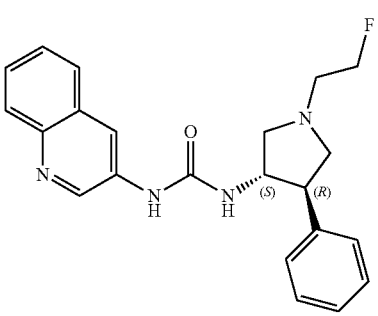
Example 90
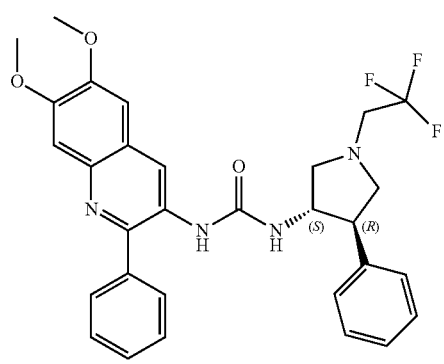
Example 91
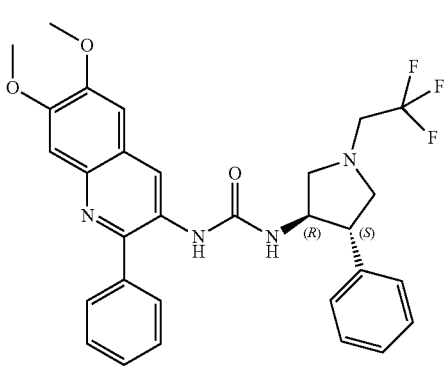
Example 92

TABLE 1-continued
Exemplary compounds from Formula I (Examples 1-202)
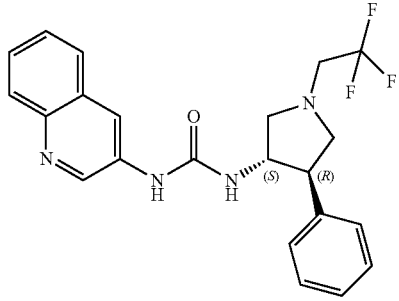
Example 93
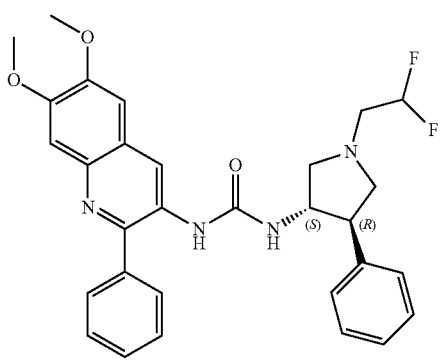
Example 94
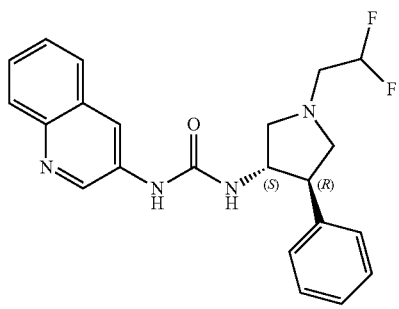
Example 95
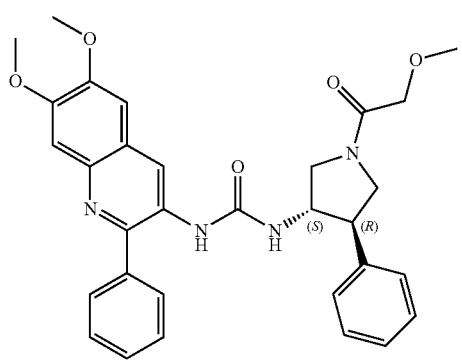
Example 96
TABLE 1-continued
Exemplary compounds from Formula I (Examples 1-202)
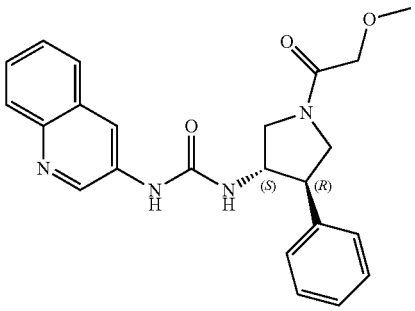
Example 97
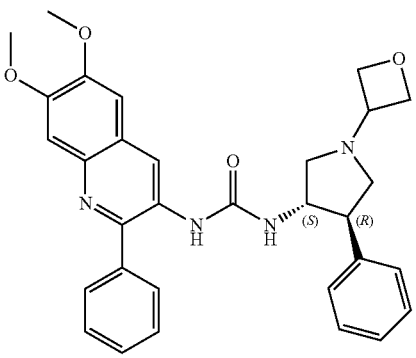
Example 98
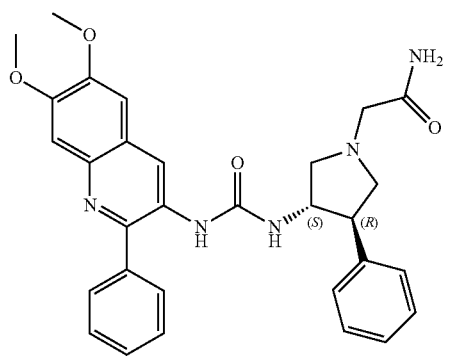
Example 99
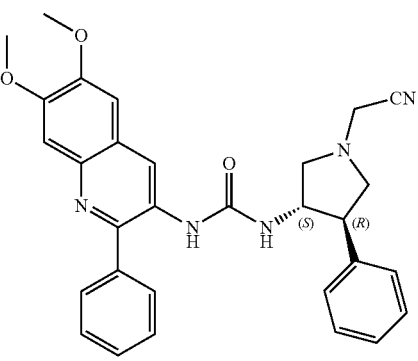
Example 100

TABLE 1-continued
Exemplary compounds from Formula I (Examples 1-202)
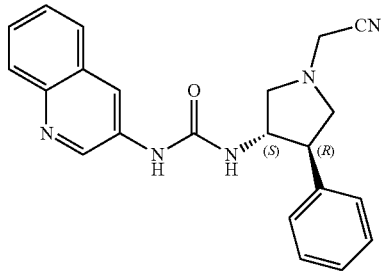
Example 101
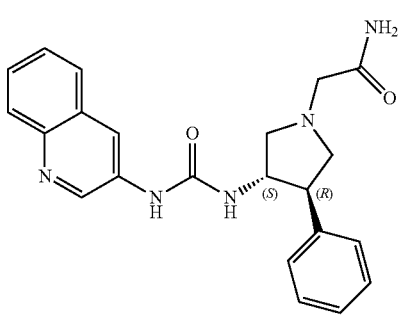
Example 102
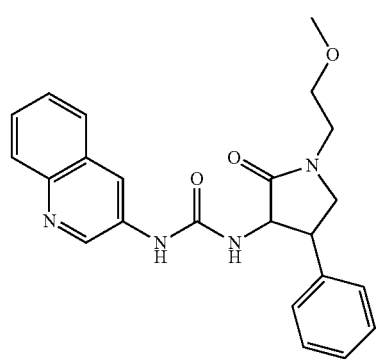
Example 103
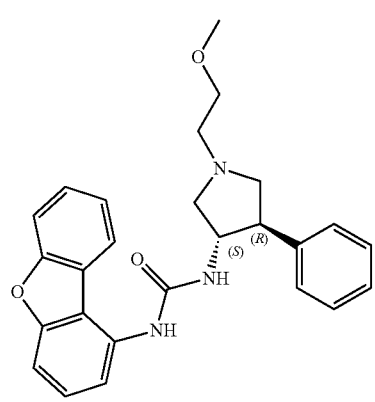
Example 104
TABLE 1-continued
Exemplary compounds from Formula I (Examples 1-202)
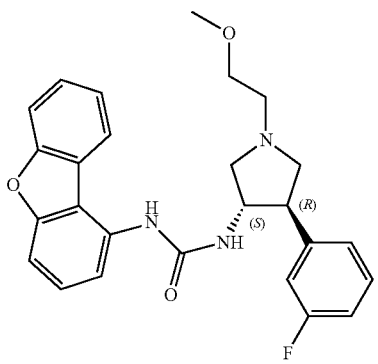
Example 105
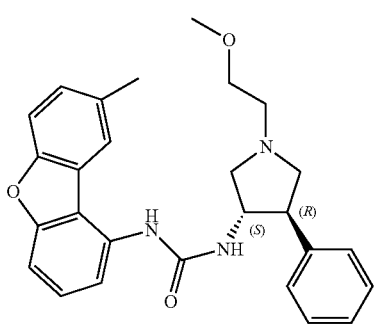
Example 106
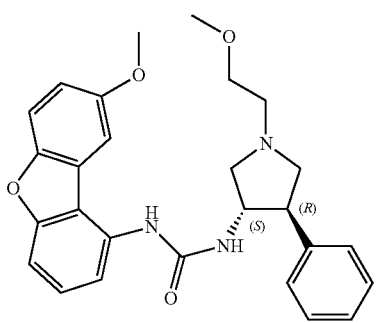
Example 107
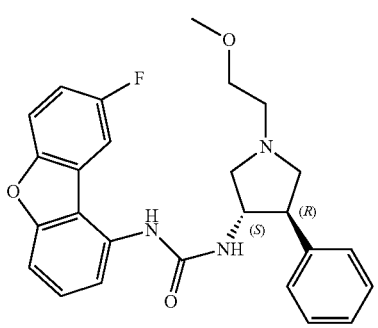
Example 108

TABLE 1-continued
Exemplary compounds from Formula I (Examples 1-202)
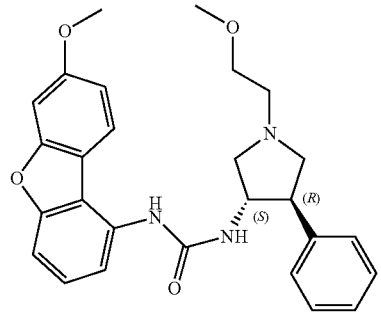
Example 109
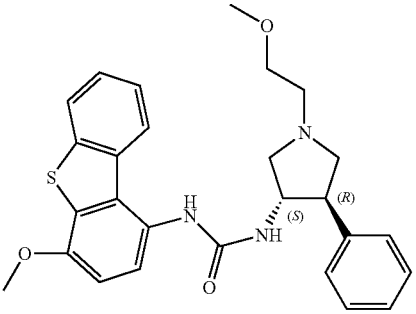
Example 113
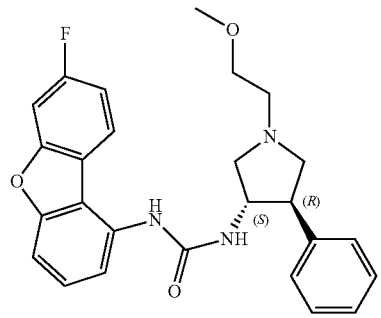
Example 110
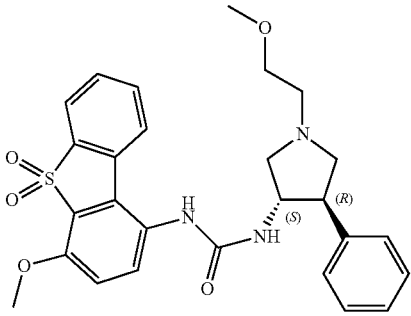
Example 114
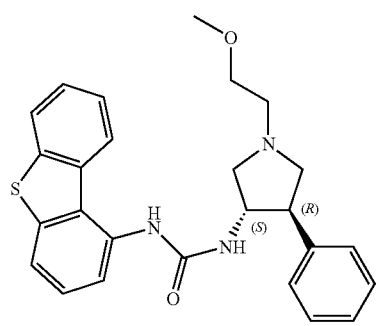
Example 111
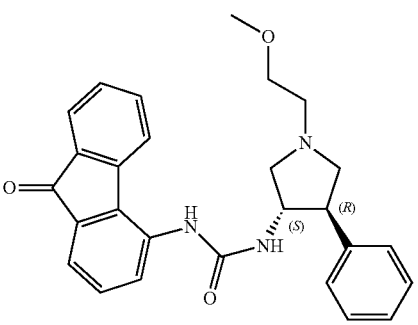
Example 115
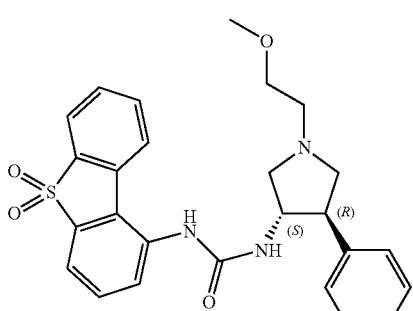
Example 112
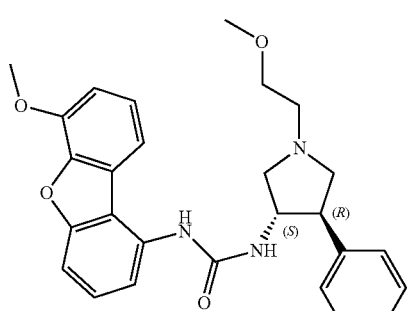
Example 116

TABLE 1-continued
Exemplary compounds from Formula I (Examples 1-202)
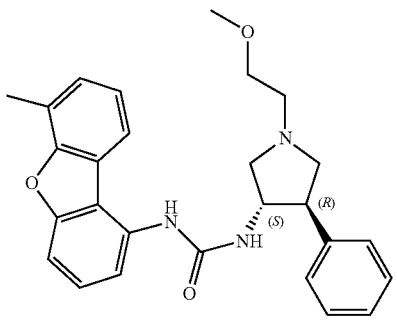
Example 117
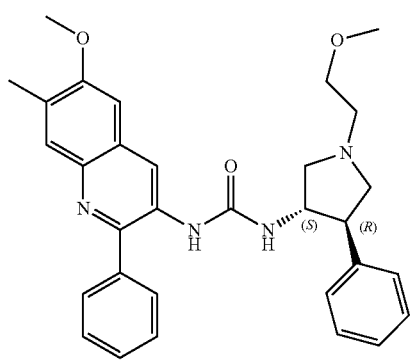
Example 118
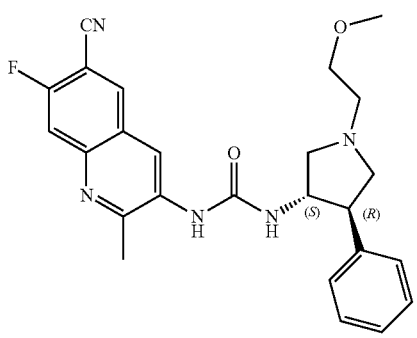
Example 119
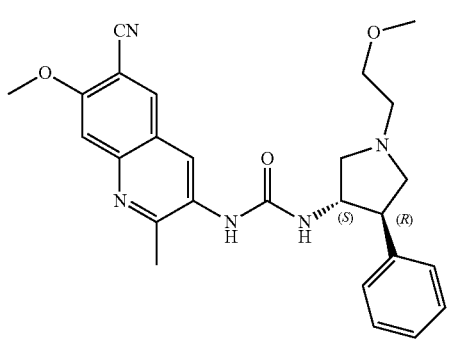
Example 120
TABLE 1-continued
Exemplary compounds from Formula I (Examples 1-202)
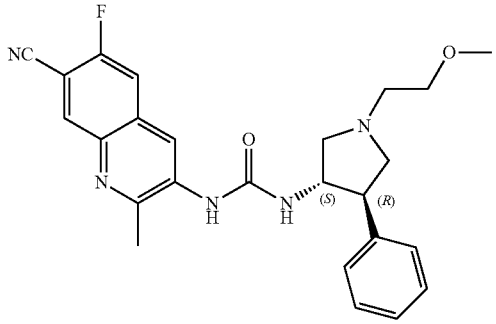
Example 121
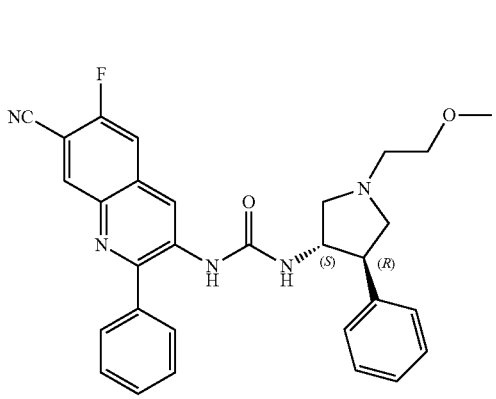
Example 122
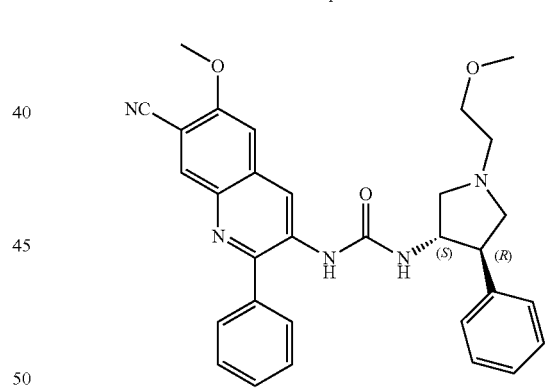
Example 123
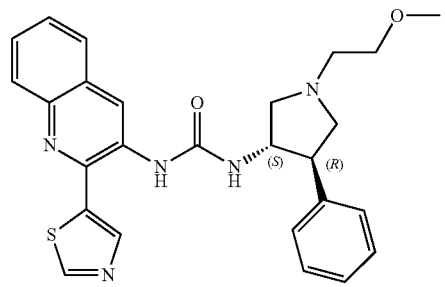
Example 124

TABLE 1-continued
Exemplary compounds from Formula I (Examples 1-202)
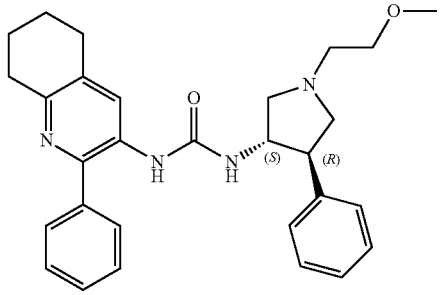
Example 125
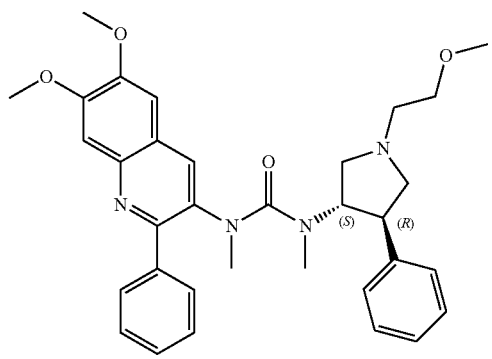
Example 126
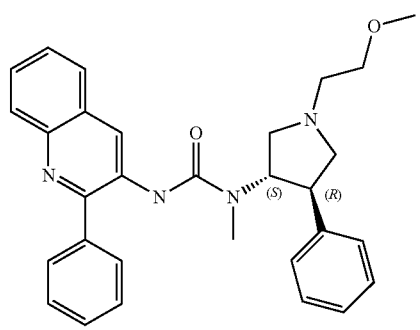
Example 127
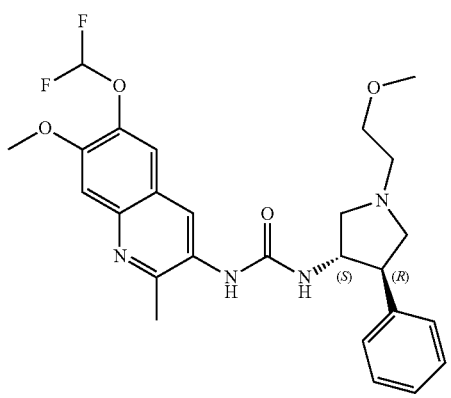
Example 128
TABLE 1-continued
Exemplary compounds from Formula I (Examples 1-202)
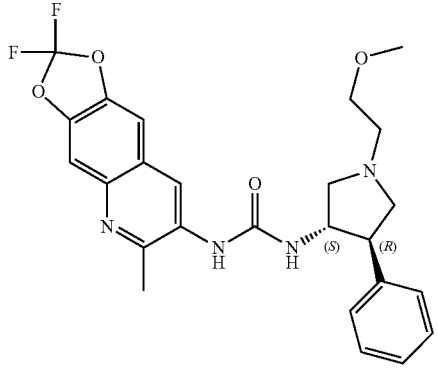
Example 129
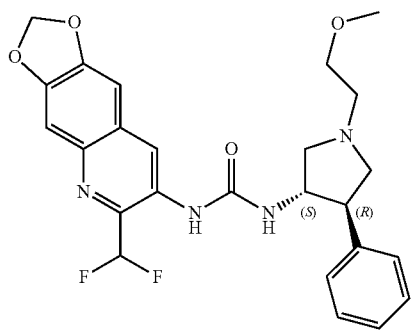
Example 130
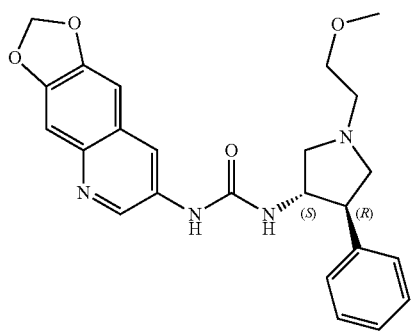
Example 131
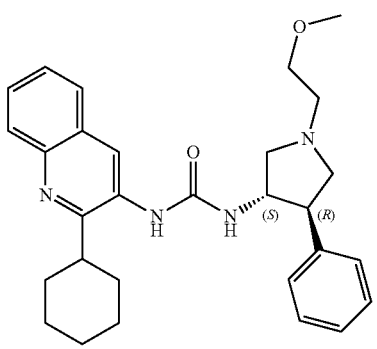
Example 132

TABLE 1-continued
Exemplary compounds from Formula I (Examples 1-202)
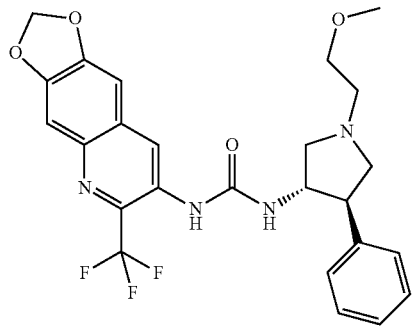
Example 133
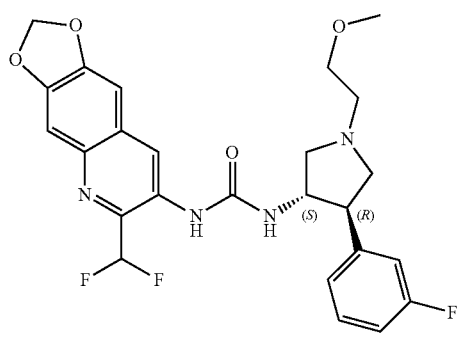
Example 134
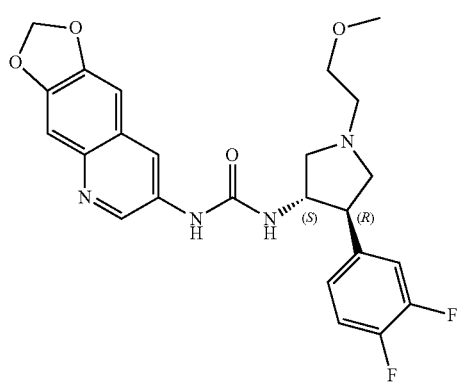
Example 135
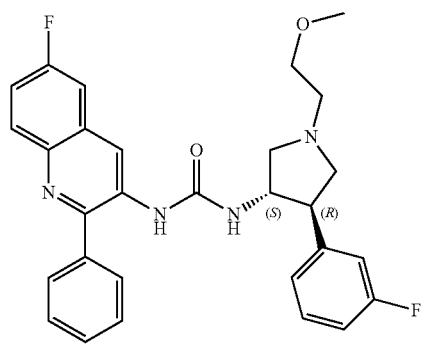
Example 136
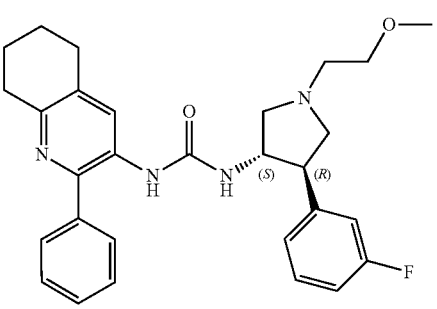
Example 137
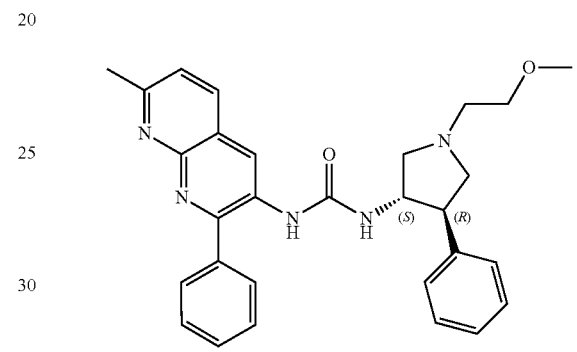
Example 138
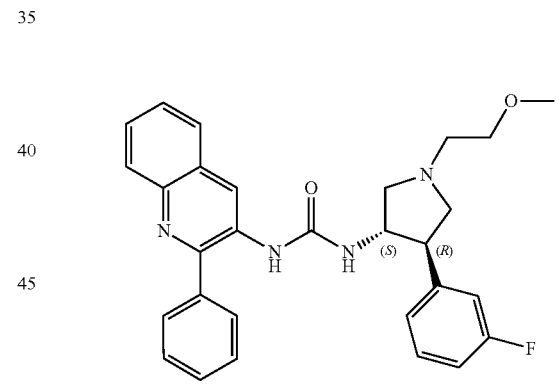
Example 139
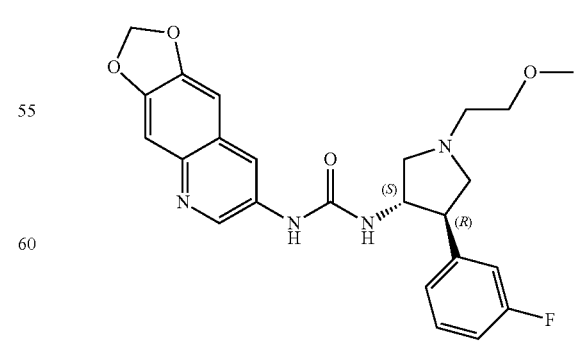
Example 140

TABLE 1-continued
Exemplary compounds from Formula I (Examples 1-202)
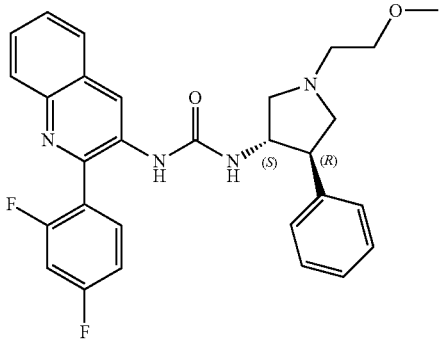
Example 141
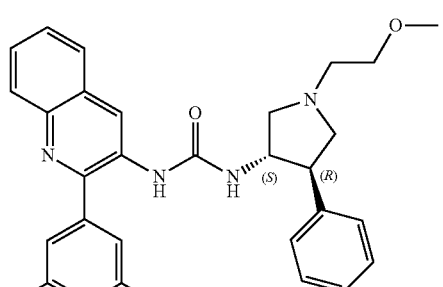
Example 142
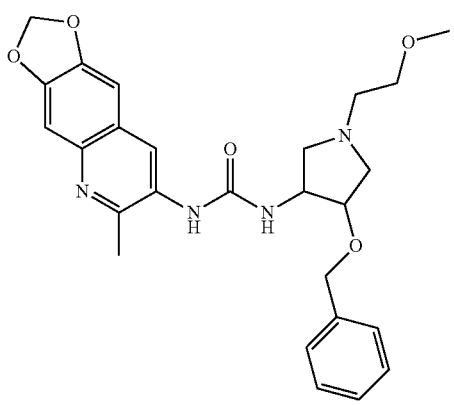
Example 143
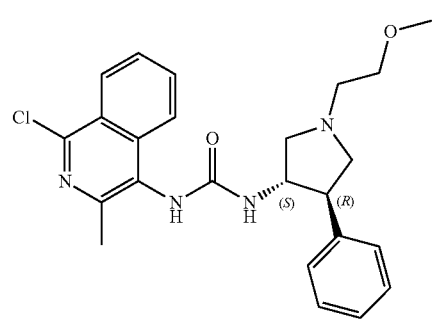
Example 144
TABLE 1-continued
Exemplary compounds from Formula I (Examples 1-202)
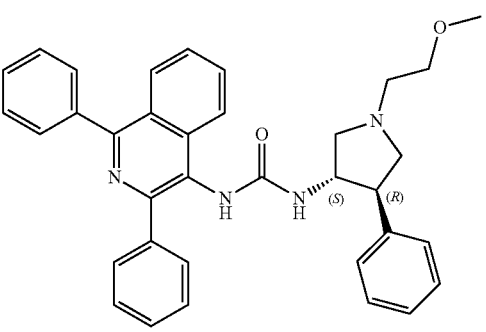
Example 145
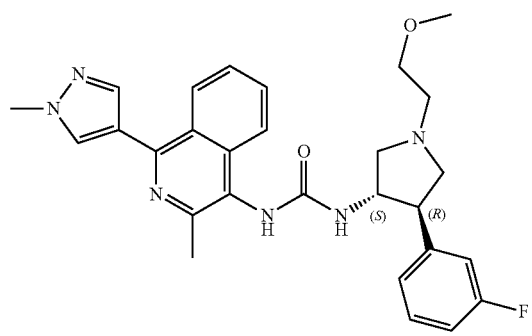
Example 146
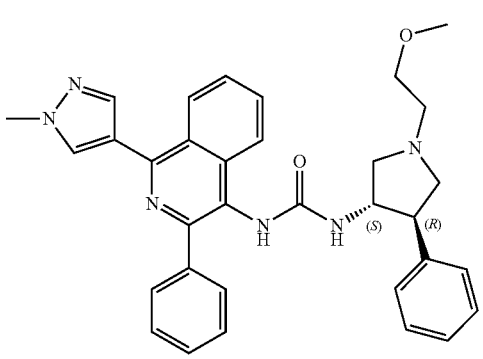
Example 147
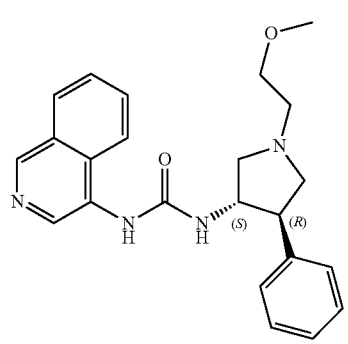
Example 148

TABLE 1-continued
Exemplary compounds from Formula I (Examples 1-202)
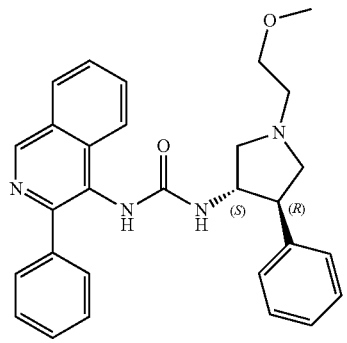
Example 149
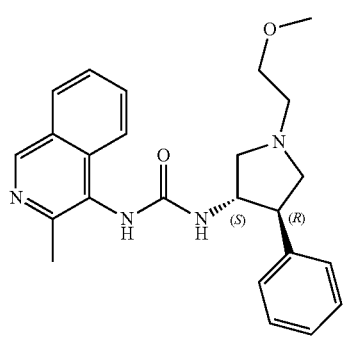
Example 150
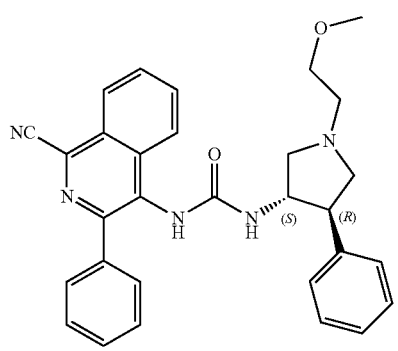
Example 151
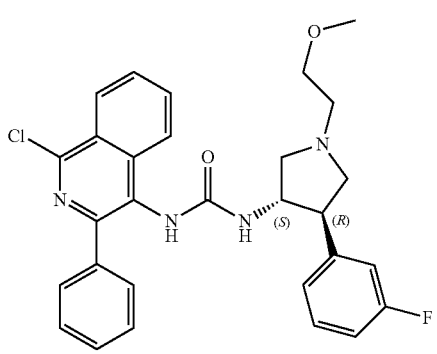
Example 152
TABLE 1-continued
Exemplary compounds from Formula I (Examples 1-202)
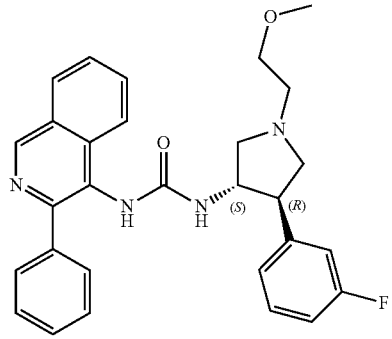
Example 153
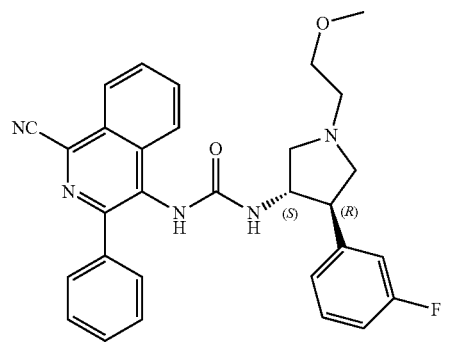
Example 154
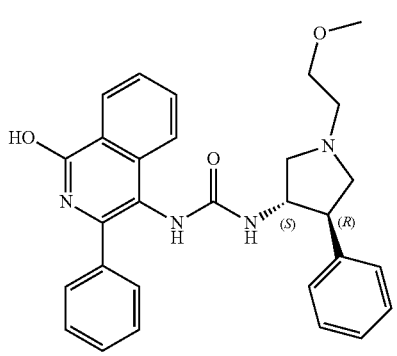
Example 155
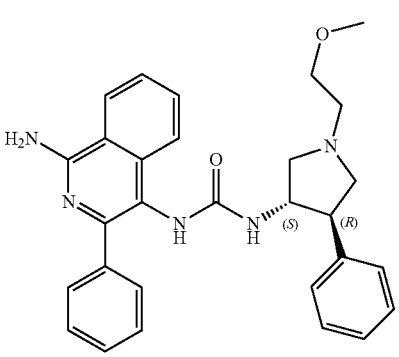
Example 156

TABLE 1-continued
Exemplary compounds from Formula I (Examples 1-202)
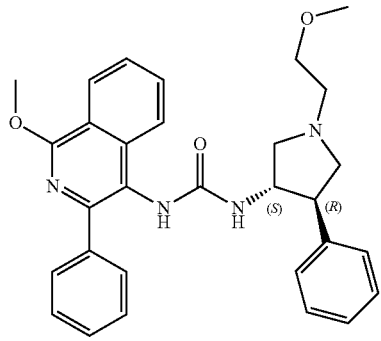
Example 157
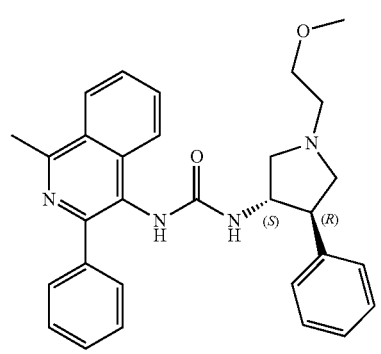
Example 158
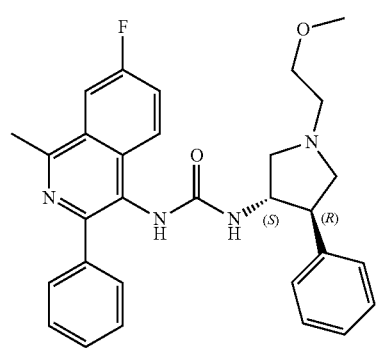
Example 159
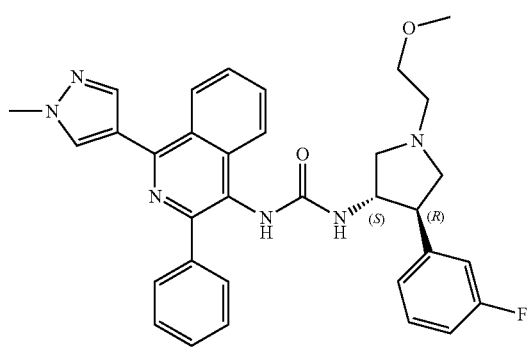
Example 160
TABLE 1-continued
Exemplary compounds from Formula I (Examples 1-202)
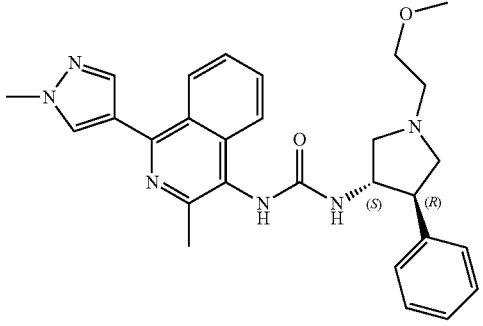
Example 161
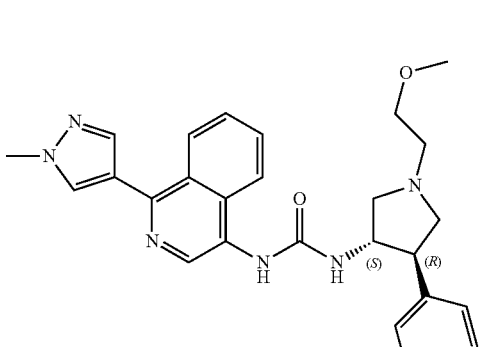
Example 162
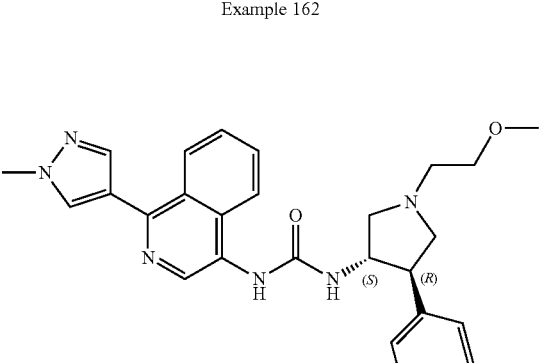
Example 163
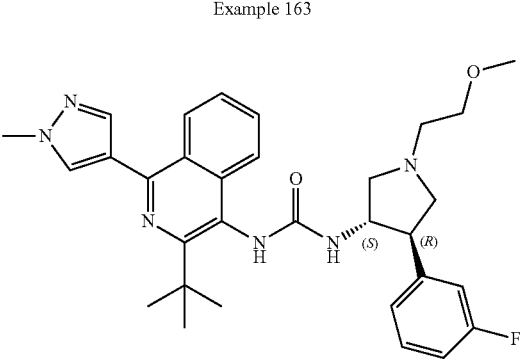
Example 164

TABLE 1-continued
Exemplary compounds from Formula I (Examples 1-202)
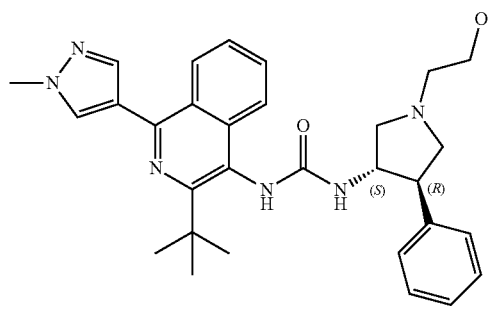
Example 165
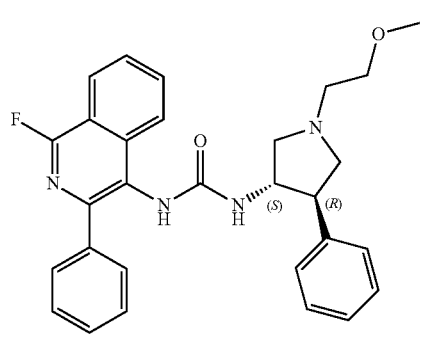
Example 166
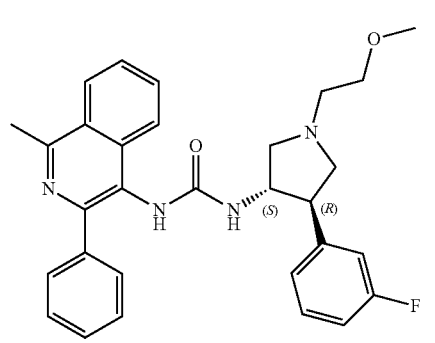
Example 167
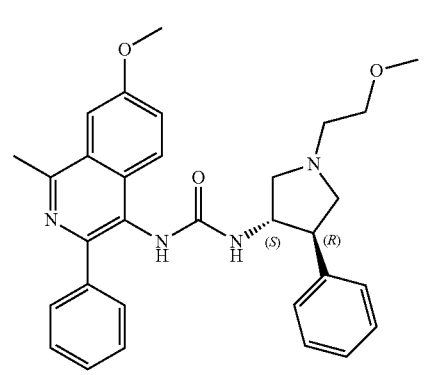
Example 168
TABLE 1-continued
Exemplary compounds from Formula I (Examples 1-202)
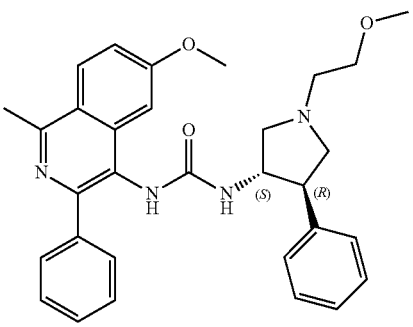
Example 169
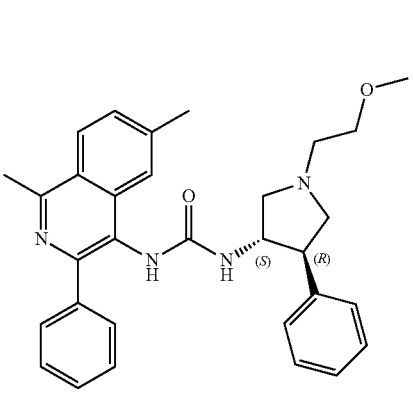
Example 170
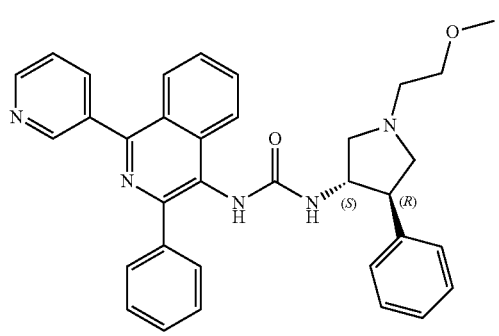
Example 171
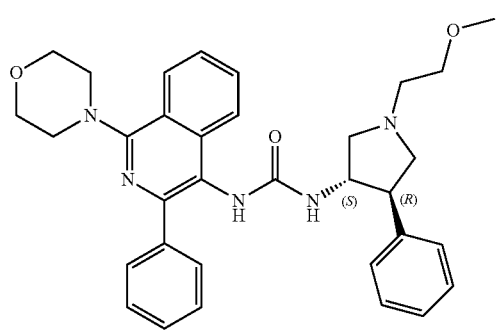
Example 172

TABLE 1-continued
Exemplary compounds from Formula I (Examples 1-202)
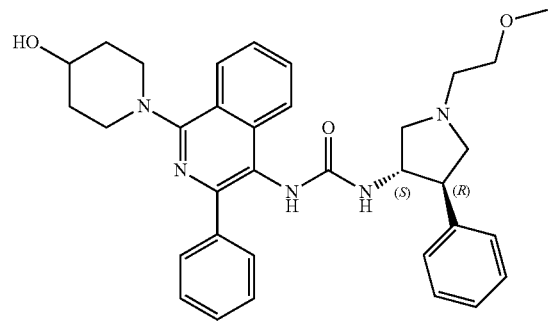
Example 173
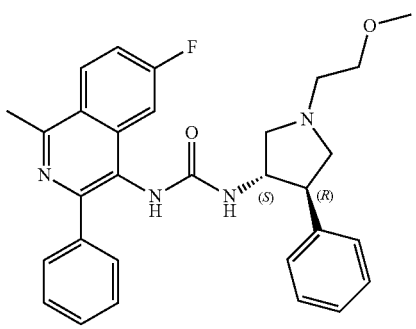
Example 177
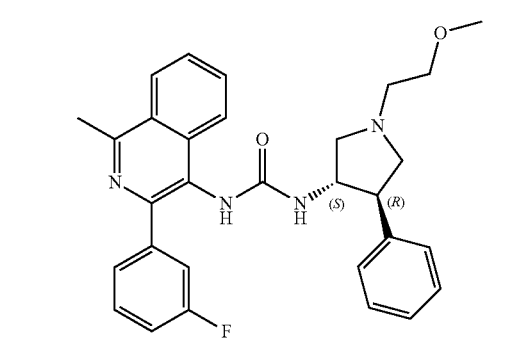
Example 174
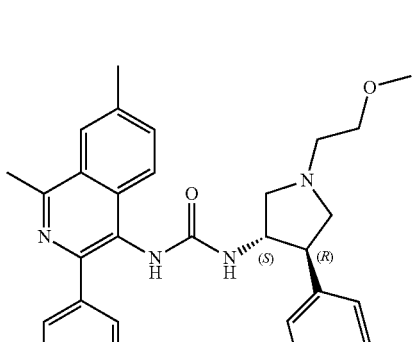
Example 178
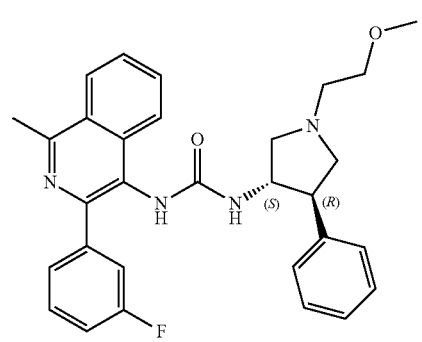
Example 175
Example 179
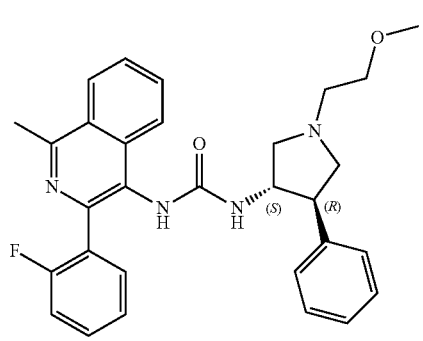
Example 176
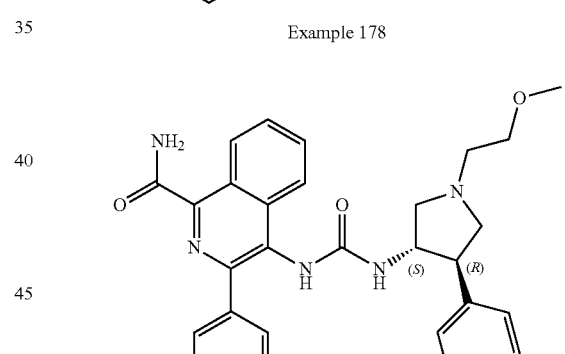
Example 180

TABLE 1-continued
Exemplary compounds from Formula I (Examples 1-202)
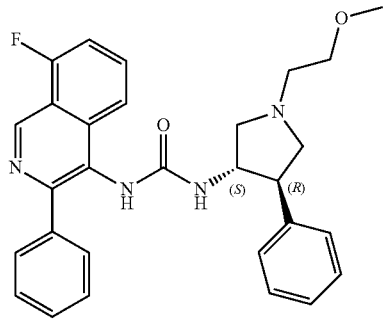
Example 181
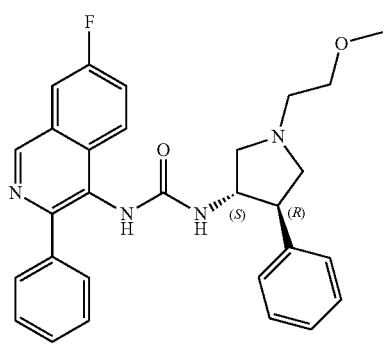
Example 182
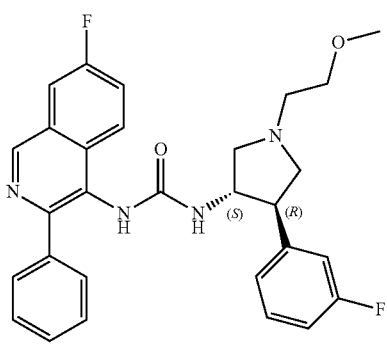
Example 183
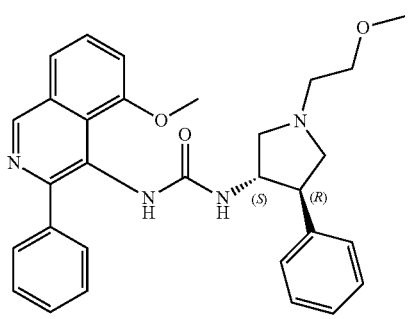
Example 184
TABLE 1-continued
Exemplary compounds from Formula I (Examples 1-202)
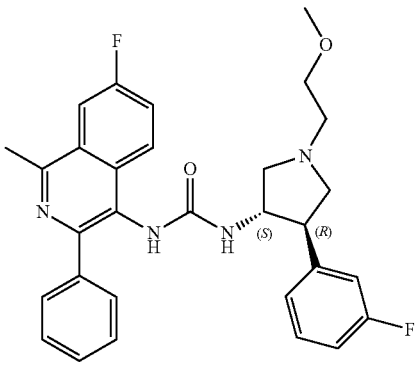
Example 185
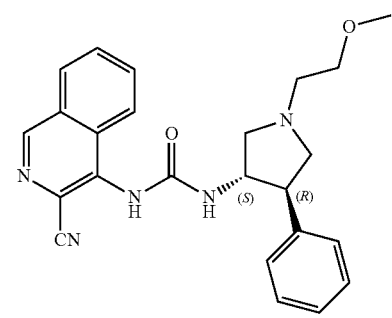
Example 186
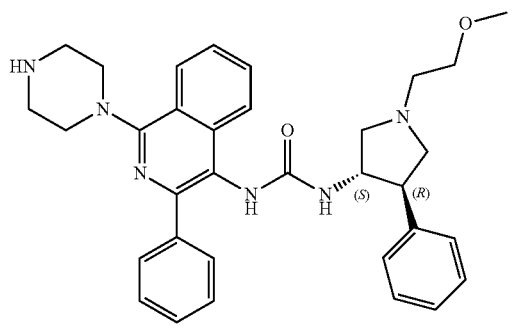
Example 187
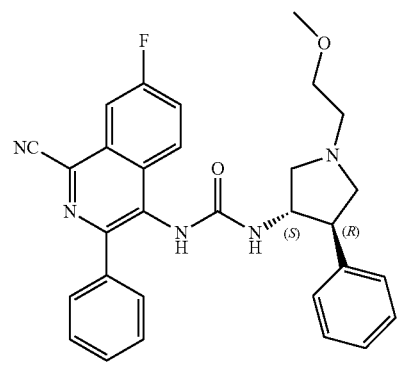
Example 188

TABLE 1-continued
Exemplary compounds from Formula I (Examples 1-202)
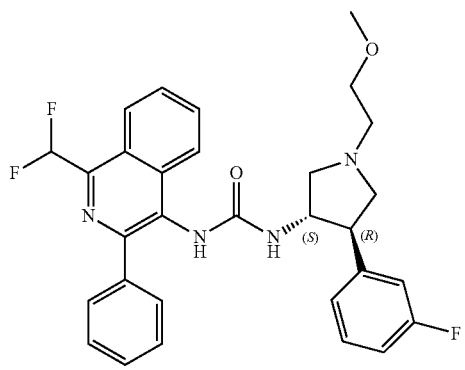
Example 189
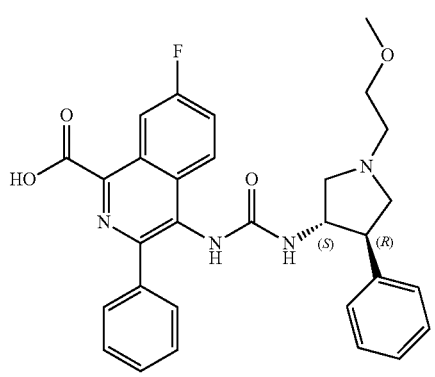
Example 190
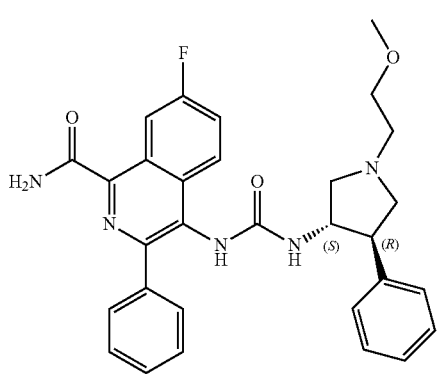
Example 191
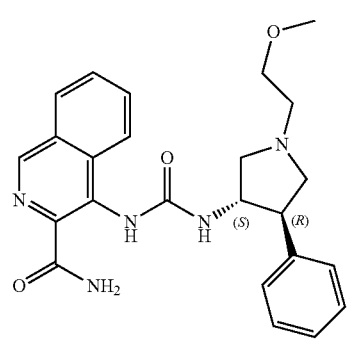
Example 192
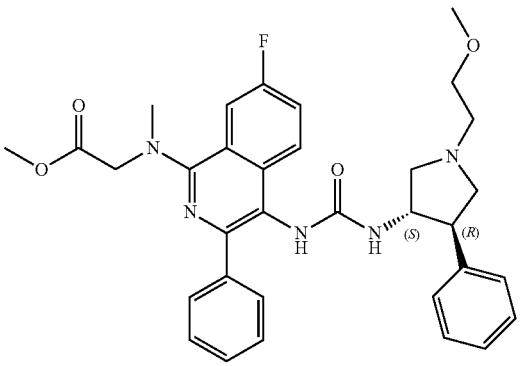
Example 193
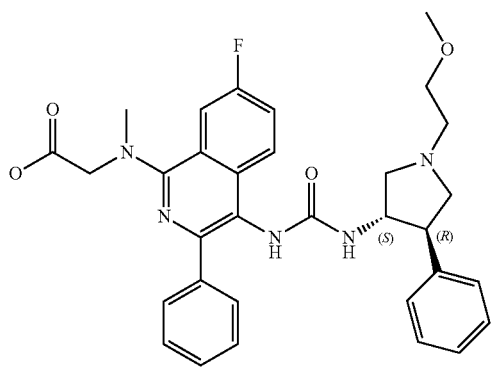
Example 194
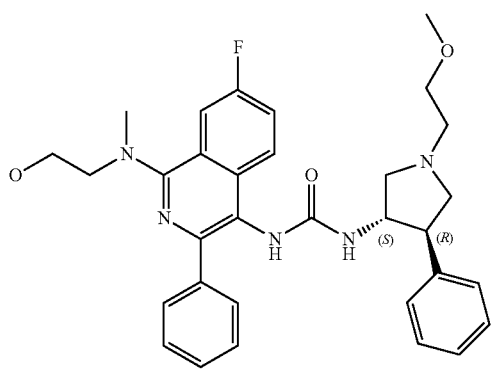
Example 195
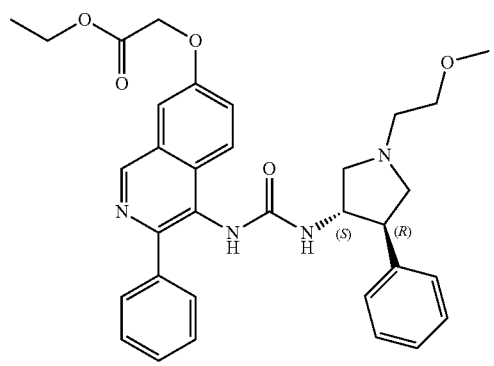
Example 196

TABLE 1-continued

Exemplary compounds from Formula I (Examples 1-202)

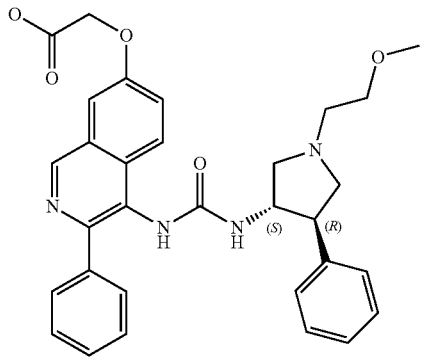

Example 197

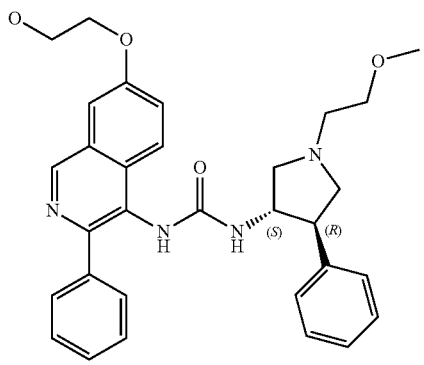

Example 198

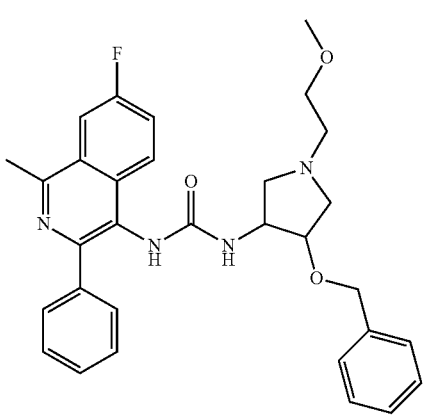

Example 199

TABLE 1-continued

Exemplary compounds from Formula I (Examples 1-202)

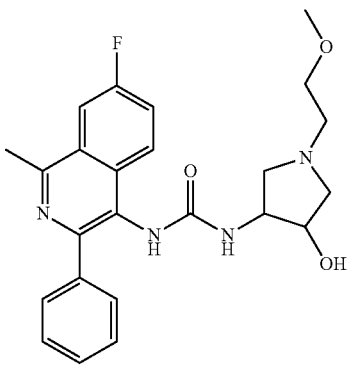

Example 200

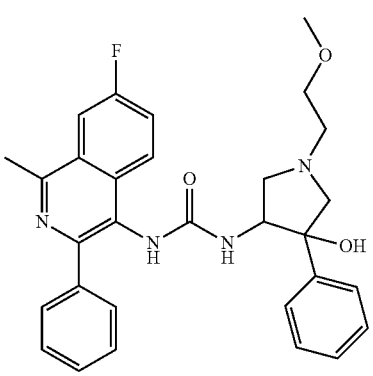

Example 201

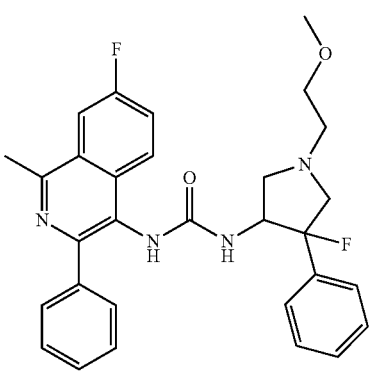

Example 202

The above mentioned compounds are just for exemplary purposes and not to limit the scope of the invention.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

Reaction Schemes:

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

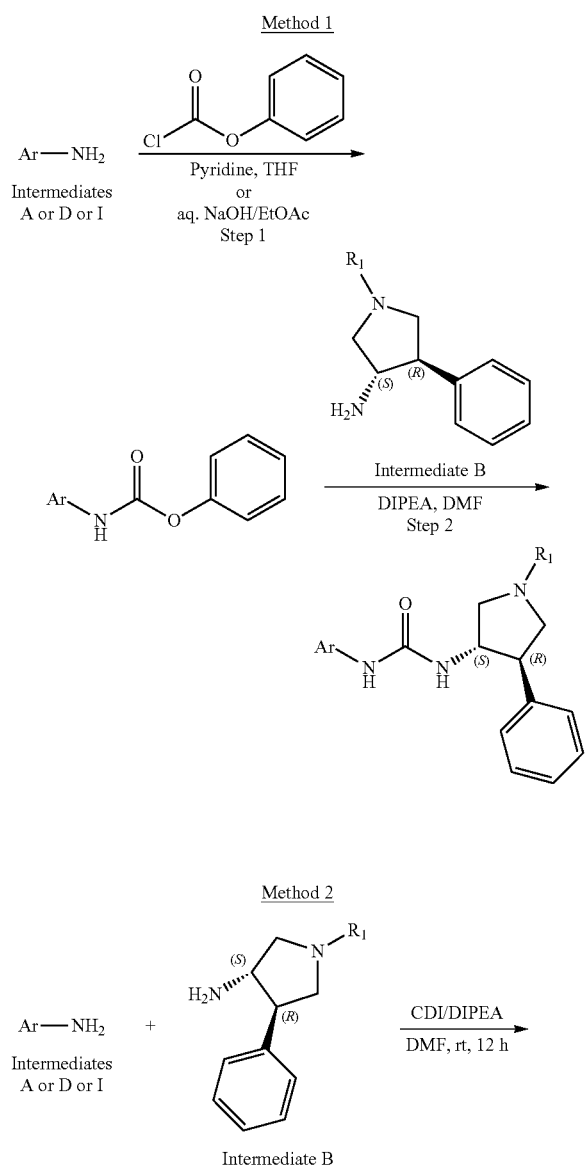

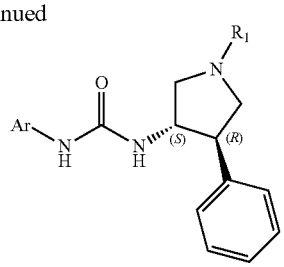

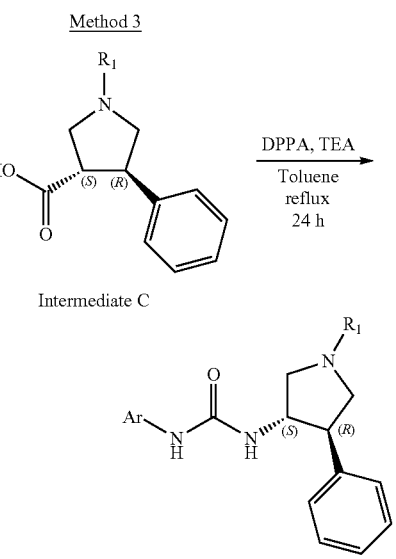

Experimental Section

All commercially available reagents and solvents were purchased from combi-blocks, Aldrich, Avra etc., and used as received. Reactions using air or moisture sensitive reagents were performed under an atmosphere of nitrogen using freshly opened drySolv solvents. Reaction progress was monitored by TLC and/or LCMS. Flash column chromatography was performed with Grace Purification System or Isco Combi Flash Companion Systems using pre-packed silica gel columns (40-60 µm particle size RediSep or 20-40 µm spherical silica gel RediSep Gold columns or reveleris columns or similar columns from other vendors). Specific optical rotation is recorded on Rudolph and melting point on Buchi instrument. Preparative reverse phase HPLC purifications were performed on Agilent or Waters instrument. NMR spectra were measured on Agilent 300 or 400 MHz spectrometer and chemical shifts were reported in ppm downfield from TMS using residual non deuterated solvent as internal standards (CHCl3, 7.26 ppm; DMSO, 2.50 ppm; MeOH, 3.31 ppm). The following abbreviations are used: br=broad signal, s=singlet, d=doublet, dd=doublet of doublets, t=triplet, q=quartet, m=multiplet. The purity of final compounds was verified by HPLC in all cases using stationary phase and a gradient of water/acetonitrile (5-95% over 10 min, 0.05% TFA in both phases) at a flow rate of 0.4 mL/min.

List of Intermediates required for synthesis of the compounds of Formula I described below.

Preparation of Intermediates

Certain intermediates were directly purchased from commercial vendors and used as such for the respective synthesis of examples of Formula I. The other intermediates were prepared either by following reported literature procedures or modified as per the requirement or applied the skills in derivatizing with appropriate substitutions.

Intermediate A: Quinoline Intermediates (A1-A72)

Scheme 1 (This scheme was described in *Chemistry-A European Journal*, 2012, 18, 5530-5535; *Tetrahedron*, 2004, 60, 2937-2942).

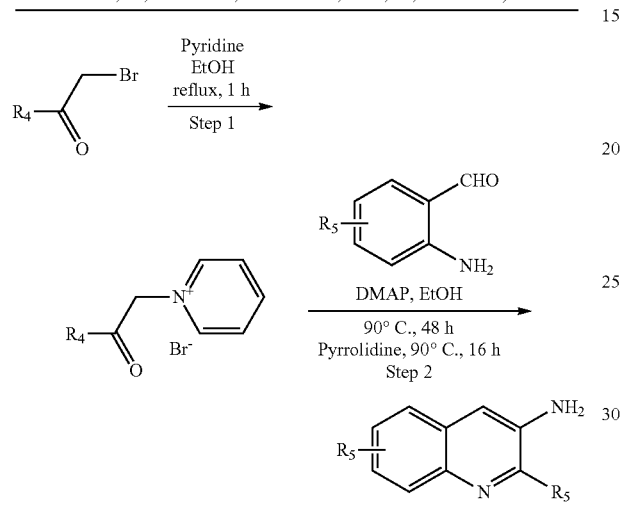

Scheme 2
(This scheme was described in *J. Org. Chem.* 2004, 69, 1565-1570)

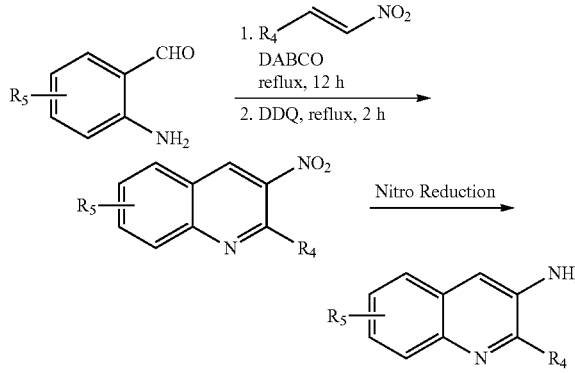

Scheme 3
(This scheme was described in WO2014062667 A1)

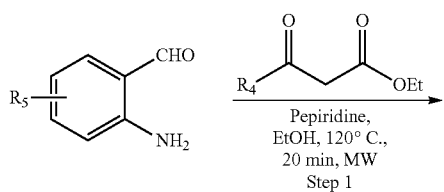

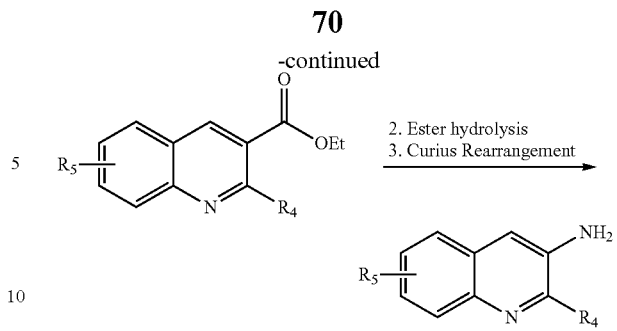

Scheme 4

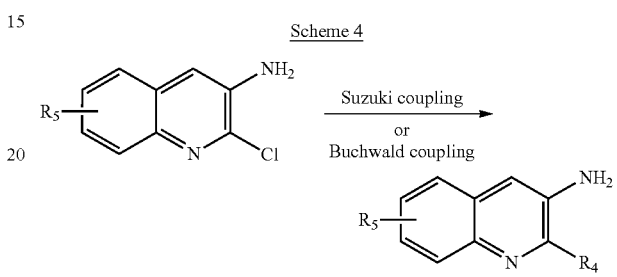

Scheme 5
(Part of this scheme was described in US2008/161340 A1)

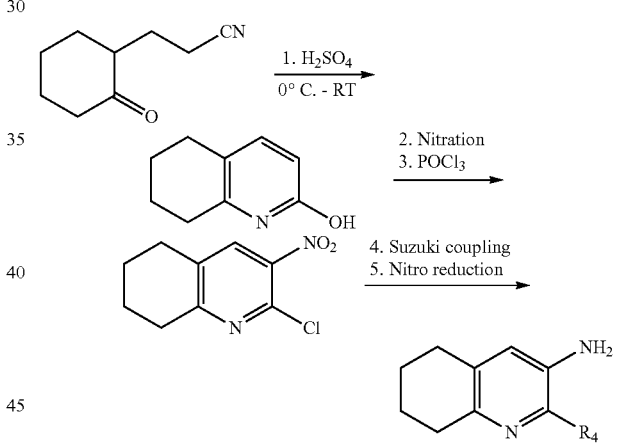

Intermediates such as A1-A5 were purchased from commercial vendors and other intermediates A6-A72 were synthesized based on the above general schemes 1-5 and the analytical data are shown below.

Intermediate A1: Quinolin-3-amine
Intermediate A2: 2-Chloroquinolin-3-amine
Intermediate A3: Quinolin-4-amine
Intermediate A4: Quinazolin-4-amine
Intermediate A5: Quinoxalinoxalin-2-amine
Intermediate A6: 2-Phenylquinolin-3-amine. LCMS (M+H): 221.10
Intermediate A7: 2-Methylquinolin-3-amine. LCMS (M+H): 158.95.
Intermediate A8: 2-Ethylquinolin-3-amine. LCMS (M+H): 173.12.
Intermediate A9: 2-(Cyclopropyl)-quinolin-3-amine. LCMS (M+H): 185.28.
Intermediate A10: 2-(Trifluoromethyl)-quinolin-3-amine. LCMS (M+H): 213.10.

Intermediate A11: 6-Fluoro-2-phenylquinolin-3-amine. LCMS (M+H): 238.95.

Intermediate A12: 7-Fluoro-2-phenylquinolin-3-amine. $^1$H NMR (DMSO-d$_6$, 300 MHz): δ 7.77-7.72 (m, 3H), 7.60-7.37 (m, 5H), 7.40-7.30 (m, 1H), 5.24 (s, 2H).

Intermediate A13: 6-Methoxy-2-phenylquinolin-3-amine. $^1$H NMR (DMSO-d$_6$, 300 MHz): δ 7.72-7.66 (m, 3H), 7.53-7.44 (m, 3H), 7.30 (s, 1H), 7.03-6.97 (m, 2H), 5.22 (s, 2H), 3.87 (s, 3H).

Intermediate A14: 6,7-Dimethoxy-2-phenylquinolin-3-amine. LCMS (M+H): 281.19.

Intermediate A15: 6,7-Dimethoxy-2-methylquinolin-3-amine. LCMS (M+H): 219.24.

Intermediate A16: 6-Fluoro-2-methylquinolin-3-amine. LCMS (M+H): 177.08.

Intermediate A17: 6-Methyl-2-methylquinolin-3-amine. LCMS (M+H): 173.12.

Intermediate A18: 7-Methyl-2-methylquinolin-3-amine. LCMS (M+H): 173.12.

Intermediate A19: 5-Methyl-2-methylquinolin-3-amine. LCMS (M+H): 173.05

Intermediate A20: 5-Fluoro-2-methylquinolin-3-amine. LCMS (M+H): 177.04.

Intermediate A21: 8-Methyl-2-methylquinolin-3-amine. LCMS (M+H): 173.30.

Intermediate A22: 8-Fluoro-2-methylquinolin-3-amine. LCMS (M+H): 177.25.

Intermediate A23: 5-Methoxy-2-methylquinolin-3-amine. LCMS (M+H): 189.29.

Intermediate A24: 6-Methoxy-2-methylquinolin-3-amine. LCMS (M+H): 189.29.

Intermediate A25: 7-Methoxy-2-methylquinolin-3-amine. LCMS (M+H): 189.03.

Intermediate A26: 8-Methoxy-2-methylquinolin-3-amine. LCMS (M+H): 189.10.

Intermediate A27: 7-Fluoro-2-methylquinolin-3-amine. LCMS (M+H): 177.08.

Intermediate A28: 6-Methoxy-2-methyl-7-morpholinoquinolin-3-amine. LCMS (M+H): 274.10.

Intermediate A29: 6-Fluoro-7-methyl-2-phenylquinolin-3-amine. LCMS (M+H): 253.31.

Intermediate A30: 6-Bromo-8-methoxy-2-methylquinolin-3-amine.

Intermediate A31: 8-Methoxy-2,7-dimethylquinolin-3-amine. LCMS (M+H): 265.46.

Intermediate A32: 6-Phenyl-[1,3]dioxolo[4,5-g]quinolin-7-amine. LCMS (M+H): 265.25.

Intermediate A33: N-(3-Amino-7-methoxy-2-phenylquinolin-6-yl)acetamide. LCMS (M+H): 308.16.

Intermediate A34: 8-Bromo-2-methylquinolin-3-amine. LCMS (M+H+2H): 238.93.

Intermediate A35: 6-Methyl-[1,3]dioxolo[4,5-g]quinolin-7-amine. LCMS (M+H): 203.07.

Intermediate A36: 7-Methyl-2,3-dihydro-[1,4]dioxino[2,3-g]quinolin-8-amine. LCMS (M+H): 217.11.

Intermediate A37: 7-Phenyl-2,3-dihydro-[1,4]dioxino[2,3-g]quinolin-8-amine. LCMS (M+H): 279.11.

Intermediate A38: N-(3-Amino-6-methoxy-2-phenylquinolin-7-yl)acetamide. LCMS (M+H): 308.16.

Intermediate A39: N-(3-Amino-6-methoxy-2-methylquinolin-7-yl)acetamide. LCMS (M+H): 246.13.

Intermediate A40: 6-Methoxy-7-methyl-2-phenylquinolin-3-amine. LCMS (M+H): 265.16.

Intermediate A41: 3-Amino-7-methoxy-2-methylquinoline-6-carbonitrile. LCMS (M+H): 202.06.

Intermediate A42: 3-Amino-7-methoxy-2-methylquinoline-6-carbonitrile.

Intermediate A43: 3-Amino-6-fluoro-2-methylquinoline-7-carbonitrile. LCMS (M+H): 202.03.

Intermediate A44: 3-Amino-6-fluoro-2-phenylquinoline-7-carbonitrile. LCMS (M+H): 264.13.

Intermediate A45: 3-Amino-6-methoxy-2-phenylquinoline-7-carbonitrile. $^1$H NMR (DMSO-d$_6$, 300 MHz): δ 8.17 (s, 1H), 7.70-7.67 (m, 2H), 7.55-7.48 (m, 3H), 7.28 (d, J=13.2 Hz, 2H), 5.81 (b s, 2H), 3.97 (s, 3H).

Intermediate A46: 6-(Difluoromethoxy)-7-methoxy-2-methylquinolin-3-amine. LCMS (M+H): 255.05.

Intermediate A47: 2,2-Difluoro-6-methyl-[1,3]dioxolo[4,5-g]quinolin-7-amine. LCMS (M+H): 239.20.

Intermediate A48: 2-Cyclohexylquinolin-3-amine. LCMS (M+H): 227.42.

Intermediate A49: 6-(Trifluoromethyl)-[1,3]dioxolo[4,5-g]quinolin-7-amine. LCMS (M+H): 257.19.

Intermediate A50: 7-Methyl-2-phenyl-1,8-naphthyridin-3-amine. LCMS (M+H): 236.22.

Intermediate A51: 6,7-Dimethoxyquinolin-3-amine. LCMS (M+H): 205.04.

Intermediate A52: [1,3]Dioxolo[4,5-g]quinolin-7-amine. LCMS (M+H): 189.07.

Intermediate A53: 6-Methyl-2-phenylquinolin-3-amine. LCMS (M+H): 235.1.

Intermediate A54: 6-Fluoro-3-amino-2-phenylquinoline. LCMS (M+H): 238.95.

Intermediate A55: 7-Methyl-3-amino-2-phenylquinoline. LCMS-(M+H): 234.99.

Intermediate A56: 7-Methoxy-2-phenylquinolin-3-amine. LCMS (M+H): 251.10.

Intermediate A57: 7-Fluoro-6-methoxy-2-phenylquinolin-3-amine. LCMS (M+H): 269.13.

Intermediate A58: 7-Fluoro-6-methyl-2-phenylquinolin-3-amine. LCMS (M+H): 253.08.

Intermediate A59: N-(3-Amino-7-fluoro-2-phenylquinolin-6-yl)acetamide.

Intermediate A60: 6-Methoxy-7-methyl-2-methylquinolin-3-amine. LCMS (M+H): 203.20.

Intermediate A61: 6-Methoxy-7-fluoro-2-methylquinolin-3-amine. LCMS (M+H): 207.03.

Intermediate A62: Tert-butyl (3-amino-7-methoxy-2-methylquinolin-6-yl)(methyl)carbamate. LCMS (M+H): 380.24.

Intermediate A63: 2-(1-Methyl-1H-pyrazol-4-yl)quinolin-3-amine. LCMS (M+H): 224.94.

Intermediate A64: 2-(Pyridin-3-yl)quinolin-3-amine. LCMS (M+H): 222.23.

Intermediate A65: 2-(Pyridin-4-yl)quinolin-3-amine. LCMS (M+H): 222.23.

Intermediate A66: 2-(Pyrimidin-5-yl)quinolin-3-amine. LCMS (M+H): 223.12.

Intermediate A67: 2-(Thiazol-5-yl)quinolin-3-amine. LCMS (M+H): 228.17.

Intermediate A68: 2-(2,4-Difluorophenyl)quinolin-3-amine. LCMS (M+H): 257.15.

Intermediate A69: 2-(3,5-difluorophenyl)quinolin-3-amine. LCMS (M+H): 257.15.

Intermediate A70: 2-Morpholinoquinolin-3-amine. LCMS (M+H): 230.29.

Intermediate A71: 2-Phenyl-5,6,7,8-tetrahydroquinolin-3-amine. LCMS: (M+H): 225.04.

Intermediate A72: 6-(Difluoromethyl)-[1,3]dioxolo[4,5-g]quinolin-7-amine. LCMS (M+H): 239.01.

Intermediate D: Dibenzofuran& Dibenzothiophene Intermediates (D1-D10)

Intermediates D1-D10 were synthesized based on the Schemes 6-8 and the analytical data for each intermediate are shown below.

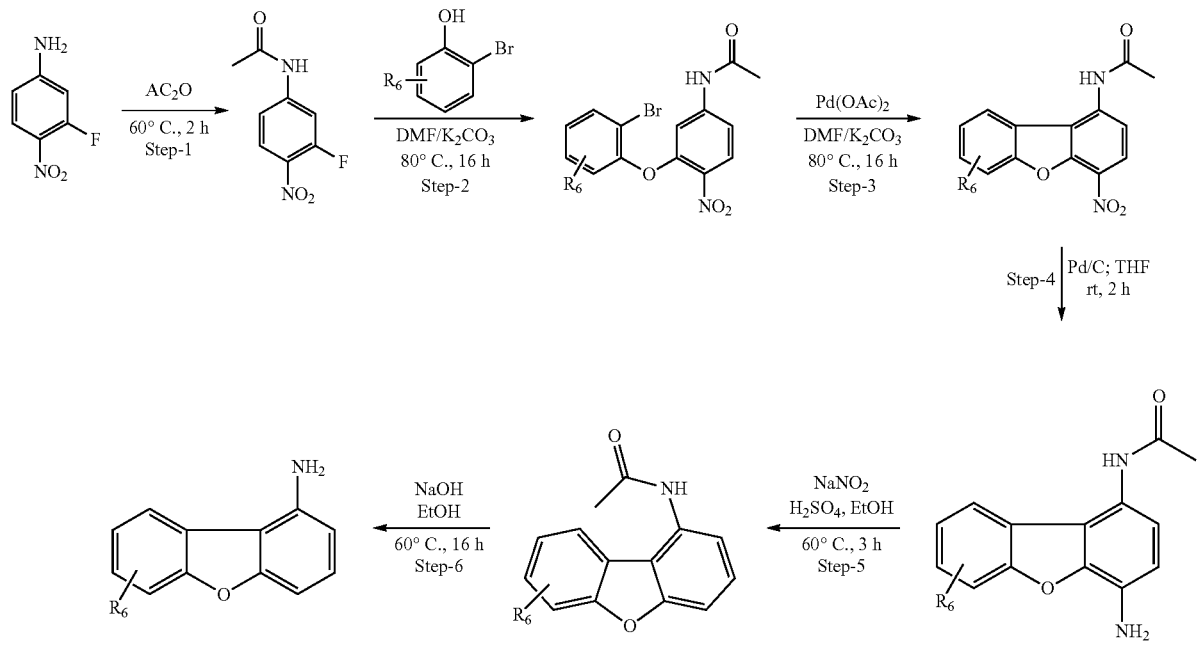
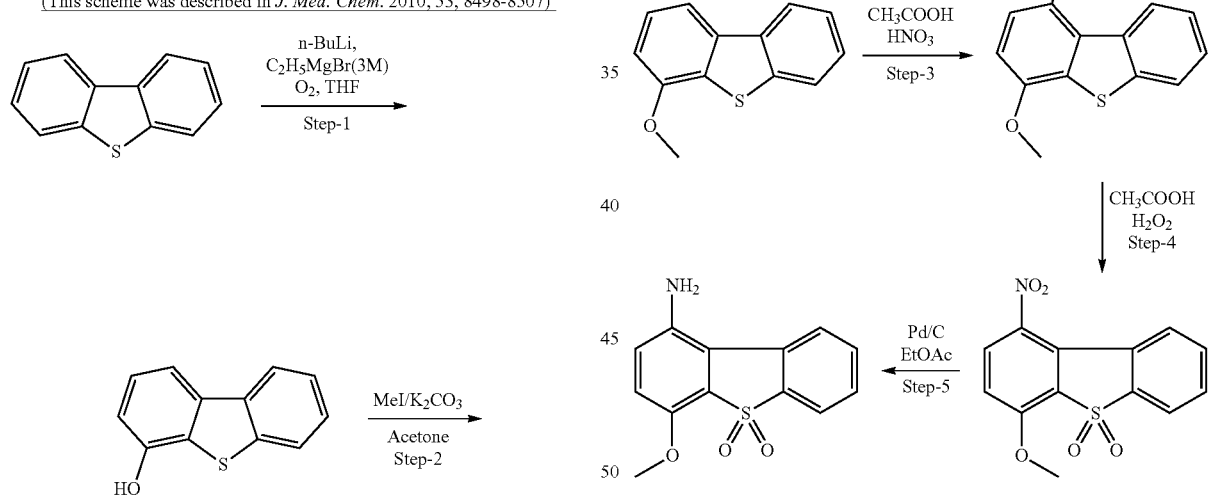
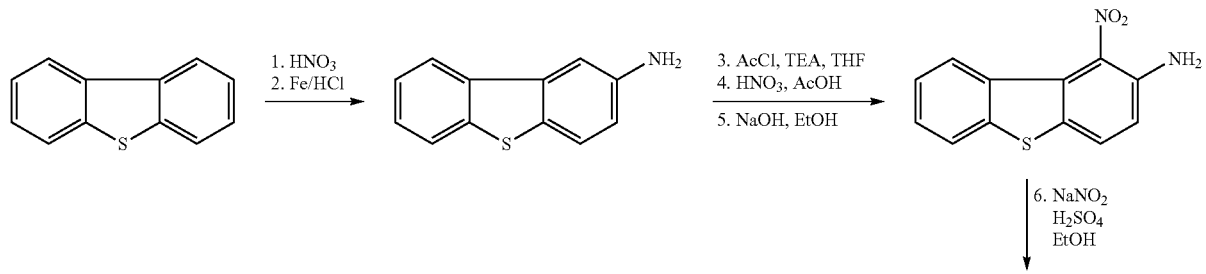

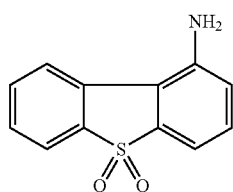 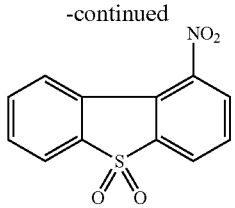 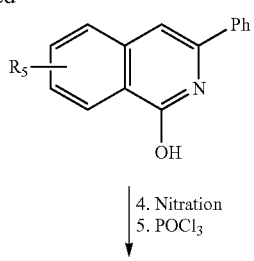

-continued

Analytical data for D1-D10

Intermediate D1: 6-Methoxydibenzo[b,d]furan-1-amine. LCMS (M+H): 214.10.

Intermediate D2: Dibenzo[b,d]furan-1-amine. LCMS (M+H): 184.10.

Intermediate D3: 8-Methyldibenzo[b,d]furan-1-amine. LCMS (M+H): 198.00.

Intermediate D4: 8-Methoxydibenzo[b,d]furan-1-amine. $^1$H NMR (CDCl$_3$, 300 MHz): δ 8.44 (s, 1H), 8.28-8.25 (m, 1H), 8.03-8.00 (m, 1H), 7.57-7.54 (m, 1H), 7.45 (m, 1H), 7.21-7.18 (m, 1H), 3.94 (s, 3H).

Intermediate D5: 8-Fluorodibenzo[b,d]furan-1-amine. $^1$H NMR (CDCl$_3$, 300 MHz): δ 7.51-7.45 (m, 2H), 7.30-7.28 (m, 1H), 7.15 (dt, J=2.4, 9.0 Hz, 1H), 7.01 (d, J=8.4 Hz, 1H), 6.63 (d, J=8.4 Hz, 1H).

Intermediate D6: 7-Fluorodibenzo[b,d]furan-1-amine. LCMS (M+H): 202.20.

Intermediate D7: 7-Methoxydibenzo[b,d]furan-1-amine. LCMS (M+H): 214.20.

Intermediate D8: 6-Methyldibenzo[b,d]furan-1-amine.

Intermediate D9: 4-Methoxy-5,5-dioxo-dibenzo[b,d]thiophen-1-ylamine. LCMS (M+H): 262.03.

Intermediate D10: 5,5-Dioxo-dibenzo[b,d]thiophen-1-ylamine. LCMS (M+H): 231.95.

Intermediate I: Isoquinoline Intermediates (I1-I30)

Intermediates I1-I30 were synthesized based on the general Schemes 9-12 and the analytical data for each intermediate are shown below.

Scheme 9
(Part of the scheme was described in WO 2007/53346 A1 and *Chemistry - A European Journal*, 2013 19, 11553-11557)

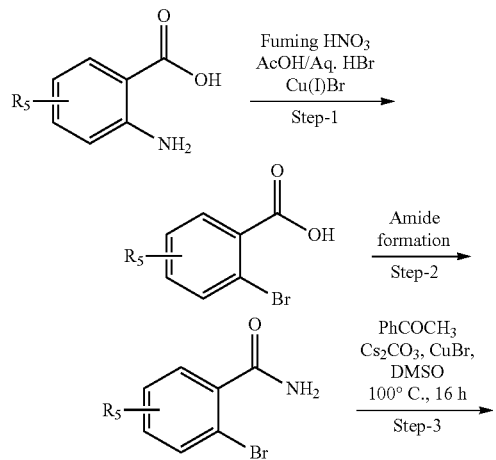

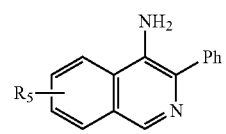

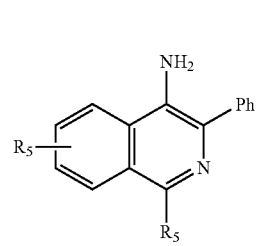

Scheme 10
(This scheme was described in WO2007/53346 A1)

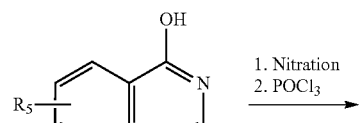

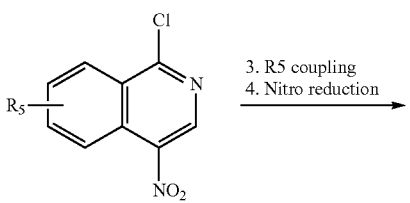

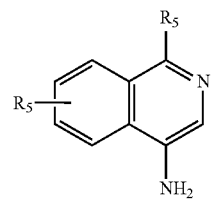

Scheme 11
(Part of the scheme was described in *Org. Lett.* 2009, 11, 2469-2472)

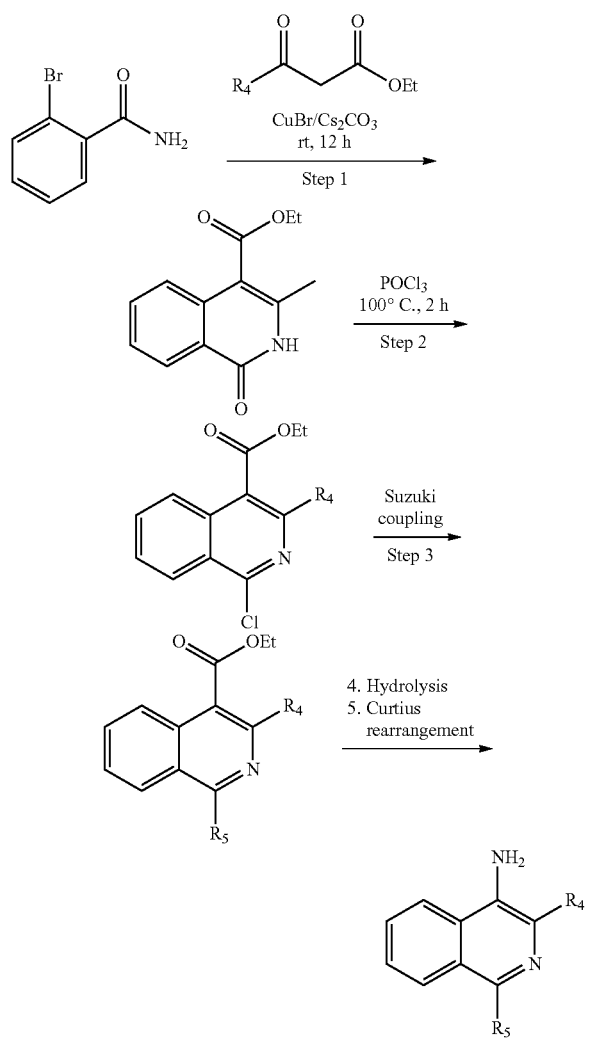

Analytical Data for I1-I30

Intermediate I1: 7-Fluoro-1-methyl-3-phenylisoquinolin-4-amine. LCMS: (M+H)=253.10.

Intermediate I2: 1-(1-Methyl-1H-pyrazol-4-yl)-3-phenylisoquinolin-4-amine. LCMS (M+H): 301.34.

Intermediate I3: 7-Methoxy-1-methyl-3-phenylisoquinolin-4-amine. LCMS: (M+H)=265.31.

Intermediate I4: 1-Methyl-3-phenylisoquinolin-4-amine. LCMS: (M+H): 235.09.

Intermediate I5: 1,7-Dimethyl-3-phenylisoquinolin-4-amine. LCMS: (M+H): 249.41.

Intermediate I6: 3-Phenyl-1-(pyridin-3-yl)isoquinolin-4-amine. LCMS: (M+H): 298.41.

Intermediate I7: 8-Methoxy-1-methyl-3-phenylisoquinolin-4-amine. LCMS: (M+H): 265.08.

Intermediate I8: 1,3-Diphenylisoquinolin-4-amine

Intermediate I9: 6-Methoxy-1-methyl-3-phenylisoquinolin-4-amine. LCMS: (M+H): 265.25.

Intermediate I10: 1,6-Dimethyl-3-phenylisoquinolin-4-amine. LCMS: (M+H): 249.23.

Intermediate I11: 6,7-Dimethoxy-1-methyl-3-phenylisoquinolin-4-amine. LCMS: (M+H): 295.39.

Intermediate I12: 6-Fluoro-1-methyl-3-phenylisoquinolin-4-amine. LCMS: (M+H)=295.39.

Intermediate I13: 1-Chloro-3-phenylisoquinolin-4-amine. ESI-MS m/z: 255.34 (M+H)⁺.

Intermediate I14: 5-Methoxy-3-phenylisoquinolin-4-amine. LCMS: (M+H): 251.07.

Intermediate I15: 8-Fluoro-3-phenylisoquinolin-4-amine. LCMS: (M+H): 239.09.

Intermediate I16: 7-Fluoro-3-phenylisoquinolin-4-amine. LCMS: (M+H)=239.07.

Intermediate I17: 1-(1-Methyl-1H-pyrazol-4-yl)isoquinolin-4-amine. LCMS: (M+H)=225.28.

Intermediate I18: 3-Methyl-1-(1-methyl-1H-pyrazol-4-yl)isoquinolin-4-amine. ESI-MS m/z: 239.36 (M+H)⁺.

Intermediate I19: 3-Phenylisoquinolin-4-amine. ESI-MS m/z: 221.08 (M+H)⁺.

Intermediate I20: 3-Methylisoquinolin-4-amine. ESI-MS m/z: 159.24 (M+H)⁺.

Scheme 12
(Part of the scheme was described in *Heterocycles*, 2000, 52, 1371-1383)

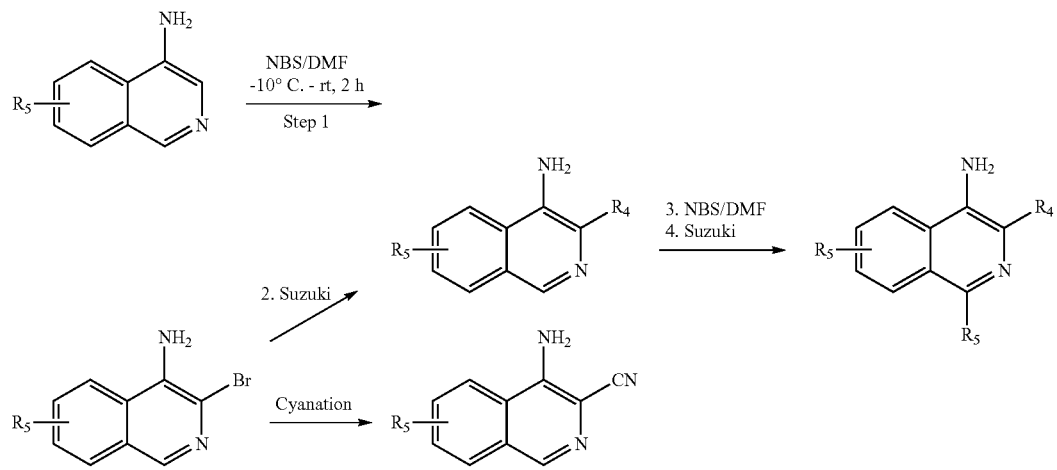

Intermediate I21: 4-Aminoisoquinoline-3-carbonitrile. ESI-MS m/z: 170.05 (M+H)+.

Intermediate I22: 3-(3-Fluorophenyl)-1-methylisoquinolin-4-amine. LC-MS (M+H)+:253.23.

Intermediate I23: 3-(2-Fluorophenyl)-1-methylisoquinolin-4-amine. LC-MS (M+H): 253.32.

Intermediate I24: 1-Methoxy-3-phenylisoquinolin-4-amine. LCMS: (M+H): 251.03

Intermediate I25: tert-Butyl (4-amino-3-phenylisoquinolin-1-yl)carbamate. LCMS: (M+H): 336.24.

Intermediate I26: 1-Fluoro-3-phenylisoquinolin-4-amine. ESI-MS m/z: 239.29 (M+H)+.

Intermediate I27: 4-Amino-3-phenylisoquinoline-1-carbonitrile. ESI-MS m/z: 246.21 (M+H)+.

Intermediate I28: 1-Morpholino-3-phenylisoquinolin-4-amine. LCMS: (M+H)=306.42.

Intermediate I29: 1-(4-Amino-3-phenylisoquinolin-1-yl)piperidin-4-ol. LCMS: (M+H)=320.26.

Intermediate I30: Methyl 4-amino-7-fluoro-3-phenylisoquinoline-1-carboxylate. LCMS: (M+H)=296.94.

Intermediate B: Pyrrolidin-3-amines (B1-B21)

Substituted pyrrolidin-3-amine intermediates were synthesized by using appropriate starting materials based on the reported literature methods (WO2012/125668, WO2014/078378, *Expert Opin. Ther. Patents*, 2014, 24(7), 731-744, *J. Med. Chem.* 2012, 55, 8903-8925, WO2011/147951, *J. Chem. Soc., Chem. Commun.* 1985, 1566-1567 and *Journal of Organic Chemistry*, 1992, 57, 4404-4414). Herein intermediates B1-B21 were used for synthesis of examples described in Formula I.

Intermediate B1: (3S,4R)-1-(2-Methoxyethyl)-4-phenylpyrrolidin-3-amine. LCMS (M+H): 221.10.

Intermediate B2: (3S,4R)-4-(3,4-Difluorophenyl)-1-(2-methoxyethyl)pyrrolidin-3-amine. HCl. LCMS-(MH): 257.20.

Intermediate B3: (3S,4R)-4-(3-Fluorophenyl)-1-(2-methoxyethyl)pyrrolidin-3-amine.HCl. LCMS (M+H): 239.40.

Intermediate B4: 3-((3R,4S)-4-amino-1-(2-methoxyethyl)pyrrolidin-3-yl)benzonitrile.HCl. LCMS (M+H): 245.98.

Intermediate B5: (3S,4R)-1-(2-Methoxyethyl)-4-(pyridin-3-yl)pyrrolidin-3-amine.HCl. LCMS (M+H): 221.98.

Intermediate B6: (3S,4R)-1-(2-Methoxyethyl)-4-(1-methyl-1H-pyrazol-4-yl)pyrrolidin-3-amine.HCl. LCMS (M+H): 225.20.

Intermediate B7: (3S,4R)-4-(tert-butyl)-1-(2-methoxyethyl)pyrrolidin-3-amine.HCl. LCMS (M+H): 201.41

Intermediate B8: Methyl 2-((3S,4R)-3-amino-4-phenylpyrrolidin-1-yl)acetate. LCMS (M+H)+: 235.19.

Intermediate B9: Methyl 2-((3R,4S)-3-Amino-4-phenylpyrrolidin-1-yl)acetate hydrochloride.

Intermediate B10: (3R,4S)-1-(2-methoxyethyl)-4-phenylpyrrolidin-3-amine hydrochloride. ¹HNMR (CD₃OD, 300 MHz): δ 7.48-7.39 (m, 5H), 4.29-4.24 (m, 1H), 4.08-4.05 (m, 2H), 3.78-3.75 (m, 2H), 3.65-3.59 (m, 4H), 3.58 (m, 1H), 3.43 (s, 3H).

Intermediate B11: (3S,4R)-1-(2-Fluoroethyl)-4-phenylpyrrolidin-3-amine hydrochloride. LCMS (M+H): 209.10.

Intermediate B12: (3R,4S)-1-(2-Fluoroethyl)-4-phenylpyrrolidin-3-amine hydrochloride. LCMS (M+H): 209.10.

Intermediate B13: 2-((3S,4R)-3-Amino-4-phenylpyrrolidin-1-yl)acetonitrile hydrochloride. LCMS (M+H): 202.31.

Intermediate B14: 2-((3S,4R)-3-Amino-4-phenylpyrrolidin-1-yl)acetamide hydrochloride. LCMS (M+H): 220.00.

Intermediate B15: (3S,4R)-4-phenyl-1-(2,2,2-trifluoroethyl) pyrrolidin-3-amine hydrochloride. LCMS (M+H)+: 244.92.

Intermediate B16: (3R,4S)-4-Phenyl-1-(2,2,2-trifluoroethyl) pyrrolidin-3-amine hydrochloride. LCMS (M+H): 245.43.

Intermediate B17: (3S,4R)-1-(2,2-Difluoroethyl)-4-phenylpyrrolidin-3-amine hydrochloride. LCMS (M+H): 227.34.

Intermediate B18: 1-((3S,4R)-3-amino-4-phenylpyrrolidin-1-yl)-2-methoxyethan-1-one hydrochloride. LCMS (M+H): 235.33.

Intermediate B19: (3S,4R)-1-(Oxetan-3-yl)-4-phenylpyrrolidin-3-amine hydrochloride. ¹HNMR (DMSO-d₆, 300 MHz): δ 8.22 (br s, 2H), 7.42-7.31 (m, 5H), 4.67-4.64 (m, 2H), 4.57-4.51 (m, 2H), 4.02 (m, 1H), 3.92-3.74 (m, 2H), 3.41-3.34 (m, 2H), 3.28-2.96 (m, 2H).

Intermediate B20: 3-Amino-1-(2-methoxyethyl)-4-phenylpyrrolidin-2-one.

Intermediate B21: 4-Amino-1-(2-methoxyethyl)-3-phenylpyrrolidin-3-ol dihydrochloride. LCMS: (M+1)= 237.17.

The present invention will now be illustrated in greater detail with reference to Examples, but the present invention should not be interpreted as being restricted thereto.

Preparation of Examples 1-202

Example 1: 1-((3S,4R)-1-(2-methoxyethyl)-4-phenylpyrrolidin-3-yl)-3-(quinolin-3-yl)urea This compound was synthesized using method 3 as mentioned in the general scheme.

To a solution of (3S,4R)-1-(2-methoxyethyl)-4-phenylpyrrolidine-3-carboxylic acid (0.15 g, 0.6 mmol) in toluene (10 mL) was added diphenylphosphoryl azide (0.24 g, 0.96 mmol), diisopropylethylamine (0.32 mL, 1.80 mmol) and the resulting mixture was heated to reflux temperature for 1 h. The reaction mixture was then cooled to room temperature followed by 3-aminoquinoline (Intermediate A1) (0.1 g, 0.72 mmol) was added and it was heated to reflux for 24 h. The reaction mixture was allowed to cool to room temperature and concentrated under reduced pressure. The residue thus obtained was diluted with 10% MeOH/dichloromethane, washed with water (10 mL), brine (10 mL), dried over anhydrous sodium sulphate, filtered and concentrated under reduced pressure. The crude product was purified by flash column chromatography by eluting with 2% MeOH/dichloromethane to afford the desired product as a pale brown gummy material. Yield: 0.035 g (6%); (¹HNMR CDCl₃, 300 M Hz): δ 8.69 (br s, 1H), 8.59 (br s, 1H), 8.01 (d, J=8.4 Hz, 1H), 7.75 (d, J=8.0 Hz, 1H), 7.56 (t, J=7.6 Hz, 1H), 7.48 (t, J=7.6 Hz, 1H), 7.35-7.31 (m, 2H), 7.28-7.24 (m, 3H), 4.22-4.13 (m, 1H), 3.58 (m, 3H), 3.50-3.45 (m, 1H), 3.33 (s, 3H), 3.28-3.26 (m, 1H), 2.92-2.84 (m, 2H), 2.79-2.75 (m, 1H), 2.46 (t, J=9.0 Hz, 1H); LCMS (M+H): 391.20.

Example 2: 1-((3S,4R)-1-(2-methoxyethyl)-4-phenylpyrrolidin-3-yl)-3-(2-phenylquinolin-3-yl)urea This compound was prepared according to the above mentioned protocol using the intermediate A6 and (3S,4R)-1-(2-methoxyethyl)-4-phenylpyrrolidine-3-carboxylic acid. ¹HNMR (CD₃OD, 300 M Hz): δ 8.64 (s, 1H), 7.98 (d, J=8.4 Hz, 1H), 7.87 (d, J=7.8 Hz, 1H), 7.68-7.52 (m, 7H), 7.33-7.24 (m, 5H), 4.30-4.26 (m, 1H), 3.56 (t, J=5.1 Hz, 2H), 3.35 (s, 3H), 3.19-3.16 (m, 3H), 2.90-2.66 (m, 4H); LCMS (M+H): 467.4.

Example 3: 1-((3S,4R)-1-(2-methoxyethyl)-4-phenylpyrrolidin-3-yl)-3-(2-methylquinolin-3-yl)urea This compound was synthesized using method 1 as mentioned in the general scheme.

Step 1: Preparation of phenyl 2-methylquinolin-3-ylcarbamate: To a solution of 2-methylquinolin-3-amine (Intermediate A7) (0.05 g, 0.31 mmol) and pyridine (0.076 mL, 0.94 mmol) in THF (5 mL) at 0° C. was added phenylchloroformate (0.076 g, 0.47 mmol) drop-wise, and the resulting mixture was stirred at room temperature for 2 h. Ice-cold water was added to the reaction mixture and it was extracted with ethyl acetate (2×25 mL). The combined organic layers were washed with water (10 mL), brine (10 mL) and dried over sodium sulphate. The organic layer was filtered and concentrated under reduced pressure to afford the title compound as a pale brown solid. Yield: 0.24 g (29%); LCMS (M+H): 278.91.

Step 2: Preparation of 1-((3S,4R)-1-(2-methoxyethyl)-4-phenylpyrrolidin-3-yl)-3-(2-methylquinolin-3-yl)urea: To a solution of (3S,4R)-1-(2-methoxyethyl)-4-phenylpyrrolidin-3-amine dihydrochloride (0.18 g, 0.64 mmol) and diisopropylethylamine (0.32 mL, 1.92 mmol) in DMF (5 mL) was added phenyl 2-methylquinolin-3-ylcarbamate (0.18 g. 0.64 mmol) slowly at 0° C., and the resulting mixture was stirred at room temperature for 12 h. The reaction mixture was diluted with water (10 mL) and extracted with ethyl acetate (25 mL). The extracts were washed with water (10 mL), brine (10 mL) and dried over sodium sulphate. The organic layer was filtered, concentrated under reduced pressure and the residue was purified by flash column chromatography eluting with 2% MeOH/CHCl$_3$ to afford the title compound as an off-white solid. Yield: 0.045 g (10%); $^1$HNMR (CD$_3$OD, 400 MHz): δ 8.51 (s, 1H), 7.90 (d, J=8.4 Hz, 1H), 7.80 (d, J=7.6 Hz, 1H), 7.62 (dt, J=0.8 Hz and 6.8 Hz, 1H), 7.51 (t, J=6.8 Hz, 1H), 7.43-7.33 (m, 4H), 7.26 (t, J=7.2 Hz, 1H), 4.45-4.40 (m, 1H), 3.59 (t, J=5.6 Hz, 2H), 3.37 (s, 3H), 3.36-3.34 (m, 1H), 3.33-3.23 (m, 1H), 3.13-2.97 (m, 1H), 2.96-2.94 (m, 1H), 2.88-2.77 (m, 2H), 2.70-2.68 (m, 1H), 2.65 (s, 3H), LCMS (M+H): 404.87.

The following examples were prepared according to the above mentioned procedure by using appropriate intermediates.

Example 4: 1-(2-Ethylquinolin-3-yl)-3-((3S,4R)-1-(2-methoxyethyl)-4-phenylpyrrolidin-3-yl)urea $^1$H NMR(CD$_3$OD, 400 MHz): δ 8.45 (s, 1H), 7.91 (d, J=8.0 Hz, 1H), 7.77 (d, J=8.4 Hz, 1H), 7.60 (dt, J=1.2 Hz and 8.4 Hz, 1H), 7.48 (t, J=7.2 Hz, 1H), 7.37-7.32 (m, 4H), 7.30-7.23 (m, 1H), 4.41-4.39 (m, 1H), 3.57 (t, J=5.2 Hz, 2H), 3.35 (s, 3H), 3.26-3.21 (m, 1H), 3.11-3.07 (m, 1H), 2.99-2.91 (m, 3H), 2.83-2.76 (m, 3H), 2.67-2.65 (m, 1H), 1.30 (t, J=8.0 Hz, 3H). LCMS (M+H): 419.22.

Example 5: 1-(2-Cyclopropylquinolin-3-yl)-3-((3S,4R)-1-(2-methoxyethyl)-4-phenylpyrrolidin-3-yl)urea $^1$H NMR(CD$_3$OD, 300 MHz): δ 8.38 (s, 1H), 7.83 (d, J=8.4 Hz, 1H), 7.72 (d, J=7.2 Hz, 1H), 7.56-7.51 (m, 1H), 7.44-7.29 (m, 5H), 7.25-7.22 (m, 1H), 4.43-4.38 (m, 1H), 3.56 (t, J=5.4 Hz, 2H), 3.35 (s, 3H), 3.23-3.08 (m, 1H), 3.08-3.05 (m, 1H), 2.93-2.88 (m, 1H), 2.83-2.71 (m, 3H), 2.65-2.59 (m, 1H), 2.23-2.18 (m, 1H), 1.15-1.09 (m, 2H), 1.07-1.01 (m, 2H). LCMS (M+H): 431.0.

Example 6: 1-(2-(Trifluoromethyl)quinolin-3-yl)-3-((3S,4R)-1-(2-methoxyethyl)-4-phenylpyrrolidin-3-yl)urea $^1$H NMR (DMSO-d$_6$, 400 MHz): δ 8.87 (s, 1H), 8.05-7.99 (m, 3H), 7.76-7.70 (m, 2H), 7.59 (d, J=7.6 Hz, 1H), 7.33-7.30 (m, 4H), 7.24-7.22 (m, 1H), 4.20-4.17 (m, 1H), 3.47 (t, J=5.6 Hz, 2H), 3.26 (s, 3H), 3.22-3.18 (m, 1H), 3.13-3.08 (m, 1H), 2.93-2.89 (m, 1H), 2.71-2.60 (m, 3H), 2.45-2.43 (m, 1H). LCMS (M+H): 459.2.

Example 7: 1-(6-Fluoro-2-phenylquinolin-3-yl)-3-((3S,4R)-1-(2-methoxyethyl)-4-phenylpyrrolidin-3-yl)urea $^1$H NMR (DMSO-d$_6$, 300 MHz): δ 8.81 (s, 1H), 7.96-7.91 (m, 1H), 7.73-7.70 (m, 1H), 7.69-7.65 (m, 1H), 7.60-7.53 (m, 5H), 7.50-7.44 (m, 1H), 7.39-7.36 (m, 1H), 7.34-7.31 (m, 4H), 7.23-7.20 (m, 1H), 4.18-4.15 (m, 1H), 3.43 (t, J=6.0 Hz, 2H), 3.23 (s, 3H), 3.17-3.11 (m, 1H), 3.05-3.00 (m, 1H), 2.88-2.82 (m, 1H), 2.62-2.59 (m, 3H), 2.43-2.37 (m, 1H). LCMS (M+H): 484.86.

Example 8: 1-(6-Fluoro-2-methylquinolin-3-yl)-3-((3S,4R)-1-(2-methoxyethyl)-4-phenylpyrrolidin-3-yl)urea $^1$H NMR (DMSO-d$_6$, 300 MHz): δ 8.62 (s, 1H), 8.32 (br s, 1H) 7.88-7.83 (m, 1H), 7.59-7.55 (m, 2H), 7.43-7.32 (m, 6H), 4.52-4.48 (m, 1H), 4.04-4.01 (m, 1H), 3.82-3.67 (m, 4H), 3.58-3.45 (m, 4H), 3.31 (s, 3H), 2.57 (s, 3H). LCMS (M+H): 423.25.

Example 9: 1-(5-Fluoro-2-methylquinolin-3-yl)-3-((3S,4R)-1-(2-methoxyethyl)-4-phenylpyrrolidin-3-yl)urea $^1$H NMR (CD$_3$OD, 400 MHz): δ 8.76 (s, 1H), 7.70 (d, J=8.8 Hz, 1H), 7.56-7.50 (m, 1H), 7.38-7.31 (m, 4H), 7.25-7.17 (m, 2H), 4.40-4.39 (m, 1H), 3.56 (t, J=6.0 Hz, 2H), 3.36 (s, 3H), 3.34-3.33 (m, 1H), 3.26-3.22 (m, 1H), 3.12-3.07 (m, 1H), 2.95-2.91 (m, 1H), 2.85-2.74 (m, 2H), 2.74-2.62 (m, 4H). LCMS (M+H): 423.33.

Example 10: 1-(8-Fluoro-2-methylquinolin-3-yl)-3-((3S,4R)-1-(2-methoxyethyl)-4-phenylpyrrolidin-3-yl)urea $^1$H NMR (DMSO-d$_6$, 300 MHz): δ 8.74 (s, 1H), 8.08 (br s, 1H), 7.59 (d, J=7.8 Hz, 1H), 7.43-7.23 (m, 8H), 4.25-4.18 (m, 1H), 3.58-3.40 (m, 2H), 3.34-3.33 (m, 1H), 3.26 (s, 3H), 3.18-3.04 (m, 2H), 2.90-2.86 (m, 2H), 2.74-2.70 (m, 2H), 2.61 (s, 3H). LCMS (M+H): 423.36.

Example 11: 1-(7-Fluoro-2-phenylquinolin-3-yl)-3-((3S,4R)-1-(2-methoxyethyl)-4-phenylpyrrolidin-3-yl)urea $^1$H NMR (CD$_3$OD, 400 MHz): δ 8.65 (s, 1H), 7.96-7.92 (m, 1H), 7.64-7.60 (m, 3H), 7.59-7.54 (m, 3H), 7.43 (dt, J=2.8 Hz and 8.8 Hz, 1H), 7.35-7.30 (m, 4H), 7.26-7.22 (m, 1H), 4.33-4.29 (m, 1H), 3.54 (t, J=5.6 Hz, 2H), 3.33 (s, 3H), 3.24-3.21 (m, 1H), 3.15-3.08 (m, 1H), 3.04-2.99 (m, 1H), 2.82-2.70 (m, 3H), 2.62-2.57 (m, 1H). LCMS (M+H): 484.80.

Example 12: 1-(7-Fluoro-2-methylquinolin-3-yl)-3-((3S,4R)-1-(2-methoxyethyl)-4-phenylpyrrolidin-3-yl)urea $^1$H NMR (CD$_3$OD, 300 MHz): δ 8.51 (br s, 1H), 7.85-7.81 (m, 1H), 7.53-7.35 (m, 7H), 4.59-4.52 (m, 1H), 4.08-3.65 (m, 5H), 3.64-3.56 (m, 2H), 3.44 (s, 3H), 3.38-3.35 (m, 1H), 3.30-3.18 (m, 1H), 2.61 (s, 3H). LCMS (M+H): 423.11.

Example 13: 1-((3S,4R)-1-(2-Methoxyethyl)-4-phenylpyrrolidin-3-yl)-3-(6-methoxy-2-phenylquinolin-3-yl)urea $^1$HNMR (CD$_3$OD, 300 MHz): δ 8.53 (s, 1H), 7.84 (d, J=9.3 Hz, 1H), 7.56-7.50 (m, 5H), 7.31-7.19 (m, 7H), 4.30-4.28 (m, 1H), 3.92 (s, 3H), 3.51 (t, J=5.7 Hz, 2H), 3.23-3.12 (m, 2H), 3.09-3.02 (m, 2H), 2.98-2.96 (m, 1H), 2.80-2.65 (m, 4H), 2.59-2.53 (m, 1H). LCMS (M+H): 496.83.

Example 14: 1-(7-Methoxy-2-phenylquinolin-3-yl)-3-((3S,4R)-1-(2-methoxyethyl)-4-phenylpyrrolidin-3-yl)urea $^1$H NMR (DMSO-d$_6$, 400 MHz): δ 8.60 (s, 1H), 7.79 (d, J=9.2 Hz, 1H), 7.64-7.60 (m, 3H), 7.55-7.50 (m, 3H), 7.33-7.28 (m, 5H), 7.23-7.13 (m, 3H), 4.15-4.10 (m, 1H), 3.87 (s, 3H), 3.43 (t, J=6.0 Hz, 2H), 3.23 (s, 3H), 3.14-3.10 (m, 1H), 3.04-2.98 (m, 1H), 2.85 (t, J=8.0 Hz, 1H), 2.67-2.55 (m, 3H), 2.44-2.40 (m, 1H). LCMS (M+H): 497.10.

Example 15: 1-(8-Methoxy-2-phenylquinolin-3-yl)-3-((3S,4R)-1-(2-methoxyethyl)-4-phenylpyrrolidin-3-yl)urea $^1$H NMR (DMSO-d$_6$, 300 MHz): δ 8.72 (s, 1H), 7.68 (br s, 1H), 7.56-7.54 (m, 4H), 7.45-7.21 (m, 9H), 7.03 (d, J=7.8 Hz, 1H), 4.23-4.14 (m, 1H), 3.91 (s, 3H), 3.49-3.34 (m, 2H), 3.24 (s, 3H), 3.14-3.13 (m, 1H), 3.03-3.00 (m, 2H), 2.62-2.60 (m, 3H), 2.49-2.48 (m, 1H). LCMS (M+H): 497.62.

Example 16: 1-(5-Methoxy-2-phenylquinolin-3-yl)-3-((3S,4R)-1-(2-methoxyethyl)-4-phenylpyrrolidin-3-yl)urea $^1$H NMR (CD$_3$OD, 300 MHz): δ 8.92 (s, 1H), 7.60-7.50 (m, 7H), 7.31-7.22 (m, 5H), 6.98 (dd, J=2.1 Hz and 6.6 Hz, 1H), 4.31-4.28 (m, 1H), 4.02 (s, 3H), 3.54-3.50 (m, 2H), 3.31 (s, 3H), 3.23-3.18 (m, 1H), 3.11-3.00 (m, 2H), 2.84-2.72 (m, 3H), 2.60-2.58 (m, 1H). LCMS (M+H): 497.55.

Example 17: 1-(5-Methoxy-2-methylquinolin-3-yl)-3-((3S,4R)-1-(2-methoxyethyl)-4-phenylpyrrolidin-3-yl)urea $^1$H NMR (CD$_3$OD, 300 MHz): δ 8.77 (s, 1H), 7.51-7.44 (m, 2H), 7.38-7.21 (m, 5H), 6.92 (d, J=6.9 Hz, 1H), 4.40-4.38 (m, 1H), 3.98 (s, 3H), 3.57 (t, J=5.4 Hz, 2H), 3.36 (s, 3H), 3.39-3.24 (m, 2H), 3.16-3.10 (m, 1H), 2.98-2.97 (m, 1H), 2.86-2.79 (m, 2H), 2.71-2.68 (m, 1H), 2.59 (s, 3H). LCMS (M+H): 435.39.

Example 18: 1-(6-Methoxy-2-methylquinolin-3-yl)-3-((3S,4R)-1-(2-methoxyethyl)-4-phenylpyrrolidin-3-yl)urea $^1$H NMR (CD$_3$OD, 400 MHz): δ 8.40 (s, 1H), 7.75 (d, J=9.2 Hz, 1H), 7.37-7.31 (m, 4H), 7.25-7.21 (m, 2H), 7.13 (d, J=2.4 Hz, 1H), 4.41-4.40 (m, 1H), 3.89 (s, 3H), 3.57 (t, J=6.0 Hz, 2H), 3.36 (s, 3H), 3.34-3.31 (m, 1H), 3.26-3.22 (m, 1H), 3.13-3.08 (m, 1H), 2.95-2.91 (m, 1H), 2.86-2.72 (m, 2H), 2.68-2.62 (m, 1H), 2.57 (s, 3H). LCMS (M+H): 435.35.

Example 19: 1-(7-Methoxy-2-methylquinolin-3-yl)-3-((3S,4R)-1-(2-methoxyethyl)-4-phenylpyrrolidin-3-yl)urea $^1$H NMR (CD$_3$OD, 400 MHz): δ 8.30 (s, 1H), 7.69 (d, J=9.6 Hz, 1H), 7.38-7.31 (m, 4H), 7.26-7.24 (m, 2H), 7.16 (dd, J=2.4 Hz and 8.8 Hz, 1H), 4.41-4.40 (m, 1H), 3.94 (s, 3H), 3.58 (t, J=5.6 Hz, 2H), 3.36 (s, 3H), 3.41-3.26 (m, 2H), 3.21-3.17 (m, 1H), 3.01-2.99 (m, 1H), 2.90-2.86 (m, 2H), 2.72-2.70 (m, 1H), 2.58 (s, 3H). LCMS (M+H): 435.39.

Example 20: 1-(8-Methoxy-2-methylquinolin-3-yl)-3-((3S,4R)-1-(2-methoxyethyl)-4-phenylpyrrolidin-3-yl)urea $^1$H NMR (CD$_3$OD, 300 MHz): δ 8.45 (s, 1H), 7.41-7.22 (m, 7H), 7.03 (d, J=7.2 Hz, 1H), 4.40-4.38 (m, 1H), 4.02 (s, 3H), 3.56 (t, J=5.7 Hz, 2H), 3.35 (s, 3H), 3.31-3.29 (m, 1H), 3.25-3.20 (m, 1H), 3.10-3.04 (m, 1H), 2.92-2.87 (m, 1H), 2.84-2.71 (m, 2H), 2.62 (s, 3H), 2.61-2.59 (m, 1H). LCMS (M+H): 435.12.

Example 21: 1-(6,7-Dimethoxy-2-phenylquinolin-3-yl)-3-((3S,4R)-1-(2-methoxyethyl)-4-phenylpyrrolidin-3-yl)urea $^1$H NMR (DMSO d$_6$, 300 MHz): δ 8.53 (s, 1H), 7.60-7.58 (m, 3H), 7.53-7.47 (m, 3H), 7.31-7.19 (m, 7H), 7.12 (d, J=7.8 Hz, 1H), 4.17-4.28 (m, 1H), 3.88 (s, 6H), 3.43 (t, J=6.0 Hz, 2H), 3.24 (s, 3H), 3.09 (t, J=8.1 Hz, 1H), 3.02 (q, J=6.9 Hz, 1H), 2.85 (t, J=7.8 Hz, 1H), 2.60-2.57 (m, 3H), 2.42 (t, J=8.4 Hz, 1H). LCMS (M+H): 527.72.

Example 22: 1-(6,7-Dimethoxy-2-methylquinolin-3-yl)-3-((3S,4R)-1-(2-methoxyethyl)-4-phenylpyrrolidin-3-yl)urea $^1$H NMR (CD$_3$OD, 300 MHz): δ 8.24 (s, 1H), 7.37-7.29 (m, 4H), 7.25-7.20 (m, 2H), 7.13 (s, 1H), 4.42-4.37 (m, 1H), 3.95 (s, 3H), 3.93 (s, 3H), 3.55 (t, J=5.4 Hz, 2H), 3.31 (s, 3H), 3.30-3.19 (m, 2H), 3.09-2.92 (m, 1H), 2.90-2.83 (m, 1H), 2.81-2.70 (m, 2H), 2.62 (t, J=9.0 Hz, 1H), 2.54 (s, 3H). LCMS (M+H): 464.91.

Example 23: 1-((3S,4R)-1-(2-Methoxyethyl)-4-phenylpyrrolidin-3-yl)-3-(6,7-dimethoxyquinolin-3-yl)urea $^1$H NMR (CD$_3$OD, 400 MHz): δ 8.51 (d, J=2.4 Hz, 1H), 8.22 (d, J=1.6 Hz, 1H), 7.37-7.30 (m, 4H), 7.25-7.23 (m, 2H), 7.15 (s, 1H), 4.43-4.37 (m, 1H), 3.95 (s, 6H), 3.58 (t, J=5.6 Hz, 2H), 3.40-3.37 (m, 4H), 3.31-3.24 (m, 1H), 3.11-3.09 (m, 1H), 2.97-2.95 (m, 1H), 2.87-2.80 (m, 2H), 2.68-2.65 (m, 1H). LCMS (M+H): 450.81.

Example 24: 1-((3S,4R)-1-(2-Methoxyethyl)-4-phenylpyrrolidin-3-yl)-3-(6-methyl-2-phenylquinolin-3-yl)urea $^1$HNMR (CD$_3$OD, 300 MHz): δ 8.53 (s, 1H), 7.86 (d, J=9.0 Hz, 1H), 7.63-7.48 (m, 7H), 7.35-7.22 (m, 5H), 4.31-4.28 (m, 1H), 3.53 (t, J=5.4 Hz, 2H), 3.32 (s, 3H), 3.23-2.98 (m, 3H), 2.82-2.71 (m, 3H), 2.61-2.58 (m, 1H), 2.53 (s, 3H). LCMS (M+H): 480.90.

Example 25: 1-(2,6-Dimethylquinolin-3-yl)-3-((3S,4R)-1-(2-methoxyethyl)-4-phenylpyrrolidin-3-yl)urea $^1$H NMR (CD$_3$OD, 400 MHz): δ 8.38 (s, 1H), 7.77 (d, J=8.4 Hz, 1H), 7.54 (s, 1H), 7.45-7.43 (m, 1H), 7.37-7.30 (m, 4H), 7.24-7.21 (m, 1H), 4.42-4.37 (m, 1H), 3.56 (t, J=5.6 Hz, 2H), 3.35 (s, 3H), 3.24-3.18 (m, 2H), 3.09-3.04 (m, 1H), 2.90-2.88 (m, 1H), 2.84-2.70 (m, 2H), 2.64-2.62 (m, 1H), 2.59 (s, 3H), 2.48 (s, 3H). LCMS (M+H): 419.33.

Example 26: 1-(2,7-Dimethylquinolin-3-yl)-3-((3S,4R)-1-(2-methoxyethyl)-4-phenylpyrrolidin-3-yl)urea $^1$H NMR (CD$_3$OD, 300 MHz): δ 8.38 (s, 1H), 7.68-7.65 (m, 2H), 7.38-7.30 (m, 5H), 7.26-7.21 (m, 1H), 4.43-4.36 (m, 1H), 3.57 (t, J=5.4 Hz, 2H), 3.38-3.31 (m, 1H), 3.36 (s, 3H), 3.25-3.20 (m, 1H), 3.15-3.09 (m, 1H), 2.97-2.92 (m, 1H), 2.90-2.74 (m, 2H), 2.70-2.64 (m, 1H), 2.59 (s, 3H), 2.51 (s, 3H). LCMS (M+H): 419.37.

Example 27: 1-(2,5-Dimethylquinolin-3-yl)-3-((3S,4R)-1-(2-methoxyethyl)-4-phenylpyrrolidin-3-yl)urea $^1$H NMR (CD$_3$OD, 400 MHz): δ 8.68 (s, 1H), 7.73 (d, J=8.8 Hz, 1H), 7.47 (t, J=8.4 Hz, 1H), 7.38-7.29 (m, 5H), 7.25-7.21 (m, 1H), 4.40-4.38 (m, 1H), 3.56 (t, J=5.2 Hz, 2H), 3.36 (s, 3H), 3.35-3.33 (m, 1H), 3.26-3.20 (m, 1H), 3.11-3.07 (m, 1H), 2.94-2.90 (m, 1H), 2.85-2.72 (m, 2H), 2.66-2.64 (m, 1H), 2.62 (s, 6H). LCMS (M+H): 419.33.

Example 28: 1-(2,8-Dimethylquinolin-3-yl)-3-((3S,4R)-1-(2-methoxyethyl)-4-phenylpyrrolidin-3-yl)urea $^1$H NMR (DMSO-d$_6$, 300 MHz): δ 8.62 (s, 1H), 7.97 (br s, 1H), 7.58 (d, J=7.8 Hz, 1H), 7.38-7.20 (m, 8H), 4.22-4.18 (m, 1H), 3.47 (t, J=5.7 Hz, 2H), 3.26 (s, 3H), 3.22-3.19 (m, 1H), 3.14-3.09 (m, 1H), 2.94-2.88 (m, 1H), 2.75-2.67 (m, 3H), 2.64 (s, 3H), 2.60 (s, 3H), 2.44-2.42 (m, 1H). LCMS (M+H): 419.37.

Example 29: 1-((3S,4R)-1-(2-Methoxyethyl)-4-phenylpyrrolidin-3-yl)-3-(7-methyl-2-phenylquinolin-3-yl)urea $^1$H NMR (DMSO-d$_6$, 300 MHz): δ 8.66 (s, 1H), 7.76 (d, J=8.7 Hz, 1H), 7.69-7.59 (m, 2H), 7.54-7.52 (m, 5H), 7.38-7.21 (m, 7H), 4.15-4.10 (m, 1H), 3.43 (t, J=6.0 Hz, 2H), 3.23 (s, 3H), 3.13-3.10 (m, 1H), 3.02-3.00 (m, 1H), 2.85-2.84 (m, 1H), 2.60-2.59 (m, 3H), 2.50 (s, 3H), 2.44-2.39 (m, 1H). LCMS (M+H): 480.83.

Example 30: 1-(2-Chloroquinolin-3-yl)-3-((3S,4R)-1-(2-methoxyethyl)-4-phenylpyrrolidin-3-yl)urea $^1$HNMR (CD$_3$OD 300 MHz): δ 8.81 (s, 1H), 7.84-7.79 (m, 2H), 7.65-7.51 (m, 2H), 7.38-7.29 (m, 4H), 7.25-7.22 (m, 1H), 4.39-4.38 (m, 1H), 3.56 (t, J=5.4 Hz, 2H), 3.34 (s, 3H), 3.30-3.20 (m, 1H), 3.13-3.08 (m, 1H), 2.92-2.74 (m, 4H), 2.69-2.63 (m, 1H). LCMS (M+H): 425.30.

Example 31: 1-((3S,4R)-1-(2-Methoxyethyl)-4-phenylpyrrolidin-3-yl)-3-(2-(1-methyl-1H-pyrazol-4-yl)quinolin-3-yl)urea $^1$HNMR (CD$_3$OD, 300 MHz): δ 8.38 (s, 1H), 8.08 (s, 1H), 8.00 (s, 1H), 7.96 (d, J=8.4 Hz, 1H), 7.83 (d, J=8.4 Hz, 1H), 7.68-7.62 (m, 1H), 7.53-7.49 (m, 1H), 7.32-7.31 (m, 4H), 7.25-7.22 (m, 1H), 4.42-4.35 (m, 1H), 3.94 (s, 3H), 3.54 (t, J=5.4 Hz, 2H), 3.34 (s, 3H), 3.31-3.30 (m, 1H), 3.23-3.13 (m, 1H), 3.07-3.01 (m, 1H), 2.89-2.84 (m, 1H), 2.80-2.75 (m, 2H), 2.63-2.57 (m, 1H). LCMS (M+H): 470.82.

Example 32: 1-((3S,4R)-1-(2-Methoxyethyl)-4-phenylpyrrolidin-3-yl)-3-(2-(pyridin-3-yl)quinolin-3-yl)urea $^1$H NMR (CD$_3$OD, 300 MHz): δ 8.83 (s, 1H), 8.64 (d, J=5.1 Hz, 1H), 8.53 (s, 1H), 8.12-8.09 (m, 1H), 8.03 (d, J=8.4 Hz, 1H), 7.90 (d, J=7.8 Hz, 1H), 7.72-7.67 (m, 1H), 7.62-7.53 (m, 2H), 7.34-7.22 (m, 5H), 4.28-4.26 (m, 1H), 3.52 (t, J=5.4 Hz, 2H), 3.32 (s, 3H), 3.24-3.21 (m, 1H), 3.11-3.08 (m, 1H), 2.96-2.95 (m, 1H), 2.80-2.71 (m, 3H), 2.56-2.55 (m, 1H). LCMS (M+H): 467.87.

Example 33: 1-((3S,4R)-1-(2-Methoxyethyl)-4-phenylpyrrolidin-3-yl)-3-(2-(pyridin-4-yl)quinolin-3-yl)urea $^1$H NMR (CD$_3$OD, 300 MHz): δ 8.67-8.65 (m, 2H), 8.53 (s, 1H), 8.03 (d, J=8.4 Hz, 1H), 7.91 (d, J=8.1 Hz, 1H), 7.74-7.69 (m, 3H), 7.64-7.59 (m, 1H), 7.36-7.23 (m, 5H), 4.30-4.29 (m, 1H), 3.56 (t, J=5.4 Hz, 2H), 3.38-3.37 (m, 1H), 3.35 (s, 3H), 3.24-3.16 (m, 2H), 2.91-2.90 (m, 3H), 2.75-2.74 (m, 1H). LCMS (M−H): 465.85.

Example 34: 1-((3S,4R)-1-(2-Methoxyethyl)-4-phenylpyrrolidin-3-yl)-3-(2-(pyrimidin-5-yl)quinolin-3-yl)urea $^1$H NMR (CD$_3$OD, 400 MHz): δ 9.22 (s, 1H), 9.11 (s, 2H), 8.44 (s, 1H), 8.05 (d, J=8.8 Hz, 1H), 7.92 (d, J=8.4 Hz, 1H), 7.74-7.71 (m, 1H), 7.64-7.60 (m, 1H), 7.32-7.21 (m, 5H), 4.32-4.29 (m, 1H), 3.53 (t, J=5.2 Hz, 2H), 3.32 (s, 3H), 3.12-3.10 (m, 1H), 2.93-2.91 (m, 1H), 2.76-2.75 (m, 4H), 2.55-2.54 (m, 1H). LCMS (M+H): 469.60.

Example 35: 1-((3S,4R)-1-(2-Methoxyethyl)-4-phenylpyrrolidin-3-yl)-3-(2-morpholinoquinolin-3-yl)urea $^1$H NMR (CD$_3$OD, 300 MHz): δ 8.48 (s, 1H), 7.80 (d, J=8.4 Hz, 1H), 7.68 (d, J=8.4 Hz, 1H), 7.53-7.47 (m, 1H), 7.40-7.29 (m, 5H), 7.25-7.22 (m, 1H), 4.41-4.40 (m, 1H), 3.90 (t, J=4.8 Hz, 4H), 3.56 (t, J=5.7 Hz, 2H), 3.36 (s, 3H), 3.22-3.16 (m, 5H), 3.12-3.06 (m, 1H), 2.90-2.71 (m, 4H), 2.67-2.61 (m, 1H). LCMS (M+H): 476.21.

Example 36: 1-((3S,4R)-1-(2-Methoxyethyl)-4-phenylpyrrolidin-3-yl)-3-(quinolin-4-yl)urea $^1$H NMR (DMSO-d$_6$, 300 MHz): δ 8.98 (s, 1H), 8.62 (d, J=5.1 Hz, 1H), 8.16-8.13 (m, 2H), 7.94 (d, J=8.1 Hz, 1H), 7.72 (t, J=7.2 Hz, 1H), 7.61 (t, J=7.8 Hz, 1H), 7.39-7.23 (m, 6H), 4.25-4.23 (m, 1H), 3.49-3.47 (m, 2H), 3.31-3.28 (m, 1H), 3.26 (s, 3H), 3.15-3.12 (m, 2H), 2.93-2.91 (m, 1H), 2.72-2.69 (m, 3H). LCMS (M+H): 391.10.

Example 37: 1-((3S,4R)-1-(2-Methoxyethyl)-4-phenylpyrrolidin-3-yl)-3-(quinazolin-4-yl)urea ¹H NMR (CD₃OD, 400 MHz): δ 8.80 (s, 1H), 8.36 (d, J=8.0 Hz, 1H), 7.95-7.87 (m, 2H), 7.69-7.65 (m, 1H), 7.45-7.38 (m, 2H), 7.32-7.29 (m, 2H), 7.23-7.17 (m, 1H), 4.85-4.52 (m, 1H), 3.60-3.58 (m, 2H), 3.46-3.37 (m, 2H), 3.30 (s, 3H), 3.18-3.13 (m, 1H), 3.08-3.04 (m, 1H), 2.92-2.71 (m, 3H). LCMS (M+H): 391.84.

Example 38: 1-(2-Chloro-6,7-dimethoxyquinazolin-4-yl)-3-((3S,4R)-1-(2-methoxyethyl)-4-phenylpyrrolidin-3-yl)urea ¹H NMR (CD₃OD, 300 MHz): δ 7.71 (s, 1H), 7.42-7.40 (m, 2H), 7.34-7.29 (m, 2H), 7.24-7.22 (m, 1H), 7.15 (s, 1H), 4.41-4.39 (m, 1H), 3.99 (s, 3H), 3.97 (s, 3H) 3.58 (t, J=5.7 Hz, 2H), 3.36 (s, 3H), 3.34-3.30 (m, 2H), 3.22-3.16 (m, 1H), 3.02-2.98 (m, 1H), 2.85-2.76 (m, 3H). LCMS (M+H): 485.81.

Example 39: 1-((3S,4R)-1-(2-Methoxyethyl)-4-phenylpyrrolidin-3-yl)-3-(quinoxalin-2-yl)urea ¹H NMR: (DMSO-d₆, 300 MHz): δ 10.05 (s, 1H), 9.07 (d, J=6.9 Hz, 1H), 8.85 (s, 1H), 7.96 (d, J=8.4 Hz, 1H), 7.88 (d, J=8.4 Hz, 1H), 7.80-7.74 (m, 1H), 7.65-7.59 (m, 1H), 7.39-7.29 (m, 4H), 7.24-7.21 (m, 1H), 4.27-4.25 (m, 1H), 3.49 (t, J=5.4 Hz, 2H), 3.31 (s, 3H), 3.27-3.25 (m, 2H) 2.99-2.98 (m, 1H), 2.80-2.69 (m, 3H), 2.50-2.49 (m, 1H). LCMS (M+H): 392.20.

Example 40: 1-(2-Isopropylquinolin-3-yl)-3-((3S,4R)-1-(2-methoxyethyl)-4-phenylpyrrolidin-3-yl)urea ¹H NMR: (CDCl₃, 400 MHz): δ 8.31 (s, 1H), 8.01 (d, J=8.4 Hz, 1H), 7.72 (d, J=8.4 Hz, 1H), 7.62-7.57 (m, 1H), 7.46-7.43 (m, 1H), 7.35-7.23 (m, 5H), 5.25 (br s, 1H), 4.43-4.34 (m, 1H), 3.51-3.48 (m, 2H), 3.47-3.44 (m, 1H), 3.34-3.29 (m, 2H), 3.26 (s, 3H), 3.14-3.12 (m, 1H), 2.91-2.87 (m, 1H), 2.81-2.79 (m, 1H), 2.71-2.70 (m, 1H), 2.49-2.47 (m, 1H), 1.35 (d, J=2.0 Hz, 3H), 1.33 (d, J=1.6 Hz, 3H). LCMS (M+H): 433.14.

Example 41: 1-(2-tert-Butylquinolin-3-yl)-3-((3S,4R)-1-(2-methoxyethyl)-4-phenylpyrrolidin-3-yl)urea ¹H NMR: (CDCl₃, 300 MHz): δ 8.14 (s, 1H), 8.01 (d, J=8.7 Hz, 1H), 7.71-7.60 (m, 2H), 7.49-7.44 (m, 1H), 7.35-7.26 (m, 5H), 6.59 (br s, 1H), 4.58-4.50 (m, 1H), 3.58-3.52 (m, 3H), 3.37-3.31 (m, 1H), 3.31 (s, 3H), 3.23-3.19 (m, 1H), 3.04-3.02 (m, 1H), 2.82-2.79 (m, 2H), 2.63-2.59 (m, 1H), 1.50 (s, 9H). LCMS (M+H): 447.13.

Example 42: 1-(6-Methoxy-2-methyl-7-morpholinoquinolin-3-yl)-3-((3S,4R)-1-(2-methoxyethyl)-4-phenylpyrrolidin-3-yl)urea ¹H NMR: (CDCl₃, 300 MHz): δ 8.37 (s, 1H), 7.36-7.26 (m, 6H), 6.98 (s, 1H), 6.79 (brs, 1H), 4.49-4.42 (m, 1H), 3.95 (s, 3H), 3.92-3.91 (m, 4H), 3.73-3.70 (m, 3H), 3.67-3.59 (m, 2H), 3.58-3.49 (m, 1H), 3.35-3.34 (m, 1H), 3.30 (s, 3H), 3.20-3.19 (m, 4H), 3.04-2.91 (m, 3H), 2.74-2.68 (m, 1H), 2.61 (s, 3H). LCMS (M+H): 520.42.

Example 43: 1-(6-Fluoro-7-methyl-2-phenylquinolin-3-yl)-3-((3S,4R)-1-(2-methoxyethyl)-4-phenylpyrrolidin-3-yl)urea ¹H NMR (CDCl₃, 300 MHz): δ 8.76 (s, 1H), 7.86 (d, J=7.5 Hz, 1H), 7.63-7.60 (m, 2H), 7.56-7.48 (m, 3H), 7.35-7.26 (m, 4H), 7.23-7.22 (m, 2H), 5.16-5.10 (br m, 1H), 4.26-4.23 (m, 1H), 3.44-3.37 (m, 2H), 3.24 (s, 3H), 3.21-3.17 (m, 2H), 3.05-3.02 (m, 1H), 2.73-2.52 (m, 3H), 2.44 (s, 3H), 2.31-2.25 (m, 1H). LCMS (M+H): 499.44.

Example 44: 1-(6-Bromo-8-methoxy-2-phenylquinolin-3-yl)-3-((3S,4R)-1-(2-methoxyethyl)-4-phenylpyrrolidin-3-yl)urea ¹H NMR (CDCl₃, 400 MHz): δ 8.51 (s, 1H), 7.45 (d, J=1.2 Hz, 1H), 7.33-7.29 (m, 2H), 7.24-7.22 (m, 3H), 6.98 (d, J=2.0 Hz, 1H), 6.04 (br s, 1H) 4.34-4.31 (m, 1H), 4.01 (s, 3H), 3.53-3.46 (m, 3H), 3.30-3.20 (m, 5H), 2.90-2.84 (m, 2H), 2.74-2.68 (m, 1H), 2.63 (s, 3H), 2.49 (t, J=9.2 Hz, 1H). LCMS (M+H): 513.33.

Example 45: 1-(7-Fluoro-6-methoxy-2-phenylquinolin-3-yl)-3-((3S,4R)-1-(2-methoxyethyl)-4-phenylpyrrolidin-3-yl)urea ¹H NMR (CDCl₃, 400 MHz): δ 8.76 (s, 1H), 7.69-7.61 (m, 3H), 7.55-7.48 (m, 3H), 7.34-7.30 (m, 3H), 7.26-7.24 (m, 2H), 7.13 (d, J=8.8 Hz, 1H), 5.22 (br s, 1H), 4.26-4.20 (m, 1H), 3.99 (s, 3H), 3.44-3.40 (m, 2H), 3.24 (s, 3H), 3.21-3.17 (m, 2H), 3.08-3.04 (m, 1H), 2.79-2.52 (m, 3H), 2.32-2.28 (m, 1H). LCMS (M+H): 515.35.

Example 46: 1-(7-Fluoro-6-methoxy-2-methylquinolin-3-yl)-3-((3S,4R)-1-(2-methoxyethyl)-4-phenylpyrrolidin-3-yl)urea ¹H NMR (CD₃OD, 300 MHz): δ 8.41 (s, 1H), 7.49 (d, J=12.0 Hz, 1H), 7.37-7.23 (m, 6H), 4.42-4.38 (m, 1H), 3.97 (s, 3H), 3.56 (t, J=5.4 Hz, 2H), 3.36 (s, 3H), 3.24-3.21 (m, 2H), 3.09-2.94 (m, 1H), 2.94-2.72 (m, 4H), 2.57 (s, 3H). LCMS (M+H): 453.26.

Example 47: 1-(8-Methoxy-7-methyl-2-phenylquinolin-3-yl)-3-((3S,4R)-1-(2-methoxyethyl)-4-phenylpyrrolidin-3-yl)urea ¹H NMR (CDCl₃, 400 MHz): δ 8.73 (s, 1H), 7.70-7.68 (m, 2H), 7.54-7.43 (m, 4H), 7.33-7.29 (m, 3H), 7.23-7.21 (m, 3H), 5.09-5.07 (d, J=8.0 Hz, 1H), 4.26-4.20 (m, 1H), 4.11 (s, 3H), 3.41 (t, J=5.2 Hz, 2H), 3.24 (s, 3H), 3.21-3.17 (m, 2H), 3.03-3.00 (m, 1H), 2.73-2.62 (m, 2H), 2.57-2.53 (m, 1H), 2.45 (s, 3H), 2.28 (t, J=8.8 Hz, 1H). LCMS (M+H): 511.39.

Example 48: 1-(6-Methoxy-2,7-dimethylquinolin-3-yl)-3-((3S,4R)-1-(2-methoxyethyl)-4-phenylpyrrolidin-3-yl)urea ¹H NMR (CD₃OD, 300 MHz): δ 8.33 (s, 1H), 7.61 (s, 1H), 7.38-7.30 (m, 4H), 7.26-7.23 (m, 1H), 7.08 (s, 1H), 4.45-4.36 (m, 1H), 3.93 (s, 3H), 3.57 (t, J=5.4 Hz, 2H), 3.36

(s, 3H), 3.25-3.09 (m, 2H), 2.96-2.78 (m, 4H), 2.70-2.64 (m, 1H), 2.55 (s, 3H), 2.34 (s, 3H). LCMS (M+H): 449.26.

Example 49: 1-(7-Fluoro-6-methyl-2-phenylquinolin-3-yl)-3-((3S,4R)-1-(2-methoxyethyl)-4-phenylpyrrolidin-3-yl)urea $^1$H NMR (CDCl$_3$, 400 MHz): δ 8.73 (s, 1H), 7.64-7.61 (m, 3H), 7.58-7.46 (m, 4H), 7.33-7.30 (m, 2H), 7.24-7.22 (m, 3H), 5.06 (br s, 1H), 4.25-4.21 (m, 1H), 3.41-3.40 (m, 2H), 3.22 (s, 3H), 3.20-3.17 (m, 2H), 3.05-3.02 (m, 1H), 2.73-2.64 (m, 2H), 2.57-2.48 (m, 1H), 2.45 (s, 3H), 2.29-2.26 (m, 1H). LCMS (M+H): 499.33.

Example 50: 1-(7-Fluoro-2,6-dimethylquinolin-3-yl)-3-((3S,4R)-1-(2-methoxyethyl)-4-phenylpyrrolidin-3-yl)urea $^1$H NMR (DMSO-d6, 300 MHz): δ 8.62 (s, 1H), 7.97 (s, 1H), 7.71 (d, J=7.8 Hz, 1H), 7.51 (d, J=10.8 Hz, 1H), 7.34-7.20 (m, 6H), 4.22-4.16 (m, 1H), 3.47 (t, J=5.7 Hz, 2H), 3.25 (s, 3H), 3.21-3.18 (m, 1H), 3.13-3.09 (m, 1H), 2.93-2.87 (m, 1H), 2.72-2.59 (m, 3H), 2.55 (s, 3H), 2.44-2.41 (m, 1H), 2.37 (s, 3H). LCMS (M+H): 437.28.

Example 51: 1-((3S,4R)-1-(2-methoxyethyl)-4-phenylpyrrolidin-3-yl)-3-(6-phenyl-[1,3]dioxolo[4,5-g]quinolin-7-yl)urea $^1$H NMR (CDCl$_3$, 300 MHz): δ 8.61 (s, 1H), 7.63-7.60 (m, 2H), 7.54-7.45 (m, 3H), 7.34-7.29 (m, 3H), 7.27-7.22 (m, 3H), 7.04 (s, 1H), 6.08 (s, 2H), 5.07 (br s, 1H), 4.24-4.22 (m, 1H), 3.41 (t, J=5.4 Hz, 2H), 3.24 (s, 3H), 3.20-3.16 (m, 2H), 3.04-3.01 (m, 1H), 2.74-2.56 (m, 3H), 2.32-2.26 (m, 1H). LCMS (M+H): 511.39.

Example 52: 1-((3S,4R)-1-(2-Methoxyethyl)-4-phenylpyrrolidin-3-yl)-3-(6-methyl-[1,3]dioxolo[4,5-g]quinolin-7-yl)urea $^1$H NMR (CD$_3$OD, 300 MHz): δ 8.23 (s, 1H), 7.39-7.32 (m, 4H), 7.29-7.26 (m, 1H), 7.16 (s, 1H), 7.05 (s, 1H), 6.08 (s, 2H), 4.42-4.39 (m, 1H), 3.61 (t, J=5.4 Hz, 2H), 3.55-3.49 (m, 1H), 3.38 (s, 3H), 3.36-3.32 (m, 1H), 3.14-3.00 (m, 3H), 2.93-2.80 (m, 2H), 2.51 (s, 3H). LCMS (M+H): 449.36.

Example 53: 1-((3S,4R)-1-(2-Methoxyethyl)-4-phenylpyrrolidin-3-yl)-3-(7-methyl-2,3-dihydro-[1,4]dioxino[2,3-g]quinolin-8-yl)urea $^1$H NMR (CD$_3$OD, 400 MHz): δ 8.18 (s, 1H), 7.36-7.30 (m, 4H), 7.27-7.23 (m, 2H), 7.14 (s, 1H), 4.42-4.37 (m, 1H), 4.33 (s, 4H), 3.56 (t, J=5.6 Hz, 2H), 3.35 (s, 3H), 3.34-3.32 (m, 1H), 3.25-3.21 (m, 1H), 3.09-3.06 (m, 1H), 2.93-2.90 (m, 1H), 2.85-2.75 (m, 2H), 2.65 (t, J=9.6 Hz, 1H), 2.52 (s, 3H). LCMS M+H: 463.25.

Example 54: 1-((3S,4R)-1-(2-Methoxyethyl)-4-phenylpyrrolidin-3-yl)-3-(7-phenyl-2,3-dihydro-[1,4]dioxino[2,3-g]quinolin-8-yl)urea $^1$H NMR (CDCl$_3$, 400 MHz): δ 8.57 (s, 1H), 7.61-7.59 (m, 2H), 7.51-7.45 (m, 4H), 7.33-7.29 (m, 2H), 7.24-7.22 (m, 3H), 7.17 (s, 1H), 5.22 (br s, 1H), 4.36 (s, 4H), 4.26-4.22 (m, 1H), 3.42-3.36 (m, 2H), 3.24 (s, 3H), 3.19-3.16 (m, 2H), 3.04-3.01 (m, 1H), 2.75-2.65 (m, 2H), 2.59-2.56 (m, 1H), 2.32-2.28 (m, 1H). LCMS (M+H): 525.32.

Example 55: 1-(6-Amino-7-methoxy-2-phenylquinolin-3-yl)-3-((3S,4R)-1-(2-methoxyethyl)-4-phenylpyrrolidin-3-yl)urea $^1$H NMR (CDCl$_3$, 400 MHz): δ 8.46 (s, 1H), 7.61-7.59 (m, 2H), 7.52-7.48 (m, 3H), 7.45-7.43 (m, 2H), 7.35-7.23 (m, 4H), 6.88 (s, 1H), 4.56-4.49 (m, 1H), 4.19 (br s, 2H), 3.96 (s, 3H), 3.66-3.60 (m, 3H), 3.46-3.44 (m, 2H), 3.32 (s, 3H), 3.16-2.98 (m, 3H), 2.78-2.52 (m, 1H). LCMS (M+H): 512.32.

Example 56: 1-(7-Methoxy-6-(methylamino)-2-phenylquinolin-3-yl)-3-((3S,4R)-1-(2-methoxyethyl)-4-phenylpyrrolidin-3-yl)urea $^1$H NMR (CD$_3$OD, 400 MHz): δ 8.18 (s, 1H), 7.55-7.53 (m, 2H), 7.48-7.44 (m, 3H), 7.33-7.27 (m, 4H), 7.24-7.20 (m, 2H), 6.64 (s, 1H), 4.29-4.21 (m, 1H), 3.98 (s, 3H), 3.52 (t, J=5.6 Hz, 2H), 3.33 (s, 3H), 3.12-2.98 (m, 2H), 2.93 (s, 3H), 2.82-2.72 (m, 4H), 2.62-2.52 (m, 1H). LCMS (M+H): 526.37.

Example 57: N-(7-Methoxy-3-(3-((3S,4R)-1-(2-methoxyethyl)-4-phenylpyrrolidin-3-yl)ureido)-2-phenylquinolin-6-yl)acetamide $^1$H NMR (CDCl$_3$, 300 MHz): δ 8.78 (s, 1H), 8.61 (s, 1H), 7.99 (br s, 1H), 7.60-7.58 (m, 2H), 7.52-7.43 (m, 3H), 7.39 (s, 1H), 7.34-7.29 (m, 2H), 7.23-7.19 (m, 2H), 5.22 (br s, 1H), 4.29-4.21 (m, 1H), 4.00 (s, 3H), 3.42 (t, J=5.7 Hz, 2H), 3.24 (s, 3H), 3.21-3.17 (m, 2H), 3.04-3.02 (m, 1H), 2.75-2.58 (m, 3H), 2.32-2.28 (m, 1H), 2.26 (s, 3H). LCMS (M+H): 554.41.

Example 58: N-(7-Methoxy-3-(3-((3S,4R)-1-(2-methoxyethyl)-4-phenylpyrrolidin-3-yl)ureido)-2-methylquinolin-6-yl)acetamide $^1$H NMR (CD$_3$OD, 300 MHz): δ 8.71 (s, 1H), 8.34 (s, 1H), 7.38-7.31 (m, 4H), 7.27-7.20 (m, 1H), 7.19 (s, 1H), 4.44-4.39 (m, 1H), 4.01 (s, 3H), 3.58 (t, J=5.4 Hz, 2H), 3.37 (s, 3H), 3.24-3.13 (m, 2H), 3.00-2.84 (m, 3H), 2.72-2.54 (m, 2H), 2.54 (s, 3H), 2.23 (s, 3H). LCMS (M+H): 492.31.

Example 59: N-(6-Methoxy-3-(3-((3S,4R)-1-(2-methoxyethyl)-4-phenylpyrrolidin-3-yl)ureido)-2-phenylquinolin-7-yl)acetamide $^1$H NMR (CD$_3$OD, 400 MHz): δ 8.76 (s, 1H), 8.45 (s, 1H), 7.57-7.48 (m, 5H), 7.32-7.23 (m, 6H), 4.29-4.24 (m, 1H), 4.04 (s, 3H), 3.53 (t, J=4.8 Hz, 2H), 3.33 (s, 3H), 3.14-3.03 (m, 3H), 2.85-2.61 (m, 4H), 2.23 (s, 3H). LCMS (M+H): 554.30.

Example 60: N-(6-methoxy-3-(3-((3S,4R)-1-(2-methoxyethyl)-4-phenylpyrrolidin-3-yl)ureido)-2-methylquinolin-7-yl)acetamide $^1$H NMR (CD$_3$OD, 300 MHz): δ 8.71 (s, 1H), 8.33 (s, 1H), 7.39-7.30 (m, 4H), 7.26-7.19 (m, 2H), 4.45-4.38 (m, 1H), 4.00 (s, 3H), 3.58 (t, J=5.4 Hz, 2H), 3.36 (s, 3H), 3.24-3.13 (m, 3H), 3.00-2.82 (m, 3H), 2.72-2.54 (m, 1H), 2.54 (s, 3H), 2.23 (s, 3H). LCMS (M+H): 492.21.

Example 61: 1-(8-Methoxy-6-(1-Methyl-1H-pyrazol-4-yl)-2-phenylquinolin-3-yl)-3-((3S,4R)-1-(2-methoxyethyl)-4-phenylpyrrolidin-3-yl)urea $^1$H NMR (CDCl$_3$, 300 MHz): δ 8.51 (s, 1H), 7.84 (s, 1H), 7.70 (s, 1H), 7.39-7.38 (m, 2H), 7.33-7.30 (m, 4H), 7.03-7.00 (m, 1H), 5.51 (br s, 1H), 4.36-4.25 (m, 1H), 4.10 (s, 3H), 3.98 (s, 3H), 3.68-3.64 (m, 1H), 3.52-3.49 (m, 2H), 3.42-3.33 (m, 1H), 3.26 (s, 3H), 3.18-3.10 (m, 2H), 2.89-2.81 (m, 2H), 2.67 (s, 3H), 2.48-2.42 (m, 1H). LCMS (M+H): 515.35.

Example 62: 1-((3S,4R)-1-(2-Methoxyethyl)-4-phenylpyrrolidin-3-yl)-3-(2-methyl-8-(1-methyl-1H-pyrazol-4-yl)quinolin-3-yl)urea $^1$H NMR (CDCl$_3$, 300 MHz): δ 8.48 (s, 1H), 8.42 (s, 1H), 8.13 (s, 1H), 7.78 (dd, J=1.2 Hz and 7.2 Hz, 1H), 7.61-7.58 (m, 1H), 7.43 (t, J=7.2 Hz, 1H), 7.34-7.28 (m, 6H), 5.66 (br s, 1H), 4.36-4.32 (m, 1H), 4.00 (s, 3H), 3.52-3.50 (m, 3H), 3.38-3.26 (m, 1H), 3.26 (s, 3H), 3.22-3.19 (m, 1H), 2.92-2.82 (m, 2H), 2.76-2.70 (m, 1H), 2.67 (s, 3H), 2.57-2.50 (m, 1H). LCMS (M+H): 485.30.

Example 63: 1-((3S,4R)-4-(3,4-Difluorophenyl)-1-(2-methoxyethyl)pyrrolidin-3-yl)-3-(quinolin-3-yl)urea $^1$H NMR: (CD$_3$OD, 300 MHz): δ 8.73 (d, J=2.4 Hz, 1H), 8.39 (d, J=2.1 Hz, 1H), 7.93 (d, J=8.4 Hz, 1H), 7.81 (d, J=7.8 Hz, 1H), 7.63-7.50 (m, 2H), 7.35-7.31 (m, 1H), 7.25-7.16 (m, 2H), 4.39-4.32 (m, 1H), 3.58-3.54 (m, 2H), 3.37 (s, 3H), 3.27-3.22 (m, 3H), 3.13-3.07 (m, 1H), 2.85-2.72 (m, 2H), 2.66-2.61 (m, 1H). LCMS: M+H): 426.85.

Example 64: 1-((3S,4R)-1-(2-methoxyethyl)-4-phenylpyrrolidin-3-yl)-3-(naphthalen-2-yl)urea $^1$H NMR (DMSO-d$_6$, 300 MHz): δ 10.21 (br s, 1H), 8.93-8.85 (m, 1H), 7.96 (s, 1H), 7.78-7.69 (m, 3H), 7.41-7.32 (m, 7H), 6.82-6.80 (m, 1H), 4.56-4.54 (m, 1H), 3.93 (s, 1H), 3.75-3.67 (m, 3H), 3.49-3.47 (m, 4H), 3.34-3.31 (m, 4H). LCMS (M+H): 390.10.

Example 65: 1-((3S,4R)-4-(3,4-Difluorophenyl)-1-(2-methoxyethyl)pyrrolidin-3-yl)-3-(2-phenylquinolin-3-yl)urea $^1$H NMR (CD$_3$OD 300 MHz): δ 8.63 (s, 1H), 7.97 (d, J=8.4 Hz, 1H), 7.87 (d, J=8.1 Hz, 1H), 7.68-7.53 (m, 7H), 7.28-7.06 (m, 3H), 4.26-4.22 (m, 1H), 3.51 (t, J=5.7 Hz, 2H), 3.31 (s, 3H), 3.29-3.05 (m, 3H), 2.79-2.73 (m, 3H), 2.67-2.54 (m, 1H). LCMS (M+H): 502.50.

Example 66: 1-((3S,4R)-4-(3,4-Difluorophenyl)-1-(2-methoxyethyl)pyrrolidin-3-yl)-3-(2-(pyridin-3-yl)quinolin-3-yl)urea $^1$H NMR (CD$_3$OD, 300 MHz): δ 8.85 (d, J=1.5 Hz, 1H), 8.65 (dd, J=1.2 Hz and 5.4 Hz, 1H), 8.52 (s, 1H), 8.15-8.11 (m, 1H), 8.02 (d, J=8.4 Hz, 1H), 7.91 (d, J=8.1 Hz, 1H), 7.73-7.67 (m, 1H), 7.62-7.55 (m, 2H), 7.26-7.17 (m, 2H), 7.08-7.05 (m, 1H), 4.21-4.19 (m, 1H), 3.51 (t, J=5.4 Hz, 2H), 3.30 (s, 3H), 3.21-3.15 (m, 1H), 3.10-2.94 (m, 2H), 2.76-2.65 (m, 3H), 2.58-2.52 (m, 1H). LCMS (M+H): 504.76.

Example 67: 1-((3S,4R)-4-(3,4-Difluorophenyl)-1-(2-methoxyethyl)pyrrolidin-3-yl)-3-(2-methylquinolin-3-yl)urea $^1$H NMR (CD$_3$OD 300 MHz): δ 8.49 (s, 1H), 7.89 (d, J=8.4 Hz, 1H), 7.78 (d, J=8.1 Hz, 1H), 7.62-7.57 (m, 1H), 7.51-7.46 (m, 1H), 7.35-7.29 (m, 1H), 7.22-7.17 (m, 2H), 4.36-4.32 (m, 1H), 3.55 (t, J=5.4 Hz, 2H), 3.36 (s, 3H), 3.22-3.17 (m, 3H), 3.13-3.07 (m, 1H), 2.84-2.73 (m, 3H), 2.63 (s, 3H). LCMS (M+H): 440.90.

Example: 68: 1-((3S,4R)-4-(3,4-Difluorophenyl)-1-(2-methoxyethyl)pyrrolidin-3-yl)-3-(6,7-dimethoxy-2-methylquinolin-3-yl)urea 1H NMR (CD$_3$OD 400 MHz): δ 8.25 (s, 1H), 7.34-7.29 (m, 1H), 7.22-7.14 (m, 4H), 4.37-4.32 (m, 1H), 3.95 (s, 3H), 3.93 (s, 3H), 3.55 (t, J=5.2 Hz, 2H), 3.35 (s, 3H), 3.25-3.11 (m, 2H), 3.09-3.07 (m, 1H), 2.82-2.70 (m, 3H), 2.65-2.61 (m, 1H), 2.55 (s, 3H). LCMS (M+H): 501.40.

Example: 69: 1-((3S,4R)-4-(3,4-Difluorophenyl)-1-(2-methoxyethyl)pyrrolidin-3-yl)-3-(6,7-dimethoxyquinolin-3-yl)urea $^1$H NMR (CD$_3$OD, 400 MHz): δ 8.51 (d, J=2.4 Hz, 1H), 8.23 (d, J=2.4 Hz, 1H), 7.34-7.29 (m, 1H), 7.25 (s, 1H), 7.21-7.14 (m, 3H), 4.34-4.32 (m, 1H), 3.95 (s, 6H), 3.56 (t, J=5.2 Hz, 2H), 3.37 (s, 3H), 3.27-3.19 (m, 2H), 3.09-3.06 (m, 1H), 2.85-2.72 (m, 3H), 2.63 (t, J=8.8 Hz, 1H). LCMS (M+H): 487.40.

Example: 70: 1-((3S,4R)-4-(3-fluorophenyl)-1-(2-methoxyethyl)pyrrolidin-3-yl)-3-(quinolin-3-yl)urea $^1$H NMR (DMSO-d$_6$, 300 MHz): δ 8.86 (s, 1H), 8.71 (d, J=2.7 Hz, 1H), 8.41 (d, J=2.7 Hz, 1H), 7.88 (d, J=7.8 Hz, 1H), 7.80 (d, J=8.4 Hz, 1H), 7.57-7.47 (m, 2H), 7.40-7.32 (m, 1H), 7.19 (d, J=7.8 Hz, 2H), 7.07-7.02 (m, 1H), 6.82 (d, J=8.1 Hz, 1H), 4.21-4.18 (m, 1H), 3.47 (t, J=5.7 Hz, 2H), 3.26 (s, 3H), 3.22-3.15 (m, 2H), 3.00-2.94 (m, 1H), 2.72-2.64 (m, 3H), 2.50-2.49 (m, 1H). LCMS (M+H): 409.40.

Example: 71: 1-((3S,4R)-4-(3-Fluorophenyl)-1-(2-methoxyethyl)pyrrolidin-3-yl)-3-(2-methylquinolin-3-yl)urea $^1$H NMR (DMSO-d$_6$, 300 MHz): δ 8.49 (s, 1H), 7.88 (d, J=8.4 Hz, 1H), 7.78 (d, J=8.4 Hz, 1H), 7.60 (t, J=6.9 Hz, 1H), 7.49 (t, J=7.5 Hz, 1H), 7.40-7.33 (m, 1H), 7.21-7.15 (m, 2H), 7.03-6.97 (m, 1H), 6.70-6.68 (d, J=7.8 Hz, 1H), 6.61 (d, J=7.8 Hz, 1H), 4.47-4.40 (m, 1H), 3.74-3.70 (m, 1H), 3.62 (t, J=5.4 Hz, 2H), 3.55-3.42 (m, 1H), 3.38 (s, 3H), 3.34-3.30 (m, 1H), 3.26-3.18 (m, 1H), 3.12-2.88 (m, 3H), 2.62 (s, 3H). LCMS (M+H): 423.33.

Example: 72: 1-(6-Fluoro-2-methylquinolin-3-yl)-3-((3S,4R)-4-(3-fluorophenyl)-1-(2-methoxyethyl)pyrrolidin-3-yl)urea $^1$H NMR (CD$_3$OD, 300 MHz): δ 8.52 (s, 1H), 7.91-7.86 (m, 1H), 7.45-7.29 (m, 3H), 7.19-7.12 (m, 2H), 6.98-6.92 (m, 1H), 4.39-4.37 (m, 1H), 3.56 (t, J=5.4 Hz, 2H), 3.36 (s, 3H), 3.31-3.22 (m, 2H), 3.12-3.06 (m, 1H), 2.87-2.64 (m, 4H), 2.62 (s, 3H). LCMS (M+H): 441.05.

Example: 73: 1-(7-Fluoro-2-methylquinolin-3-yl)-3-((3S,4R)-4-(3-fluorophenyl)-1-(2-methoxyethyl)pyrrolidin-3-yl)urea $^1$H NMR (CD$_3$OD, 400 MHz): δ 8.49 (s, 1H), 7.85-7.81 (m, 1H), 7.51 (dd, J=2.4 Hz and 10.0 Hz, 1H), 7.36-7.30 (m, 2H), 7.19-7.12 (m, 2H), 6.99-6.94 (m, 1H), 4.39-4.37 (m, 1H), 3.56 (t, J=5.2 Hz, 2H), 3.36 (s, 3H), 3.27-3.23 (m, 1H), 3.13-3.08 (m, 1H), 2.89-2.73 (m, 4H), 2.68-2.64 (m, 1H), 2.62 (s, 3H). LCMS (M+H): 441.37.

Example: 74: 1-(6,7-Dimethoxy-2-phenylquinolin-3-yl)-3-((3S,4R)-4-(3-fluorophenyl)-1-(2-methoxyethyl)pyrrolidin-3-yl)urea $^1$H NMR (DMSO-d$_6$, 400 MHz): δ 8.52 (s, 1H), 7.63-7.58 (m, 3H), 7.53-7.45 (m, 3H), 7.38-7.32 (m, 1H), 7.27 (d, J=7.2 Hz, 2H), 7.16-7.11 (m, 3H), 7.06-7.02 (m, 1H), 4.16-4.10 (m, 1H), 3.89 (s, 3H), 3.88 (s, 3H), 3.44 (t, J=5.6 Hz, 2H), 3.24 (s, 3H), 3.12-3.04 (m, 2H), 2.91-2.87 (m, 1H), 2.62-2.51 (m, 3H), 2.50-2.45 (m, 1H). LCMS (M+H): 545.30.

Example: 75: 1-((3S,4R)-4-(3-fluorophenyl)-1-(2-methoxyethyl)pyrrolidin-3-yl)-3-(6-phenyl-[1,3]dioxolo[4,5-g]quinolin-7-yl)urea $^1$H NMR (CD$_3$OD, 400 MHz): δ 8.37 (s, 1H), 7.57-7.48 (m, 5H), 7.34-7.29 (m, 1H), 7.24 (s, 1H), 7.14-7.04 (m, 3H), 6.98-6.94 (m, 1H), 6.11 (s, 2H), 4.24-4.22 (m, 1H), 3.51 (t, J=6.0 Hz, 2H), 3.33 (s, 3H), 3.18-3.16 (m, 1H), 3.13-3.07 (m, 1H), 3.02-2.96 (m, 1H), 2.76-2.68 (m, 3H), 2.59-2.57 (m, 1H). LCMS (M+H): 529.29.

Example: 76: 1-((3S,4R)-4-(3-Fluorophenyl)-1-(2-methoxyethyl)pyrrolidin-3-yl)-3-(6-methyl-[1,3]dioxolo[4,5-g]quinolin-7-yl)urea $^1$H NMR (CD$_3$OD, 300 MHz): δ 8.23 (s, 1H), 7.37-7.29 (m, 1H), 7.18-7.11 (m, 3H), 7.06 (s, 1H), 6.99-6.93 (m, 1H), 6.08 (s, 2H), 4.40-4.34 (m, 1H), 3.55 (t, J=5.7 Hz, 2H), 3.35 (s, 3H), 3.26-3.18 (m, 2H), 3.10-3.04 (m, 1H), 2.86-2.70 (m, 3H), 2.66-2.60 (m, 1H), 2.53 (s, 3H). LCMS (M+H): 467.30.

Example: 77: 1-((3S,4R)-4-(3-Cyanophenyl)-1-(2-methoxyethyl)pyrrolidin-3-yl)-3-(quinolin-3-yl)urea $^1$H NMR (CD$_3$OD, 400 MHz): δ 8.72 (s, 1H), 8.38 (s, 1H), 7.91 (d, J=8.4 Hz, 1H), 7.81-7.74 (m, 2H), 7.71 (d, J=7.6 Hz, 1H), 7.61-7.58 (m, 2H), 7.55-7.49 (m, 2H), 4.41-4.38 (m, 1H), 3.58-3.51 (m, 2H), 3.49-3.45 (m, 1H), 3.39-3.35 (m, 3H), 3.15-3.11 (m, 1H), 2.84-2.68 (m, 5H). LCMS (M+H): 416.00.

Example: 78: 1-((3S,4R)-4-(3-Cyanophenyl)-1-(2-methoxyethyl)pyrrolidin-3-yl)-3-(6,7-dimethoxy-2-phenylquinolin-3-yl)urea $^1$H NMR (CD$_3$OD, 300 MHz): δ 8.38 (s, 1H), 7.67-7.59 (m, 5H), 7.54-7.47 (m, 4H), 7.33 (s, 1H), 7.23 (s, 1H), 4.25-4.23 (m, 1H), 3.98 (s, 3H), 3.96 (s, 3H), 3.57-3.50 (m, 2H), 3.37 (s, 3H), 3.25-3.09 (m, 3H), 2.78-2.59 (m, 4H). LCMS (M+H): 551.70.

Example: 79: 1-((3S,4R)-1-(2-Methoxyethyl)-4-(pyridin-3-yl)pyrrolidin-3-yl)-3-(quinolin-3-yl)urea $^1$H NMR (CD$_3$OD, 400 MHz): δ 8.73 (d, J=2.4 Hz, 1H), 8.54 (d, J=2.0 Hz, 1H), 8.42 (dd, J=1.6 Hz and 8.4 Hz, 1H), 8.38 (d, J=2.4 Hz, 1H), 7.94-7.90 (m, 2H), 7.80 (d, J=7.6 Hz, 1H), 7.62-7.51 (m, 2H), 7.44-7.41 (m, 1H), 4.42-4.41 (m, 1H), 3.58 (t, J=5.2 Hz, 2H), 3.38 (s, 3H), 3.35-3.31 (m, 2H), 3.21-3.16 (m, 1H), 2.92-2.73 (m, 4H). LCMS (M+H): 392.48.

Example: 80: 1-(6,7-Dimethoxy-2-phenylquinolin-3-yl)-3-((3S,4R)-1-(2-methoxyethyl)-4-(pyridin-3-yl)pyrrolidin-3-yl)urea $^1$H NMR (CD$_3$OD, 300 MHz): δ 8.46 (d, J=1.5 Hz, 1H), 8.42 (d, J=4.8 Hz, 1H), 8.38 (s, 1H), 7.86-7.83 (m, 1H), 7.59-7.48 (m, 5H), 7.43-7.39 (m, 1H), 7.33 (s, 1H), 7.22 (s, 1H), 4.29-4.27 (m, 1H), 3.97 (s, 3H), 3.96 (s, 3H), 3.54-3.51 (m, 2H), 3.34 (s, 3H), 3.24-3.15 (m, 1H), 3.13-3.03 (m, 2H), 2.82-2.62 (m, 4H). LCMS (M+H): 528.55.

Example: 81: 1-((3S,4R)-4-tert-Butyl-1-(2-methoxyethyl)pyrrolidin-3-yl)-3-(quinolin-3-yl)urea $^1$H NMR (CDCl$_3$, 400 MHz): δ 8.79 (s, 1H), 8.50 (br s, 1H), 8.01 (d, J=8.0 Hz, 1H), 7.75 (d, J=8.4 Hz, 1H), 7.55-7.47 (m, 2H), 6.86-6.82 (m, 1H), 3.76-3.72 (m, 2H), 3.58-3.42 (m, 4H), 3.35 (s, 3H), 3.02-2.98 (m, 2H), 2.38-2.24 (m, 2H), 0.97 (s, 9H). LCMS (M+H): 371.34.

Example: 82: 1-(6,7-Dimethoxy-2-phenylquinolin-3-yl)-3-((3S,4R)-1-(2-methoxyethyl)-4-(1-methyl-1H-pyrazol-4-yl)pyrrolidin-3-yl)urea $^1$H NMR (CD$_3$OD, 300 MHz): δ 8.43 (s, 1H), 7.60-7.57 (m, 2H), 7.54-7.48 (m, 4H), 7.38 (s, 1H), 7.34 (s, 1H), 7.24 (s, 1H), 4.18-4.14 (m, 1H), 3.98 (s, 3H), 3.96 (s, 3H), 3.84 (s, 3H), 3.51 (t, J=5.4 Hz, 2H), 3.33 (s, 3H), 3.30-3.20 (m, 1H), 3.07-2.90 (m, 2H), 2.77-2.71 (m, 3H), 2.52-2.49 (m, 1H). LCMS (M+H): 538.41.

Example: 83: 1-((3S,4R)-1-(2-Methoxyethyl)-4-(1-methyl-1H-pyrazol-4-yl)pyrrolidin-3-yl)-3-(quinolin-3-yl)urea $^1$H NMR (CD$_3$OD, 300 MHz): δ 8.75 (d, J=2.4 Hz, 1H), 8.42 (d, J=2.4 Hz, 1H), 7.93 (d, J=8.1 Hz, 1H), 7.82 (d, J=7.8 Hz, 1H), 7.63-7.51 (m, 3H), 7.44 (s, 1H), 4.28-4.26 (m, 1H), 3.84 (s, 3H), 3.55 (t, J=5.4 Hz, 2H), 3.36 (s, 3H), 3.22-3.16 (m, 1H), 3.01-2.95 (m, 1H), 2.88-2.73 (m, 4H), 2.52 (t, J=9.0 Hz, 1H). LCMS (M+H): 395.14.

Example 84: 1-((3S,4R)-1-(2-Methoxyethyl)-4-phenylpyrrolidin-3-yl)-3-(2-phenyl-1,8-naphthyridin-3-yl)urea

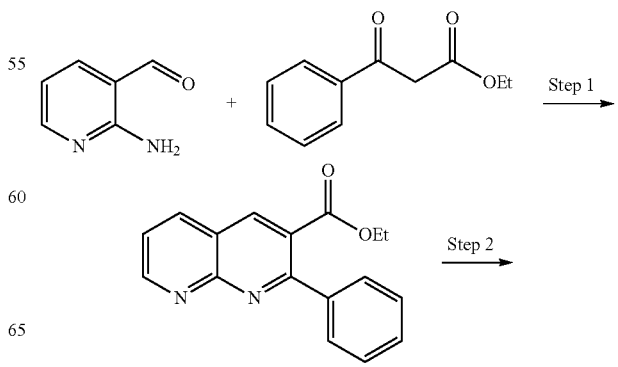

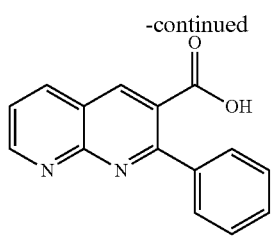

Step 3 →

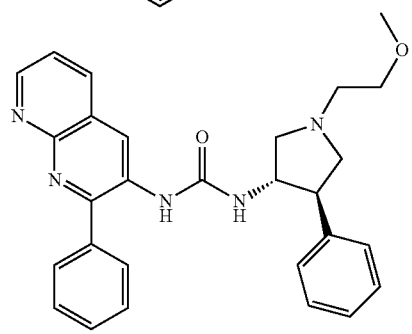

Step 1: Synthesis of ethyl 2-phenyl-1,8-naphthyridine-3-carboxylate: To a solution of 2-aminonicotinaldehyde (1.5 g, 12.29 mmol) in piperidine (7.5 mL) was added ethyl 3-oxo-3-phenylpropanoate (2.59 g, 13.52 mmol) and was stirred at 90° C. for 3 h. The reaction mixture was cooled to ambient temperature and poured into cold water. The resulting solid was filtered and washed with ether to get the required compound as an off-white solid. Yield: 2.87 g (84%); $^1$H NMR (DMSO-$d_6$, 400 MHz): δ 9.21-9.2 (m, 1H), 8.95 (s, 1H), 8.65 (dd, J=8.4 and 2.0 Hz, 1H), 7.75-7.72 (m, 2H), 7.65-7.63 (m, 2H), 7.54-7.52 (m, 2H), 4.21-4.16 (m, 2H), 1.07 (t, J=6.8 Hz, 3H).

Step 2: Synthesis of 2-phenyl-1,8-naphthyridine-3-carboxylic acid: To a solution of ethyl 2-phenyl-1,8-naphthyridine-3-carboxylate (1 g, 3.59 mmol) in EtOH (10 mL) was added H$_2$O (10 mL) followed by NaOH (0.79 g, 17.9 mmol) The reaction mixture was then refluxed for 4 hours, cooled to room temperature and solvents were evaporated under reduced pressure. The residue thus obtained was neutralized with 2N HCl (pH-3 to 4) at 0° C. and the resulting solid was filtered, washed with pentane and dried in vacuum to get the required compound as a white solid. Yield: 0.81 g (89%). $^1$H NMR (DMSO-$d_6$, 300 MHz): δ 13.5 (s, 1H), 9.19-9.17 (m, 1H), 8.62 (dd, J=8.1 and 1.8 Hz, 1H), 7.74-7.69 (m, 4H), 7.54-7.5 (m, 3H).

Step 3: Synthesis of 1-((3S,4R)-1-(2-methoxyethyl)-4-phenylpyrrolidin-3-yl)-3-(2-phenyl-1,8-naphthyridin-3-yl)urea: To a solution of 2-phenyl-1,8-naphthyridine-3-carboxylic acid (0.2 g, 0.8 mmol) in Toluene (4 mL) was added DPPA (0.261 g, 0.96 mmol) followed by TEA (0.57 mL, 4 mmol). The reaction mixture was stirred at room temperature for 16 hours. Then (3S,4R)-1-(2-methoxyethyl)-4-phenylpyrrolidin-3-amine (Intermediate B1) (0.22 g, 1.03 mmol) was added to the reaction mixture and was refluxed for 2 hours. The reaction mixture was evaporated under vacuum and the resulting residue was extracted twice with EtOAc (2×25 mL). The combined organic layers were washed with water (25 mL), brine (25 mL), dried over sodium sulphate, filtered and concentrated under reduced pressure. The crude product was purified by column chromatography (2% MeOH/DCM) to get the title compound as a colorless semi solid. Yield: 0.033 g. $^1$H NMR (DMSO-$d_6$, 300 MHz): δ 8.97-8.89 (m, 1H), 8.75 (S, 1H), 8.35 (dd, J=1.2 Hz and 8.1 Hz, 1H), 7.68-7.60 (m, 2H), 7.59-7.47 (m, 5H), 7.37-7.32 (m, 4H), 7.26-7.17 (m, 2H), 4.35-4.33 (m, 1H), 3.55 (t, J=5.4 Hz, 2H), 3.37-3.31 (m, 4H), 3.22-3.14 (m, 2H), 2.95-2.84 (m, 3H), 2.77-2.70 (m, 1H). LCMS (M+H): 468.1.

Example 85: Methyl 2-((3S,4R)-3-(3-(6,7-dimethoxy-2-phenylquinolin-3-yl)ureido)-4-phenylpyrrolidin-1-yl)acetate $^1$H NMR (DMSO-$d_6$, 300 MHz): δ 8.52 (s, 1H), 7.62-7.57 (m, 3H), 7.53-7.48 (m, 3H), 7.32-7.22 (m, 7H), 7.12 (d, J=7.5 Hz, 1H), 4.22-4.18 (m, 1H), 3.88 (s, 6H), 3.63 (s, 3H), 3.41-3.38 (m, 2H), 3.18-2.98 (m, 3H), 2.72-2.60 (m, 2H). LCMS (M+H)$^+$: 540.71.

Example 86: Methyl 2-((3R,4S)-3-phenyl-4-(3-(quinolin-3-yl)ureido)pyrrolidin-1-yl)acetate $^1$H NMR (DMSO-$d_6$, 300 MHz): δ 8.86 (s, 1H), 8.71 (d, J=2.4 Hz, 1H), 8.40 (d, J=2.1 Hz, 1H), 7.88 (d, J=7.8 Hz, 1H), 7.81 (d, J=7.5 Hz, 1H), 7.55-7.49 (m, 2H), 7.37-7.30 (m, 4H), 7.24-7.22 (m, 1H), 6.81 (d, J=7.8 Hz, 1H), 4.28-4.23 (m, 1H), 3.64 (s, 3H), 3.51-3.36 (m, 2H), 3.23-3.19 (m, 2H), 3.11-3.06 (m, 1H), 2.80-2.69 (m, 2H). LCMS (M+H): 405.29.

Example 87: 1-((3S,4R)-1-(2-Fluoroethyl)-4-phenylpyrrolidin-3-yl)-3-(6,7-dimethoxy-2-phenylquinolin-3-yl)urea $^1$H NMR (DMSO-$d_6$, 300 MHz): δ 8.53 (s, 1H), 7.60-7.57 (m, 3H), 7.53-7.49 (m, 3H), 7.32-7.25 (m, 7H), 7.14 (d, J=7.5 Hz, 1H), 4.62 (t, J=5.1 Hz, 1H), 4.46 (t, J=4.8 Hz, 1H), 4.19-4.15 (m, 1H), 3.89 (s, 3H), 3.88 (s, 3H), 3.31-3.16 (m, 1H), 3.05-3.03 (m, 1H), 2.90-2.88 (m, 1H), 2.81-2.79 (m, 1H), 2.71-2.61 (m, 3H). LCMS (M+H): 515.52.

Example 88: 1-((3R,4S)-1-(2-Fluoroethyl)-4-phenylpyrrolidin-3-yl)-3-(6,7-dimethoxy-2-phenylquinolin-3-yl)urea $^1$H NMR (DMSO-$d_6$, 300 MHz): δ 8.53 (s, 1H), 7.61-7.58 (m, 3H), 7.53-7.49 (m, 3H), 7.32-7.22 (m, 7H), 7.14-7.12 (m, 1H), 4.62 (t, J=5.1 Hz, 1H), 4.46 (t, J=5.1 Hz, 1H), 4.17-4.16 (m, 1H), 3.88 (s, 6H), 3.19-3.13 (m, 1H), 3.08-3.03 (m, 1H), 2.93-2.88 (m, 1H), 2.81-2.79 (m, 1H), 2.71-2.61 (m, 3H). LCMS (M+H): 514.76.

Example 89: 1-((3S,4R)-1-(2-Fluoroethyl)-4-phenylpyrrolidin-3-yl)-3-(2-phenylquinolin-3-yl)urea $^1$H NMR (CD$_3$OD, 300 MHz): δ 8.64 (s, 1H), 7.96 (d, J=8.4 Hz, 1H), 7.86 (d, J=8.1 Hz, 1H), 7.67-7.52 (m, 7H), 7.31-7.30 (m, 4H), 7.25-7.22 (m, 1H), 4.63 (t, J=4.8 Hz, 1H), 4.47 (t, J=5.1 Hz, 1H), 4.32-4.30 (m, 1H), 3.24-3.21 (m, 1H), 3.15-3.04 (m, 2H), 2.91-2.77 (m, 3H), 2.63 (t, J=9.0 Hz, 1H). SOR: −33.636° (c=1, MeOH). LCMS (M+H): 454.82.

Example 90: 1-((3S,4R)-1-(2-Fluoroethyl)-4-phenylpyrrolidin-3-yl)-3-(quinolin-3-yl)urea $^1$H NMR (CD$_3$OD, 300 MHz): δ 8.72 (d, J=2.7 Hz, 1H), 8.38 (d, J=2.4 Hz, 1H), 7.92 (d, J=8.4 Hz, 1H), 7.80 (d, J=8.4 Hz, 1H), 7.62-7.50 (m, 2H), 7.38-7.29 (m, 4H), 7.24-7.20 (m, 1H), 4.68 (t, J=4.8 Hz, 1H), 4.52 (t, J=5.1 Hz, 1H), 4.45-4.38 (m, 1H), 3.38-3.35 (m, 1H), 3.26-3.20 (m, 1H), 3.13-3.07 (m, 1H), 2.97-2.81 (m, 3H), 2.67 (t, J=8.7 Hz, 1H). SOR: −28.000° (c=1, MeOH). LCMS (M+H): 379.76.

Example 91: 1-((3S,4R)-1-(2,2,2-Trifluoroethyl)-4-phenylpyrrolidin-3-yl)-3-(6,7-dimethoxy-2-phenylquinolin-3-yl)urea $^1$H NMR (DMSO-d$_6$, 300 MHz): δ 8.49 (s, 1H), 7.61-7.57 (m, 3H), 7.51-7.47 (m, 3H), 7.33-7.23 (m, 7H), 7.09 (d, J=7.8 Hz, 1H), 4.24-4.20 (m, 1H), 3.88 (s, 6H), 3.37-3.32 (m, 1H), 3.31-3.22 (m, 2H), 3.14-3.09 (m, 2H), 2.77-2.70 (m, 2H). LCMS (M+H): 550.73.

Example 92: 1-((3R,4S)-1-(2,2,2-Trifluoroethyl)-4-phenylpyrrolidin-3-yl)-3-(6,7-dimethoxy-2-phenylquinolin-3-yl)urea $^1$H NMR (DMSO-d$_6$, 300 MHz): δ 8.50 (s, 1H), 7.61-7.57 (m, 3H), 7.51-7.47 (m, 3H), 7.33-7.23 (m, 7H), 7.09 (d, J=7.5 Hz, 1H), 4.24-4.20 (m, 1H), 3.89 (s, 3H), 3.88 (s, 3H), 3.37-3.34 (m, 1H), 3.28-3.23 (m, 2H), 3.14-3.09 (m, 2H) 2.77-2.70 (m, 2H). LCMS (M+H): 551.53.

Example 93: 1-((3S,4R)-1-(2,2,2-Trifluoroethyl)-4-phenylpyrrolidin-3-yl)-3-(quinolin-3-yl)urea $^1$H NMR (DMSO-d$_6$, 300 MHz): δ 8.85 (s, 1H), 8.71 (d, J=2.4 Hz, 1H), 8.40 (d, J=2.7 Hz, 1H), 7.88 (d, J=7.8 Hz, 1H), 7.81 (d, J=7.8 Hz, 1H), 7.56-7.47 (m, 2H), 7.37-7.30 (m, 4H), 7.26-7.21 (m, 1H), 6.81 (d, J=7.8 Hz, 1H), 4.31-4.22 (m, 1H), 3.46-3.33 (m, 2H), 3.28-3.16 (m, 3H), 2.86-2.72 (m, 2H). LCMS (M+H): 415.35.

Example 94: 1-((3S,4R)-1-(2,2-Difluoroethyl)-4-phenylpyrrolidin-3-yl)-3-(6,7-dimethoxy-2-phenylquinolin-3-yl)urea $^1$H NMR (CD$_3$OD, 400 MHz): δ 8.40 (s, 1H), 7.56-7.48 (m, 5H), 7.33-7.30 (m, 5H), 7.28-7.21 (m, 2H), 6.08-5.80 (m, 1H), 4.30-4.27 (m, 1H), 3.97 (s, 3H), 3.95 (s, 3H), 3.26-3.21 (m, 1H), 3.11-3.06 (m, 2H), 2.97-2.65 (m, 4H). LCMS (M+H): 533.79.

Example 95: 1-((3S,4R)-1-(2,2-Difluoroethyl)-4-phenylpyrrolidin-3-yl)-3-(quinolin-3-yl)urea $^1$H NMR (DMSO-d$_6$, 400 MHz): δ 8.85 (s, 1H), 8.71 (d, J=2.4 Hz, 1H), 8.40 (d, J=2.4 Hz, 1H), 7.88 (d, J=7.6 Hz, 1H), 7.82 (dd, J=1.2 Hz and 8.0 Hz, 1H), 7.56-7.48 (m, 2H), 7.36-7.30 (m, 4H), 7.25-7.20 (m, 1H), 6.82 (d, J=8.0 Hz, 1H), 6.29-6.60 (m, 1H), 4.27-4.20 (m, 1H), 3.26-3.16 (m, 2H), 3.10-3.03 (m, 1H), 3.01-2.83 (m, 2H), 2.79-2.75 (m, 1H), 2.68-2.64 (m, 1H). LCMS (M+H): 397.45.

Example 96: 1-(6,7-Dimethoxy-2-phenylquinolin-3-yl)-3-((3S,4R)-1-(2-methoxyacetyl)-4-phenylpyrrolidin-3-yl)urea $^1$H NMR (DMSO-d$_6$, 400 MHz): δ 8.46 (br s, 1H), 7.65-7.62 (m, 1H), 7.56-7.54 (m, 2H), 7.46-7.45 (m, 3H), 7.35-7.27 (m, 7H), 7.00-6.95 (m, 1H), 4.37-4.28 (m, 1H), 4.03 (s, 2H), 3.90 (s, 6H), 3.85-3.80 (m, 2H), 3.37-3.35 (m, 1H), 3.31 (s, 3H), 3.20-3.17 (m, 1H), 3.13-3.10 (m, 1H). LCMS (M+H): 540.78.

Example 97: 1-((3S,4R)-1-(2-Methoxyacetyl)-4-phenylpyrrolidin-3-yl)-3-(quinolin-3-yl)urea $^1$H NMR (DMSO-d$_6$, 400 MHz): δ 8.91 (d, J=9.2 Hz, 1H), 8.71-8.69 (m, 1H), 8.41 (br s, 1H), 7.88 (d, J=8.4 Hz, 1H), 7.82 (d, J=8.0 Hz, 1H), 7.57-7.49 (m, 2H), 7.40-7.35 (m, 4H), 7.28-7.25 (m, 1H), 6.78-6.72 (m, 1H), 4.44-4.34 (m, 1H), 4.05 (s, 2H), 3.99-3.89 (m, 2H), 3.88-3.46 (m, 1H), 3.36-3.35 (m, 1H), 3.32 (s, 3H), 3.28-3.17 (m, 1H). LCMS (M+H): 405.50.

Example 98: 1-(6,7-Dimethoxy-2-phenylquinolin-3-yl)-3-((3S,4R)-1-(oxetan-3-yl)-4-phenylpyrrolidin-3-yl)urea $^1$H NMR (DMSO-d$_6$, 300 MHz): δ 8.51 (s, 1H), 7.62-7.58 (m, 3H), 7.53-7.47 (m, 3H), 7.33-7.31 (m, 4H), 7.28-7.22 (m, 3H), 7.14 (d, J=7.8 Hz, 1H), 4.59 (t, J=6.3 Hz, 2H), 4.50-4.45 (m, 2H), 4.20-4.18 (m, 1H), 3.88 (s, 6H), 3.66-3.62 (m, 1H), 3.12-3.06 (m, 2H), 2.88-2.82 (m, 1H), 2.55-2.53 (m, 1H), 2.45-2.41 (m, 1H). LCMS (M+H): 524.53.

Example 99: 2-((3S,4R)-3-(3-(6,7-Dimethoxy-2-phenylquinolin-3-yl)ureido)-4-phenylpyrrolidin-1-yl)acetamide $^1$H NMR (DMSO-d$_6$, 300 MHz): δ 8.50 (br s, 1H), 7.61-7.58 (m, 3H), 7.51-7.48 (m, 3H), 7.33-7.31 (m, 4H), 7.28 (d, J=6.0 Hz, 2H), 7.25-7.21 (m, 2H), 7.10-7.07 (m, 2H), 4.20-4.18 (m, 1H), 3.88 (s, 6H), 3.15-2.97 (m, 5H), 2.60-2.57 (m, 2H). LCMS (M+H): 526.54.

Example 100: 1-((3S,4R)-1-(Cyanomethyl)-4-phenylpyrrolidin-3-yl)-3-(6,7-dimethoxy-2-phenylquinolin-3-yl)urea $^1$H NMR (DMSO-d$_6$, 400 MHz): δ 8.52 (br s, 1H), 7.62-7.58 (m, 3H), 7.58-7.45 (m, 3H), 7.35-7.22 (m, 7H), 7.15 (d, J=7.2 Hz, 1H), 4.23-4.19 (m, 1H), 3.88 (s, 6H), 3.40-3.31 (m, 1H), 3.17-3.08 (m, 3H), 3.05-3.01 (m, 1H) 2.63-2.45 (m, 2H). LCMS (M+H): 508.57.

Example 101: 1-((3S,4R)-1-(Cyanomethyl)-4-phenylpyrrolidin-3-yl)-3-(quinolin-3-yl)urea $^1$H NMR (DMSO-d$_6$, 400 MHz): δ 8.85 (br s, 1H), 8.71 (d, J=2.4 Hz, 1H), 8.40 (d, J=2.4 Hz, 1H), 7.88 (d, J=8.4 Hz, 1H), 7.82 (dd, 1.2 Hz and 8.0 Hz, 1H), 7.56-7.48 (m, 2H), 7.34-7.32 (m, 4H), 7.26-7.22 (m, 1H), 6.88 (d, J=8.0 Hz, 1H), 4.23-4.19 (m, 1H), 3.90 (s, 2H), 3.31-3.17 (m, 2H), 3.13-3.09 (m, 1H), 2.70-2.64 (m, 2H). LCMS (M+H): 371.76.

Example 102: 2-((3R,4S)-3-Phenyl-4-(3-(quinolin-3-yl)ureido)pyrrolidin-1-yl)acetamide $^1$H NMR (DMSO-d$_6$, 400 MHz): δ 8.85 (br s, 1H), 8.72 (d, J=2.8 Hz, 1H), 8.40 (d, J=2.4 Hz, 1H), 7.88 (d, J=8.0 Hz, 1H), 7.81 (d, 8.0 Hz, 1H), 7.54-7.50 (m, 2H), 7.37-7.22 (m, 6H), 7.16 (br s, 1H), 6.85 (d, J=8.0 Hz, 1H), 4.25-4.24 (m, 1H), 3.31-3.12 (m, 3H), 3.05-3.00 (m, 2H), 2.73-2.64 (m, 1H) 2.61-2.55 (m, 1H). LCMS (M+H): 389.87.

Example 103: 1-(1-(2-Methoxyethyl)-2-oxo-4-phenylpyrrolidin-3-yl)-3-(quinolin-3-yl)urea $^1$H NMR (CD$_3$OD, 400 MHz): δ 8.74 (d, J=3.2 Hz, 1H), 8.40 (d, J=2.4 Hz, 1H), 7.92 (d, J=8.0 Hz, 1H), 7.80 (d, J=8.4 Hz, 1H), 7.62-7.58 (m, 1H), 7.55-7.51 (m, 1H), 7.43-7.41 (m, 2H), 7.37-7.33 (m, 2H), 7.29-7.25 (m, 1H), 4.71 (d, J=10.8 Hz, 1H), 3.84-3.82 (m, 1H), 3.73-3.46 (m, 6H), 3.38 (s, 3H). LCMS (M+H): 405.2.

Example 104: 1-(Dibenzo[b,d]furan-1-yl)-3-((3S,4R)-1-(2-methoxyethyl)-4-phenylpyrrolidin-3-yl)urea Step 1: Preparation of phenyl dibenzo[b,d]furan-1-ylcarbamate: To a solution of dibenzo[b,d]furan-1-amine (0.2 g, 1.09 mmol) and pyridine (0.17 g, 2.18 mmol) in THF (20 mL) at 0° C. was added phenylchloroformate (0.17 g, 1.09 mmol) drop-wise, and the resulting mixture was stirred at room temperature for 2 h. Cold water was added to the reaction mixture and it was extracted with ethyl acetate (2×25 mL). The combined organic layers were washed with water (10 mL), brine (10 mL) and dried over sodium sulphate. The organic layer was filtered and concentrated under reduced pressure to afford the title compound as a pale brown solid. Yield: 0.2 g (61%); LCMS (M+H): 304.27.

Step 2: Preparation of 1-(dibenzo[b,d]furan-1-yl)-3-((3S,4R)-1-(2-methoxyethyl)-4-phenylpyrrolidin-3-yl)urea: To a solution of (3S,4R)-1-(2-methoxyethyl)-4-phenylpyrrolidin-3-amine dihydrochloride (0.2 g, 0.78 mmol) and diisopropylethylamine (0.30 g, 2.34 mmol) in DMF (4 mL) was added phenyl dibenzo[b,d]furan-1-ylcarbamate (0.23 g. 0.78 mmol) slowly at 0° C., and the resulting mixture was stirred at room temperature for 12 h. The reaction mixture was diluted with water (10 mL) and extracted with ethyl acetate (25 mL). The organic layers were washed with water (10 mL), brine (10 mL) and dried over sodium sulfate. The organic layers were filtered, concentrated under reduced pressure and the residue was purified by flash column chromatography eluting with 2% MeOH/CHCl$_3$ to afford the title compound as an off-white solid. Yield: 0.03 g (9%); $^1$H NMR (CDCl$_3$, 300 MHz): δ 8.01 (d, J=8.1 Hz, 1H), 7.93 (d, J=7.2 Hz, 1H), 7.61 (d, J=8.1 Hz, 1H), 7.51 (d, J=8.1 Hz, 1H), 7.44 (dt, J=1.2 and 8.4 Hz, 1H), 7.36 (d, J=8.4 Hz, 1H), 7.31-7.25 (m, 5H), 7.22-7.20 (m, 1H), 5.35 (d, J=7.8 Hz, 1H), 4.36-4.32 (m, 1H), 3.52 (t, J=6.0 Hz, 2H), 3.49-3.46 (m, 1H), 3.38-3.33 (m, 1H), 3.30 (s, 3H), 3.14-3.11 (m, 1H), 2.92-2.70 (m, 3H), 2.46 (t, J=9.0 Hz, 1H). (M+H): 430.35.

The following examples were prepared according to the above mentioned procedure by using appropriate intermediates.

Example 105: 1-(Dibenzo[b,d]furan-1-yl)-3-((3S,4R)-4-(3-fluorophenyl)-1-(2-methoxyethyl)pyrrolidin-3-yl)urea $^1$H NMR (DMSO-d$_6$, 300 MHz): δ 8.68 (br s, 1H), 8.10 (t, J=7.5 Hz, 2H), 7.70 (d, J=6.6 Hz, 1H), 7.66 (dd, J=1.2 and 7.8 Hz, 1H), 7.53 (dt, J=1.2 and 7.8 Hz, 1H), 7.42 (d, J=7.2 Hz, 1H), 7.40-7.32 (m, 1H), 7.26 (d, J=7.8 Hz, 1H), 7.21-7.17 (m, 3H), 7.09-7.01 (m, 1H), 4.22-4.16 (m, 1H), 3.47 (t, J=6.0 Hz, 2H), 3.26 (s, 3H), 3.16-3.11 (m, 2H), 2.98 (t, J=7.5 Hz, 1H), 2.74-2.60 (m, 4H). LCMS (M+H): 448.24.

Example 106: 1-((3S,4R)-1-(2-Methoxyethyl)-4-phenylpyrrolidin-3-yl)-3-(8-methyldibenzo[b,d]furan-1-yl)urea $^1$H NMR (CD$_3$OD, 300 MHz): δ 7.71 (s, 1H), 7.43 (d, J=8.4 Hz, 1H), 7.39-7.22 (m, 9H), 4.48-4.40 (m, 1H), 3.95-3.90 (m, 1H), 3.54 (t, J=5.4 Hz, 2H), 3.34 (s, 3H), 3.25-3.20 (m, 1H), 3.10-3.05 (m, 1H), 2.98-2.92 (m, 1H), 2.85-2.75 (m, 2H), 2.61 (t, J=9.0 Hz, 1H), 2.41 (s, 3H). LCMS (M+H): 444.26.

Example 107: 1-((3S,4R)-1-(2-Methoxyethyl)-4-phenylpyrrolidin-3-yl)-3-(8-methoxydibenzo[b,d]furan-1-yl)urea $^1$H NMR (CD$_3$OD, 300 MHz): δ 7.46 (d, J=9.0 Hz, 1H), 7.40-7.35 (m, 3H), 7.31-7.22 (m, 6H), 7.06 (dd, J=3.0 and 9.0 Hz, 1H), 4.46-4.42 (m, 1H), 3.72 (s, 3H), 3.54 (t, J=5.4 Hz, 2H), 3.38-3.36 (m, 1H), 3.34 (s, 3H), 3.24-3.20 (m, 1H), 3.12-3.07 (m, 1H), 3.02-2.96 (m, 1H), 2.87-2.80 (m, 2H), 2.63 (t, J=9.0 Hz, 1H). LCMS (M+H): 460.28.

Example 108: 1-((3S,4R)-1-(2-Methoxyethyl)-4-phenylpyrrolidin-3-yl)-3-(8-fluorodibenzo[b,d]furan-1-yl)urea $^1$H NMR (CDCl$_3$, 300 MHz): δ 7.58 (dd, J=2.7 and 8.4 Hz, 1H), 7.46-7.29 (m, 5H), 7.25-7.18 (m, 5H), 7.10 (dt, J=2.1 and 9.0 Hz, 1H), 5.71 (br s, 1H), 4.45-4.35 (m, 1H), 3.40 (t, J=5.4 Hz, 2H), 3.37-3.33 (m, 1H), 3.21 (s, 3H), 3.20-3.19 (m, 1H), 3.07 (d, J=10.2 Hz, 1H), 2.83 (t, J=7.5 Hz, 1H), 2.73-2.59 (m, 2H), 2.37 (t, J=9.6 Hz, 1H). LCMS (M+H): 448.25.

Example 109: 1-((3S,4R)-1-(2-Methoxyethyl)-4-phenylpyrrolidin-3-yl)-3-(7-methoxydibenzo[b,d]furan-1-yl)urea $^1$H NMR (CD$_3$OD, 400 MHz): δ 7.66 (d, J=8.8 Hz, 1H), 7.36-7.22 (m, 8H), 7.13 (d, J=2.0 Hz, 1H), 6.82 (dd, J=2.4 and 8.8 Hz, 1H), 4.50-4.40 (m, 1H), 3.88 (s, 3H), 3.53 (t, J=5.2 Hz, 2H), 3.34 (s, 3H), 3.22-3.18 (m, 1H), 3.03 (t, J=7.6 Hz, 1H), 2.91-2.87 (m, 1H), 2.80-2.72 (m, 3H), 2.58 (t, J=9.2 Hz, 1H). LCMS (M+H): 460.28.

Example 110: 1-((3S,4R)-1-(2-Methoxyethyl)-4-phenylpyrrolidin-3-yl)-3-(7-fluorodibenzo[b,d]furan-1-yl)urea $^1$H NMR (DMSO-d$_6$, 300 MHz): δ 8.24 (br s, 1H), 8.14-8.09 (m, 1H), 7.68-7.63 (m, 2H), 7.40-7.28 (m, 7H), 7.25-7.20 (m, 2H), 4.32-4.20 (m, 1H), 3.48 (t, J=5.7 Hz, 2H), 3.26 (s, 3H), 3.22-3.13 (m, 2H), 3.00-2.90 (m, 1H), 2.80-2.60 (m, 3H), 2.43-2.40 (m, 1H). LCMS (M+H): 448.29.

Example 111: 1-(Dibenzo[b,d]thiophen-1-yl)-3-((3S,4R)-1-(2-methoxyethyl)-4-phenylpyrrolidin-3-yl)urea $^1$H NMR (DMSO-d$_6$, 400 MHz): δ 8.32 (d, J=6.8 Hz, 2H), 8.01 (d, J=7.2 Hz, 1H), 7.78-7.76 (m, 1H), 7.50 (t, J=7.2 Hz, 1H), 7.45-7.41 (m, 3H), 7.36-7.29 (m, 4H), 7.23-7.20 (m, 1H), 7.07 (d, J=7.6 Hz, 1H), 4.25-4.16 (m, 1H), 3.47 (t, J=6.0 Hz, 2H), 3.26 (s, 3H), 3.19-3.15 (m, 2H), 2.93 (t, J=7.6 Hz, 1H), 2.72-2.60 (m, 3H), 2.54-2.50 (m, 1H). LCMS (M+H): 446.20.

Example 112: 1-(5,5-Dioxodibenzo[b,d]thiophen-1-yl)-3-[1-(2-methoxy-ethyl)-4-phenyl-pyrrolidin-3-yl]-urea $^1$H NMR (CDCl$_3$, 300 MHz): δ 8.07-8.04 (m, 1H), 7.82-7.79 (m, 1H), 7.66 (t, J=7.5 Hz, 2H), 7.48-7.42 (m, 3H), 7.34-7.28 (m, 2H), 7.23-7.20 (m, 3H), 7.05-7.01 (m, 1H), 6.40 (br s, 1H), 4.50-4.35 (m, 1H), 3.56 (t, J=8.1 Hz, 2H), 3.48-3.44 (m, 2H), 3.35-3.32 (m, 1H), 3.22 (s, 3H), 2.95 (t, J=7.8 Hz, 1H), 2.81-2.77 (m, 2H), 2.56 (t, J=9.6 Hz, 1H). LCMS (M+H): 478.13.

Example 113: 1-(4-Methoxydibenzo[b,d]thiophen-1-yl)-3-((3S,4R)-1-(2-methoxyethyl)-4-phenylpyrrolidin-3-yl)urea $^1$H NMR (DMSO-d$_6$, 300 MHz): δ 8.29 (d, J=8.1 Hz, 1H), 8.12 (br s, 1H), 8.02 (d, J=7.8 Hz, 1H), 7.50 (t, J=7.2 Hz, 1H), 7.39 (t, J=7.2 Hz, 1H), 7.32-7.19 (m, 6H), 7.06 (d, J=8.4 Hz, 1H), 6.84 (d, J=8.1 Hz, 1H), 4.25-4.15 (m, 1H), 3.97 (s, 3H), 3.46 (t, J=6.0 Hz, 2H), 3.25 (s, 3H), 3.21-3.11 (m, 2H), 2.93-2.89 (m, 2H), 2.67-2.57 (m, 3H). LCMS (M+H): 476.15.

Example 114: 1-(4-Methoxy-5,5-Dioxodibenzo[b,d]thiophen-1-yl)-3-[1-(2-methoxy-ethyl)-4-phenyl-pyrrolidin-3-yl]-urea $^1$H NMR (DMSO-d$_6$, 300 MHz): δ 8.16 (br s, 1H), 7.98 (d, J=8.1 Hz, 1H), 7.91-7.88 (m, 1H), 7.63-7.61 (m, 2H), 7.50 (d, J=8.7 Hz, 1H), 7.32-7.28 (m, 4H), 7.23 (d, J=9.0 Hz, 2H), 7.01 (d, J=7.8 Hz, 1H), 4.20-4.10 (m, 1H), 3.95 (s, 3H), 3.46 (t, J=5.1 Hz, 2H), 3.25 (s, 3H), 3.18-3.14 (m, 2H), 2.96-2.85 (m, 1H), 2.70-2.62 (m, 3H), 2.58-2.54 (m, 1H). LCMS (M+H): 508.26.

Example 115: 1-((3S,4R)-1-(2-Methoxyethyl)-4-phenylpyrrolidin-3-yl)-3-(9-oxo-9H-fluoren-4-yl)urea $^1$H NMR (DMSO-d$_6$, 300 MHz): δ 8.13 (br s, 1H), 7.73-7.54 (m, 4H), 7.38-7.21 (m, 9H), 4.22-4.18 (m, 1H), 3.47 (t, J=6.0 Hz, 2H), 3.26 (s, 3H), 3.21-3.15 (m, 2H), 2.95-2.89 (m, 1H), 2.72-2.61 (m, 3H), 2.43-2.41 (m, 1H). LCMS (M+H): 442.21.

Example 116: 1-(6-Methoxydibenzo[b,d]furan-1-yl)-3-((3S,4R)-1-(2-methoxyethyl)-4-phenylpyrrolidin-3-yl)urea $^1$H NMR (CD$_3$OD, 400 MHz): δ 7.46 (d, J=8.0 Hz, 1H), 7.42 (d, J=8.4 Hz, 1H), 7.40-7.30 (m, 6H), 7.26-7.23 (m, 1H), 7.19 (t, J=8.8 Hz, 1H), 7.08 (d, J=7.2 Hz, 1H), 4.46-4.43 (m, 1H), 4.02 (s, 3H), 3.54 (t, J=5.2 Hz, 2H), 3.38-3.36 (m, 1H), 3.35 (s, 3H), 3.26-3.22 (m, 1H), 3.07 (t, J=8.4 Hz, 1H), 2.95-2.91 (m, 1H), 2.85-2.76 (m, 2H), 2.63 (t, J=9.2 Hz, 1H). LCMS (M+H): 460.24.

Example 117: 1-(6-Methyldibenzo[b,d]furan-1-yl)-3-((3S,4R)-1-(2-methoxyethyl)-4-phenylpyrrolidin-3-yl)urea $^1$H NMR (CD$_3$OD, 300 MHz): δ 7.71 (s, 1H), 7.43 (d, J=8.4 Hz, 1H), 7.39-7.20 (m, 9H), 4.48-4.40 (m, 1H), 3.54 (t, J=5.4 Hz, 2H), 3.38-3.36 (m, 1H), 3.34 (s, 3H), 3.25-3.20 (m, 1H), 3.08-3.03 (m, 1H), 2.95-2.92 (m, 1H), 2.80-2.74 (m, 2H), 2.59 (t, J=9.3 Hz, 1H), 2.41 (s, 3H). LCMS (M+H: 444.21.

The following compounds were synthesized by following the synthetic method 1 and procedure described in Example 3 by using appropriate starting materials.

Example 118: 1-(6-Methoxy-7-methyl-2-phenylquinolin-3-yl)-3-((3S,4R)-1-(2-methoxyethyl)-4-phenylpyrrolidin-3-yl)urea $^1$H NMR (CD$_3$OD, 300 MHz): δ 8.46 (s, 1H), 7.70 (br s, 1H), 7.56-7.49 (m, 5H), 7.31-7.30 (m, 5H), 7.16 (s, 1H), 4.36-4.30 (m, 1H), 3.97 (s, 3H), 3.52 (t, J=4.8 Hz, 2H), 3.31 (s, 3H), 3.12-3.02 (m, 2H), 2.82-2.74 (m, 5H), 2.36 (s, 3H). LCMS (M+H): 511.39.

Example 119: 1-(6-Cyano-7-fluoro-2-methylquinolin-3-yl)-3-((3S,4R)-1-(2-methoxyethyl)-4-phenylpyrrolidin-3-yl)urea $^1$H NMR (DMSO d$_6$, 400 MHz): δ 8.85 (s, 1H), 8.60 (d, J=7.6 Hz, 1H), 8.13 (s, 1H), 7.84 (d, J=10.8 Hz, 1H), 7.63-7.52 (m, 1H), 7.38-7.30 (m, 5H), 7.24-7.21 (m, 1H), 4.25-4.22 (m, 1H), 3.47 (t, J=6.0 Hz, 2H), 3.26 (s, 3H), 3.23-3.22 (m, 2H), 3.12-3.10 (m, 1H), 2.93-2.90 (m, 1H), 2.72-2.66 (m, 2H), 2.64 (s, 3H), 2.44-2.43 (m, 1H). LCMS (M+H): 448.21.

Example 120: 1-(6-Cyano-7-methoxy-2-methylquinolin-3-yl)-3-((3S,4R)-1-(2-methoxyethyl)-4-phenylpyrrolidin-3-yl)urea $^1$H NMR (DMSO d$_6$, 400 MHz): δ 8.67 (s, 1H), 8.39 (s, 1H), 8.03 (s, 1H), 7.43 (s, 1H), 7.35-7.22 (m, 6H), 4.25-4.22 (m, 1H), 3.98 (s, 3H), 3.47 (t, J=6.4 Hz, 2H), 3.26 (s, 3H), 3.23-3.21 (m, 1H), 3.14-3.10 (m, 1H), 2.94-2.88 (m, 1H), 2.75-2.65 (m, 3H), 2.59 (s, 3H), 2.50-2.49 (m, 1H). LCMS (M+H): 460.25.

Example 121: 1-(7-Cyano-6-fluoro-2-methylquinolin-3-yl)-3-((3S,4R)-1-(2-methoxyethyl)-4-phenylpyrrolidin-3-yl)urea $^1$H NMR (CD$_3$OD, 400 MHz): δ 8.73 (s, 1H), 8.26 (d, J=6.0 Hz, 1H), 7.66 (d, J=9.6 Hz, 1H), 7.38-7.31 (m, 4H), 7.25-7.23 (m, 1H), 4.42-4.40 (m, 1H), 3.58 (t, J=6.4 Hz, 2H), 3.37 (s, 3H), 3.26-3.21 (m, 2H), 3.18-3.13 (m, 1H), 2.98-2.94 (m, 1H), 2.90-2.78 (m, 2H), 2.73-2.68 (m, 1H), 2.65 (s, 3H). LCMS (M+H): 448.29.

Example 122: 1-(7-Cyano-6-fluoro-2-phenylquinolin-3-yl)-3-((3S,4R)-1-(2-methoxyethyl)-4-phenylpyrrolidin-3-yl)urea $^1$H NMR (CD$_3$OD, 400 MHz): δ 8.85 (s, 1H), 8.37 (d, J=6.0 Hz, 1H), 7.75 (d, J=10.0 Hz, 1H), 7.62-7.56 (m, 5H), 7.34-7.30 (m, 4H), 7.24-7.20 (m, 1H), 4.40-4.38 (m, 1H), 3.53 (t, J=5.6 Hz, 2H), 3.31 (s, 3H), 3.13-3.05 (m, 2H), 2.84-2.71 (m, 4H), 2.62-2.60 (m, 1H). LCMS (M+H): 510.30.

Example 123: 1-(7-Cyano-6-methoxy-2-phenylquinolin-3-yl)-3-((3S,4R)-1-(2-methoxyethyl)-4-phenylpyrrolidin-3-yl)urea $^1$H NMR (CD$_3$OD, 400 MHz): δ 8.75 (s, 1H), 8.22 (s, 1H), 7.59-7.54 (m, 5H), 7.39 (s, 1H), 7.31-7.30 (m, 4H), 7.24-7.21 (m, 1H), 4.38-4.36 (m, 1H), 4.05 (s, 3H), 3.53 (t, J=6.0 Hz, 2H), 3.33 (s, 3H), 3.15-3.07 (m, 2H), 2.84-2.74 (m, 4H), 2.62-2.60 (m, 1H). LCMS (M+H): 522.30.

Example 124: 1-((3S,4R)-1-(2-Methoxyethyl)-4-phenylpyrrolidin-3-yl)-3-(2-(thiazol-5-yl)quinolin-3-yl)urea $^1$H NMR (CD$_3$OD, 400 MHz): δ 9.08 (s, 1H), 8.49 (s, 1H), 8.31 (s, 1H), 8.01 (d, J=8.8 Hz, 1H), 7.86 (d, J=8.0 Hz, 1H), 7.73-7.68 (m, 1H), 7.58-7.54 (m, 1H), 7.32-7.24 (m, 4H), 7.23-7.21 (m, 1H), 4.40-4.35 (m, 1H), 3.54 (t, J=5.6

Hz, 2H), 3.38-3.35 (m, 1H), 3.35 (s, 3H), 3.24-3.13 (m, 1H), 3.12-3.06 (m, 1H), 2.93-2.77 (m, 3H), 2.69-2.64 (m, 1H). LCMS (M+H): 474.37.

Example 125: 1-((3S,4R)-1-(2-Methoxyethyl)-4-phenylpyrrolidin-3-yl)-3-(2-phenyl-5,6,7,8-tetrahydroquinolin-3-yl)urea $^1$H NMR (CDCl$_3$, 400 MHz): δ 7.94 (s, 1H), 7.52 (s, 1H), 7.50 (s, 1H), 7.44 (t, J=7.2 Hz, 2H), 7.39 (d, J=6.8 Hz, 1H), 7.32-7.29 (m, 2H), 7.22-7.21 (m, 3H), 5.32 (br s, 1H), 4.28 (br s, 1H), 3.48-3.44 (m, 2H), 3.31-3.30 (m, 1H), 3.28 (s, 3H), 3.20-3.18 (m, 1H), 3.04-3.02 (m, 1H), 2.90 (t, J=6.4 Hz, 2H), 2.82-2.61 (m, 5H), 2.35-2.33 (m, 1H), 1.89-1.88 (m, 2H), 1.82-1.80 (m, 2H). LCMS (M+H): 471.33.

Example 126: 1-(6,7-Dimethoxy-2-phenylquinolin-3-yl)-3-((3S,4R)-1-(2-methoxyethyl)-4-phenylpyrrolidin-3-yl)-1,3-dimethylurea

LCMS (M+H): 555.39.

Example 127: 1-((3S,4R)-1-(2-Methoxyethyl)-4-phenylpyrrolidin-3-yl)-1-methyl-3-(2-phenylquinolin-3-yl)urea $^1$H NMR (CDCl$_3$, 400 MHz): δ 9.20 (br s, 1H), 8.71 (s, 1H), 8.06 (d, J=8.4 Hz, 1H), 7.80 (d, J=8.4 Hz, 1H), 7.74 (d, J=7.2 Hz, 2H), 7.60 (t, J=6.8 Hz, 1H), 7.53-7.42 (m, 4H), 7.34-7.30 (m, 2H), 7.24-7.19 (m, 2H), 4.28-4.25 (m, 1H), 3.50 (br s, 1H), 3.34-3.17 (m, 4H), 2.98 (s, 3H), 2.93 (s, 3H), 2.76-2.74 (m, 1H), 2.57-2.49 (m, 2H), 2.25-2.22 (m, 1H), 2.13 (t, J=10.0 Hz, 1H). LCMS (M+H): 481.47.

Example 128: 1-(6-(Difluoromethoxy)-7-methoxy-2-methylquinolin-3-yl)-3-((3S,4R)-1-(2-methoxyethyl)-4-phenylpyrrolidin-3-yl)urea $^1$H NMR (CD$_3$OD, 300 MHz): δ 8.33 (s, 1H), 7.49 (s, 1H), 7.37-7.33 (m, 5H), 7.28-7.25 (m, 1H), 7.10-6.66 (m, 1H), 4.40-4.39 (m, 1H), 3.99 (s, 3H), 3.57 (t, J=5.4 Hz, 2H), 3.38-3.37 (m, 1H), 3.36 (s, 3H), 3.26-3.23 (m, 1H), 3.13-3.10 (m, 1H), 2.98-2.82 (m, 3H), 2.72-2.69 (m, 1H), 2.58 (s, 3H). LCMS (M+H): 501.25.

Example 129: 1-(2,2-Difluoro-6-methyl-[1,3]dioxolo[4,5-g]quinolin-7-yl)-3-((3S,4R)-1-(2-methoxyethyl)-4-phenylpyrrolidin-3-yl)urea 1H NMR (CDCl$_3$, 400 MHz): δ 8.48 (s, 1H), 7.50 (s, 1H), 7.35-7.31 (m, 5H), 7.25-7.23 (m, 2H), 5.79-5.78 (m, 1H), 4.26-4.24 (m, 1H), 3.53-3.50 (m, 4H), 3.22-3.20 (m, 1H), 3.19 (s, 3H), 2.86-2.80 (m, 2H), 2.70-2.64 (m, 1H), 2.57 (s, 3H), 2.45-2.40 (m, 1H). LCMS (M+H): 485.01.

Example 130: 1-(6-(Difluoromethyl)-[1,3]dioxolo[4,5-g]quinolin-7-yl)-3-((3S,4R)-1-(2-methoxyethyl)-4-phenylpyrrolidin-3-yl)urea $^1$H NMR (CD$_3$OD, 400 MHz): δ 8.39 (s, 1H), 7.36-7.20 (m, 6H), 7.12 (s, 1H), 6.96-6.69 (m, 1H), 6.13 (s, 2H), 4.37-4.34 (m, 1H), 3.55 (t, J=4.4 Hz, 2H), 3.35 (s, 3H), 3.24-3.18 (m, 2H), 3.07-3.03 (m, 1H), 2.88-2.86 (m, 1H), 2.85-2.70 (m, 2H), 2.65-2.60 (m, 1H). LCMS (M+H): 484.94.

Example 131: 1-([1,3]Dioxolo[4,5-g]quinolin-7-yl)-3-((3S,4R)-1-(2-methoxyethyl)-4-phenylpyrrolidin-3-yl)urea $^1$H NMR (CDCl$_3$, 400 MHz): δ 8.46 (s, 1H), 8.39 (s, 1H), 7.35-7.32 (m, 2H), 7.29-7.26 (m, 5H), 6.99 (s, 1H), 6.07 (s, 2H), 5.48-5.46 (m, 1H), 4.15-4.12 (m, 1H), 3.59-3.56 (m, 3H), 3.45-3.42 (m, 1H), 3.32 (s, 3H), 3.26-3.23 (m, 1H), 2.89-2.84 (m, 2H), 2.79-2.74 (m, 1H), 2.49-2.45 (m, 1H). LCMS (M+H): 435.39.

Example 132: 1-(2-Cyclohexylquinolin-3-yl)-3-((3S,4R)-1-(2-methoxyethyl)-4-phenylpyrrolidin-3-yl)urea $^1$H NMR (CD$_3$OD, 400 MHz): δ 8.25 (s, 1H), 7.96 (d, J=8.4 Hz, 1H), 7.75 (d, J=7.2 Hz, 1H), 7.60 (t, J=7.2 Hz 1H), 7.46 (t, J=7.2 Hz, 1H), 7.37-7.29 (m, 4H), 7.25-7.22 (m, 1H), 4.40-4.39 (m, 1H), 3.56 (t, J=5.6 Hz, 2H), 3.35 (s, 3H), 3.12-3.05 (m, 2H), 3.02-2.96 (m, 1H), 2.84-2.77 (m, 3H), 2.70-2.69 (m, 1H), 2.66 (t, J=8.8 Hz, 1H), 1.86-1.73 (m, 7H), 1.48-1.35 (m, 3H). LCMS (M+H): 473.45.

Example 133: 1-((3S,4R)-1-(2-Methoxyethyl)-4-phenylpyrrolidin-3-yl)-3-(6-(trifluoromethyl)-[1,3]dioxolo[4,5-g]quinolin-7-yl)urea $^1$H NMR (CDCl$_3$, 400 MHz): δ 8.57 (s, 1H), 7.35-7.30 (m, 5H), 7.24-7.22 (m, 1H), 7.02 (s, 1H), 6.12 (s, 2H), 5.68-5.66 (m, 1H), 4.35-4.30 (m, 1H), 3.53-3.49 (m, 3H), 3.39-3.27 (m, 1H) 3.26 (s, 3H), 3.18-3.16 (m, 1H), 2.88-2.69 (m, 3H), 2.46-2.42 (m, 1H). LCMS (M+H): 503.35.

Example 134: 1-(6-(Difluoromethyl)-[1,3]dioxolo[4,5-g]quinolin-7-yl)-3-((3S,4R)-4-(3-fluorophenyl)-1-(2-methoxyethyl)pyrrolidin-3-yl)urea 1H NMR (DMSO-d$_6$, 300 MHz): δ 8.58 (s, 1H), 8.00 (s, 1H), 7.45-7.31 (m, 4H), 7.21-7.17 (m, 2H), 7.07-7.02 (m, 2H), 6.21 (s, 2H), 4.19-4.16 (m, 1H), 3.46 (t, J=5.7 Hz, 2H), 3.25 (s, 3H), 3.16-3.14 (m, 2H), 2.98-2.92 (m, 1H), 2.72-2.63 (m, 4H). LCMS (M+H): 503.35.

Example 135: 1-([1,3]Dioxolo[4,5-g]quinolin-7-yl)-3-((3S,4R)-4-(3,4-difluorophenyl)-1-(2-methoxyethyl)pyrrolidin-3-yl)urea $^1$H NMR (CDCl$_3$, 400 MHz): δ 8.51 (s, 1H), 8.36 (s, 1H), 7.29 (s, 1H), 7.14-7.08 (m, 2H), 7.07-7.00 (m, 2H), 6.07 (s, 2H), 5.48-5.46 (m, 1H), 4.15-4.12 (m, 1H), 3.59-3.56 (m, 2H), 3.45-3.42 (m, 2H), 3.34 (s, 3H), 3.26-3.23 (m, 1H), 2.91-2.86 (m, 2H), 2.82-2.78 (m, 1H), 2.49-2.44 (m, 1H). LCMS (M+H): 471.34.

Example 136: 1-(6-Fluoro-2-phenylquinolin-3-yl)-3-((3S,4R)-4-(3-fluorophenyl)-1-(2-methoxyethyl)pyrrolidin-3-yl)urea $^1$HNMR (CD$_3$OD, 300 MHz): 8.65 (s, 1H), 8.00-7.95 (m, 1H), 7.61-7.41 (m, 7H), 7.35-7.28 (m, 1H), 7.13-7.05 (m, 2H), 6.99-6.93 (m, 1H), 4.32-4.26 (m, 1H), 3.54 (t, J=5.7 Hz, 2H), 3.32 (s, 3H), 3.23-3.00 (m, 3H), 2.79-2.58 (m, 4H). LCMS (M+H): 503.48.

Example 137: 1-((3S,4R)-4-(3-Fluorophenyl)-1-(2-methoxyethyl)pyrrolidin-3-yl)-3-(2-phenyl-5,6,7,8-tetrahydroquinolin-3-yl)urea $^1$HNMR (CD$_3$OD, 300 MHz): 7.77 (s, 1H), 7.48-7.41 (m, 5H), 7.35-7.28 (m, 1H), 7.10-7.03 (m, 2H), 6.98-6.92 (m, 1H), 4.27-4.22 (m, 1H), 3.53 (t, J=5.7 Hz, 2H), 3.33 (s, 3H), 3.24-3.18 (m, 1H), 3.12-2.97 (m, 2H), 2.85-2.71 (m, 7H), 2.67-2.57 (m, 1H), 1.90-1.82 (m, 4H). LCMS (M+H): 489.48.

Example 138: 1-((3S,4R)-1-(2-Methoxyethyl)-4-phenylpyrrolidin-3-yl)-3-(7-methyl-2-phenyl-1,8-naphthyridin-3-yl)urea $^1$HNMR (CDCl$_3$, 300 MHz): δ 8.89-8.88 (m, 1H), 8.05 (d, J=8.1 Hz, 1H), 7.74 (d, J=6.0 Hz, 2H), 7.54-7.47 (m, 3H), 7.35-7.30 (m, 3H), 7.26-7.24 (m, 3H), 4.30-4.28 (m, 1H), 3.48-3.44 (m, 2H), 3.33-3.28 (m, 1H), 3.24 (s, 3H), 3.22-3.13 (m, 2H), 2.76 (s, 3H), 2.54-2.50 (m, 3H), 2.48-2.30 (m, 1H). LCMS (M+H): 482.46.

Example 139: 1-((3S,4R)-4-(3-Fluorophenyl)-1-(2-methoxyethyl)pyrrolidin-3-yl)-3-(2-phenylquinolin-3-yl)urea $^1$HNMR (CDCl$_3$, 400 MHz): δ 8.85 (s, 1H), 8.05 (d, J=8.8 Hz, 1H), 7.81 (d, J=8.0 Hz, 1H), 7.64-7.49 (m, 7H), 7.30-7.26 (m, 1H), 7.04 (d, J=8.0 Hz, 1H), 6.97-6.90 (m, 2H), 5.22-5.21 (m, 1H), 4.26-4.24 (m, 1H), 3.47-3.37 (m, 2H), 3.26 (s, 3H), 3.20-3.15 (m, 2H) 3.01-2.98 (m, 1H), 2.73-2.65 (m, 2H), 2.59-2.56 (m, 1H), 2.31-2.37 (m, 1H). LCMS (M+H): 485.47.

Example 140: 1-([1,3]Dioxolo[4,5-g]quinolin-7-yl)-3-((3S,4R)-4-(3-fluorophenyl)-1-(2-methoxyethyl)pyrrolidin-3-yl)urea $^1$HNMR (CDCl$_3$, 300 MHz): δ 8.49 (s, 1H), 8.38 (s, 1H), 7.32-7.27 (m, 3H), 7.07 (d, J=7.5 Hz, 1H), 6.97-6.92 (m, 3H), 6.07 (s, 2H), 5.48-5.46 (m, 1H), 4.18-4.15 (m, 1H), 3.58-3.52 (m, 3H), 3.42-3.40 (m, 1H), 3.33 (s, 3H), 3.21-3.18 (m, 1H), 2.87-2.72 (m, 3H), 2.45-2.39 (m, 1H). LCMS (M+H): 453.38.

Example 141: 1-(2-(2,4-Difluorophenyl)quinolin-3-yl)-3-((3S,4R)-1-(2-methoxyethyl)-4-phenylpyrrolidin-3-yl)urea $^1$H NMR (CDCl$_3$, 400 MHz): δ 8.70 (s, 1H), 8.05 (d, J=8.8 Hz, 1H), 7.82 (d, J=7.6 Hz, 1H), 7.65-7.51 (m, 3H), 7.34-7.30 (m, 2H), 7.26-7.22 (m, 4H), 7.08-7.04 (m, 1H), 6.99-6.94 (m, 1H), 5.32-5.29 (m, 1H), 4.28-4.25 (m, 1H), 3.45 (t, J=4.8 Hz, 2H), 3.36-3.29 (m, 2H), 3.23 (s, 3H), 3.09-3.06 (m, 1H), 2.76-2.69 (m, 2H), 2.63-2.59 (m, 1H), 2.36-2.32 (m, 1H). LCMS (M+H): 503.48.

Example 142: 1-(2-(3,5-Difluorophenyl)quinolin-3-yl)-3-((3S,4R)-1-(2-methoxyethyl)-4-phenylpyrrolidin-3-yl)urea $^1$HNMR (CDCl$_3$, 300 MHz): δ 8.75 (s, 1H), 8.05 (d, J=8.4 Hz, 1H), 7.82 (d, J=8.1 Hz, 1H), 7.65-7.60 (m, 1H), 7.55-7.50 (m, 1H), 7.35-7.30 (m, 8H), 6.96-6.90 (m, 1H), 5.40-5.38 (m, 1H), 4.19-4.16 (m, 1H), 3.38 (t, J=5.4 Hz, 2H), 3.24-3.21 (m, 3H), 3.13 (s, 3H), 2.73-2.67 (m, 2H), 2.60-2.55 (m, 1H), 2.30-2.28 (m, 1H). LCMS (M+H): 502.99.

Example 143: 1-(4-(Benzyloxy)-1-(2-methoxyethyl)pyrrolidin-3-yl)-3-(6-methyl-[1,3]dioxolo[4,5-g]quinolin-7-yl)urea $^1$H NMR (CD$_3$OD, 300 MHz): δ 8.29 (s, 1H), 7.38-7.25 (m, 5H), 7.17 (s, 1H), 7.09 (s, 1H), 6.09 (s, 2H), 4.70 (d, J=10.4 Hz, 1H), 4.59 (d, J=12.0 Hz, 1H), 4.28-4.25 (m, 1H), 3.98-3.94 (m, 1H), 3.52 (t, J=5.4 Hz, 2H), 3.33 (s, 3H), 3.16-3.10 (m, 1H), 3.04-2.99 (m, 1H), 2.74-2.60 (m, 4H), 2.56 (s, 3H). LCMS (M+H)$^+$:479.15.

Example 144: 1-(1-Chloro-3-methylisoquinolin-4-yl)-3-((3S,4R)-1-(2-methoxyethyl)-4-phenylpyrrolidin-3-yl)urea $^1$H NMR (CD$_3$OD, 400 MHz): δ 8.31 (d, J=8.4 Hz, 1H), 7.87-7.85 (m, 1H), 7.80-7.77 (m, 1H), 7.72-7.68 (m, 1H), 7.33-7.32 (m, 4H), 7.26-7.22 (m, 1H), 4.45-4.41 (m, 1H), 3.55-3.47 (m, 2H), 3.33 (s, 3H), 3.20-3.06 (m, 2H), 2.90-2.64 (m, 5H), 2.48 (s, 3H). LCMS 439.08.

Example 145: 1-(1,3-Diphenylisoquinolin-4-yl)-3-((3S,4R)-1-(2-methoxyethyl)-4-phenylpyrrolidin-3-yl)urea $^1$H NMR (CD$_3$OD, 400 MHz): δ 8.04 (d, J=8.4 Hz, 2H), 7.78 (t, J=6.8 Hz, 1H), 7.68-7.67 (m, 4H), 7.62-7.54 (m, 5H), 7.38-7.24 (m, 7H), 4.40-4.36 (m, 1H), 3.50-3.47 (m, 2H), 3.30 (s, 3H), 3.25-3.24 (m, 1H), 2.80-2.68 (m, 5H), 2.50-2.48 (m, 1H). LCMS (M+H): 543.99.

Example 146: 1-((3S,4R)-4-(3-Fluorophenyl)-1-(2-methoxyethyl)pyrrolidin-3-yl)-3-(3-methyl-1-(1-methyl-1H-pyrazol-4-yl)isoquinolin-4-yl)urea $^1$H NMR (CD$_3$OD, 400 MHz): δ 8.29 (d, J=8.8 Hz, 1H), 8.12 (s, 1H), 7.93 (s, 1H), 7.89 (d, J=7.6 Hz, 1H), 7.75-7.71 (m, 1H), 7.62-7.58 (m, 1H), 7.36-7.31 (m, 1H), 7.15-7.09 (m, 2H), 6.99-6.95 (m, 1H), 4.45-4.40 (m, 1H), 4.03 (s, 3H) 3.54-3.51 (m, 3H), 3.33 (s, 3H), 3.12-3.05 (m, 1H), 2.77-2.64 (m, 5H), 2.55 (s, 3H). LCMS (M+H): 503.44.

Example 147: 1-((3S,4R)-1-(2-Methoxyethyl)-4-phenylpyrrolidin-3-yl)-3-(1-(1-methyl-1H-pyrazol-4-yl)-3-phenylisoquinolin-4-yl)urea $^1$H NMR (DMSO d$_6$, 300 MHz): δ 8.41 (s, 1H), 8.38-8.37 (m, 1H), 8.00 (s, 1H), 7.91 (d, J=8.1 Hz, 2H), 7.80-7.64 (m, 4H), 7.40-7.39 (m, 3H), 7.34-7.22 (m, 5H), 6.70 (br s, 1H), 4.19-4.11 (m, 1H), 3.96 (s, 3H) 3.46-3.43 (m, 2H), 3.25 (s, 3H), 3.19-3.12 (m, 2H), 2.91-2.75 (m, 1H), 2.71-2.54 (m, 4H). LCMS (M+H): 547.12.

Example 148: 1-(Isoquinolin-4-yl)-3-((3S,4R)-1-(2-methoxyethyl)-4-phenylpyrrolidin-3-yl)urea $^1$H NMR (DMSO d$_6$, 300 MHz): δ 9.07 (d, J=9.9 Hz 1H), 8.96 (d, J=6.9 Hz, 1H), 8.54 (br s 1H), 8.25-8.16 (m, 1H), 8.07 (t, J=9.0 Hz, 2H), 7.84-7.66 (m, 2H), 7.37-7.22 (m, 4H), 7.07 (d, J=7.5 Hz 1H), 4.25-4.20 (m, 1H), 3.48 (t, J=5.4 Hz, 2H), 3.26 (s, 3H), 3.18-3.08 (m, 2H), 2.98-2.85 (m, 1H), 2.78-2.60 (m, 3H), 2.48-2.39 (m, 1H). LCMS (M+H): 391.47.

Example 149: 1-((3S,4R)-1-(2-Methoxyethyl)-4-phenylpyrrolidin-3-yl)-3-(3-phenylisoquinolin-4-yl)urea $^1$H NMR (DMSO d$_6$, 300 MHz): δ 9.29 (s, 1H), 8.15 (d, J=8.1 Hz, 1H), 7.95 (br s, 1H), 7.86-7.75 (m, 2H), 7.70-7.65 (m, 3H), 7.41-7.20 (m, 8H), 6.67 (br s, 1H), 4.20-4.08 (m, 1H), 3.44 (t, J=5.7 Hz, 2H), 3.25 (s, 3H), 3.13-3.06 (m, 2H), 2.84 (t, J=8.7 Hz, 1H), 2.65-2.58 (m, 3H), 2.46-2.42 (m, 1H). LCMS (M+H): 467.03.

Example 150: 1-((3S,4R)-1-(2-Methoxyethyl)-4-phenylpyrrolidin-3-yl)-3-(3-methylisoquinolin-4-yl)urea $^1$H NMR (DMSO d$_6$, 300 MHz): δ 9.09 (s, 1H), 8.08 (s, 1H), 8.05-8.02 (m, 1H), 7.80-7.69 (m, 2H), 7.58 (t, J=7.8 Hz, 1H), 7.33-7.31 (m, 5H), 7.24-7.23 (m, 1H), 6.70 (d, J=8.1 Hz, 1H), 4.32-4.11 (m, 1H), 3.48-3.45 (m, 2H), 3.25 (s, 3H), 3.21-3.11 (m, 2H), 2.98-2.91 (m, 1H), 2.68-2.62 (m, 4H), 2.46 (s, 3H). LCMS (M+H): 405.02.

Example 151: 1-(1-Cyano-3-phenylisoquinolin-4-yl)-3-((3S,4R)-1-(2-methoxyethyl)-4-phenylpyrrolidin-3-yl)urea $^1$H NMR (DMSO d$_6$, 300 MHz): δ 8.52-8.39 (m, 1H), 8.27-8.24 (m, 1H), 8.04-8.02 (m, 1H), 7.97-7.91 (m, 2H), 7.65-7.62 (m, 2H), 7.46-7.44 (m, 3H), 7.33-7.19 (m, 5H), 6.88 (d, J=8.4 Hz, 1H), 4.09-4.07 (m, 1H), 3.45-3.41 (m, 2H), 3.24 (s, 3H), 3.17-3.05 (m, 3H), 2.82-2.76 (m, 1H), 2.63-2.56 (m, 3H). LCMS (M+H): 492.25.

Example 152: 1-(1-Chloro-3-phenylisoquinolin-4-yl)-3-((3S,4R)-4-(3-fluorophenyl)-1-(2-methoxyethyl)pyrrolidin-3-yl)urea $^1$H NMR (DMSO d$_6$, 400 MHz): δ 8.30 (d, J=8.4 Hz, 1H), 8.15-8.02 (m, 1H), 7.95-7.88 (m, 2H), 7.85-7.80 (m, 1H), 7.66-7.65 (m, 2H), 7.42-7.41 (m, 3H), 7.37-7.31 (m, 1H), 7.09-7.02 (m, 3H), 6.78-6.65 (m, 1H), 4.19-4.05 (m, 1H), 3.45-3.41 (m, 2H), 3.24 (s, 3H), 3.17-3.05 (m, 3H), 2.92-2.83 (m, 1H), 2.66-2.56 (m, 3H). LCMS (M+H): 519.38.

Example 153: 1-((3S,4R)-4-(3-Fluorophenyl)-1-(2-methoxyethyl)pyrrolidin-3-yl)-3-(3-phenylisoquinolin-4-yl)urea $^1$H NMR (CD$_3$OD, 300 MHz): δ 9.22 (s, 1H), 8.17 (d, J=8.4 Hz, 1H), 7.98 (d, J=8.1 Hz, 1H), 7.84-7.79 (m, 1H), 7.73-7.67 (m, 1H), 7.62-7.61 (m, 2H), 7.42-7.40 (m, 3H), 7.36-7.29 (m, 1H), 7.08-6.95 (m, 3H), 4.22-4.32 (m, 1H), 3.51-3.48 (m, 2H), 3.29 (s, 3H), 3.22-3.19 (m, 1H), 3.08-3.02 (m, 1H), 2.95-2.85 (m, 1H), 2.72-2.67 (m, 3H), 2.55-2.48 (m, 1H). LCMS (M+H): 485.38.

Example 154: 1-(1-Cyano-3-phenylisoquinolin-4-yl)-3-((3S,4R)-4-(3-fluorophenyl)-1-(2-methoxyethyl)pyrrolidin-3-yl)urea $^1$H NMR (CD$_3$OD, 400 MHz): δ 8.35-8.32 (m, 1H), 8.09 (d, J=7.2 Hz, 1H), 7.91-7.87 (m, 2H), 7.67-7.64 (m, 2H), 7.44-7.43 (m, 3H), 7.33-7.30 (m, 1H), 7.09-6.97 (m, 3H), 4.32-4.21 (m, 1H), 3.50-3.47 (m, 2H), 3.30 (s, 3H), 3.22-3.20 (m, 1H), 3.13-3.08 (m, 2H), 2.92-2.90 (m, 1H), 2.74-2.69 (m, 2H), 2.52-2.50 (m, 1H). LCMS (M+H): 510.41.

Example 155: 1-(1-Hydroxy-3-phenylisoquinolin-4-yl)-3-((3S,4R)-1-(2-methoxyethyl)-4-phenylpyrrolidin-3-yl)urea $^1$H NMR (DMSO d$_6$, 300 MHz): δ 11.38 (s, 1H), 8.21 (d, J=9.0 Hz, 1H), 7.72 (t, J=7.2 Hz, 1H), 7.53-7.48 (m, 4H), 7.42-7.38 (m, 3H), 7.30-7.21 (m, 6H), 6.50 (br s, 1H), 4.10-4.06 (m, 1H), 3.43-3.39 (m, 2H), 3.23 (s, 3H), 3.08-3.02 (m, 2H), 2.83-2.78 (m, 1H), 2.66-2.52 (m, 3H), 2.47-2.43 (m, 1H). LCMS (M+H): 483.49.

Example 156: 1-(1-Amino-3-phenylisoquinolin-4-yl)-3-((3S,4R)-1-(2-methoxyethyl)-4-phenylpyrrolidin-3-yl)urea $^1$H NMR (CD$_3$OD, 300 MHz): δ 8.13 (d, J=8.1 Hz, 1H), 7.77-7.73 (m, 1H), 7.71-7.64 (m, 1H), 7.62-7.48 (m, 3H), 7.42-7.30 (m, 3H), 7.29-7.18 (m, 5H), 4.34-4.28 (m, 1H), 3.50-3.46 (m, 2H), 3.31 (s, 3H), 3.28-3.22 (m, 1H), 2.94-2.90 (m, 2H), 2.64-2.59 (m, 3H), 2.54-2.48 (m, 1H). LCMS (M+H): 482.07.

Example 157: 1-(1-Methoxy-3-phenylisoquinolin-4-yl)-3-((3S,4R)-1-(2-methoxyethyl)-4-phenylpyrrolidin-3-yl)urea $^1$H NMR (DMSO d$_6$, 300 MHz): δ 8.19 (d, J=8.1 Hz, 1H), 7.75-7.59 (m, 6H), 7.39-7.22 (m, 8H), 6.66 (br s, 1H), 4.22-4.10 (m, 1H), 4.09 (s, 3H), 3.45-3.42 (m, 2H), 3.25 (s, 3H), 3.08-3.06 (m, 2H), 2.84-2.80 (m, 1H), 2.62-2.54 (m, 4H). LCMS (M+H): 497.49.

Example 158: 1-((3S,4R)-1-(2-Methoxyethyl)-4-phenylpyrrolidin-3-yl)-3-(1-methyl-3-phenylisoquinolin-4-yl)urea $^1$H NMR (CD$_3$OD, 300 MHz): δ 8.25 (d, J=8.4 Hz, 1H), 7.95 (d, J=7.8 Hz, 1H), 7.77 (t, J=8.1 Hz, 1H), 7.68 (t, J=7.2 Hz, 1H), 7.62-7.56 (m, 2H), 7.42-7.36 (m, 3H), 7.34-7.23 (m, 5H), 4.33-4.28 (m, 1H), 3.49 (t, J=5.7 Hz, 2H), 3.30 (s, 3H), 3.26-3.23 (m, 1H), 3.10-3.05 (m, 1H), 2.97 (s, 3H), 2.93-2.90 (m, 1H), 2.74-2.64 (m, 2H), 2.54-2.47 (m, 1H). LCMS (M+H): 481.42.

Example 159: 1-(7-Fluoro-1-methyl-3-phenylisoquinolin-4-yl)-3-((3S,4R)-1-(2-methoxyethyl)-4-phenylpyrrolidin-3-yl)urea $^1$H NMR (DMSO d$_6$, 400 MHz): δ 7.95 (dd, J=2.0 and 9.6 Hz, 1H), 7.92-7.88 (m, 2H), 7.68 (dd, J=2.4 and 9.2 Hz, 1H), 7.64-7.62 (m, 2H), 7.39-7.38 (m, 3H), 7.33-7.26 (m, 4H), 7.23 (d, J=6.8 Hz 1H), 6.65 (br s, 1H), 4.14-4.10 (m, 1H), 3.44 (t, J=5.6 Hz, 2H), 3.25 (s, 3H), 3.11-3.05 (m, 2H), 2.87 (s, 3H), 2.84-2.82 (m, 1H), 2.65-2.55 (m, 3H), 2.46 (t, J=7.2 Hz, 1H). LCMS (M+H): 499.38.

Example 160: 1-((3S,4R)-4-(3-Fluorophenyl)-1-(2-methoxyethyl)pyrrolidin-3-yl)-3-(1-(1-methyl-1H-pyrazol-4-yl)-3-phenylisoquinolin-4-yl)urea $^1$H NMR (CD$_3$OD, 300 MHz): δ 8.41 (d, J=8.4 Hz, 1H), 8.19 (s, 1H), 8.05-7.98 (m, 2H), 7.79 (t, J=8.1 Hz 1H), 7.70-7.66 (m, 3H), 7.41-7.28 (m, 4H), 7.03-6.94 (m, 3H), 4.33-4.26 (m, 1H), 4.02 (s, 3H), 3.49 (t, J=5.4 Hz 2H), 3.29 (s, 3H), 3.22-3.18 (m, 2H), 2.94-2.88 (m, 1H), 2.71-2.64 (m, 3H), 2.53-2.48 (m, 1H). LCMS (M+H): 565.18.

Example 161: 1-((3S,4R)-1-(2-Methoxyethyl)-4-phenylpyrrolidin-3-yl)-3-(3-methyl-1-(1-methyl-1H-pyrazol-4-yl)isoquinolin-4-yl)urea $^1$H NMR (CD$_3$OD, 300 MHz): δ 8.29 (d, J=8.4 Hz, 1H), 8.12 (s, 1H), 7.93 (s, 1H), 7.87 (d, J=8.1 Hz, 1H), 7.72 (t, J=8.1 Hz, 1H), 7.59 (t, J=6.9 Hz, 1H), 7.41-7.32 (m, 4H), 7.27-7.22 (m, 1H), 4.46-4.43 (m, 1H), 4.03 (s, 3H), 3.54 (t, J=5.1 Hz, 2H), 3.33 (s, 3H), 3.23-3.19 (m, 2H), 3.09-3.06 (m, 1H), 2.95-2.92 (m, 1H), 2.82-2.78 (m, 2H), 2.54 (s, 3H). LCMS (M+H): 485.20.

Example 162: 1-((3S,4R)-1-(2-Methoxyethyl)-4-phenylpyrrolidin-3-yl)-3-(1-(1-methyl-1H-pyrazol-4-yl)isoquinolin-4-yl)urea $^1$H NMR (CDCl$_3$, 300 MHz): δ 8.60 (s, 1H), 8.37 (d, J=8.4 Hz, 1H), 7.96-7.90 (m, 3H), 7.70-7.57 (m, 2H), 7.34-7.29 (m, 2H), 7.23-7.21 (m, 3H), 5.57 (br s, 1H), 4.48-4.46 (m, 1H), 4.03 (s, 3H), 3.46 (t, J=5.4 Hz, 2H), 3.41-3.38 (m, 1H), 3.31-3.27 (m, 1H), 3.24 (s, 3H), 3.14-3.10 (m, 1H), 2.94-2.88 (m, 1H), 2.77-2.70 (m, 2H), 2.47 (t, J=9.3 Hz, 1H). LCMS (M+H): 471.38.

Example 163: 1-((3S,4R)-4-(3-Fluorophenyl)-1-(2-methoxyethyl)pyrrolidin-3-yl)-3-(1-(1-methyl-1H-pyrazol-4-yl)isoquinolin-4-yl)urea $^1$H NMR (CDCl$_3$, 400 MHz): δ 8.58 (s, 1H), 8.39 (d, J=8.8 Hz, 1H), 7.98-7.92 (m, 3H), 7.71 (t, J=7.2 Hz, 1H), 7.63 (t, J=7.2 Hz, 1H), 7.29-7.27 (m, 2H), 7.03 (d, J=8.0 Hz, 1H), 6.95-6.91 (m, 2H), 5.25 (br s, 1H), 4.44-4.41 (m, 1H), 4.04 (s, 3H), 3.43 (t, J=5.2 Hz, 2H), 3.34 (t, J=8.8 Hz, 1H), 3.25 (s, 3H), 3.17-3.14 (m, 1H), 2.99-2.97 (m, 1H), 2.86 (t, J=8.0 Hz, 1H), 2.73-2.62 (m, 2H), 2.40 (t, J=9.2 Hz, 1H). LCMS (M+H): 489.48.

Example 164: 1-(3-(tert-Butyl)-1-(1-methyl-1H-pyrazol-4-yl)isoquinolin-4-yl)-3-((3S,4R)-4-(3-fluorophenyl)-1-(2-methoxyethyl)pyrrolidin-3-yl)urea $^1$H NMR (CD$_3$OD 300 MHz): 8.43-8.40 (m, 1H), 8.33 (d, J=7.5 Hz, 1H), 8.08-8.01 (m, 1H), 7.91-7.78 (m, 1H), 7.72-7.48 (m, 2H), 7.42-7.24 (m, 1H), 7.22-7.14 (m, 1H), 7.08-6.82 (m, 2H), 4.48-4.40 (m, 1H), 4.01 (s, 3H), 3.57 (t, J=5.7 Hz, 2H), 3.37 (s, 3H), 3.26-3.21 (m, 1H), 3.11-3.05 (m, 1H), 2.94-2.78 (m, 1H), 2.76-2.68 (m, 1H), 2.63-2.59 (m, 1H), 2.48-2.33 (m, 1H), 1.49 (s, 9H). LCMS (M+H): 545.53.

Example 165: 1-(3-(tert-Butyl)-1-(1-methyl-1H-pyrazol-4-yl)isoquinolin-4-yl)-3-((3S,4R)-1-(2-methoxyethyl)-4-phenylpyrrolidin-3-yl)urea $^1$H NMR (CD$_3$OD, 300 MHz): δ 8.42-8.01 (m, 3H), 7.79-7.55 (m, 3H), 7.35-7.10 (m, 5H), 4.48-4.44 (m, 1H), 4.01 (s, 3H), 3.57-3.53 (m, 2H), 3.37 (s, 3H), 3.22-3.08 (m, 2H), 2.83-2.70 (m, 4H), 2.37-2.32 (m, 1H), 1.48 (s, 9H). LCMS (M+H): 527.52.

Example 166: 1-(1-Fluoro-3-phenylisoquinolin-4-yl)-3-((3S,4R)-1-(2-methoxyethyl)-4-phenylpyrrolidin-3-yl)urea $^1$H NMR (DMSO d$_6$ 400 MHz): 8.17 (d, J=8.4 Hz, 1H), 7.96 (br s, 1H), 7.99-7.89 (m, 2H), 7.78 (t, J=8.0 Hz, 1H), 7.68-7.64 (m, 2H), 7.44-7.39 (m, 3H), 7.33-7.20 (m, 5H), 6.71 (br s, 1H), 4.15-4.10 (m, 1H), 3.44 (t, J=4.8 Hz, 2H), 3.38-3.34 (m, 1H), 3.24 (s, 3H), 3.14-3.05 (m, 2H), 2.86-2.80 (m, 1H), 2.69-2.58 (m, 3H). LCMS (M+H): 485.40.

Example 167: 1-((3S,4R)-4-(3-Fluorophenyl)-1-(2-methoxyethyl)pyrrolidin-3-yl)-3-(1-methyl-3-phenyl isoquinolin-4-yl)urea $^1$H NMR (CD$_3$OD, 300 MHz): 8.27 (d, J=8.4 Hz, 1H), 7.96 (d, J=7.5 Hz, 1H), 7.79 (t, J=5.1 Hz, 1H), 7.69 (t, J=7.2 Hz, 1H), 7.62-7.56 (m, 2H), 7.41-7.28 (m, 4H), 7.03-6.94 (m, 3H), 4.29-4.25 (m, 1H), 3.49 (t, J=5.4 Hz, 2H), 3.34 (s, 3H), 3.28-3.16 (m, 2H), 3.09-3.04 (m, 1H), 2.97 (s, 3H), 2.92-2.86 (m, 1H), 2.68-2.64 (m, 2H), 2.53-2.48 (m, 1H). LCMS (M+H): 499.43.

Example 168: 1-(7-Methoxy-1-methyl-3-phenylisoquinolin-4-yl)-3-((3S,4R)-1-(2-methoxyethyl)-4-phenylpyrrolidin-3-yl)urea $^1$H NMR (CD$_3$OD 400 MHz): 7.85 (d, J=8.4 Hz, 1H), 7.58-7.54 (m, 2H), 7.46 (d, J=2.0 Hz, 1H), 7.41-7.37 (m, 4H), 7.31 (d, J=6.8 Hz, 2H), 7.25 (J=6.8 Hz, 2H), 7.23-7.19 (m, 1H), 4.31-4.26 (m, 1H), 3.99 (s, 3H), 3.52-3.48 (m, 2H), 3.42-3.38 (m, 1H), 3.30 (s, 3H), 3.28-3.20 (m, 1H), 3.12-3.06 (m, 1H), 2.93 (s, 3H), 2.78-2.74 (m, 3H), 2.58-2.54 (m, 1H). LCMS (M+H): 511.45.

Example 169: 1-(6-Methoxy-1-methyl-3-phenylisoquinolin-4-yl)-3-((3S,4R)-1-(2-methoxyethyl)-4-phenylpyrrolidin-3-yl)urea $^1$H NMR (CDCl$_3$, 400 MHz): δ 8.07 (d, J=9.6 Hz, 1H), 7.65 (d, J=7.2 Hz, 2H), 7.42-7.35 (m, 3H), 7.28-7.25 (m, 1H), 7.22-7.19 (m, 4H), 7.09 (d, J=6.8 Hz, 2H), 4.86 (br s, 1H), 4.38-4.33 (m, 1H), 3.78 (s, 3H), 3.37-3.35 (m, 2H), 3.23 (s, 3H), 3.18-3.16 (m, 1H), 2.98 (s, 3H), 2.89-2.87 (m, 1H), 2.82-2.76 (m, 2H), 2.63-2.55 (m, 2H), 2.29 (t, J=9.6 Hz, 1H). LCMS (M+H): 511.45.

Example 170: 1-(1,6-Dimethyl-3-phenylisoquinolin-4-yl)-3-((3S,4R)-1-(2-methoxyethyl)-4-phenylpyrrolidin-3-yl)urea $^1$H NMR (CDCl$_3$ 400 MHz): 8.05 (d, J=8.4 Hz, 1H), 7.79 (s, 1H), 7.67 (d, J=7.2 Hz, 2H), 7.46-7.34 (m, 5H), 7.29-7.26 (m, 2H), 7.22 (d, J=7.2 Hz, 1H), 7.12 (d, J=7.2 Hz, 2H), 4.85 (br s, 1H), 4.42-4.28 (m, 1H), 3.39-3.35 (m, 2H), 3.21 (s, 3H), 2.99 (s, 3H), 2.92-2.85 (m, 1H), 2.83-2.74 (m, 2H), 2.64-2.60 (m, 2H), 2.51 (s, 3H), 2.33-2.29 (m, 2H). LCMS (M+H): 495.47.

Example 171: 1-((3S,4R)-1-(2-Methoxyethyl)-4-phenylpyrrolidin-3-yl)-3-(3-phenyl-1-(pyridin-3-yl)isoquinolin-4-yl)urea $^1$H NMR (DMSO d$_6$, 300 MHz): δ 8.91 (d, J=1.5 Hz, 1H), 8.75 (dd, J=1.5 and 4.8 Hz, 1H), 8.15 (dt, J=1.8 and 3.6 Hz, 1H), 8.00-7.96 (m, 3H), 7.83 (t, J=6.9 Hz, 1H), 7.73-7.59 (m, 4H), 7.42-7.21 (m, 8H), 6.73 (br s, 1H), 4.22-4.13 (m, 1H), 3.45 (t, J=5.7 Hz, 2H), 3.26 (s, 3H), 3.17-3.12 (m, 2H), 2.86-2.83 (m, 1H), 2.70-2.55 (m, 3H), 2.49-2.47 (m, 1H). LCMS (M+H): 544.51.

Example 172: 1-((3S,4R)-1-(2-Methoxyethyl)-4-phenylpyrrolidin-3-yl)-3-(1-morpholino-3-phenylisoquinolin-4-yl)urea $^1$H NMR (CD$_3$OD, 400 MHz): 8.19 (d, J=7.6 Hz, 1H), 7.88-7.82 (m, 3H), 7.69 (d, J=6.4 Hz, 1H), 7.57 (t, J=7.2 Hz, 1H), 7.36-7.28 (m, 4H), 7.30-7.25 (m, 2H), 7.23 (d, J=7.2 Hz, 2H), 4.33-4.28 (m, 1H), 3.96 (t, J=4.4 Hz, 4H), 3.68-3.52 (m, 2H), 3.55-3.44 (m, 4H), 3.30 (s, 3H), 3.27-3.18 (m, 2H), 2.96-2.82 (m, 2H), 2.74-2.63 (m, 2H), 2.53-2.48 (m, 1H). LCMS (M+H): 552.52.

Example 173: 1-(1-(4-Hydroxypiperidin-1-yl)-3-phenylisoquinolin-4-yl)-3-((3S,4R)-1-(2-methoxyethyl)-4-phenylpyrrolidin-3-yl)urea ¹H NMR (CD₃OD 400 MHz): 8.13 (d, J=8.0 Hz, 1H), 7.88-7.82 (m, 1H), 7.74-7.63 (m, 3H), 7.56 (t, J=8.4 Hz, 1H), 7.42-7.28 (m, 5H), 7.25-7.19 (m, 3H), 4.33-4.29 (m, 1H), 3.86-3.79 (m, 3H), 3.52-3.46 (m, 2H), 3.30 (s, 3H), 3.15 (t, J=9.6 Hz, 4H), 2.96-2.88 (m, 2H), 2.74-2.65 (m, 2H), 2.53-2.47 (m, 1H), 2.07-2.05 (m, 2H), 1.86-1.79 (m, 2H). LCMS (M+H): 566.56.

Example 174: 1-(3-(3-Fluorophenyl)-1-methylisoquinolin-4-yl)-3-((3S,4R)-1-(2-methoxyethyl)-4-phenylpyrrolidin-3-yl)urea ¹H NMR (CD₃OD, 400 MHz): δ 8.27 (d, J=8.4 Hz, 1H), 7.97-7.95 (m, 1H), 7.79 (t, J=7.2 Hz, 1H), 7.70 (t, J=8.0 Hz, 1H), 7.44-7.38 (m, 3H), 7.32-7.20 (m, 5H), 7.12 (t, J=6.8 Hz, 1H), 4.31-4.26 (m, 1H), 3.52-3.47 (m, 2H), 3.30 (s, 3H), 3.25-3.14 (m, 2H), 2.98 (s, 3H), 2.88-2.82 (m, 1H), 2.78-2.62 (m, 3H), 2.52-2.47 (m, 1H). LCMS (M+H): 499.47.

Example 175: 1-(3-(2-Fluorophenyl)-1-methylisoquinolin-4-yl)-3-((3S,4R)-1-(2-methoxyethyl)-4-phenylpyrrolidin-3-yl)urea ¹H NMR (CDCl₃, 400 MHz): δ 8.18 (d, J=8.4 Hz, 1H), 8.03 (d, J=8.4 Hz, 1H), 7.73-7.64 (m, 2H), 7.57-7.51 (m, 1H), 7.39-7.35 (m, 1H), 7.29-7.28 (m, 2H), 7.23-7.20 (m, 2H), 7.16-7.08 (m, 3H), 4.82 (br s, 1H), 4.25-4.22 (m, 1H), 3.41-3.43 (m, 2H), 3.28-3.26 (m, 1H), 3.21 (s, 3H), 3.03 (s, 3H), 2.94-2.90 (m, 2H), 2.71-2.54 (m, 3H), 2.33-2.30 (m, 1H). LCMS (M+H): 499.47.

Example 176: 1-(6,7-Dimethoxy-1-methyl-3-phenylisoquinolin-4-yl)-3-((3S,4R)-1-(2-methoxyethyl)-4-phenylpyrrolidin-3-yl)urea ¹H NMR (CDCl₃, 300 MHz): δ 7.63 (d, J=6.9 Hz, 2H), 7.42-7.32 (m, 5H), 7.23-7.19 (m, 3H), 7.09 (d, J=6.6 Hz, 2H), 4.85 (br s, 1H), 4.45-4.37 (m, 1H), 4.08 (s, 3H), 3.83 (s, 3H), 3.40-3.36 (m, 2H), 3.24 (s, 3H), 3.23-3.22 (m, 1H), 2.96 (s, 3H), 2.87-2.77 (m, 3H), 2.61-2.56 (m, 2H), 2.30 (t, J=8.4 Hz, 1H). LCMS (M+H): 541.50.

Example 177: 1-(6-Fluoro-1-methyl-3-phenylisoquinolin-4-yl)-3-((3S,4R)-1-(2-methoxyethyl)-4-phenylpyrrolidin-3-yl)urea ¹H NMR (CD₃OD, 400 MHz): δ 8.36-8.32 (m, 1H), 7.57-7.45 (m, 4H), 7.39-7.38 (m, 3H), 7.33-7.22 (m, 5H), 4.30-4.28 (m, 1H), 3.52-3.51 (m, 2H), 3.31 (s, 3H), 3.31-3.30 (m, 2H), 3.11-3.09 (m, 1H), 2.96 (s, 3H), 2.79-2.73 (m, 3H), 2.57-2.55 (m, 1H). LCMS (M+H): 499.51.

Example 178: 1-(1,7-Dimethyl-3-phenylisoquinolin-4-yl)-3-((3S,4R)-1-(2-methoxyethyl)-4-phenylpyrrolidin-3-yl)urea ¹H NMR (CD₃OD, 400 MHz): δ 8.03 (s, 1H), 7.84 (d, J=8.0 Hz, 1H), 7.62 (d, J=8.8 Hz, 1H), 7.58-7.56 (m, 2H), 7.39-7.36 (m, 3H), 7.33-7.29 (m, 2H), 7.25-7.21 (m, 3H), 4.32-4.28 (m, 1H), 3.52-3.48 (m, 2H), 3.30 (s, 3H), 3.24-3.22 (m, 1H), 3.12-2.99 (m, 1H), 2.95-2.93 (m, 2H), 2.92 (s, 3H), 2.80-2.70 (m, 3H), 2.59 (s, 3H), 2.53-2.48 (m, 1H). LCMS (M+H): 495.55.

Example 179: 4-(3-((3S,4R)-1-(2-Methoxyethyl)-4-phenylpyrrolidin-3-yl)ureido)-3-phenylisoquinoline-1-carboxamide ¹H NMR CD₃OD, 300 MHz): δ 8.95 (dd, J=2.7 Hz and 10.8 Hz, 1H), 8.08-8.03 (m, 1H), 7.71-7.69 (m, 3H), 7.63-7.56 (m, 2H), 7.41-7.33 (m, 5H), 7.31-7.25 (m, 2H), 4.32-4.27 (m, 1H), 3.52 (t, J=4.5 Hz, 2H), 3.31 (s, 3H), 3.17-3.11 (m, 2H), 2.97 (t, J=8.1 Hz, 1H), 2.82-2.74 (m, 3H), 2.59 (t, J=9.3 Hz, 1H). LCMS (M+H): 510.54.

Example 180: 1-(8-Methoxy-1-methyl-3-phenylisoquinolin-4-yl)-3-((3S,4R)-1-(2-methoxyethyl)-4-phenylpyrrolidin-3-yl)urea ¹H NMR (CD₃OD, 400 MHz): δ 8.00 (d, J=8.4 Hz, 2H), 7.91 (s, 1H), 7.60 (d, J=8.4 Hz, 1H), 7.49-7.42 (m, 3H), 7.29-7.26 (m, 3H), 7.23 (d, J=8.0 Hz, 1H), 7.20 (d, J=6.8 Hz 1H), 7.03 (d, J=8.4 Hz 1H), 4.44-4.39 (m, 1H), 4.02 (s, 3H), 3.54 (t, J=5.6 Hz, 2H), 3.48-3.46 (m, 1H), 3.33 (s, 3H), 3.14 (s, 3H), 3.08-3.02 (m, 1H), 2.91-2.87 (m, 3H), 2.80-2.71 (m, 2H). LCMS (M+H): 510.94.

Example 181: 1-(8-Fluoro-3-phenylisoquinolin-4-yl)-3-((3S,4R)-1-(2-methoxyethyl)-4-phenylpyrrolidin-3-yl)urea ¹H NMR (CD₃OD, 400 MHz): δ 9.22 (s, 1H), 8.15 (d, J=8.0 Hz, 1H), 7.98-7.86 (m, 1H), 7.82-7.78 (m, 1H), 7.70-7.68 (m, 1H), 7.62-7.58 (m, 1H), 7.45-7.39 (m, 3H), 7.34-7.29 (m, 1H), 7.26-7.15 (m, 3H) 7.02-6.94 (m, 1H), 4.35-4.22 (m, 1H), 3.50 (t, J=4.4 Hz, 2H), 3.37-3.35 (m, 1H), 3.30 (s, 3H), 3.26-3.22 (m, 1H), 3.12-3.08 (m, 1H), 2.95-2.92 (m, 1H), 2.78-2.66 (m, 2H), 2.56 (t, J=7.6 Hz, 1H). LCMS (M+H): 485.35.

Example 182: 1-(7-Fluoro-3-phenylisoquinolin-4-yl)-3-((3S,4R)-1-(2-methoxyethyl)-4-phenylpyrrolidin-3-yl)urea ¹H NMR (CD₃OD, 300 MHz): δ 9.20 (s, 1H), 8.01-7.96 (m, 1H), 7.84 (dd, J=2.4 and 9.0 Hz, 1H), 7.64-7.57 (m, 3H), 7.41-7.39 (m, 3H), 7.35-7.23 (m, 5H), 4.32-4.28 (m, 1H), 3.53-3.50 (m, 2H), 3.33 (s, 3H), 3.24-3.22 (m, 1H), 3.12-3.07 (m, 1H), 2.98-2.94 (m, 1H), 2.80-2.74 (m, 3H), 2.56-2.54 (m, 1H). LCMS (M+H): 484.88.

Example 183: 1-(7-fluoro-3-phenylisoquinolin-4-yl)-3-((3S,4R)-4-(3-fluorophenyl)-1-(2-methoxyethyl)pyrrolidin-3-yl)urea ¹H NMR (CD₃OD, 300 MHz): δ 9.21 (s, 1H), 8.04-7.99 (m, 1H), 7.84 (dd, J=2.4 and 9.0 Hz, 1H), 7.65-7.58 (m, 3H), 7.42-7.29 (m, 4H), 7.09-6.95 (m, 3H), 4.32-4.28 (m, 1H), 3.50 (t, J=5.7 Hz, 2H), 3.31 (s, 3H), 3.24-3.19 (m, 1H), 3.10-3.07 (m, 1H), 2.95-2.90 (m, 1H), 2.79-2.65 (m, 3H), 2.56-2.54 (m, 1H).). LCMS (M+H): 502.82.

Example 184: 1-(5-Methoxy-3-phenylisoquinolin-4-yl)-3-((3S,4R)-1-(2-methoxyethyl)-4-phenylpyrrolidin-3-yl)urea ¹H NMR (CD₃OD, 400 MHz): δ 8.99 (s, 1H), 7.58 (d, J=8.0 Hz, 1H), 7.53-7.52 (m, 2H), 7.48 (d, J=8.0 Hz, 1H), 7.28-7.26 (m, 3H), 7.19 (d, J=7.2 Hz, 2H), 7.15-7.10 (m, 4H), 4.07-4.09 (m, 1H), 3.69 (s, 3H), 3.42-3.41 (m, 2H), 3.31-3.29 (m, 1H), 3.21 (s, 3H), 3.04-3.02 (m, 1H), 2.86-2.82 (m, 1H), 2.72-2.64 (m, 3H), 2.50-2.48 (m, 1H). LCMS (M+H): 497.39.

Example 185: 1-(7-Fluoro-1-methyl-3-phenylisoquinolin-4-yl)-3-((3S,4R)-4-(3-fluorophenyl)-1-(2-methoxyethyl)pyrrolidin-3-yl)urea $^1$H NMR (CD$_3$OD, 300 MHz): δ 8.03-7.98 (m, 1H), 7.91 (dd, J=2.4 and 9.9 Hz, 1H), 7.61-7.57 (m, 3H), 7.40-7.28 (m, 4H), 7.07-6.94 (m, 3H), 4.27-4.24 (m, 1H), 3.49 (m, J=5.1 Hz, 2H), 3.31 (s, 3H), 3.29-3.21 (m, 2H), 3.20-3.05 (m, 1H), 2.93 (s, 3H), 2.75-2.65 (m, 3H), 2.54-2.50 (m, 1H). LCMS (M+H): 517.10.

Example 186: 1-(3-Cyanoisoquinolin-4-yl)-3-((3S,4R)-1-(2-methoxyethyl)-4-phenylpyrrolidin-3-yl)urea $^1$H NMR (CD$_3$OD, 300 MHz): δ 8.83 (s, 1H), 8.68-8.65 (m, 1H), 8.06-8.03 (m, 1H), 7.84-7.80 (m, 2H), 7.37-7.19 (m, 4H), 6.46-6.41 (m, 1H), 3.90-3.84 (m, 1H), 3.82-3.76 (m, 1H), 3.64 (t, J=5.1 Hz, 2H), 3.56 (d, J=8.7 Hz 1H), 3.42 (s, 3H), 3.35-3.31 (m, 1H), 3.07-2.94 (m, 2H), 2.87-2.79 (m, 1H), 2.58 (t, J=9.6 Hz, 1H). LCMS (M+H): 415.91.

Example 187: 1-((3S,4R)-1-(2-Methoxyethyl)-4-phenylpyrrolidin-3-yl)-3-(3-phenyl-1-(piperazin-1-yl)isoquinolin-4-yl)urea $^1$H NMR (CD$_3$OD, 400 MHz): δ 8.16 (d, J=8.0 Hz, 1H), 7.89-7.85 (m, 1H), 7.70-7.66 (m, 3H), 7.58 (t, J=8.0 Hz, 1H), 7.33-7.22 (m, 8H), 4.33-4.29 (m, 1H), 3.52-3.49 (m, 6H), 3.35-3.50 (m, 4H), 3.25-3.12 (m, 5H), 2.91-2.68 (m, 5H). LCMS (M+H): 551.39.

Example 188: 1-(1-Cyano-7-fluoro-3-phenylisoquinolin-4-yl)-3-((3S,4R)-1-(2-methoxyethyl)-4-phenylpyrrolidin-3-yl)urea $^1$H NMR (DMSO d$_6$, 400 MHz): δ 8.40 (br s, 1H), 8.12-8.09 (m, 1H), 7.93-7.85 (m, 2H), 7.63-7.61 (m, 2H), 7.52-7.45 (m, 3H), 7.33-7.20 (m, 5H), 6.90 (d, J=8.0 Hz, 1H), 4.09-4.04 (m, 1H), 3.43 (t, J=5.6 Hz, 2H), 3.24 (s, 3H), 3.13-3.04 (m, 2H), 2.80 (t, J=8.0 Hz, 1H), 2.65-2.55 (m, 3H), 2.44 (t, J=8.4 Hz, 1H). LCMS (M+H): 510.36.

Example 189: 1-(1-(Difluoromethyl)-3-phenylisoquinolin-4-yl)-3-(4-(3-fluorophenyl)-1-(2-methoxyethyl)pyrrolidin-3-yl)urea Step 1: Synthesis of 1-(4-(3-fluorophenyl)-1-(2-methoxyethyl)pyrrolidin-3-yl)-3-(1-formyl-3-phenylisoquinolin-4-yl)urea: To a stirred solution of 1-(4-(3-fluorophenyl)-1-(2-methoxyethyl)pyrrolidin-3-yl)-3-(1-methyl-3-phenylisoquinolin-4-yl)urea (0.1 g, 0.200 mmol) in 1,4 dioxane (30 mL) was added selenium dioxide (0.033 g, 0.301 mmol) and the reaction mixture was refluxed for 4 h. The reaction mixture was allowed to room temperature, concentrated under reduced pressure and the resultant crude compound was purified by flash chromatography using 5% methanol in dichloromethane as an eluent to afford intermediate 1-(4-(3-fluorophenyl)-1-(2-methoxyethyl)pyrrolidin-3-yl)-3-(1-formyl-3-phenylisoquinolin-4-yl)urea (0.05 g, 49%) as a white solid. ESI-MS m/z: 513.47 (M+H)$^+$.

Step 2: Synthesis of 1-(1-(difluoromethyl)-3-phenylisoquinolin-4-yl)-3-(4-(3-fluorophenyl)-1-(2-methoxyethyl) pyrrolidin-3-yl)urea: Deoxo-Fluor® solution 50% in THF (0.064 g, 0.292 mmol) was added to a solution of 1-(4-(3-fluorophenyl)-1-(2-methoxyethyl)pyrrolidin-3-yl)-3-(1-formyl-3-phenylisoquinolin-4-yl)urea (0.05 g, 0.097 mmol) in DCM (20 mL) at 0° C. and stirred at rt for 12 h. The reaction mixture was diluted with dichloromethane and washed with water. The separated organic layer was dried over anhydrous Na$_2$SO$_4$, filtered and the filtrate was evaporated under reduced pressure. The crude compound was purified by flash chromatography using 5% methanol in dichloromethane as an eluent to afford the title compound (0.01 g, 19%) as an off-white solid. $^1$H NMR (DMSO d$_6$ 300 MHz): 8.41 (d, J=8.4 Hz, 1H), 8.17 (br s, 1H), 8.00 (d, J=7.5 Hz, 1H), 7.90-7.77 (m, 2H), 7.69-7.65 (m, 2H), 7.58-7.38 (m, 4H), 7.35-7.31 (m, 1H), 7.11-7.01 (m, 3H), 6.79 (d, J=7.8 Hz, 1H), 4.15-4.03 (m, 1H), 3.44 (t, J=5.7 Hz, 2H), 3.24 (s, 3H), 3.09-3.05 (m, 2H), 2.86 (t, J=7.5 Hz, 1H), 2.74-2.71 (m, 1H), 2.66-2.57 (m, 2H), 2.28-2.24 (m, 1H). ESI-MS m/z: 535.49 (M+H)$^+$.

Example 190: 7-Fluoro-4-(3-(1-(2-methoxyethyl)-4-phenylpyrrolidin-3-yl)ureido)-3-phenylisoquinoline-1-carboxylic acid To a stirred solution of methyl 7-fluoro-4-(3-(1-(2-methoxyethyl)-4-phenylpyrrolidin-3-yl)ureido)-3-phenylisoquinoline-1-carboxylate (0.02 g, 0.036 mmol) in THF: MeOH (1:1) (6 mL) was added LiOH.H$_2$O (0.003 g 0.073 mmol) and the reaction mixture was stirred for 2 h at rt. Then, it was concentrated under vacuum and the resulting residue was neutralized with 2N HCl, the formed solid was filtered and dried under reduced pressure to get the title compound as grey solid. Yield: 0.010 g (53%). $^1$H NMR (CD$_3$OD, 400 MHz): δ 8.22-8.14 (m, 1H), 8.02-7.94 (m, 1H), 7.65-7.53 (m, 3H), 7.36-7.29 (m, 8H), 4.42-4.36 (m, 1H), 3.89-3.85 (m, 1H), 3.66-3.63 (m, 2H), 3.59-3.47 (m, 2H), 3.38 (s, 3H), 3.35-3.31 (m, 3H), 3.28-3.21 (m, 1H). LC-MS (M+H): 529.69.

Example 191: 7-Fluoro-4-(3-((3S,4R)-1-(2-methoxyethyl)-4-phenylpyrrolidin-3-yl)ureido)-3-phenylisoquinoline-1-carboxamide To a stirred solution of 7-fluoro-4-(3-(1-(2-methoxyethyl)-4-phenylpyrrolidin-3-yl)ureido)-3-phenylisoquinoline-1-carboxylic acid (Example 190, 0.075 g, 0.142 mmol) in DMF (5 mL) were added HATU (0.081 g 0.213 mmol), DIPEA (0.075 mL, 0.426 mmol) and THF solution of ammonia (5 mL) and was stirred for 1 h at rt. The reaction mixture was diluted with water (10 mL) and extracted with ethyl acetate (2×20 mL). The combined organic layers were washed with water (10 mL), brine (10 mL) and dried over sodium sulphate. The solvents were filtered, concentrated under reduced pressure and the residue was purified by flash column chromatography eluting with 3% methanol/dichloromethane to afford the title compound as a yellow solid. Yield: 0.008 g (11%). $^1$H NMR (CD$_3$OD, 300 MHz): δ 8.95 (dd, J=2.7 Hz and 10.8 Hz, 1H), 8.08-8.03 (m, 1H), 7.71-7.69 (m, 2H), 7.63-7.56 (m, 2H), 7.41-7.33 (m, 5H), 7.31-7.25 (m, 2H), 4.32-4.27 (m, 1H), 3.52 (t, J=4.5 Hz, 2H), 3.31 (s, 3H), 3.17-3.11 (m, 2H), 2.97 (t, J=8.1 Hz, 1H), 2.82-2.74 (m, 3H), 2.59 (t, J=9.3 Hz, 1H). LC-MS (M+H): 528.38.

Example 192: 4-(3-((3S,4R)-1-(2-Methoxyethyl)-4-phenylpyrrolidin-3-yl)ureido)isoquinoline-3-carboxamide $^1$H NMR (CD$_3$OD, 400 MHz): δ 8.98 (s, 1H), 8.65 (d, J=8.0 Hz 1H), 7.80 (d, J=8.4 Hz, 1H), 7.72-7.64 (m, 2H), 7.40-7.33 (m, 4H), 7.25 (t, J=6.8 Hz, 1H), 4.44-4.38 (m, 1H), 3.58 (t, J=5.4 Hz 2H), 3.37 (s, 3H), 3.35-3.34 (m, 2H), 3.18 (t, J=9.2 Hz, 1H), 2.99-2.95 (m, 1H), 2.91-2.80 (m, 3H). LC-MS (M+H): 434.24.

Example 193: Methyl 2-((7-fluoro-4-(3-((3S,4R)-1-(2-methoxyethyl)-4-phenylpyrrolidin-3-yl)ureido)-3-phenylisoquinolin-1-yl)(methyl)amino)acetate $^1$H NMR (DMSO-d$_6$, 300 MHz): δ 7.84 (dd, J=2.4, 10.2 Hz, 1H), 7.80-7.78 (m, 1H), 7.73-7.68 (m, 1H), 7.65-7.58 (m, 3H), 6.63 (br s, 1H), 7.36-7.21 (m, 8H), 4.21-4.16 (m, 1H), 4.13 (s, 2H), 3.64 (s, 3H), 3.44 (t, J=5.4 Hz, 2H), 3.31 (s, 3H), 3.25 (s, 3H), 3.11-3.04 (m, 2H), 2.88-2.85 (m, 1H), 2.67-2.58 (m, 3H), 2.49 (t, J=1.8 Hz, 1H). LC-MS (M+H): 586.08.

Example 194: 2-((7-Fluoro-4-(3-((3S,4R)-1-(2-methoxyethyl)-4-phenylpyrrolidin-3-yl)ureido)-3-phenylisoquinolin-1-yl)(methyl)amino)acetic acid $^1$H NMR (DMSO-d$_6$, 300 MHz): δ 7.85-7.82 (m, 1H), 7.78 (d, J=8.0 Hz, 1H), 7.62-7.55 (m, 3H), 7.34-7.32 (m, 9H), 6.62 (br s, 1H), 4.16-4.10 (m, 1H), 4.04 (s, 2H), 3.44 (t, J=5.7 Hz, 2H), 3.32 (s, 3H), 3.24 (s, 3H), 3.13-3.02 (m, 2H), 2.88-2.85 (m, 1H), 2.66-2.55 (m, 3H). LC-MS (M+H): 572.35.

Example 195: 1-(7-Fluoro-1-((2-hydroxyethyl)(methyl)amino)-3-phenylisoquinolin-4-yl)-3-((3S,4R)-1-(2-methoxyethyl)-4-phenylpyrrolidin-3-yl)urea $^1$H NMR (CD$_3$OD, 400 MHz): δ 8.06 (d, J=9.6 Hz, 1H), 7.93-7.88 (m, 1H), 7.86-7.79 (m, 1H), 7.66-7.60 (m, 2H), 7.48-7.42 (m, 1H), 7.36-7.28 (m, 7H), 4.68-4.59 (m, 1H), 3.92-3.89 (m, 4H), 3.78-3.72 (m, 1H), 3.70-3.61 (m, 3H), 3.59 (s, 3H), 3.52-3.45 (m, 2H), 3.38-3.34 (m, 3H), 3.12 (s, 3H). LC-MS (M+H): 558.45.

Example 196: Ethyl 2-((4-(3-((3S,4R)-1-(2-methoxyethyl)-4-phenylpyrrolidin-3-yl)ureido)-3-phenylisoquinolin-7-yl)oxy)acetate $^1$H NMR (CD$_3$OD, 400 MHz): δ 9.10 (s, 1H), 7.87 (d, J=9.2 Hz, 1H), 7.57-7.56 (m, 2H), 7.48 (d, J=9.6 Hz, 2H), 7.39-7.21 (m, 8H), 4.91 (s, 2H), 4.35-4.32 (m, 1H) 4.28 (q, J=7.2 Hz, 2H), 3.50 (t, J=10.8 Hz, 2H), 3.30 (s, 3H), 3.24-3.19 (m, 1H), 3.12-3.04 (m, 1H), 2.92-2.90 (m, 1H), 2.76-2.70 (m, 3H), 2.53 (t, J=10.8 Hz, 1H), 1.30 (t, J=6.8 Hz, 3H). LC-MS: (M+H): 569.31.

Example 197: 2-((4-(3-((3S,4R)-1-(2-Methoxyethyl)-4-phenylpyrrolidin-3-yl)ureido)-3-phenylisoquinolin-7-yl)oxy)acetic acid $^1$H NMR (CD$_3$OD, 300 MHz): δ 9.09 (s, 1H), 7.82-7.76 (m, 1H), 7.60-7.54 (m, 1H), 7.50-7.45 (m, 3H), 7.42-7.36 (m, 5H), 7.32-7.28 (m, 3H), 4.58 (s, 2H), 4.42-4.34 (m, 1H), 3.75-3.71 (m, 1H), 3.62 (t, J=4.8 Hz, 2H), 3.52-3.44 (m, 2H), 3.38 (s, 3H), 3.23-3.18 (m, 1H), 3.12-3.05 (m, 3H). LC-MS (M+H): 541.35.

Example 198: 1-(7-(2-hydroxyethoxy)-3-phenylisoquinolin-4-yl)-3-((3S,4R)-1-(2-methoxyethyl)-4-phenylpyrrolidin-3-yl)urea $^1$H NMR (CD$_3$OD, 300 MHz): 9.10 (s, 1H), 7.84 (d, J=9.3 Hz, 1H), 7.57-7.51 (m, 3H), 7.47 (dd, J=2.4 and 9.3 Hz, 1H), 7.39-7.24 (m, 8H), 4.32-4.28 (m, 1H), 4.24 (t, J=4.2 Hz, 2H), 3.96 (t, J=4.8 Hz, 2H), 3.50 (t, J=5.4 Hz, 2H), 3.31 (s, 3H), 3.26-3.22 (m, 1H), 3.12-3.05 (m, 1H), 2.93 (t, J=6.9 Hz, 1H), 2.76-2.71 (m, 3H), 2.54 (t, J=9.3 Hz, 1H). LC-MS (M+H): 527.46.

Example 199: 1-(4-(Benzyloxy)-1-(2-methoxyethyl)pyrrolidin-3-yl)-3-(7-fluoro-1-methyl-3-phenylisoquinolin-4-yl)urea $^1$H NMR (CD$_3$OD, 400 MHz): δ 8.13-8.09 (m, 1H), 7.94 (dd, J=2.4 and 9.6 Hz, 1H), 7.64-7.59 (m, 3H), 7.42-7.33 (m, 3H), 7.28-7.25 (m, 5H), 4.57-4.54 (m, 1H), 4.44-4.40 (m, 1H), 4.34-4.10 (m, 1H), 3.78-3.60 (m, 2H), 3.44 (s, 3H), 3.30-3.25 (m, 1H), 3.10-2.98 (m, 1H), 2.94 (s, 3H), 2.87-2.78 (m, 1H), 2.68-2.57 (m, 2H), 2.49-2.42 (m, 2H). LCMS (M+H): 529.08.

Example 200: 1-(7-Fluoro-1-methyl-3-phenylisoquinolin-4-yl)-3-(4-hydroxy-1-(2-methoxyethyl)pyrrolidin-3-yl)urea $^1$H NMR (DMSO-d$_6$, 400 MHz): δ 8.50-7.79 (m, 2H), 7.76-7.67 (m, 3H), 7.45 (t, =7.2 Hz, 2H), 7.39 (t, J=7.6 Hz, 1H), 6.54-6.48 (m, 2H), 4.00-3.89 (m, 1H), 3.87-3.79 (m, 2H), 3.51-3.42 (m, 3H), 3.25 (s, 3H), 3.23-3.20 (m, 1H), 3.10-3.00 (m, 2H), 2.89 (s, 3H), 2.64-2.58 (m, 1H). LCMS (M+H): 439.25.

Example 201: 1-(7-Fluoro-1-methyl-3-phenylisoquinolin-4-yl)-3-(4-hydroxy-1-(2-methoxyethyl)-4-phenylpyrrolidin-3-yl)urea $^1$H NMR (DMSO-d$_6$, 300 MHz): δ 7.91 (dd, J=2.1 and 9.9 Hz, 1H), 7.69 (br s, 1H), 7.53-7.50 (m, 5H), 7.41-7.35 (m, 7H), 6.28 (br s, 1H), 5.44 (br s, 1H), 4.30-4.23 (m, 1H), 3.51-3.47 (m, 2H), 3.28 (s, 3H), 3.24-3.15 (m, 3H), 2.84 (s, 3H), 2.80-2.75 (m, 3H), 2.61-2.58 (m, 1H). LCMS (M+H): 515.35.

Example 202: 1-(4-Fluoro-1-(2-methoxyethyl)-4-phenylpyrrolidin-3-yl)-3-(7-fluoro-1-methyl-3-phenylisoquinolin-4-yl)urea $^1$H NMR (CDCl$_3$, 300 MHz): δ 7.67 (d, J=7.5 Hz, 2H), 7.50-7.42 (m, 4H), 7.40-7.33 (m, 5H), 7.22-7.17 (m, 3H), 5.91 (brs, 1H), 4.63-4.53 (m, 1H), 3.46 (t, J=5.4 Hz, 2H), 3.32 (s, 3H), 3.16-3.06 (m, 2H), 3.01-2.97 (m, 1H), 2.93 (s, 3H), 2.75-2.73 (m, 2H), 2.63-2.61 (m, 1H). LCMS (M+H): 517.33.

Biological Activity

Example A: TrkA Cell Based Phosphorylation Assay

Recombinant AD293 cells overexpressing human TrkA were used to determine TrkA Y490 phosphorylation upon NGF stimulation. 25 k cells plated in serum free DMEM medium in a 96 well plate were serum starved for 2 hours at 37° C. in 5% CO2 incubator. Test compounds were added to the plate at a final concentration of 2.5% DMSO and incubated for 20 min at 37° C. 6 nM NGF was added and incubated for 5 min at 37° C. The plate was immediately centrifuged at 2000 rpm for 1 min and media removed. Lysis buffer containing 1% NP-40 Substitute, 20 mM Tris (pH 8.0), 137 mM NaCl final concentrations was added, mixed for one minute and kept on ice for 15 min with shaking every 5 minutes. 100 ul of the cell lysate was added to the PathScan® Phospho-TrkA (Tyr490) Sandwich ELISA plate with precoated wells and ELISA performed according to the manufacturer's instructions for color development. $IC_{50}$ was generated in Graph Pad Prism software in non linear regression format.

$IC_{50}$ for representative compounds of this invention are provided below in Table 2.

TABLE 2

TrkA Cell based activity for representative compounds

| Example | TrkA Cell based activity |
|---------|--------------------------|
| 2       | +++                      |
| 16      | ++                       |
| 33      | +                        |
| 74      | +++                      |
| 104     | ++                       |
| 125     | +++                      |
| 149     | +++                      |
| 165     | ++                       |
| 172     | +++                      |
| 190     | ++                       |

The +++ represents $IC_{50}$ of <100 nM, the ++ represents $IC_{50}$ range between 100 nM to 1000 nM and the + represents $IC_{50}$ of >1000 nM.

We claim:
1. A compound of Formula I:

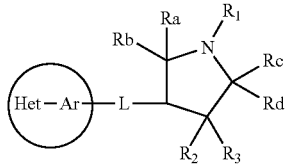

Formula I or stereoisomers, tautomers, or pharmaceutically acceptable salts, isotopologues, solvates, or prodrugs thereof, wherein:

Ra and Rb are each independently selected from H, alkyl, alkenyl, alkynyl, haloalkyl, halogen, hydroxy, hydroxyalkyl, alkoxy, haloalkoxy, optionally substituted phenyl, optionally substituted 5-6 membered aromatic ring having 1-3 heteroatoms selected from O, N, and S or Ra and Rb together forms carbonyl group, optionally substituted phenyl which is further optionally substituted with a halogen;

Rc and Rd is H, alkyl, alkenyl, alkynyl, haloalkyl, hydroxy, alkoxy, haloalkoxy, optionally substituted phenyl, optionally substituted 5-6 membered aromatic ring having 1-3 heteroatoms selected from O, N, or S or Rc and Rd together form a ring (4-6 membered) with or without a hetero atom;

R1 is alkenyl, alkynyl, haloalkyl, hydroxy, alkoxy, haloalkoxy, (1-3C alkoxy)(1-3C)alkyl, (1-4C alkoxycarbonyl) (1-6Calkyl), mono, di, tri halo(1-4C alkyl), alkoxy (1-3C) carbonyl, (1-3C alkyl)aminocarbonyl, cyano(1-3C alkyl), (1-3C haloalkoxy)(1-3C)alkyl, 3-6 membered heterocyclic ring with one or more heteroatom selected from O, N or S and optionally substituted with one or more substituents independently selected from H, alkyl, alkenyl, alkynyl, haloalkyl, halogen, hydroxy, alkoxy, haloalkoxy, nitro or amino, a 9-10 membered bicyclic heteroaryl having 1-3 ring nitrogen atoms;

R2 and R3 are independently selected from H, alkyl, alkenyl, alkynyl, isopropyl, tert butyl, haloalkyl, halogen, hydroxy, alkoxy, haloalkoxy, optionally substituted phenyl, or optionally substituted 5-6 membered aromatic ring having 1-3 heteroatoms selected from O, N, or S with the provision that R2 and R3 cannot be hydrogen atoms at the same time;

L is a NR'C(O)N(R') wherein each R' is independently selected from H or alkyl;

Het-Ar ring is selected from the group consisting of H1A-H1G;

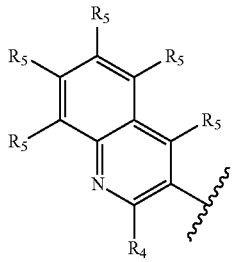

H1A

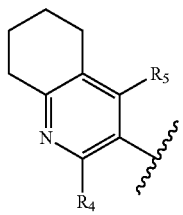

H1B

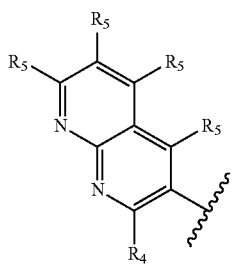

H1C

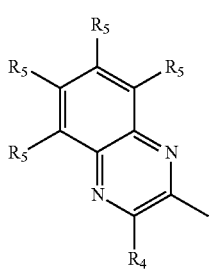

H1D

-continued

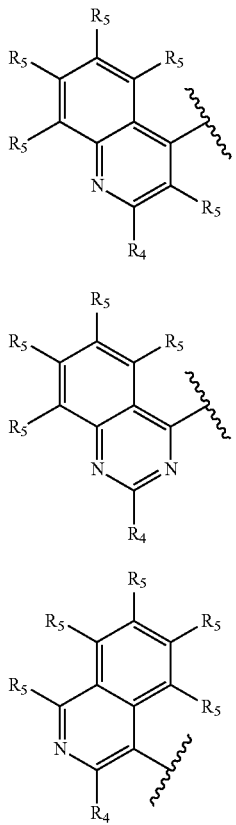

H1E

H1F

H1G

R4 and R5 are each independently selected from the group consisting of H, alkyl, alkenyl, alkynyl, isopropyl, tert-butyl, haloalkyl, halogen, mono, di, tri halo(1-4C alkyl)hydroxy, alkoxy, haloalkoxy, cyano, cycloalkyl(3-7 carbon), optionally substituted phenyl, optionally substituted 5-6 membered heterocyclic ring having 1-3 heteroatoms selected from O, N, or S or 3-6 membered carbocyclic ring having one or more heteroatom selected from O, N or S, —NH$_2$, —N(H)(alkyl), —N(alkyl)$_2$, —N(H)C(O)alkyl, —N(alkyl)C(O)alkyl, —N(H)C(O)O alkyl, —N(alkyl)C(O)Oalkyl, —N(H)SO$_2$(alkyl), —N(alkyl)SO$_2$(alkyl), —C(O)alkyl, —C(O)OH, —(O)Oalkyl, —C(O)NH$_2$, —C(O)N(H)(alkyl), —C(O)N(alkyl)$_2$, —S(alkyl), —S(O)alkyl, —S(O)$_2$alkyl, —S(O)$_2$N(H)2, —S(O)$_2$N(H)(alkyl) and —S(O)$_2$N(alkyl)$_2$.

2. A pharmaceutical composition comprising a therapeutically effective amount of a compound of Formula I in claim 1 or a pharmaceutically acceptable salt thereof.

3. A compound which is:
1-((3S,4R)-1-(2-methoxyethyl)-4-phenylpyrrolidin-3-yl)-3-(quinolin-3-yl)urea
1-((3S,4R)-1-(2-methoxyethyl)-4-phenylpyrrolidin-3-yl)-3-(2-phenylquinolin-3-yl)urea
1-((3S,4R)-1-(2-methoxyethyl)-4-phenylpyrrolidin-3-yl)-3-(2-methylquinolin-3-yl)urea
1-(2-Ethylquinolin-3-yl)-3-((3S,4R)-1-(2-methoxyethyl)-4-phenylpyrrolidin-3-yl)urea
1-(2-Cyclopropylquinolin-3-yl)-3-((3S,4R)-1-(2-methoxyethyl)-4-phenylpyrrolidin-3-yl)urea
1-(2-(Trifluoromethyl)quinolin-3-yl)-3-((3S,4R)-1-(2-methoxyethyl)-4-phenylpyrrolidin-3-yl)urea
1-(6-Fluoro-2-phenylquinolin-3-yl)-3-((3S,4R)-1-(2-methoxyethyl)-4-phenylpyrrolidin-3-yl)urea
1-(6-Fluoro-2-methylquinolin-3-yl)-3-((3S,4R)-1-(2-methoxyethyl)-4-phenylpyrrolidin-3-yl)urea
1-(5-fluoro-2-methylquinolin-3-yl)-3-((3S,4R)-1-(2-methoxyethyl)-4-phenylpyrrolidin-3-yl)urea
1-(8-fluoro-2-methylquinolin-3-yl)-3-((3S,4R)-1-(2-methoxyethyl)-4-phenylpyrrolidin-3-yl)urea
1-(7-fluoro-2-phenylquinolin-3-yl)-3-((3S,4R)-1-(2-methoxyethyl)-4-phenylpyrrolidin-3-yl)urea
1-(7-fluoro-2-methylquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(6-methoxy-2-phenylquinolin-3-yl)urea
1-(7-methoxy-2-phenylquinolin-3-yl)-3-((3S,4R)-1-(2-methoxyethyl)-4-phenylpyrrolidin-3-yl)urea
1-(8-methoxy-2-phenylquinolin-3-yl)-3-((3S,4R)-1-(2-methoxyethyl)-4-phenylpyrrolidin-3-yl)urea
1-(5-methoxy-2-phenylquinolin-3-yl)-3-((3S,4R)-1-(2-methoxyethyl)-4-phenylpyrrolidin-3-yl)urea
1-(5-methoxy-2-methylquinolin-3-yl)-3-((3S,4R)-1-(2-methoxyethyl)-4-phenylpyrrolidin-3-yl)urea
1-(6-methoxy-2-methylquinolin-3-yl)-3-((3S,4R)-1-(2-methoxyethyl)-4-phenylpyrrolidin-3-yl)urea
1-(7-methoxy-2-methylquinolin-3-yl)-3-((3S,4R)-1-(2-methoxyethyl)-4-phenylpyrrolidin-3-yl)urea
1-(8-methoxy-2-methylquinolin-3-yl)-3-((3S,4R)-1-(2-methoxyethyl)-4-phenylpyrrolidin-3-yl)urea
1-(6,7-dimethoxy-2-phenylquinolin-3-yl)-3-((3S,4R)-1-(2-methoxyethyl)-4-phenylpyrrolidin-3-yl)urea
1-(6,7-dimethoxy-2-methylquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(6,7-dimethoxyquinolin-3-yl)urea
1-((3S,4R)-1-(2-methoxyethyl)-4-phenylpyrrolidin-3-yl)-3-(6-methyl-2-phenylquinolin-3-yl)urea
1-(2,6-dimethylquinolin-3-yl)-3-((3S,4R)-1-(2-methoxyethyl)-4-phenylpyrrolidin-3-yl)urea
1-(2,7-dimethylquinolin-3-yl)-3-((3S,4R)-1-(2-methoxyethyl)-4-phenylpyrrolidin-3-yl)urea
1-(2,5-dimethylquinolin-3-yl)-3-((3S,4R)-1-(2-methoxyethyl)-4-phenylpyrrolidin-3-yl)urea
1-(2,8-dimethylquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(7-methyl-2-phenylquinolin-3-yl)urea
1-(2-chloroquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(2-(1-methyl-1H-pyrazol-4-yl)quinolin-3-yl)urea
1-((3S,4R)-1-(2-methoxyethyl)-4-phenylpyrrolidin-3-yl)-3-(2-(pyridin-3-yl)quinolin-3-yl)urea
1-((3S,4R)-1-(2-methoxyethyl)-4-phenylpyrrolidin-3-yl)-3-(2-(pyridin-4-yl)quinolin-3-yl)urea
1-((3S,4R)-1-(2-methoxyethyl)-4-phenylpyrrolidin-3-yl)-3-(2-(pyrimidin-5-yl)quinolin-3-yl)urea
1-((3S,4R)-1-(2-methoxyethyl)-4-phenylpyrrolidin-3-yl)-3-(2-morpholinoquinolin-3-yl)urea
1-((3S,4R)-1-(2-methoxyethyl)-4-phenylpyrrolidin-3-yl)-3-(quinolin-4-yl)urea
1-((3S,4R)-1-(2-methoxyethyl)-4-phenylpyrrolidin-3-yl)-3-(quinazolin-4-yl)urea
1-(2-chloro-6,7-dimethoxyquinazolin-4-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(quinoxalin-2-yl)urea 1-(2-isopropylquinolin-3-yl)-3-((3S,4R)-1-(2-methoxyethyl)-4-phenylpyrrolidin-3-yl)urea
1-(2-tert-butylquinolin-3-yl)-3-((3S,4R)-1-(2-methoxyethyl)-4-phenylpyrrolidin-3-yl)urea
1-(6-methoxy-2-methyl-7-morpholinoquinolin-3-yl)-3-((3S,4R)-1-(2-methoxyethyl)-4-phenylpyrrolidin-3-yl)urea
1-(6-fluoro-7-methyl-2-phenylquinolin-3-yl)-3-((3S,4R)-1-(2-methoxyethyl)-4-phenylpyrrolidin-3-yl)urea
1-(6-bromo-8-methoxy-2-phenylquinolin-3-yl)-3-((3S,4R)-1-(2-methoxyethyl)-4-phenylpyrrolidin-3-yl)urea
1-(7-fluoro-6-methoxy-2-phenylquinolin-3-yl)-3-((3S,4R)-1-(2-methoxyethyl)-4-phenylpyrrolidin-3-yl)urea
1-(7-fluoro-6-methoxy-2-methylquinolin-3-yl)-3-((3S,4R)-1-(2-methoxyethyl)-4-phenylpyrrolidin-3-yl)urea
1-(8-methoxy-7-methyl-2-phenylquinolin-3-yl)-3-((3S,4R)-1-(2-methoxyethyl)-4-phenylpyrrolidin-3-yl)urea
1-(6-methoxy-2,7-dimethylquinolin-3-yl)-3-((3S,4R)-1-(2-methoxyethyl)-4-phenylpyrrolidin-3-yl)urea
1-(7-fluoro-6-methyl-2-phenylquinolin-3-yl)-3-((3S,4R)-1-(2-methoxyethyl)-4-phenylpyrrolidin-3-yl)urea
1-(7-fluoro-2,6-dimethylquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(6-phenyl-[1,3]dioxolo[4,5-g]quinolin-7-yl)urea
1-((3S,4R)-1-(2-methoxyethyl)-4-phenylpyrrolidin-3-yl)-3-(6-methyl-[1,3]dioxolo[4,5-g]quinolin-7-yl)urea
1-((3S,4R)-1-(2-methoxyethyl)-4-phenylpyrrolidin-3-yl)-3-(7-methyl-2,3-dihydro-[1,4]dioxino[2,3-g]quinolin-8-yl)urea
1-((3S,4R)-1-(2-methoxyethyl)-4-phenylpyrrolidin-3-yl)-3-(7-phenyl-2,3-dihydro-[1,4]dioxino[2,3-g]quinolin-8-yl)urea
1-(6-amino-7-methoxy-2-phenylquinolin-3-yl)-3-((3S,4R)-1-(2-methoxyethyl)-4-phenylpyrrolidin-3-yl)urea
1-(7-methoxy-6-(methylamino)-2-phenylquinolin-3-yl)-3-((3S,4R)-1-(2-methoxyethyl)-4-phenylpyrrolidin-3-yl)urea
N-(7-methoxy-3-(3-((3S,4R)-1-(2-methoxyethyl)-4-phenylpyrrolidin-3-yl)ureido)-2-phenylquinolin-6-yl)acetamide
N-(7-methoxy-3-(3-((3S,4R)-1-(2-methoxyethyl)-4-phenylpyrrolidin-3-yl)ureido)-2-methylquinolin-6-yl)acetamide
N-(6-methoxy-3-(3-((3S,4R)-1-(2-methoxyethyl)-4-phenylpyrrolidin-3-yl)ureido)-2-phenylquinolin-7-yl)acetamide
N-(6-methoxy-3-(3-((3S,4R)-1-(2-methoxyethyl)-4-phenylpyrrolidin-3-yl)ureido)-2-methylquinolin-7-yl)acetamide
1-(8-methoxy-6-(1-methyl-1H-pyrazol-4-yl)-2-phenylquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(2-methyl-8-(1-methyl-1H-pyrazol-4-yl)quinolin-3-yl)urea
1-((3S,4R)-4-(3,4-Difluorophenyl)-1-(2-methoxyethyl)pyrrolidin-3-yl)-3-(quinolin-3-yl)urea
1-((3S,4R)-1-(2-methoxyethyl)-4-phenylpyrrolidin-3-yl)-3-(naphthalen-2-yl)urea
1-((3R,4S)-1-(2-methoxyethyl)-4-phenylpyrrolidin-3-yl)-3-(naphthalen-2-yl)urea
1-((3S,4R)-4-(3,4-difluorophenyl)-1-(2-methoxyethyl)pyrrolidin-3-yl)-3-(2-(pyridin-3-yl)quinolin-3-yl)urea
1-((3S,4R)-4-(3,4-difluorophenyl)-1-(2-methoxyethyl)pyrrolidin-3-yl)-3-(2-methylquinolin-3-yl)urea
1-((3S,4R)-4-(3,4-difluorophenyl)-1-(2-methoxyethyl)pyrrolidin-3-yl)-3-(6,7-dimethoxy-2-methylquinolin-3-yl)urea
1-((3S,4R)-4-(3,4-difluorophenyl)-1-(2-methoxyethyl)pyrrolidin-3-yl)-3-(6,7-dimethoxyquinolin-3-yl)urea
1-((3S,4R)-4-(3-fluorophenyl)-1-(2-methoxyethyl)pyrrolidin-3-yl)-3-(quinolin-3-yl)urea
1-((3S,4R)-4-(3-fluorophenyl)-1-(2-methoxyethyl)pyrrolidin-3-yl)-3-(2-methylquinolin-3-yl)urea
1-(6-fluoro-2-methylquinolin-3-yl)-3-((3S,4R)-4-(3-fluorophenyl)-1-(2-methoxyethyl)pyrrolidin-3-yl)urea
1-(7-fluoro-2-methylquinolin-3-yl)-3-((3S,4R)-4-(3-fluorophenyl)-1-(2-methoxyethyl)pyrrolidin-3-yl)urea
1-(6,7-Dimethoxy-2-phenylquinolin-3-yl)-3-((3S,4R)-4-(3-fluorophenyl)-1-(2-methoxyethyl)pyrrolidin-3-yl)urea
1-((3S,4R)-4-(3-fluorophenyl)-1-(2-methoxyethyl)pyrrolidin-3-yl)-3-(6-phenyl-[1,3]dioxolo[4,5-g]quinolin-7-yl)urea
1-((3S,4R)-4-(3-fluorophenyl)-1-(2-methoxyethyl)pyrrolidin-3-yl)-3-(6-methyl-[1,3]dioxolo[4,5-g]quinolin-7-yl)urea
1-((3S,4R)-4-(3-Cyanophenyl)-1-(2-methoxyethyl)pyrrolidin-3-yl)-3-(quinolin-3-yl)urea
1-((3S,4R)-4-(3-cyanophenyl)-1-(2-methoxyethyl)pyrrolidin-3-yl)-3-(6,7-dimethoxy-2-phenylquinolin-3-yl)urea
1-((3S,4R)-1-(2-methoxyethyl)-4-(pyridin-3-yl)pyrrolidin-3-yl)-3-(quinolin-3-yl)urea
1-(6,7-dimethoxy-2-phenylquinolin-3-yl)-3-((3S,4R)-1-(2-methoxyethyl)-4-(pyridin-3-yl)pyrrolidin-3-yl)urea
1-((3S,4R)-4-tert-butyl-1-(2-methoxyethyl)pyrrolidin-3-yl)-3-(quinolin-3-yl)urea
1-(6,7-dimethoxy-2-phenylquinolin-3-yl)-3-((3S,4R)-1-(2-methoxyethyl)-4-(1-methyl-1H-pyrazol-4-yl)pyrrolidin-3-yl)urea
1-((3S,4R)-1-(2-methoxyethyl)-4-(1-methyl-1H-pyrazol-4-yl)pyrrolidin-3-yl)-3-(quinolin-3-yl)urea
1-((3S,4R)-1-(2-Methoxyethyl)-4-phenylpyrrolidin-3-yl)-3-(2-phenyl-1,8-naphthyridin-3-yl)urea
Methyl 2-((3S,4R)-3-(3-(6,7-dimethoxy-2-phenylquinolin-3-yl)ureido)-4-phenylpyrrolidin-1-yl)acetate
Methyl 2-((3R,4S)-3-phenyl-4-(3-(quinolin-3-yl)ureido)pyrrolidin-1-yl)acetate
1-((3S,4R)-1-(2-fluoroethyl)-4-phenylpyrrolidin-3-yl)-3-(6,7-dimethoxy-2-phenylquinolin-3-yl)urea
1-((3R,4S)-1-(2-fluoroethyl)-4-phenylpyrrolidin-3-yl)-3-(6,7-dimethoxy-2-phenylquinolin-3-yl)urea
1-((3S,4R)-1-(2-fluoroethyl)-4-phenylpyrrolidin-3-yl)-3-(2-phenylquinolin-3-yl)urea
1-((3S,4R)-1-(2-fluoroethyl)-4-phenylpyrrolidin-3-yl)-3-(quinolin-3-yl)urea
1-((3S,4R)-1-(2,2,2-trifluoroethyl)-4-phenylpyrrolidin-3-yl)-3-(6,7-dimethoxy-2-phenylquinolin-3-yl)urea
1-((3R,4S)-1-(2,2,2-trifluoroethyl)-4-phenylpyrrolidin-3-yl)-3-(6,7-dimethoxy-2-phenylquinolin-3-yl)urea
1-((3S,4R)-1-(2,2,2-trifluoroethyl)-4-phenylpyrrolidin-3-yl)-3-(quinolin-3-yl)urea
1-((3S,4R)-1-(2,2-difluoroethyl)-4-phenylpyrrolidin-3-yl)-3-(6,7-dimethoxy-2-phenylquinolin-3-yl)urea
1-((3S,4R)-1-(2,2-difluoroethyl)-4-phenylpyrrolidin-3-yl)-3-(quinolin-3-yl)urea
1-(6,7-dimethoxy-2-phenylquinolin-3-yl)-3-((3S,4R)-1-(2-methoxyacetyl)-4-phenylpyrrolidin-3-yl)urea
1-((3S,4R)-1-(2-methoxyacetyl)-4-phenylpyrrolidin-3-yl)-3-(quinolin-3-yl)urea 1-(6,7-dimethoxy-2-phenylquinolin-3-yl)-3-((3S,4R)-1-(oxetan-3-yl)-4-phenylpyrrolidin-3-yl)urea
2-((3S,4R)-3-(3-(6,7-dimethoxy-2-phenylquinolin-3-yl)ureido)-4-phenylpyrrolidin-1-yl)acetamide
1-((3S,4R)-1-(cyanomethyl)-4-phenylpyrrolidin-3-yl)-3-(6,7-dimethoxy-2-phenylquinolin-3-yl)urea
1-((3S,4R)-1-(cyanomethyl)-4-phenylpyrrolidin-3-yl)-3-(quinolin-3-yl)urea
2-((3R,4S)-3-phenyl-4-(3-(quinolin-3-yl)ureido)pyrrolidin-1-yl)acetamide
1-(1-(2-Methoxyethyl)-2-oxo-4-phenylpyrrolidin-3-yl)-3-(quinolin-3-yl)urea
1-(6-methoxy-7-methyl-2-phenylquinolin-3-yl)-3-((3S,4R)-1-(2-methoxyethyl)-4-phenylpyrrolidin-3-yl)urea
1-(6-cyano-7-fluoro-2-methylquinolin-3-yl)-3-((3S,4R)-1-(2-methoxyethyl)-4-phenylpyrrolidin-3-yl)urea
1-(6-cyano-7-methoxy-2-methylquinolin-3-yl)-3-((3S,4R)-1-(2-methoxyethyl)-4-phenylpyrrolidin-3-yl)urea
1-(7-cyano-6-fluoro-2-methylquinolin-3-yl)-3-((3S,4R)-1-(2-methoxyethyl)-4-phenylpyrrolidin-3-yl)urea
1-(7-cyano-6-fluoro-2-phenylquinolin-3-yl)-3-((3S,4R)-1-(2-methoxyethyl)-4-phenylpyrrolidin-3-yl)urea
1-(7-cyano-6-methoxy-2-phenylquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(2-(thiazol-5-yl)quinolin-3-yl)urea
1-((3S,4R)-1-(2-methoxyethyl)-4-phenylpyrrolidin-3-yl)-3-(2-phenyl-5,6,7,8-tetrahydroquinolin-3-yl)urea
1-(6,7-dimethoxy-2-phenylquinolin-3-yl)-3-((3S,4R)-1-(2-methoxyethyl)-4-phenylpyrrolidin-3-yl)-1,3-dimethylurea
1-((3S,4R)-1-(2-methoxyethyl)-4-phenylpyrrolidin-3-yl)-1-methyl-3-(2-phenylquinolin-3-yl)urea
1-(6-(difluoromethoxy)-7-methoxy-2-methylquinolin-3-yl)-3-((3S,4R)-1-(2-methoxyethyl)-4-phenylpyrrolidin-3-yl)urea
1-(2,2-difluoro-6-methyl-[1,3]dioxolo[4,5-g]quinolin-7-yl)-3-((3S,4R)-1-(2-methoxyethyl)-4-phenylpyrrolidin-3-yl)urea
1-(6-(difluoromethyl)-[1,3]dioxolo[4,5-g]quinolin-7-yl)-3-((3S,4R)-1-(2-methoxyethyl)-4-phenylpyrrolidin-3-yl)urea
1-([1,3]dioxolo[4,5-g]quinolin-7-yl)-3-((3S,4R)-1-(2-methoxyethyl)-4-phenylpyrrolidin-3-yl)urea
1-(2-cyclohexylquinolin-3-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(6-(trifluoromethyl)-[1,3]dioxolo[4,5-g]quinolin-7-yl)urea
1-(6-(difluoromethyl)-[1,3]dioxolo[4,5-g]quinolin-7-yl)-3-((3S,4R)-4-(3-fluorophenyl)-1-(2-methoxyethyl)pyrrolidin-3-yl)urea
1-([1,3]dioxolo[4,5-g]quinolin-7-yl)-3-((3S,4R)-4-(3,4-difluorophenyl)-1-(2-methoxyethyl)pyrrolidin-3-yl)urea
1-(6-fluoro-2-phenylquinolin-3-yl)-3-((3S,4R)-4-(3-fluorophenyl)-1-(2-methoxyethyl)pyrrolidin-3-yl)urea
1-((3S,4R)-4-(3-fluorophenyl)-1-(2-methoxyethyl)pyrrolidin-3-yl)-3-(2-phenyl-5,6,7,8-tetrahydroquinolin-3-yl)urea
1-((3S,4R)-1-(2-methoxyethyl)-4-phenylpyrrolidin-3-yl)-3-(7-methyl-2-phenyl-1,8-naphthyridin-3-yl)urea
1-((3S,4R)-4-(3-fluorophenyl)-1-(2-methoxyethyl)pyrrolidin-3-yl)-3-(2-phenylquinolin-3-yl)urea
1-([1,3]dioxolo[4,5-g]quinolin-7-yl)-3-((3S,4R)-4-(3-fluorophenyl)-1-(2-methoxyethyl)pyrrolidin-3-yl)urea
1-(2-(2,4-difluorophenyl)quinolin-3-yl)-3-((3S,4R)-1-(2-methoxyethyl)-4-phenylpyrrolidin-3-yl)urea
1-(2-(3,5-difluorophenyl)quinolin-3-yl)-3-((3S,4R)-1-(2-methoxyethyl)-4-phenylpyrrolidin-3-yl)urea
1-(4-(benzyloxy)-1-(2-methoxyethyl)pyrrolidin-3-yl)-3-(6-methyl-[1,3]dioxolo[4,5-g]quinolin-7-yl)urea
1-(1-chloro-3-methylisoquinolin-4-yl)-3-((3S,4R)-1-(2-methoxyethyl)-4-phenylpyrrolidin-3-yl)urea
1-(1,3-diphenylisoquinolin-4-yl)-3-((3S,4R)-1-(2-methoxyethyl)-4-phenylpyrrolidin-3-yl)urea
1-((3S,4R)-4-(3-fluorophenyl)-1-(2-methoxyethyl)pyrrolidin-3-yl)-3-(3-methyl-1-(1-methyl-1H-pyrazol-4-yl)isoquinolin-4-yl)urea
1-((3S,4R)-1-(2-methoxyethyl)-4-phenylpyrrolidin-3-yl)-3-(1-(1-methyl-1H-pyrazol-4-yl)-3-phenylisoquinolin-4-yl)urea
1-(isoquinolin-4-yl)-3S,4R)-1-(2-methoxyethyl)-4-phenylpyrrolidin-3-yl)urea
1-((3S,4R)-1-(2-methoxyethyl)-4-phenylpyrrolidin-3-yl)-3-(3-phenylisoquinolin-4-yl)urea
1-((3S,4R)-1-(2-methoxyethyl)-4-phenylpyrrolidin-3-yl)-3-(3-methylisoquinolin-4-yl)urea
1-(1-cyano-3-phenylisoquinolin-4-yl)-3-((3S,4R)-1-(2-methoxyethyl)-4-phenylpyrrolidin-3-yl)urea
1-(1-chloro-3-phenylisoquinolin-4-yl)-3-((3S,4R)-4-(3-fluorophenyl)-1-(2-methoxyethyl)pyrrolidin-3-yl)urea
1-((3S,4R)-4-(3-fluorophenyl)-1-(2-methoxyethyl)pyrrolidin-3-yl)-3-(3-phenylisoquinolin-4-yl)urea
1-(1-cyano-3-phenylisoquinolin-4-yl)-3-((3S,4R)-4-(3-fluorophenyl)-1-(2-methoxyethyl)pyrrolidin-3-yl)urea
1-(1-Hydroxy-3-phenylisoquinolin-4-yl)-3-((3S,4R)-1-(2-methoxyethyl)-4-phenylpyrrolidin-3-yl)urea
1-(1-amino-3-phenylisoquinolin-4-yl)-3-((3S,4R)-1-(2-methoxyethyl)-4-phenylpyrrolidin-3-yl)urea
1-(1-methoxy-3-phenylisoquinolin-4-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(1-methyl-3-phenylisoquinolin-4-yl)urea
1-(7-fluoro-1-methyl-3-phenylisoquinolin-4-yl)-3-((3S,4R)-1-(2-methoxyethyl)-4-phenylpyrrolidin-3-yl)urea
1-((3S,4R)-4-(3-fluorophenyl)-1-(2-methoxyethyl)pyrrolidin-3-yl)-3-(1-(1-methyl-1H-pyrazol-4-yl)-3-phenylisoquinolin-4-yl)urea
1-((3S,4R)-1-(2-methoxyethyl)-4-phenylpyrrolidin-3-yl)-3-(3-methyl-1-(1-methyl-1H-pyrazol-4-yl)isoquinolin-4-yl)urea
1-((3S,4R)-1-(2-methoxyethyl)-4-phenylpyrrolidin-3-yl)-3-(1-(1-methyl-1H-pyrazol-4-yl)isoquinolin-4-yl)urea
1-((3S,4R)-4-(3-fluorophenyl)-1-(2-methoxyethyl)pyrrolidin-3-yl)-3-(1-(1-methyl-1H-pyrazol-4-yl)isoquinolin-4-yl)urea
1-(3-(tert-butyl)-1-(1-methyl-1H-pyrazol-4-yl)isoquinolin-4-yl)-3-((3S,4R)-4-(3-fluorophenyl)-1-(2-methoxyethyl)pyrrolidin-3-yl)urea
1-(3-(tert-butyl)-1-(1-methyl-1H-pyrazol-4-yl)isoquinolin-4-yl)-3-((3S,4R)-1-(2-methoxyethyl)-4-phenylpyrrolidin-3-yl)urea
1-(1-fluoro-3-phenylisoquinolin-4-yl)-3S,4R)-1-(2-methoxyethyl)-4-phenylpyrrolidin-3-yl)urea
1-((3S,4R)-4-(3-fluorophenyl)-1-(2-methoxyethyl)pyrrolidin-3-yl)-3-(1-methyl-3-phenylisoquinolin-4-yl)urea
1-(7-methoxy-1-methyl-3-phenylisoquinolin-4-yl)-3-((3S,4R)-1-(2-methoxyethyl)-4-phenylpyrrolidin-3-yl)urea
1-(6-methoxy-1-methyl-3-phenylisoquinolin-4-yl)-3-((3S,4R)-1-(2-methoxyethyl)-4-phenylpyrrolidin-3-yl)urea 1-(1,6-dimethyl-3-phenylisoquinolin-4-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(3-phenyl-1-(pyridin-3-yl)isoquinolin-4-yl)urea
1-((3S,4R)-1-(2-methoxyethyl)-4-phenylpyrrolidin-3-yl)-3-(1-morpholino-3-phenylisoquinolin-4-yl)urea
1-(1-(4-hydroxypiperidin-1-yl)-3-phenylisoquinolin-4-yl)-3-((3S,4R)-1-(2-methoxyethyl)-4-phenylpyrrolidin-3-yl)urea
1-(3-(3-fluorophenyl)-1-methylisoquinolin-4-yl)-3-((3S,4R)-1-(2-methoxyethyl)-4-phenylpyrrolidin-3-yl)urea
1-(3-(2-fluorophenyl)-1-methylisoquinolin-4-yl)-3-((3S,4R)-1-(2-methoxyethyl)-4-phenylpyrrolidin-3-yl)urea
1-(6,7-dimethoxy-1-methyl-3-phenylisoquinolin-4-yl)-3-((3S,4R)-1-(2-methoxyethyl)-4-phenylpyrrolidin-3-yl)urea
1-(6-fluoro-1-methyl-3-phenylisoquinolin-4-yl)-3-((3S,4R)-1-(2-methoxyethyl)-4-phenylpyrrolidin-3-yl)urea
1-(1,7-dimethyl-3-phenylisoquinolin-4-yl)-3-((3S,4R)-1-(2-methoxyethyl)-4-phenylpyrrolidin-3-yl)urea
4-(3-((3S,4R)-1-(2-methoxyethyl)-4-phenylpyrrolidin-3-yl)ureido)-3-phenylisoquinoline-1-carboxamide
1-(8-methoxy-1-methyl-3-phenylisoquinolin-4-yl)-3S,4R)-1-(2-methoxyethyl)-4-phenylpyrrolidin-3-yl)urea
1-(8-fluoro-3-phenylisoquinolin-4-yl)-3S,4R)-1-(2-methoxyethyl)-4-phenylpyrrolidin-3-yl)urea
1-(7-fluoro-3-phenylisoquinolin-4-yl)-3S,4R)-1-(2-methoxyethyl)-4-phenylpyrrolidin-3-yl)urea
1-(7-fluoro-3-phenylisoquinolin-4-yl)-3S,4R)-4-(3-fluorophenyl)-1-(2-methoxyethyl)pyrrolidin-3-yl)urea
1-(5-methoxy-3-phenylisoquinolin-4-yl)-3-((3S,4R)-1-(2-methoxyethyl)-4-phenylpyrrolidin-3-yl)urea
1-(7-fluoro-1-methyl-3-phenylisoquinolin-4-yl)-3-((3S,4R)-4-(3-fluorophenyl)-1-(2-methoxyethyl)pyrrolidin-3-yl)urea
1-(3-cyanoisoquinolin-4-yl)-3-((3S,4R)-1-(2-methoxyethyl)-4-phenylpyrrolidin-3-yl)urea
1-((3S,4R)-1-(2-methoxyethyl)-4-phenylpyrrolidin-3-yl)-3-(3-phenyl-1-(piperazin-1-yl)isoquinolin-4-yl)urea
1-(1-cyano-7-fluoro-3-phenylisoquinolin-4-yl)-3S,4R)-1-(2-methoxyethyl)-4-phenylpyrrolidin-3-yl)urea
1-(1-(difluoromethyl)-3-phenylisoquinolin-4-yl)-3-((3S,4R)-4-(3-fluorophenyl)-1-(2-methoxyethyl)pyrrolidin-3-yl)urea
7-fluoro-4-(3-((3S,4R)-1-(2-methoxyethyl)-4-phenylpyrrolidin-3-yl)ureido)-3-phenylisoquinoline-1-carboxylic acid
7-fluoro-4-(3-((3S,4R)-1-(2-methoxyethyl)-4-phenylpyrrolidin-3-yl)ureido)-3-phenylisoquinoline-1-carboxamide
4-(3-((3S,4R)-1-(2-methoxyethyl)-4-phenylpyrrolidin-3-yl)ureido)isoquinoline-3-carboxamide
methyl 2-((7-fluoro-4-(3-((3S,4R)-1-(2-methoxyethyl)-4-phenylpyrrolidin-3-yl)ureido)-3-phenylisoquinolin-1-yl)(methyl)amino)acetate
2-((7-fluoro-4-(3-((3S,4R)-1-(2-methoxyethyl)-4-phenylpyrrolidin-3-yl)ureido)-3-phenylisoquinolin-1-yl)(methyl)amino)acetic acid
1-(7-fluoro-1-((2-hydroxyethyl)(methyl)amino)-3-phenylisoquinolin-4-yl)-3-((3S,4R)-1-(2-methoxyethyl)-4-phenylpyrrolidin-3-yl)urea
ethyl 2-((4-(3-((3S,4R)-1-(2-methoxyethyl)-4-phenylpyrrolidin-3-yl)ureido)-3-phenylisoquinolin-7-yl)oxy)acetate
2-((4-(3-((3S,4R)-1-(2-methoxyethyl)-4-phenylpyrrolidin-3-yl)ureido)-3-phenylisoquinolin-7-yl)oxy)acetic acid
1-(7-(2-hydroxyethoxy)-3-phenylisoquinolin-4-yl)-3-((3S,4R)-1-(2-methoxyethyl)-4-phenylpyrrolidin-3-yl)urea
1-(4-(benzyloxy)-1-(2-methoxyethyl)pyrrolidin-3-yl)-3-(7-fluoro-1-methyl-3-phenylisoquinolin-4-yl)urea
1-(7-fluoro-1-methyl-3-phenylisoquinolin-4-yl)-3-(4-hydroxy-1-(2-methoxyethyl)pyrrolidin-3-yl)urea
1-(7-fluoro-1-methyl-3-phenylisoquinolin-4-yl)-3-(4-hydroxy-1-(2-methoxyethyl)-4-phenylpyrrolidin-3-yl)urea
1-(4-fluoro-1-(2-methoxyethyl)-4-phenylpyrrolidin-3-yl)-3-(7-fluoro-1-methyl-3-phenylisoquinolin-4-yl)urea or stereoisomers, tautomers, or pharmaceutically acceptable salts, isotopologues, solvates, or prodrugs thereof.

4. A method for treating a disease or disorder mediated by Trk receptors or associated with abnormal or dysregulated TrkA kinase activity wherein said disease or disorder is selected from the group consisting of Pain, inflammation or inflammatory diseases, Cancer, atherosclerosis, restenosis, thrombosis, Neurodegenerative diseases, Erectile Dysfunction (ED), Skin disorders, Autoimmune disease, Sjogren's syndrome, diabetic peripheral neuropathy, prostatitis, Infectious diseases, diseases related to an imbalance of the regulation of bone remodeling, endometriosis, pelvic pain syndrome and diseases resulting from abnormal tissue remodelling and fibrotic disorders; or a disease, disorder, injury, or malfunction relating to dysmyelination or demyelination or a disease or disorder associated with abnormal activities of nerve growth factor (NGF) receptor Trk-A in a patient in need thereof, comprising administering to the patient a therapeutically effective amount of a compound of claim 1 or a pharmaceutically acceptable salt thereof, and a pharmaceutically acceptable carrier.

5. The method of claim 4, wherein the cancer is selected from the group consisting of lung adenocarcinomas, breast cancer, thyroid carcinoma, pancreatic cancer, papillary thyroid carcinoma, ovarian carcinoma, gastric carcinoma, malignant mesothelioma, prostate carcinoma, neuroblastic tumors, colorectal carcinoma, spitzoid melanoma, salivary adenoid cystic carcinoma glioblastoma multiforme, stomach cancer, kidney cancer, urethral cancer, oral squamous cell carcinoma, mastocytosis, extramammary Paget's disease, Acute Myeloid Leukemia, cholangiocarcinoma and sarcoma.

6. The method of claim 4, wherein the cancer is related to dysregulation of TrkA.

7. The method of claim 6, wherein the dysregulation of TrkA is characterized by one or more chromosome translocations or inversions resulting in TrkA gene fusions.

8. The method of claim 7, wherein the TrkA gene fusion is LMNA-TrkA, TFG-TrkA, TPM3-TrkA, CD74-TrkA, NFASC-TrkA, MPRIP-TrkA, BCAN-TrkA, TP53-TrkA, RNF213-TrkA, RABGAP1L-TrkA, IRF2BP2-TrkA, SQSTM1-TrkA, SSBP2-TrkA, or TPR-TrkA.

9. The method of claim 6, wherein the dysregulation of TrkA is characterized by one or more deletions, insertions or mutations in the TrkA protein.

* * * * *